(12) United States Patent
Dellamary

(10) Patent No.: US 11,819,499 B2
(45) Date of Patent: Nov. 21, 2023

(54) SINGLE-DOSE, READY-TO-USE INJECTABLE FORMULATIONS

(71) Applicant: BioSplice Therapeutics, Inc., San Diego, CA (US)

(72) Inventor: Luis A. Dellamary, San Marcos, CA (US)

(73) Assignee: BioSplice Therapeutics, Inc., San Diego, CA (US)

( * ) Notice: Subject to any disclaimer, the term of this patent is extended or adjusted under 35 U.S.C. 154(b) by 0 days.

(21) Appl. No.: 17/873,818

(22) Filed: Jul. 26, 2022

(65) Prior Publication Data

US 2023/0139639 A1 May 4, 2023

Related U.S. Application Data

(60) Continuation of application No. 16/939,713, filed on Jul. 27, 2020, now Pat. No. 11,446,288, which is a
(Continued)

(51) Int. Cl.
*A61K 31/444* (2006.01)
*A61K 9/00* (2006.01)
(Continued)

(52) U.S. Cl.
CPC .......... *A61K 31/444* (2013.01); *A61K 9/0019* (2013.01); *A61K 9/10* (2013.01);
(Continued)

(58) Field of Classification Search
None
See application file for complete search history.

(56) References Cited

U.S. PATENT DOCUMENTS

| 4,164,559 A | 8/1979 | Miyata et al. |
| 4,474,752 A | 10/1984 | Haslam et al. |

(Continued)

FOREIGN PATENT DOCUMENTS

| CN | 1394205 | 1/2003 |
| CN | 1671710 | 9/2005 |

(Continued)

OTHER PUBLICATIONS

"Application of Hamish Christopher Swan Wood, Norman Whittaker, Irene Stirling and Kyuji Ohta," 582 F.2d 638 (Fed. Cir. 1978), 2 pages.
(Continued)

*Primary Examiner* — Dominic Lazaro
(74) *Attorney, Agent, or Firm* — Fish & Richardson P.C.

(57) ABSTRACT

Provided are single-dose, ready-to-use formulations and methods for preparing the formulations that include a compound of Formula (I)
(Continued)

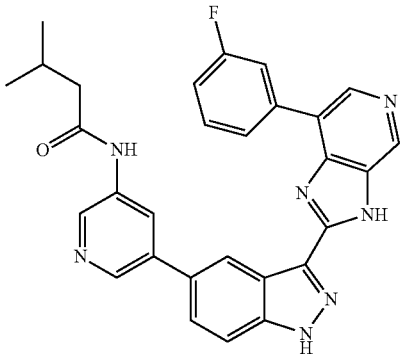

including pharmaceutically acceptable salts and amorphous and polymorph forms thereof.

45 Claims, 31 Drawing Sheets

Related U.S. Application Data division of application No. 15/806,321, filed on Nov. 7, 2017, now Pat. No. 10,758,523.

(60) Provisional application No. 62/418,688, filed on Nov. 7, 2016.

(51) Int. Cl.
*A61K 9/10* (2006.01)
*A61K 31/437* (2006.01)
*A61P 19/02* (2006.01)
*A61K 47/02* (2006.01)
*A61K 47/38* (2006.01)

(52) U.S. Cl.
CPC ............ *A61K 31/437* (2013.01); *A61K 47/02* (2013.01); *A61K 47/38* (2013.01); *A61P 19/02* (2018.01)

(56) References Cited

U.S. PATENT DOCUMENTS

| | | | |
|---|---|---|---|
| 4,603,139 A | 7/1986 | King | |
| 5,037,844 A | 8/1991 | Hamminga et al. | |
| 5,922,733 A | 7/1999 | Forbes et al. | |
| 6,120,484 A | 9/2000 | Silverstein | |
| 6,358,978 B1 | 3/2002 | Ritzeler et al. | |
| 6,377,849 B1 | 4/2002 | Lenarz et al. | |
| 6,440,102 B1 | 8/2002 | Arenberg et al. | |
| 6,555,539 B2 | 4/2003 | Reich et al. | |
| 6,648,873 B2 | 11/2003 | Arenberg et al. | |
| 6,831,175 B2 | 12/2004 | Li et al. | |
| 6,884,890 B2 | 4/2005 | Kania et al. | |
| 6,897,208 B2 | 5/2005 | Edwards et al. | |
| 6,911,211 B2 | 6/2005 | Eini et al. | |
| 6,919,461 B2 | 7/2005 | Reich et al. | |
| 7,008,953 B2 | 3/2006 | Kephart et al. | |
| 7,064,215 B2 | 6/2006 | Renhowe et al. | |
| 7,232,912 B2 | 6/2007 | Reich et al. | |
| 7,285,565 B2 | 10/2007 | Zhu et al. | |
| 7,390,815 B2 | 6/2008 | Davies et al. | |
| 7,429,609 B2 | 9/2008 | Ohi et al. | |
| 7,452,993 B2 | 11/2008 | Arnold et al. | |
| 7,468,376 B2 | 12/2008 | Rosales et al. | |
| 7,482,342 B2 | 1/2009 | D'Orchymont et al. | |
| 7,488,737 B2 | 2/2009 | Xie et al. | |
| 7,491,710 B2 | 2/2009 | Cherrier et al. | |
| 7,541,367 B2 | 6/2009 | Chiu et al. | |
| 7,626,021 B2 | 12/2009 | Arnold et al. | |
| 7,642,278 B2 | 1/2010 | Jansen et al. | |
| 7,666,867 B2 | 2/2010 | Makriyannis et al. | |
| 7,812,043 B2 | 10/2010 | Lau et al. | |
| 7,829,558 B2 | 11/2010 | Arnold et al. | |
| 7,842,711 B2 | 11/2010 | D'Orchymont et al. | |
| 7,902,217 B2 | 3/2011 | Xie et al. | |
| 7,943,616 B2 | 5/2011 | Cox et al. | |
| 8,008,481 B2 | 8/2011 | Ericsson et al. | |
| 8,088,772 B2 | 1/2012 | Garcia et al. | |
| 8,129,519 B2 | 3/2012 | Cholody et al. | |
| 8,158,647 B2 | 4/2012 | Blaney et al. | |
| 8,252,812 B2 | 8/2012 | Hood et al. | |
| 8,288,425 B2 | 10/2012 | Edwards et al. | |
| 8,304,408 B2 | 11/2012 | Wrasidlo et al. | |
| 8,450,340 B2 | 5/2013 | Hood et al. | |
| 8,604,052 B2 | 12/2013 | Hood et al. | |
| 8,618,128 B1 | 12/2013 | Hood et al. | |
| 8,637,508 B2 | 1/2014 | Badiger et al. | |
| 8,664,241 B2 | 3/2014 | Hood et al. | |
| 8,673,936 B2 | 3/2014 | Hood et al. | |
| 8,697,887 B2 | 4/2014 | Hood et al. | |
| 8,703,794 B2 | 4/2014 | Hood et al. | |
| 8,815,897 B2 | 8/2014 | Hood et al. | |
| 8,822,478 B2 | 9/2014 | Hood et al. | |
| 8,846,714 B2 | 9/2014 | Hood et al. | |
| 8,883,822 B2 | 11/2014 | Hood et al. | |
| 8,901,150 B2 | 12/2014 | Hood et al. | |
| 8,987,298 B2 | 3/2015 | Hood et al. | |
| 9,012,472 B2 | 4/2015 | Hood et al. | |
| 9,056,874 B2 | 6/2015 | Adams et al. | |
| 9,067,939 B2 | 6/2015 | Hood et al. | |
| 9,090,613 B2 | 7/2015 | Hood et al. | |
| 9,174,967 B2 | 11/2015 | Körber et al. | |
| 9,199,991 B2 | 12/2015 | Hood et al. | |
| 9,221,793 B2 | 12/2015 | Hood et al. | |
| 9,233,104 B2 | 1/2016 | Hood et al. | |
| 9,381,192 B2 | 7/2016 | Hood et al. | |
| 9,538,272 B2 | 1/2017 | Auclair et al. | |
| 9,540,398 B2 | 1/2017 | Kc et al. | |
| 9,586,977 B2 | 3/2017 | Hood et al. | |
| 9,745,271 B2 | 8/2017 | Hood et al. | |
| 9,763,927 B2 | 9/2017 | Hood et al. | |
| 9,763,951 B2 | 9/2017 | Kc et al. | |
| 9,802,916 B2 | 10/2017 | Hood et al. | |
| 9,815,854 B2 | 11/2017 | Kc et al. | |
| 9,828,372 B2 | 11/2017 | Kc et al. | |
| 9,844,536 B2 | 12/2017 | Kc et al. | |
| 9,855,272 B2 | 1/2018 | Hood et al. | |
| 9,889,140 B2 | 2/2018 | Kc et al. | |
| 10,131,677 B2 | 11/2018 | Sunil et al. | |
| 10,407,425 B2 | 9/2019 | Hood et al. | |
| 10,758,523 B2 | 9/2020 | Dellamary | |
| 10,899,757 B2 | 1/2021 | Hood et al. | |
| 10,947,228 B2 | 3/2021 | Hood et al. | |
| 10,981,909 B2 | 4/2021 | Kc | |
| 11,066,388 B2 | 7/2021 | Hood et al. | |
| 11,446,288 B2 | 9/2022 | Dellamary | |
| 11,560,378 B2 | 1/2023 | Hood et al. | |
| 11,667,632 B2 | 6/2023 | Hood et al. | |
| 11,684,615 B2 | 6/2023 | Deshmukh et al. | |
| 11,697,649 B2 | 7/2023 | Hood et al. | |
| 2002/0103229 A1 | 8/2002 | Bhagwat et al. | |
| 2002/0161022 A1 | 10/2002 | Reich et al. | |
| 2003/0199516 A1 | 10/2003 | Moser et al. | |
| 2004/0048868 A1 | 3/2004 | Edwards et al. | |
| 2004/0077681 A1 | 4/2004 | Rawlings et al. | |
| 2004/0176325 A1 | 9/2004 | Munson et al. | |
| 2004/0236101 A1 | 11/2004 | Makriyannis et al. | |
| 2005/0009894 A1 | 1/2005 | Babin et al. | |
| 2005/0026960 A1 | 2/2005 | Kephart et al. | |
| 2005/0070546 A1 | 3/2005 | Arrington et al. | |
| 2005/0090529 A1 | 4/2005 | McAlpine et al. | |
| 2005/0192262 A1 | 9/2005 | Hagstrom et al. | |
| 2005/0208582 A1 | 9/2005 | Ohi et al. | |
| 2005/0261339 A1 | 11/2005 | Ohi et al. | |
| 2006/0004000 A1 | 1/2006 | D'Orchymont et al. | |

(56) References Cited

U.S. PATENT DOCUMENTS

| | | |
|---|---|---|
| 2006/0014756 A1 | 1/2006 | Edwards et al. |
| 2006/0079564 A1 | 4/2006 | Jansen et al. |
| 2006/0094706 A1 | 5/2006 | Paruch et al. |
| 2006/0111322 A1 | 5/2006 | Reich et al. |
| 2006/0116519 A1 | 6/2006 | Ma et al. |
| 2006/0135589 A1 | 6/2006 | Berdino et al. |
| 2006/0142345 A1 | 6/2006 | Kephart et al. |
| 2006/0167056 A1 | 7/2006 | Rynberg et al. |
| 2006/0264897 A1 | 11/2006 | Lobl |
| 2007/0027140 A1 | 2/2007 | Lau et al. |
| 2007/0049598 A1 | 3/2007 | Billedeau et al. |
| 2007/0060616 A1 | 3/2007 | Bennett et al. |
| 2007/0078147 A1 | 4/2007 | Schumacher et al. |
| 2007/0185187 A1 | 8/2007 | D'Orchymont et al. |
| 2007/0219257 A1 | 9/2007 | Beachy et al. |
| 2007/0282101 A1 | 12/2007 | Ericsson et al. |
| 2008/0004270 A1 | 1/2008 | Gill et al. |
| 2008/0132495 A1 | 6/2008 | Berdini et al. |
| 2008/0255085 A1 | 10/2008 | Arvidsson et al. |
| 2008/0262205 A1 | 10/2008 | Haar et al. |
| 2008/0287452 A1 | 11/2008 | Bursavich et al. |
| 2009/0005356 A1 | 1/2009 | Blaney et al. |
| 2009/0005377 A1 | 1/2009 | Almansa Rosales et al. |
| 2009/0048249 A1 | 2/2009 | Chiu et al. |
| 2009/0054397 A1 | 2/2009 | Ohi et al. |
| 2009/0099062 A1 | 4/2009 | Lee et al. |
| 2009/0203690 A1 | 8/2009 | Akritopoulou-Zanze et al. |
| 2009/0247504 A1 | 10/2009 | Churcher et al. |
| 2009/0264446 A9 | 10/2009 | Rosales et al. |
| 2009/0286983 A1 | 11/2009 | Almansa Rosales et al. |
| 2010/0280063 A1 | 11/2010 | Price et al. |
| 2010/0298377 A1 | 11/2010 | Aletru et al. |
| 2011/0009353 A1 | 1/2011 | Chen-Kiang et al. |
| 2011/0021467 A1 | 1/2011 | D'Orchymont et al. |
| 2011/0034441 A1 | 2/2011 | Hood et al. |
| 2011/0034497 A1 | 2/2011 | Hood et al. |
| 2011/0082144 A1 | 4/2011 | Lau et al. |
| 2011/0178075 A1 | 7/2011 | Xie et al. |
| 2011/0190290 A1 | 8/2011 | Hood et al. |
| 2012/0053345 A1 | 3/2012 | Ericson et al. |
| 2012/0059047 A1 | 3/2012 | Prins et al. |
| 2012/0129837 A1 | 5/2012 | Cholody et al. |
| 2012/0277229 A1 | 11/2012 | Bearss et al. |
| 2013/0039906 A1 | 2/2013 | Do et al. |
| 2013/0267495 A1* | 10/2013 | Hood ............... A61P 3/04 514/210.21 |
| 2013/0267548 A1 | 10/2013 | Follmann et al. |
| 2014/0194441 A1 | 7/2014 | Kc et al. |
| 2014/0263319 A1 | 9/2014 | Fazi et al. |
| 2014/0364451 A1 | 12/2014 | John et al. |
| 2015/0087687 A1 | 3/2015 | Brown et al. |
| 2015/0111872 A1 | 4/2015 | Desroy et al. |
| 2016/0068529 A1 | 3/2016 | Kc et al. |
| 2016/0068547 A1 | 3/2016 | Kc et al. |
| 2016/0068548 A1 | 3/2016 | Kc et al. |
| 2016/0068549 A1 | 3/2016 | Kc et al. |
| 2016/0068550 A1 | 3/2016 | Kc et al. |
| 2016/0068551 A1 | 3/2016 | Kc et al. |
| 2016/0075701 A1 | 3/2016 | Kc |
| 2016/0090380 A1 | 3/2016 | Kc |
| 2016/0101092 A1 | 4/2016 | Hood et al. |
| 2016/0297812 A1 | 10/2016 | Hood et al. |
| 2016/0304488 A1 | 10/2016 | Hood et al. |
| 2017/0333409 A1 | 11/2017 | Hood et al. |
| 2017/0349584 A1 | 12/2017 | Kc et al. |
| 2018/0086754 A1 | 3/2018 | Kc et al. |
| 2018/0133199 A1 | 5/2018 | Dellamary |
| 2018/0141963 A1 | 5/2018 | Kc et al. |
| 2018/0148444 A1 | 5/2018 | Kc et al. |
| 2018/0153873 A1 | 6/2018 | Hood et al. |
| 2018/0162840 A1 | 6/2018 | Kc et al. |
| 2018/0177787 A1 | 6/2018 | Kc et al. |
| 2018/0185343 A1 | 7/2018 | Deshmukh et al. |
| 2018/0201624 A1 | 7/2018 | Kc et al. |
| 2018/0207141 A1 | 7/2018 | Kc et al. |
| 2018/0214427 A1 | 8/2018 | Kc et al. |
| 2018/0214428 A1 | 8/2018 | Kc et al. |
| 2018/0214429 A1 | 8/2018 | Kc et al. |
| 2018/0215753 A1 | 8/2018 | Kc et al. |
| 2018/0221341 A1 | 8/2018 | Kc et al. |
| 2018/0221350 A1 | 8/2018 | Kc et al. |
| 2018/0221351 A1 | 8/2018 | Kc et al. |
| 2018/0221352 A1 | 8/2018 | Kc et al. |
| 2018/0221353 A1 | 8/2018 | Kc et al. |
| 2018/0221354 A1 | 8/2018 | Kc et al. |
| 2018/0222891 A1 | 8/2018 | Kc et al. |
| 2018/0222923 A1 | 8/2018 | Kc et al. |
| 2018/0228780 A1 | 8/2018 | Kc et al. |
| 2018/0228781 A1 | 8/2018 | Kc et al. |
| 2018/0228782 A1 | 8/2018 | Kc et al. |
| 2018/0228783 A1 | 8/2018 | Kc et al. |
| 2018/0228784 A1 | 8/2018 | Kc et al. |
| 2018/0228785 A1 | 8/2018 | Kc et al. |
| 2018/0230142 A1 | 8/2018 | Kc et al. |
| 2018/0237416 A1 | 8/2018 | Hood et al. |
| 2018/0250269 A1 | 9/2018 | Kc et al. |
| 2018/0256588 A1 | 9/2018 | Hood et al. |
| 2018/0318292 A1 | 11/2018 | Hood et al. |
| 2019/0071440 A1 | 3/2019 | Hood et al. |
| 2021/0002273 A1 | 1/2021 | Kc |
| 2021/0121448 A1 | 4/2021 | Deshmukh et al. |
| 2021/0145807 A1 | 5/2021 | Dellamary |
| 2021/0292318 A1 | 9/2021 | Hood et al. |
| 2021/0292319 A1 | 9/2021 | Hood et al. |
| 2022/0024914 A1 | 1/2022 | Kc |
| 2023/0013144 A1 | 1/2023 | Hood et al. |
| 2023/0047396 A1 | 2/2023 | Hood et al. |

FOREIGN PATENT DOCUMENTS

| | | |
|---|---|---|
| CN | 1829713 | 9/2006 |
| CN | 101440092 | 5/2009 |
| EA | 200200768 | 2/2003 |
| KR | 20150004803 | 1/2015 |
| KZ | 20122 | 1/2010 |
| RU | 2331640 | 8/2008 |
| RU | 2350271 | 3/2009 |
| RU | 2416610 | 4/2011 |
| WO | WO 1987/05297 | 9/1987 |
| WO | WO 1996/02537 | 2/1996 |
| WO | WO 2001/02369 | 1/2001 |
| WO | WO 2001/053268 | 7/2001 |
| WO | WO 2003/004488 | 1/2003 |
| WO | WO 2003/035005 | 5/2003 |
| WO | WO 2003/035065 | 5/2003 |
| WO | WO 2003/035644 | 5/2003 |
| WO | WO 2003/051366 | 6/2003 |
| WO | WO 2003/070236 | 8/2003 |
| WO | WO 2003/070706 | 8/2003 |
| WO | WO 2003/097610 | 11/2003 |
| WO | WO 2003/101968 | 12/2003 |
| WO | WO 2003/101993 | 12/2003 |
| WO | WO 2004/014864 | 2/2004 |
| WO | WO 2004/031158 | 4/2004 |
| WO | WO 2004/076450 | 9/2004 |
| WO | WO 2005/009997 | 2/2005 |
| WO | WO 2005/012301 | 2/2005 |
| WO | WO 2005/014554 | 2/2005 |
| WO | WO 2005/047266 | 5/2005 |
| WO | WO 2005/049019 | 6/2005 |
| WO | WO 2005/092890 | 10/2005 |
| WO | WO 2005/099703 | 10/2005 |
| WO | WO 2005/110410 | 11/2005 |
| WO | WO 2006/001894 | 1/2006 |
| WO | WO 2006/015124 | 2/2006 |
| WO | WO 2006/024945 | 3/2006 |
| WO | WO 2006/054143 | 5/2006 |
| WO | WO 2006/054151 | 5/2006 |
| WO | WO 2006/063302 | 6/2006 |
| WO | WO 2006/063841 | 6/2006 |
| WO | WO 2006/130673 | 12/2006 |
| WO | WO 2007/061360 | 5/2007 |
| WO | WO 2007/107346 | 9/2007 |
| WO | WO 2007/117465 | 10/2007 |

(56) References Cited

FOREIGN PATENT DOCUMENTS

| WO | WO 2007/147874 | 12/2007 |
|----|----------------|---------|
| WO | WO 2008/061109 | 5/2008  |
| WO | WO 2008/071397 | 6/2008  |
| WO | WO 2008/071398 | 6/2008  |
| WO | WO 2008/071451 | 6/2008  |
| WO | WO 2008/124848 | 10/2008 |
| WO | WO 2008/137408 | 11/2008 |
| WO | WO 2008/140792 | 11/2008 |
| WO | WO 2008/147713 | 12/2008 |
| WO | WO 2008/150914 | 12/2008 |
| WO | WO 2008/154241 | 12/2008 |
| WO | WO 2008/156757 | 12/2008 |
| WO | WO 2009/011850 | 1/2009  |
| WO | WO 2009/016072 | 2/2009  |
| WO | WO 2009/029609 | 3/2009  |
| WO | WO 2009/061345 | 5/2009  |
| WO | WO 2009/152868 | 12/2009 |
| WO | WO 2010/064875 | 6/2010  |
| WO | WO 2010/107765 | 9/2010  |
| WO | WO 2010/111060 | 9/2010  |
| WO | WO 2010/132725 | 11/2010 |
| WO | WO 2011/011722 | 1/2011  |
| WO | WO 2011/019648 | 2/2011  |
| WO | WO 2011/019651 | 2/2011  |
| WO | WO 2011/050245 | 4/2011  |
| WO | WO 2011/079076 | 6/2011  |
| WO | WO 2011/084486 | 7/2011  |
| WO | WO 2011/123890 | 10/2011 |
| WO | WO 2012/068589 | 5/2012  |
| WO | WO 2012/104388 | 8/2012  |
| WO | WO 2012/129562 | 9/2012  |
| WO | WO 2013/024011 | 2/2013  |
| WO | WO 2013/030138 | 3/2013  |
| WO | WO 2013/113722 | 8/2013  |
| WO | WO 2015/143380 | 9/2015  |
| WO | WO 2017/079765 | 5/2017  |

OTHER PUBLICATIONS

Adaimy et al., "Mutation in WNT10A Is Associated with an Autosomal Recessive Ectodermal Dysplasia: The Odonto-onychodermal Dysplasia," Am. J. Hum. Genet., (Oct. 2007), 81(4), 821-828.
"Adult Brain Tumors Treatment," National Cancer Institute, pp. 1-21 (Jan. 24, 2013), 21 pages.
Ai et al., "Optimal Method to Stimulate Cytokine Production and Its Use in Immunotoxicity Assessment," Int J Environ Res Public Health, Sep. 2013, 10(9):3834-3842.
Anastas and Moon, "WNT signalling pathways as therapeutic targets in cancer," Nat Rev Cancer, 13(1):11-26, Jan. 2013.
Andres, "Molecular genetics and animal models in autistic disorder," Brain Research Bulletin, (2002), 57(1), 109-119.
Ator et al., "Overview of Drug Discovery and Development," Current Protocols in Pharmacology, 2006, Unit 9.9, 26 pages.
Barker and Clevers, "Mining the Wnt pathway for cancer therapeutics," Nat Rev Drug Discov., 5(12):997-1014, Dec. 2006.
Barroga et al., "Discovery of an Intra-Articular Injection Small Molecule Inhibitor of the Wnt Pathway (SM04690) as a Potential Disease Modifying Treatment for Knee Osteoarthritis," 2015 ACR/ARHP Annual Meeting, Abst. No. 2007, Sep. 29, 2015, retrieved on Sep. 27, 2018, URL <https://acrabstracts.org/abstract/discovery-of-an-intra-articular-injection-small-molecule-inhibitor-of- the-wnt-pathway-sm04690-as-a-potential-disease-modifying-treatment-for-knee-osteoarthritis/>, 3 pages.
Bass, "Why the difference between tendinitis and tendinosis matters," International Journal of Therapeutic Massage and Bodywork, vol. 5, No. 1, Mar. 2012.
Bendele, "Animal Models of Arthritis: Relevance to Human Disease," Toxicol Pathol 1999 27: 134-142.
Bernstein, "Polymorphism in Molecular Crystals," Analytical Techniques for Polymorphs, 2002, 115-118, 272.
Beyer et al., "Extended report: ß-catenin is a central mediator of pro-fibrotic Wnt signaling in systemic sclerosis," Ann Rheum Dis, 71:761-767, online Feb. 2012.
Bharath et al., "Evaluation of Myofibroblasts by Expression of Alpha Smooth Muscle Actin: A Marker in Fibrosis, Dysplasia and Carcinoma," Journal of Clinical and Diagnostic Research, 2014, 8(4):ZC14-ZC17.
Biason-Lauber et al., "A WNT4 Mutation Associated with Müllerian-Duct Regression and Virilization in a 46,XX Woman," N. Engl. J. Med., (Aug. 2004), 351(8), 792-798.
Blaydon et al., "The gene encoding R-spondin 4 (RSPO4), a secreted protein implicated in Wnt signaling, is mutated in inherited anonychia," Nat. Genet., (Nov. 2006), 38(11), 1245-1247.
Blom et al., "Involvement of the Wnt signaling pathway in experimental and human osteoarthritis: prominent role of Wnt-induced signaling protein 1," Arthritis Rheum., 60(2):501-512, Feb. 2009.
Bollong et al., "Small molecule-mediated inhibition of myofibroblast transdifferentiation for the treatment of fibrosis," PNAS, 2017, 114:18:4679-4684.
"Bone fractures," https://my.clevelandclinic.org/health/diseases/15241-bone-fractures, Jun. 2018, 5 pages.
Boyden et al., "High Bone Density Due to a Mutation in LDL-Receptor-Related Protein 5," N. Engl. J. Med., (May 2002), 346(20):1513-1521.
Brack et al., "Increased Wnt signaling during aging alters muscle stem cell fate and increases fibrosis," Science, 317(5839):807-810, Aug. 2007.
Braga et al., "Making crystals from crystals: a green route to crystal engineering and polymorphism," J. Royal Soc. Chem. Commun., 2005, 3635-3645.
Brown et al., "Toxicity and toxicokinetics of the cyclin-dependent kinase inhibitor AG-024322 in cynomolgus monkeys following intravenous infusion," Cancer Chemother Pharmacol., 62(6):1091-1101, Epub May 2008.
Caira, "Crystalline Polymorphism of Organic Compounds," Topics in Current Chemistry, Jan. 1998, 198:163-208.
Cancer definition in MedicineNet.com—2005, 1 page.
"Cancer Drug Design and Discovery," Neidle, Stephen, ed. (Elsevier/Academic Press, 2008), 5 pages.
Carpino et al., "Alpha-SMA expression in hepatic stellate cells and quantitative analysis of hepatic fibrosis in cirrhosis and in recurrent chronic hepatitis after liver transplantation," Digestive and Liver Disease, 2005, 37:349-356.
Cecil Textbook of Medicine, edited by Bennet, J.C., and Plum F., 20th edition, vol. 1, 1004-1010, 1996.
Chanput et al., "Transcription profiles of LPS-stimulated THP-1 monocytes and macrophages: a tool to study inflammation modulating effects of food-derived compounds," Food Funct, Dec. 2010, 1(3):254-61.
Chilosi et al., "The pathogenesis of COPD and IPF: Distinct horns of the same devil?" Respiratory Research, 13:3, 2012.
Chockalingam et al., "Elevated aggrecanase activity in a rat model of joint injury is attenuated by an aggrecanase specific inhibitor," Osteoarthritis Cartilage, Mar. 2011, 19(3): 315-323.
Chou et al., "Quantitative analysis of dose-effect relationships: the combined effects of multiple drugs or enzyme inhibitors," Advances in Enzyme Regulation (1984), 22, 27-55.
Chou, "Drug combination studies and their synergy quantification using the Chou-Talalay method," Cancer Res., 70(2):440-446, Jan. 2010.
Chou, "Graphic rule for drug metabolism systems," Current Drug Metabolism, (May 2010) 11(4): 369-378.
Christodoulides et al., "WNT10B mutations in human obesity," Diabetologia, (2006) 49(4):678-684.
Clevers and Nusse, "Wnt/β-catenin signaling and disease," Cell, (Jun. 2012), 149(6):1192-1205.
Clevers, "Wnt/β-catenin signaling in development and disease," Cell, Nov. 3, 2006, 127(3):469-480.
clinicaltrials.gov [online], ClinicalTrials.gov Identifier: NCT02095548, "Phase 1, Dose Escalation Study Evaluating the Safety, Tolerability, Pharmacokinetics and Pharmacodynamics of SM04690 in Moderate to Severe Knee Osteoarthritis (OA)," Mar. 26, 2014, [retrieved on

(56) References Cited

OTHER PUBLICATIONS

Aug. 1, 2018]. Retrieved from the Internet: URL<https://clinicaltrials.gov/ct2/show/NCT02095548?term=NCT02095548&rank=1>, 7 pages.
clinicaltrials.gov [online], ClinicalTrials.gov Identifier: NCT02536833, "A Study Evaluating the Safety, Tolerability, and Efficacy of SM04690 Injected in the Target Knee Joint of Moderately to Severely Symptomatic Osteoarthritis Subjects," Sep. 1, 2015, [retrieved on Aug. 1, 2018]. Retrieved from the Internet: URL<https://clinicaltrials.gov/ct2/show/NCT02536833?term=NCT02536833&rank=1>, X pages.
Corr, "Wnt-beta-catenin signaling in the pathogenesis of osteoarthritis," Nat Clin Pract Rheumatol., 4(10):550-556, Oct. 2008.
D'Alessio et al., "Benzodipyrazoles: a new class of potent CDK2 inhibitors," Bioorganic & Medicinal Chemistry Letters (2005), 15(5), 1315-1319.
Damia, "Contemporary pre-clinical development of anticancer agents—What are the optimal preclinical models?" European Journal of Cancer 2009, 45, 2768-2781 p. 2778.
Dann et al., "Insights into Wnt binding and signaling from the structures of two Frizzled cysteine-rich domains," Nature, (Jul. 2001), 412, pp. 86-90.
Datta et al., "Novel therapeutic approaches for pulmonary fibrosis," Br J Pharmacol., 163(1):141-172, May 2011.
Davidovich et al., "Detection of Polymorphism by Powder X-Ray Diffraction: Interferences by Preferred Orientation," American Pharmaceutical Review, 2004, 7:(1):10, 12, 14, 16, and 100.
Davidson et al., "Emerging links between CDK cell cycle regulators and Wnt signaling," Trends Cell Biol., Aug. 2010, 20(8):453-460.
De Ferrari and Inestrosa, "Wnt signaling function in Alzheimer's disease," Brain Research Reviews, (2000), 33(1): 1-12.
De Ferrari and Moon, "The ups and downs of Wnt signaling in prevalent neurological disorders," Oncogene, (2006) 25(57): 7545-7553.
De Ferrari et al., "Common genetic variation within the Low-Density Lipoprotein Receptor-Related Protein 6 and late-onset Alzheimer's disease," Proc. Natl. Acad. Sci. USA, (May 2007), 104(22):9434-9439.
Dean, Analytical Chemistry Handbook,. 1995, 10.24-10.26.
Deep et al., "New Combination Therapies with Cell Cycle Agents," Curr. Opin. Investig. Drugs, Jun. 2008, 9(6):591-604.
Dermer et al., "Another Anniversary for the War on Cancer," Bio/Technology, Mar. 1994, 12:320.
Deshmkukh et al., "Abstract: A Small Molecule Inhibitor of the Wnt Pathway (SM04755) as a Potential Topical Treatment for Tendinopathy," Abstract from the Orthobiologic Institute (TOBI) Annual Symposium, Las Vegas, Nevada, Jun. 7, 2018, 1 page.
Deshmkukh et al., "Abstract: Discovery of a Small Molecule Inhibitor of the Wnt Pathway (SM04755) as a Potential Topical Treatment for Tendinopathy," Abstract from Osteoarthritis Research Society International (OARSI), Las Vegas, Nevada, Apr. 27, 2017, 2 pages.
Deshmkukh et al., "Abstract: Discovery of a Small Molecule Inhibitor of the Wnt Pathway (SM04755) as a Potential Topical Treatment for Tendinopathy," Abstract from the World Congress on Osteoporosis Osteoarthritis and Musculoskeletal Disease, Florence, Italy, Mar. 23, 2017, 2 pages.
Deshmkukh et al., "Abstract: Experimental Tendinopathy Treatment with SM04755, a Topical Small Molecule Inhibitor of the Wnt Pathway," Abstract from Osteoarthritis Research Society International (OARSI), Liverpool, England, Apr. 26, 2018, 3 pages.
Deshmkukh et al., "Abstract: Experimental Tendinopathy Treatment with SM04755, a Topical Small Molecule Wnt Pathway Inhibitor," Abstract from the Orthobiologic Institute (TOBI) Annual Symposium, Las Vegas, Nevada, Jun. 7, 2018, 2 pages.
Deshmkukh et al., "Poster: A Small Molecule Inhibitor of the Wnt Pathway (SM04755) as a Potential Topical Treatment for Tendinopathy," Poster from the Orthobiologic Institute (TOBI) Annual Symposium, Las Vegas, Nevada, Jun. 7, 2018, 1 page.
Deshmkukh et al., "Poster: Discovery of a Small Molecule Inhibitor of the Wnt Pathway (SM04755) as a Potential Topical Treatment for Tendinopathy," Poster from the World Congress on Osteoporosis Osteoarthritis and Musculoskeletal Disease, Florence, Italy, Mar. 23, 2017, 1 page.
Deshmkukh et al., "Poster: Experimental Tendinopathy Treatment with SM04755, a Topical Small Molecule Wnt Pathway Inhibitor," Poster from the Orthobiologic Institute (TOBI) Annual Symposium, Las Vegas, Nevada, Jun. 7, 2018, 2 pages.
Deshmkukh et al., "Presentation: Experimental Tendinopathy Treatment with SM04755, a Topical Small Molecule Inhibitor of the Wnt Pathway," Presentation from Osteoarthritis Research Society International (OARSI), Liverpool, England, Apr. 26, 2018, 17 pages.
Deshmukh et al., Abstract #EULAR-6427: "Discovery of a Small Molecule Inhibitor of the Wnt Pathway (SM04755) as a Potential Topical Treatment for Tendinopathy," Abstract from Annual European Congress of Rheumatology (EULAR), Madrid, Spain, Jun. 14, 2017, 2 pages.
Deshmukh et al., "Abstract #THU0522: Experimental Tendinopathy Treatment with SM04755, a Topical Small Molecule Inhibitor of the Wnt Pathway," Abstract from Annual European Congress of Rheumatology (EULAR), Amsterdam, Netherlands, Jun. 13-16, 2018, 2 pages.
Deshmukh et al., "Abstract: Discovery of a Small Molecule Inhibitor of the Wnt Pathway (SM04755) as a Potential Topical Treatment for Tendinopathy," Abstract from Orthopaedic Research Society Annual Meeting, New Orleans, Louisiana, Mar. 19, 2017, 1 page.
Deshmukh et al., "Abstract: Discovery of a Small Molecule Inhibitor of the Wnt Pathway (SM04755) as a Potential Topical Treatment for Tendinopathy," Abstract from Regenerative Medicine and Biology From Development to Regeneration, St. Louis, Missouri, May 4, 2017, 2 pages.
Deshmukh et al., "Abstract: Experimental tendinopathy treatment with SM04755, a topical small molecule inhibitor of the Wnt pathway," Abstract from Orthopaedic Research Society Annual Meeting, New Orleans, Louisiana, Mar. 10, 2018, 2 pages.
Deshmukh et al., "Poster # 1459: Experimental tendinopathy treatment with SM04755, a topical small molecule inhibitor of the Wnt pathway," Poster from Orthopaedic Research Society Annual Meeting, New Orleans, Louisiana, Mar. 19, 2018, 1 page.
Deshmukh et al., "Poster #443: Discovery of a Small Molecule Inhibitor of the Wnt Pathway (SM04755) as a Potential Topical Treatment for Tendinopathy," Poster from Osteoarthritis Research Society International (OARSI), Las Vegas, Nevada, Apr. 27, 2017, 1 page.
Deshmukh et al., "Poster #SAT067: Discovery of a Small Molecule Inhibitor of the Wnt Pathway (SM04755) as a Potential Topical Treatment for Tendinopathy," Poster from Annual European Congress of Rheumatology (EULAR), Madrid, Spain, Jun. 14, 2017, 1 page.
Deshmukh et al., "Poster #THU0522: Experimental Tendinopathy Treatment with SM04755, a Topical Small Molecule Inhibitor of the Wnt Pathway," Poster from Annual European Congress of Rheumatology (EULAR), Amsterdam, Netherlands, Jun. 13-16, 2018, 1 page.
Deshmukh et al., "Poster: Discovery of a Small Molecule Inhibitor of the Wnt Pathway (SM04755) as a Potential Topical Treatment for Tendinopathy," Poster from Regenerative Medicine and Biology From Development to Regeneration, St. Louis, Missouri, May 4, 2017, 2 pages.
Deshmukh et al., "Presentation: Discovery of a Small Molecule Inhibitor of the Wnt Pathway (SM04755) as a Potential Topical Treatment for Tendinopathy," Presentation from Orthopaedic Research Society Annual Meeting, New Orleans, Louisiana, Mar. 19, 2017, 19 pages.
Deshmukh et al., A Small Molecule, SM04690, Has Inhibitory Effects on the Wnt Pathway and Inflammation in Vitro, with Potential Implications for the Treatment of Osteoarthritis [abstract]. Arthritis Rheumatol. 2016; 68 (suppl 10). https://acrabstracts.org/abstract/a-small-molecule-sm04690-has-inhibitory-effects-on-the-wnt-pathway-and-inflammation-in-vitro-with-potential-implications-for-the-treatment-of-osteoarthritis/. Accessed Dec. 28, 2020.
Deshmukh et al., "A small-molecule inhibitor of the Wnt pathway (SM04690) as a potential disease modifying agent for the treatment of osteoarthritis of the knee," Osteoarthritis and Cartilage, Jan. 2018, 26(1):18-27.

(56) References Cited

OTHER PUBLICATIONS

Deshmukh et al., "Abstract #1104: Discovery of a Small Molecule Inhibitor of the Wnt Pathway (SM04755) as a Potential Topical Treatment for Chronic Tendinopathy," Abstract from 2016 ACR/ARHP Annual Meeting, Nov. 14, 2016, 3 pages.
Deshmukh et al., "Experimental Tendinopathy Treatment with SM04755, a Topical, Small Molecule Inhibitor of the Wnt Pathway," Abstract of Oral Presentation at #1952 at the American College of Rheumatology (ACR) Conference 2018, Chicago, Illinois, Oct. 19-24, 2018, 2 pages.
Deshmukh et al., "Experimental Tendinopathy Treatment with SM04755, a Topical, Small Molecule Inhibitor of the Wnt Pathway," Slides Present at #1952 at the American College of Rheumatology (ACR) Conference 2018, Chicago, Illinois, Oct. 19-24, 2018, 22 pages.
Deshmukh et al., "Poster #1104: Discovery of a Small Molecule Inhibitor of the Wnt Pathway (SM04755) as a Potential Topical Treatment for Chronic Tendinopathy," Poster from 2016 ACR/ARHP Annual Meeting, Nov. 14, 2016, 3 pages.
Dessalew et al., "3D-QSAR CoMFA and CoMSIA study on benzodipyrazoles as cyclin dependent kinase 2 inhibitors," Medicinal Chemistry, (2008), 4(4), 313-321.
Dong et al., "QSAR study of Akt/protein kinase B (PKB) inhibitors using support vector machine," European Journal of Medicinal Chemistry, (Oct. 2009), pp. 44(10): 4090-4097.
Doumpas et al., "TCF/LEF dependent and independent transcriptional regulation of Wnt/b-catenin target genes" The EMBO Journal Nov. 13, 2018 1-14.
Du Bois, "Strategies for treating idiopathic pulmonary fibrosis," Nature Reviews Drug Discovery, 9(2): 129-140 (Feb. 2010).
Edamoto et al., "Alterations of RB1, p53 and Wnt pathways in hepatocellular carcinomas associated with hepatitis C, hepatitis B and alcoholic liver cirrhosis," Int J Cancer., 106(3):334-341, Sep. 1, 2003.
Egloff et al., "Gastrin-releasing peptide receptor expression in non-cancerous bronchial epithelia is associated with lung cancer: a case-control study," Respiratory Research, 13:9, Feb. 2012.
Enzo et al., "The Wnt/β-catenin pathway in human fibrotic-like diseases and its eligibility as a therapeutic target," Molecular and Cellular Therapies, 2015, 3(1), 13 pages.
Espada et al., "Wnt signalling and cancer stem cells," Clin. Transl. Oncol., (2009), 11(7), 411-27.
Ewan et al., "A useful approach to identify novel small-molecule inhibitors of Wnt-dependent transcription," Cancer Res. (2010), 70(14), 5963-5973.
Exhibit A: *Otsuka Pharmaceutical Co., Ltd., v. Sandoz, Inc., Sun Pharmaceutical Industries, Ltd., Synton BV, Synthon Holding BV, Synthon Laboratories, Inc., and Synton Pharmaceuticals, Inc., and Apotex Inc. and Apotex Corp., and Teva Pharmaceuticals USA, Inc., Barr Laboratories, Inc., and Barr Pharmaceuticals, Inc.*, Decision on Appeal, 2011-1126, -1127, May 7, 2012, 33 pages.
Florez et al., "TCF7L2 Polymorphisms and Progression to Diabetes in the Diabetes Prevention Program," N. Engl. J. Med., (Jul. 2006), 355(3):241-250.
Forestier et al., "Prevalence of generalized osteoarthritis in a population with knee osteoarthritis," Joint Bone Spine, May 2011, 78(3):275-278.
Freese et al., "Wnt signaling in development and disease," Neurobiology of Disease, (2010) 38(2): 148-153.
Freshney et al., "Culture of Animal Cells, A Manual of Basic Technique," Alan R. Liss, Inc., 1983, New York, p. 1-6.
Fujii et al., "An antagonist of dishevelled protein-protein interaction suppresses beta-catenin-dependent tumor cell growth," Cancer Res., 67(2):573-579, Jan. 2007.
Fukuzawa et al., "Beckwith-Wiedemann Syndrome-associated Hepatoblastoma: Wnt Signal Activation Occurs Later in Tumorigenesis in Patients with 11p15.5 Uniparental Disomy," Pediatric and Developmental Pathology (2003), 6(4): 299-306.
"Gastric MALT Lymphoma," Lymphoma Association, 2011, 10 pages.

Giles et al., "Caught up in a Wnt storm: Wnt signaling in cancer," Biochim Biophys Acta, Jun. 2003, 1653(1):1-24.
Gitter et al., "Characteristics of human synovial fibroblast activation by IL-1 beta and TNF alpha," Immunology, Feb. 1989, 66(2):196-200.
Golub et al., "Molecular Classification of Cancer: Class Discovery and Class Prediction by Gene Expression Monitoring," Science, Oct. 1999, 286(5439):531-537.
Guillory (in Brittain ed.), "Polymorphism in Pharmaceutical Solids," NY: Marcel Dekker, Inc., 1999, 1-2, 125-181, 183-226.
Gunther et al., "Prevalence of generalised osteoarthritis in patients with advanced hip and knee osteoarthritis: the Ulm Osteoarthritis Study," Ann. Rheum. Dis., Dec. 1998, 57(12):717-723.
Guo et al., "Wnt/β-Catenin Signaling: a Promising New Target for Fibrosis Diseases," Physiol. Res., 2012, 61:337-346.
Handeli and Simon, "A small-molecule inhibitor of Tcf/beta-catenin signaling down-regulates PPAR gamma and PPARdelta activities," Mol Cancer Ther., 7(3):521-529, Mar. 2008.
Hayami et al., "Characterization of articular cartilage and subchondral bone changes in the rat anterior cruciate ligament transection and meniscectomized models of osteoarthritis," Bone, Feb. 2006, 38(2):234-243.
Henderson Jr. et al., "Inhibition of Wnt/beta-catenin/CREB binding protein (CBP) signaling reverses pulmonary fibrosis," Proc Natl Acad Sci U S A., 107(32):14309-14314, Epub Jul. 2010.
Hengstschlager et al., "Cyclin-dependent kinases at the G1-S transition of the mammalian cell cycle," Mutation Research, 1999, 436:1-9.
Hood et al., "Discovery of a small molecule inhibitor of the Wnt pathway (SM04690) as a potential disease modifying treatment for knee osteoarthritis," Osteoarthritis and Cartilage, Apr. 1, 2016, 24:S14-15.
Hu et al., "Discovery of indazoles as inhibitors of Tpl2 kinase," Bioorganic & Medicinal Chemistry Letters, (Aug. 2011) 21(16): 4758-4761.
Huang et al., "Tankyrase inhibition stabilizes axin and antagonizes Wnt signaling," Nature, (Oct. 2009), 461(7264): 614-620.
Huang et al., "Synthesis of 3-(1H-benzimidazol-2-y1)-5-isoquinolin-4-ylpyrazolo[1,2-b]pyridine, a potent cyclin dependent kinase 1 (CDK1) inhibitor," Bioorganic & Medicinal Chemistry Letters, (2007) 17(5): 1243-1245.
Hübner et al., "Standardized quantification of pulmonary fibrosis in histological samples," Biotechniques, 44(4):507-511, 514-517, Apr. 2008.
Ikejima et al., "Interleukin-1 induces tumor necrosis factor (TNF) in human peripheral blood mononuclear cells in vitro and a circulating TNF-like activity in rabbits," J Infect Dis, Jul. 1990, 162(1):215-23.
Im et al., "Wnt inhibitors enhance chondrogenesis of human mesenchymal stem cells in a long-term pellet culture," Biotechnol Lett., 33(5):1061-1068, Epub Jan. 2011.
Inestrosa and Toledo, "The role of Wnt signaling in neuronal dysfunction in Alzheimer's Disease," Mol Neurodegener, 3:9, doi: 10.1186/1750-1326-3-9, 13 pages, Jul. 2008.
International Preliminary Report on Patentability for International Application No. PCT/US2017/035411, dated Dec. 4, 2018, 11 pages.
International Preliminary Report on Patentability in International Application No. PCT/US2017/057536, dated Apr. 23, 2019, 9 pages.
International Search Report and Writtent Opinion for PCT/US2017/060481, dated Mar. 6, 2018, 13 pages.
Ivanisevic et al. Use of X-ray Powder Diffraction In the Pharmaceutical Industry, Pharm. Sci. Encycl., 2010, p. 1-42.
Jain & Mohammedi, "Polymorphism in Pharmacy," Indian Drugs, 1986, 23:(6):315-329.
Janssens et al., "The Wnt-dependent signaling pathways as target in oncology drug discovery," Invest New Drugs., 24(4):263-280, Jul. 2006.
Jenkins et al., "Germline mutations in WTX cause a sclerosing skeletal dysplasia but do not predispose to tumorigenesis," Nat. Genet. (Jan. 2009), 41(1), 95-100.

(56) References Cited

OTHER PUBLICATIONS

Jessen et al., "Peripheral white blood cell toxicity induced by broad spectrum cyclin-dependent kinase inhibitors," Journal of Applied Toxicology (Jan. 2007), 27(2), 133-142.
Johnson et al., "A stem cell-based approach to cartilage repair," Science, 336(6082):717-721, Epub Apr. 5, 2012.
Johnson, et al. "Relationships between drug activity in NCI preclinical in vitro and in vivo models and early clinical trials," British Journal of Cancer 2001, 84, 1424-1431.
Jordan, "Tamoxifen: A Most Unlikely Pioneering Medicine," Nature Reviews, Mar. 2003, 2:205-213.
Kanazawa et al., "Association of the Gene Encoding Wingless-Type Mammary Tumor Virus Integration-Site Family Member 5B (WNT5B) with Type 2 Diabetes," Am. J. Hum. Genet. (2004), 75(5), 832-843.
Karlberg et al., "Structural basis for the interaction between tankyrase-2 and a potent Wnt-signaling inhibitor," J. Med. Chem. (2010), 53(14), 5352-5.
Kibar et al., "Mutations in VANGL1 Associated with Neural-Tube Defects," N. Engl. J. Med., (Apr. 2007), 356(14):1432-1437.
Kim et al., "Blockade of the Wnt/β-Catenin Pathway Attenuates Bleomycin-Induced Pulmonary Fibrosis," Tohoku J. Exp. Med., 2011, 223:45-54.
King et al., "BUILD-3: a randomized, controlled trial of bosentan in idiopathic pulmonary fibrosis," Am J Respir Crit Care Med., 184(1):92-99, Epub Apr. 2011.
Kishimoto et al., "Wnt/beta-catenin signaling suppresses expressions of Ses, Mkx and Tnmd in tendon-derived cells," PLOS ONE, Jul. 27, 2017, 12(7), E0182051, pp. 1-17.
Kojima et al., "Optimization of development form in drug development," Pharmacia, 2016, 52(5): 387-391.
Kuwajima et al., "Necdin Promotes GABAergic Neuron Differentiation in Cooperation with Dlx Homeodomain Proteins," Journal of Neuroscience (May 2006), 26(20), 5383-5392.
Lacy et al., "Generation and characterization of ABT-981, a dual variable domain immunoglobulin (DVD-Ig(TM)) molecule that specifically and potently neutralizes both IL-1α and IL-1β," Mabs, May 2015, 7(3): 605-619.
Lala and Orucevic, "Role of nitric oxide in tumor progression: lessons from experimental tumors," Cancer and Metastasis Review, vol. 17, Mar. 1998, pp. 91-106.
Lammi et al., "Mutations in AXIN2 Cause Familial Tooth Agenesis and Predispose to Colorectal Cancer," Am. J. Hum. Genet. (2004), 74(5), 1043-1050.
Lapenna et al., "Cell cycle kinases as therapeutic targets for cancer," Nature Review—Drug Discovery, Jul. 2009, 8:547-566.
Ledford, "US cancer institute overhauls cell lines," Nature, Feb. 25, 2016, vol. 530, p. 391.
Leyns et al., "Frzb-1 Is a Secreted Antagonist of Wnt Signaling Expressed in the Spemann Organizer," Cell (Mar. 1997), 88(6), 747-756.
Li et al., "Artesunate attenuates the growth of human colorectal carcinoma and inhibits hyperactive Wnt/beta-catenin pathway," Int J Cancer, 121(6): 1360-1365, Sep. 2007.
Lin et al., "Synthesis and evaluation of pyrazolo[3,4-b]pyridine CDK1 inhibitors as anti-tumor agents," Bioorganic & Medicinal Chemistry Letters, (Aug. 2007), 17(15): 4297-4302.
Liu et al., "Fibrotic lung fibroblasts show blunted inhibition by cAMP due to deficient cAMP response element-binding protein phosphory lation," J Pharmacol Exp Ther., 315(2):678-687, Epub Aug. 3, 2005.
Lories et al., "To Wnt or not to Wnt: the bone and joint health dilemma," Nat Rev Rheumatol., 9(6):328-339, Epub Mar. 2013.
Low et al., "Phenotypic fingerprinting of small molecule cell cycle kinase inhibitors for drug discovery," Curr Chem Genomics., 3:13-21, Mar. 2009.
Lu et al., "Structure-activity relationship studies of small-molecule inhibitors of Wnt response," Bioorganic & Medicinal Chemistry Letters, (Jul. 2009), 19(14):3825-3827.

Lui et al., "Expression of Wnt pathway mediators in metaplastic tissue in animal model and clinical samples of tendinopathy," Rheumatology, Sep. 1, 2013, 52(9):1609-1618.
Lui, "Histopathological changes in tendinopathy—potential roles of BMPs?" Rheumatology, May 2013, 52:2116-2126.
Luo et al., "Fragile X Mental Retardation Protein Regulates Proliferation and Differentiation of Adult Neural Stem/Progenitor Cells," PLOS Genetics, (Apr. 2010), 6(4):e1000898, 15 pages.
Luu et al., "Wnt/beta-catenin signaling pathway as a novel cancer drug target," Curr Cancer Drug Targets., 4(8):653-671, Dec. 2004.
Luyten et al., "Wnt signaling and osteoarthritis," Bone, Apr. 1, 2009, 44(4):522-527.
MacDonald et al., "Wnt/beta-catenin signaling: components, mechanisms, and diseases," Dev. Cell (Jul. 2009), 17(1), 9-26.
Malumbres et al., "CDK inhibitors in cancer therapy: what is next?" TRENDS in Pharmacological Sciences, Dec. 2007, 29(1):16-21.
Mandel et al., "SERKAL Syndrome: An Autosomal-Recessive Disorder Caused by a Loss-of-Function Mutation in WNT4," Am. J. Hum. Genet., (Jan. 2008), 82(1), 39-47.
Mani, et al., "LRP6 Mutation in a Family with Early Coronary Disease and Metabolic Risk Factors," Science, (Mar. 2007), 315(5816), 1278-1282.
McBride et al., "Design and structure-activity relationship of 3-benzimidazol-2-yl-1H-indazoles as inhibitors of receptor tyrosine kinases," Bioorganic & Medicinal Chemistry Letters (2006), 16(13), 3595-3599.
McMahon et al., "VEGF receptor signaling in tumor angiogenesis," The Oncologist, 2005, pp. 3-10.
med.unc.edu [online], "Buffers," 2006, retrieved on Oct. 12, 2021, retrieved from URL<https://www.med.unc.edu/pharm/sondeklab/wp-content/uploads/sites/868/2018/10/buffers_calbiochem.pdf>, 38 pages.
MedlinePlus, [online] "Cancer," [retrieved on Jul. 6, 2007]. Retrieved from the internet, URL http://www.nlnn.nih.govinnedlineplus/cancer.html>.
Misra et al., "1H-Pyrazolo[3,4-b]pyridine inhibitors of cyclin-dependent kinases: highly potent 2,6- Difluorophenacyl analogues," Bioorganic & Medicinal Chemistry Letters, (2003), 13:2405-2408.
Monner et al., "Induction of lymphokine synthesis in peripheral blood mononuclear cells with phorbol ester and calcium ionophore allows precise measurement of individual variations in capacity to produce IL 2," Lymphokine Res. 1986;5 Suppl 1:S67-73.
Mora et al., "Emerging therapies for idiopathic pulmonary fibrosis, a progressive age-related disease," Nat Rev Drug Discov. Oct. 3, 20170; 16(11): 810.
Morrisey, "Wnt signaling and pulmonary fibrosis," Am J Pathol., 162(5):1393-1397, May 2003.
Muddassar et al., "Elucidation of binding mode and three dimensional quantitative structure-activity relationship studies of a novel series of protein kinase B/Akt inhibitors," Journal of Molecular Modeling, (2009), 15(2): 183-192.
Nakagami, "Preformation and Drug Development," Pharmacia, Mar. 1, 2003, 39 (3): 204-208.
Ngkelo et al., "LPS induced inflammatory responses in human peripheral blood mononuclear cells is mediated through NOX4 and Gia dependent PI-3 kinase signaling," Journal of Inflammation, Dec. 2012, 9(1):1, 7 pages.
Niemann et al., "Homozygous WNT3 Mutation Causes Tetra-Amelia in a Large Consanguineous Family," Am. J. Hum. Genet. (2004), 74(3), 558-563.
Nigg, "Mitotic Kinases as Regulators of Cell Division and its Checkpoints," Nature Reviews—Molecular Cell Biology, Jan. 2001, 2:21-32.
Nishisho et al., "Mutations of chromosome 5q21 genes in FAP and colorectal cancer patients," Science, (Aug. 1991), 253(5020):665-669.
Nusse, "Wnt signaling in disease and in development," Cell Res., 15(1):28-32, Jan. 2005.
Oates et al., "Increased DNA Methylation at the AXIN1 Gene in a Monozygotic Twin from a Pair Discordant for a Caudal Duplication Anomaly," Am. J. Hum. Genet. (2006 ), 79(1), 155-162.
Ocana, A., "Preclinical development of molecular targeted agents for cancer," Nat. Rev. Clin. Oncol. 2011, 8, 200-209.

(56) References Cited

OTHER PUBLICATIONS

Oduor et al., "Trypanosoma brucei glycogen synthase kinase-3, a target for anti-trypanosomal drug development: a public-private partnership to identify novel leads," PLOS Negl Trop Dis., 5(4):e1017, Apr. 2011.
Okerlund and Cheyette, "Synaptic Wnt signaling-a contributor to major psychiatric disorders?" J Neurodev Disord., (2011) 3(2): 162-174.
"Osteoarthritis," https://www.rnayoclinic.org/diseases-conditions/osteoarthritis/diagnosis-treatment/drc-20351930, Sep. 2018, 8 pages.
Park et al., "Optimized THP-1 differentiation is required for the detection of responses to weak stimuli," Inflamm Res, Jan. 2007, 56(1):45-50.
Parsons et al., "Benzo[d]imidazole Transient Receptor Potential Vanilloid 1 Antagonists for the Treatment of Pain: Discovery of trans-2-(2-{2-[2-(4-Trifluoromethyl-phenyl)-vinyl]-1H-benzimidazol-5-yl}-phenyl)-propan-2-ol (Mavatrep)," J Med Chem, May 2015, 58(9): 3859-3874.
Patani and Lavoie, "Bioisosterism: A Rational Approach in Drug Design," Chem. Rev, Jul. 25, 1996, vol. 96, p. 3147-3176.
Pharmacology, 10th ed., Kharkevich (ed)., 2010, pp. 73-74 (English Translation).
Pharmacology, Zhulenko (ed)., 2008, pp. 34-35 (English Translation).
Piersanti et al., "Synthesis of benzo[1,2-d;3,4-d']diimidazole and 1 H-pyrazolo[4,3-b]pyridine as putative A2A receptor antagonists," Organic and Biomolecular Chemistry, Aug. 2007, 5(16):2567-2571.
Pinedo & Slamon, "Translational Research: the role of VEGF in tumor angiogenesis," The Oncologist, 2005, pp. 1-2.
Polakis, "Wnt signaling and cancer," Genes Dev., 14: 1837-1851, 2000.
Pritzker et al., "Osteoarthritis cartilage histopathology: grading and staging," Osteoarthr. Cartil., Jan. 2006, 14(1):13-29.
PUBCHEM. Substance Record for SID 164345938. Deposit Date: Nov. 4, 2013. [retrieved on Nov. 16, 2015]. Retrieved from the Internet. < URL: https://pubchem.ncbi.nlm.nih.gov/substance/164345938#section=Top>, 5 pages.
Qin et al. "Complexity of the genotype-phenotype correlation in familial exudative vitreoretinopathy with mutations in the LRP5 and/or FZD4 genes," Hum. Mutat. (2005), 26(2), 104-112.
Reya and Clevers, "Wnt signalling in stem cells and cancer," Nature 434: 843-850, Apr. 2005.
Richards et al., "Peripheral blood proteins predict mortality in idiopathic pulmonary fibrosis," Am J Respir Crit Care Med., 185(1):67-76, Jan. 2012.
Rivera et al., "An X Chromosome Gene, WTX, Is Commonly Inactivated in Wilms Tumor," Science, (Feb. 2007), 315(5812):642-645, published online Jan. 4, 2007.
Robitaille et al., "Mutant frizzled-4 disrupts retinal angiogenesis in familial exudative vitreoretinopathy," Nat. Genet., (Sep. 2002), 32(2):326-330.
Rother et al., "Efficacy and safety of epicutaneous ketoprofen in Transfersome (IDEA-033) versus oral celecoxib and placebo in osteoarthritis of the knee: multicentre randomised controlled trial," Annals of the Rheumatic Diseases, Sep. 2007, 66(9): 1178-1183.
Ryu et al., "Natural derivatives of curcumin attenuate the Wnt/beta-catenin pathway through down- regulation of the transcriptional coactivator p300," Biochem Biophys Res Commun., 377(4):1304-1308, print Dec. 2008, Epub Nov. 2008.
Salinas, "Wnt signaling in the vertebrate central nervous system: from axon guidance to synaptic function," Cold Spring Harb Perspect Biol., (2012) 4(2). pii: a008003, 15 pages.
Santamaria et al., "Cdk1 is sufficient to drive the mammalian cell cycle," Nature, Aug. 16, 2007, 448:811-815.
Sato, "Upregulation of the Wnt/beta-catenin pathway induced by transforming growth factor-beta in hypertrophic scars and keloids," Acta Derm Venereol., 86(4):300-307, 2006.
Seah et al., "Neuronal Death Resulting from Targeted Disruption of the Snf2 Protein ATRX Is Mediated by p53," Journal of Neuroscience (Nov. 2008), 28(47), 12570-12580.
Seddon, "Pseudopolymorph: A Polemic," Crystal Growth & Design, 2004, v.4(6) p. 1087.
Sharma et al., "Inhibitors of Cyclin Dependent Kinases: Useful Targets for Cancer Treatment," Current Cancer Drug Targets, 2008, 8(1):53-75.
Shi et al., "Uniaxial mechanical tension promoted osteogenic differentiation of rat tendon-derived stem cells (rTDSCs) via the Wnt5a-RhoA pathway," Journal of Cellular Biochemistry, Oct. 2012, 113(10):3133-3142.
Shih et al., "Pharmacophore modeling and virtual screening to identify potential RET kinase inhibitors," Bioorg Med Chem Lett., 21(15):4490-4497, Epub Jun. 2011.
Shruster et al., "Wnt signaling enhances neurogenesis and improves neurological function after focal ischemic injury," PLOS One, (Jul. 2012), 7(7):e40843, 11 pages.
Silva et al., "Advances in Prodrug Design," Mini-Revs. In Med. Chem. (2005), 5: 893-914.
Solowiej et al., "Characterizing the Effects of the Juxtamembrane Domain on Vascular Endothelial Growth Factor Receptor-2 Enzymatic Activity, Autophosphorylation, and Inhibition by Axitinib," Biochemistry, (2009), 48(29), 7019-7031.
Sperber et al., "Cytokine secretion induced by superantigens in peripheral blood mononuclear cells, lamina propria lymphocytes, and intraepithelial lymphocytes," Clin Diagn Lab Immunol, Jul. 1995, 2(4):473-477.
Stahly, "The Importance of Salt Selection and Polymorph Screening for the Drug Product," Journal of Pharmaceutical Science and Technology Japan, 2006, 66(6):435-439.
Staines et al., "Cartilage development and degeneration: a Wnt situation," Cell Biochem Funct., 30(8):633-642, Epub Jun. 2012.
"Stomach cancer," Mayoclinic.com, Apr. 9, 2011, 8 pages.
Sutherland et al., "A robust high-content imaging approach for probing the mechanism of action and phenotypic outcomes of cell-cycle modulators," Molecular Cancer Therapeutics, (Feb. 2011), 10(2): 242-254.
Swaney et al., "A novel, orally active LPA(1) receptor antagonist inhibits lung fibrosis in the mouse bleomycin model," Br J Pharmacol., 160(7):1699-1713, Aug. 2010.
Takahashi-Yanaga et al., "Celecoxib-induced degradation of T-cell factors-1 and -4 in human colon cancer cells," Biochem Biophys Res Commun., 377(4):1185-1190, print Dec. 2008, Epub Nov. 2008.
Tamamura et al., "Developmental regulation of Wnt/beta-catenin signals is required for growth plate assembly, cartilage integrity, and endochondral ossification," J Biol Chem., 280(19):19185-95, Epub Mar. 2005.
Thompson et al., "WNT/beta-catenin signaling in liver health and disease," Hepatology, 45(5): 1298-1305, May 2007.
Trujillo et al., "2-(6-Phenyl-1H-indazol-3-yl)-1H-benzo[d]imidazoles: design and synthesis of a potent and isoform selective PKC-zeta inhibitor," Bioorg Med Chem Lett., 19(3):908-911, Epub Dec. 6, 2008.
"Types of Brain Cancer," at http://www.cancercenter.corn/brain-cancer/types-of-brain-cancer.cfrn (Mar. 12, 2013), 3 pages.
"Types of Breast Cancer," published in breastcancer.org (Sep. 30, 2012), 1 page.
Ugur et al., "Homozygous WNT10b mutation and complex inheritance in Split-Hand/Foot Malformation," Hum. Mol. Genet. (2008), 17(17), 2644-2653.
United States Court of Appeals for the Federal Circuit, *Eli Lilly and Company*, Plaintiff—Appellant, v. *Actavis Elizabeth LLC*, Defendant—Appellee, *and Sun Pharmaceutical Industries, Ltd.*, Defendant—Appellee, and *Sandoz, Inc.*, Defendant—Appellee, *and Mylan Pharmaceuticals Inc.*, Defendant—Appellee, *and Apotex Inc.*, Defendant—Appellee, *and Aurobindo Pharma Ltd.*, Defendant—Appellee, *and Teva Pharmaceuticals USA, Inc.*, Defendant—Appellee, Appeal from the United States District Court for the District of New Jersey in Case No. 07-CV-3770, Judge Dennis M. Cavanaugh, decided on Jul. 29, 2011, 20 pages.
Vippagunta et al., "Crystalline solids," Advanced Drug Delivery Reviews, 2001, 48:3-26.

(56) References Cited

OTHER PUBLICATIONS

Vulpetti et al., "Structure-Based Approaches to Improve Selectivity: CDK2-GSK3β Binding Site Analysis," Journal of Chemical Information and Modeling (2005), 45(5), 1282-1290.
Wagner et al., "The therapeutic potential of the Wnt signaling pathway in bone disorders," Curr Mol Pharmacol., 4(1):14-25, Jan. 2011.
Walters and Kleeberger, "Mouse models of bleomycin-induced pulmonary fibrosis," Current Protocols in Pharmacology, (2008) Chapter 5: Unit 5.46, 1-17.
Wang et al., "Mutations in X-linked PORCN, a putative regulator of Wnt signaling, cause focal dermal hypoplasia," Nat. Genet. (Jul. 2007), 39(7), 836-838.
Wantanabe and Dai, "Winning WNT: race to Wnt signaling inhibitors," Proc Natl Acad Sci U S A. 108(15):5929-5930, Epub Mar. 2011.
Watts et.al., "RhoA signaling modulates cyclin D1 expression in human lung fibroblasts; implications for idiopathic pulmonary fibrosis," Respir Res., 7:88, Jun. 15, 2006.
Weng et al., "Control of Dkk-1 ameliorates chondrocyte apoptosis, cartilage destruction, and subchondral bone deterioration in osteoarthritic knees," Arthritis Rheum., 62(5):1393-1402, May 2010.
Witherington et al., "5-Aryl-pyrazolo[3,4-b]pyridazines: potent inhibitors of glycogen synthase kinase-3 (GSK-3)," Bioorganic & Medicinal Chemistry Letters, (May 2003), 13(9):1581-1584.
Woods, S. et al., "Mutations in WNT7A Cause a Range of Limb Malformations, Including Fuhrmann Syndrome and Al-Awadi/Raas-Rothschild/Schinzel Phocomelia Syndrome," Am. J. Hum. Genet. (Aug. 2006), 79(2), 402-408.
Yamada et al., "Emergence of TNIK inhibitors in cancer therapeutics," Cancer Sci, May 2017, 108(5):818-823.
Yan et al., "Discovery of small molecule inhibitors of the Wnt/b-catenin signaling pathway by targeting b-catenin/Tcf4 interactions," Experimental Biology and Medicine, vol. 242, Jun. 2017, 1185-1197.
Yardy and Brewster, "Wnt signalling and prostate cancer," Prostate Cancer Prostatic Dis, 8(2):119-126, 2005.
Yazici et al., "Abstract #: 312: Safety, Efficacy and Biomarker Outcomes of a Novel, Intra-Articular, Injectable, Wnt Inhibitor (SM04690) in the Treatment of Osteoarthritis of the Knee: Interim, Exploratory Analysis of Results from a Randomized, Double-Blind, Placebo-Controlled Phase 1 Study," Poster, Presented at 2015 ACR/American College of Rheumatology Annual Meeting, San Francisco CA, Nov. 6-11, 2015; Arthritis Rheumatol. 2015; 67 (suppl 10): 1 page.
Yazici et al., "Abstract #: 313: Magnetic Resonance Imaging Outcomes Using an Intra-Articular Injection (SM04690) in the Treatment of Osteoarthritis of the Knee: Interim, Exploratory Analysis of Results from a Randomized, Double-Blind, Placebo-Controlled, Phase 1 Study," Poster, Presented at 2015 ACR/American College of Rheumatology Annual Meeting, San Francisco CA, Nov. 6-11, 2015; Arthritis Rheumatol. 2015; 67 (suppl 10): 1 page.
Yu et al., "Physical characterization of polymorphic drugs: an integrated characterization strategy," PSTT, 1998, 1(3):118-127.
Zhan et al., "Wnt signaling in cancer" Oncogene (2017) 36, 1461-1473.
Zhang et al., "Small-molecule synergist of the Wnt/beta-catenin signaling pathway," Proc Natl Acad Sci U S A., 104(18):7444-7448, Epub Apr. 2007 and correction 104(30):12581, Jul. 2007.
Zheng, "Small-molecule inhibitors of Wnt signaling pathway: towards novel anticancer therapeutics," Future Med. Chem. (2015) 7(18), 2485-2505.
Zhong et al., "Characterization of in vitro and in vivo metabolism of AG-024322, a novel cyclin-dependent kinase (CDK) inhibitor," Health (2009), 1(4): 249-262.
Zhu et al. "Design and synthesis of pyridine-pyrazolopyridine-based inhibitors of protein kinase B/Akt," Bioorganic & Medicinal Chemistry, Mar. 2007, 15(6):2441-2452.

* cited by examiner

SINGLE-DOSE, READY-TO-USE INJECTABLE FORMULATIONS

RELATED APPLICATIONS

This application is a continuation of U.S. Ser. No. 16/939,713, filed on Jul. 27, 2020, which claims the benefit of U.S. Ser. No. 15/806,321, filed on Nov. 7, 2017, which claims the benefit of U.S. Provisional Application No. 62/418,688, filed Nov. 7, 2016, each of which is incorporated herein by reference in its entirety.

TECHNICAL FIELD

Provided herein are single-dose, ready-to-use formulations that contain a compound of Formula (I), including pharmaceutically acceptable salts, polymorphs and amorphous forms thereof. Further provided herein are processes for preparing the same.

BACKGROUND

The compound of Formula (I)

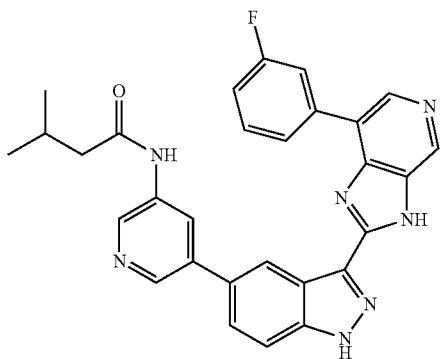

N-(5-(3-(7-(3-fluorophenyl)-3H-imidazo[4,5-c]pyridin-2-yl)-1H-indazol-5-yl)pyridin-3-yl)-3-methylbutanamide, is a Wnt inhibitor. The compound of Formula (I) can be prepared as disclosed in U.S. Pat. No. 8,252,812, incorporated by reference herein in its entirety. The compound of Formula (I), including pharmaceutically acceptable salts and polymorph and amorphous forms thereof can be used in the treatment of disorders characterized by the activation of Wnt pathway signaling (e.g., cancer, abnormal cellular proliferation, angiogenesis, Alzheimer's disease, lung disease and osteoarthritis), the modulation of cellular events mediated by Wnt pathway signaling, as well as genetic diseases and neurological conditions/disorders/diseases due to mutations or dysregulation of the Wnt pathway and/or of one or more of Wnt signaling components. There exists a need for formulations containing a compound of Formula (I), including pharmaceutically acceptable salts and polymorph and amorphous forms thereof, such as a ready-to-use, single-dose formulation.

SUMMARY

Provided herein is a process for preparing a single-dose, ready-to-use formulation comprising a compound of Formula (I)

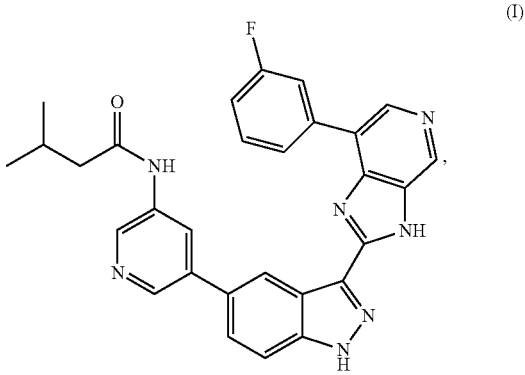 [SMILES: CC(C)CC(=O)Nc1cncc(-c2ccc3[nH]nc(-c4nc5c(-c6cccc(F)c6)cncc5[nH]4)c3c2)c1]

or a pharmaceutically acceptable salt or amorphous or polymorph form thereof, the process comprising:
(a) providing an aqueous solution comprising water;
(b) providing a slurry comprising a compound of Formula (I), or a pharmaceutically acceptable salt or amorphous or polymorph form thereof;
(c) mixing the aqueous solution and the slurry to form a suspension; and
(d) filling a container with the suspension to prepare a single-dose, ready-to-use formulation.

The process provided herein comprises providing an aqueous solution comprising water. In some embodiments of the process provided herein, the aqueous solution comprises a buffer. In some embodiments, the aqueous buffer is a phosphate buffer. In some embodiments, the phosphate buffer is selected from the group consisting of sodium phosphate dibasic, sodium phosphate monobasic, potassium phosphate monobasic, potassium phosphate dibasic, and mixtures thereof. In some embodiments, the phosphate buffer is a mixture of sodium phosphate dibasic heptahydrate and sodium phosphate monobasic monohydrate. In some embodiments, the buffer is phosphate buffered saline.

In some embodiments of the process provided herein, the aqueous solution comprises an excipient. In some embodiments, the excipient comprises a surfactant, a viscosity enhancer, or a mixture thereof. In some embodiments, the viscosity enhancer is a water-soluble polymer. In some embodiments, the viscosity enhancer is a cellulose derivative. In some embodiments, the cellulose derivative is sodium carboxymethylcellulose. In some embodiments, the aqueous solution comprises about 0.01 g/kg to about 50 g/kg; about 0.5 g/kg to about 50 g/kg; about 1.0 g/kg to about 50 g/kg; about 1 g/kg to about 25 g/kg; about 1 g/kg to about 10 g/kg; about 1 g/kg to about 7.5 g/kg; about 1 g/kg to about 5.5 g/kg; about 1 g/kg to about 2.5 g/kg; about 2.5 g/kg to about 50 g/kg; about 5 g/kg to about 50 g/kg; about 10 g/kg to about 50 g/kg; about 25 g/kg to about 50 g/kg; about. 0.1 to about 5 g/kg; about 2.5 g/kg to about 7.5 g/kg; about 5 g/kg to about 10 g/kg; or about 10 g/kg to about 20 g/kg of a viscosity enhancer. In some embodiments, the aqueous solution comprises about 5.5 g/kg of a cellulose derivative.

In some embodiments of the process provided herein, the surfactant is a polysorbate. In some embodiments, the aqueous solution comprises about 0.01 g/kg to about 5 g/kg; about 0.01 g/kg to about 2.5 g/kg; about 0.01 g/kg to about 1 g/kg; about 0.01 g/kg to about 0.75 g/kg; about 0.01 g/kg to about 0.5 g/kg; about 0.01 g/kg to about 0.25 g/kg; about 0.025 g/kg to about 5 g/kg; about 0.05 g/kg to about 5 g/kg; about 1 g/kg to about 5 g/kg; about 0.1 g/kg to about 5 g/kg; 0.1 g/kg to about 2.5 g/kg; about 0.1 g/kg to about 1 g/kg; about 0.1 g/kg to about 0.75 g/kg; about 0.1 g/kg to about 0.5 g/kg; about 0.1 g/kg to about 0.25 g/kg; about 0.25 g/kg to about 5 g/kg; about 0.25 g/kg to about 2.5 g/kg; about 0.25 g/kg to about 0.75 g/kg; about 0.5 g/kg to about 2.5 g/kg; about 0.5 g/kg to about 1 g/kg; or about 1 g/kg to about 2 g/kg of a surfactant. In some embodiments, the aqueous solution comprises about 0.5 g/kg of a surfactant. In some embodiments, the aqueous solution comprises about 5.55 g/kg of sodium carboxymethylcellulose and about 0.5 g/kg of polysorbate 80.

The process provided herein comprises providing a slurry comprising a compound of Formula (I), or a pharmaceutically acceptable salt or amorphous or polymorph form thereof. In some embodiments of the process provided herein, the slurry comprises about 0.001 g/kg to about 5 g/kg; about 0.001 g/kg to about 2.5 g/kg; about 0.001 g/kg to about 1 g/kg; about 0.001 g/kg to about 0.75 g/kg; about 0.001 g/kg to about 0.5 g/kg; about 0.001 g/kg to about 0.25 g/kg; about 0.001 g/kg to about 0.01 g/kg; about 0.01 g/kg to about 5 g/kg; about 0.01 g/kg to about 2.5 g/kg; about 0.01 g/kg to about 1 g/kg; about 0.01 g/kg to about 0.75 g/kg; about 0.01 g/kg to about 0.5 g/kg; about 0.01 g/kg to about 0.25 g/kg; about 0.1 g/kg to about 2.5 g/kg; about 0.1 g/kg to about 1 g/kg; about 0.1 g/kg to about 0.75 g/kg; about 0.1 g/kg to about 0.5 g/kg; about 0.1 g/kg to about 0.25 g/kg; about 0.25 g/kg to about 5 g/kg; about 0.5 g/kg to about 5 g/kg; about 1 g/kg to about 5 g/kg; about 2.5 g/kg to about 5 g/kg; about 0.25 g/kg to about 0.75 g/kg; about 0.5 g/kg to about 1 g/kg; or about 1 g/kg to about 2 g/kg of the compound of Formula (I), or a salt or amorphous or polymorph form thereof. In some embodiments, the slurry comprises about 0.15 g/kg, about 0.35 g/kg, or about 1.15 g/kg of the compound of Formula (I), or a salt or amorphous or polymorph form thereof. In some embodiments, the compound of Formula (I) comprises a polymorph form. In some embodiments, the polymorph is Form 1 and has an X-ray powder diffraction pattern comprising peaks at ° 2θ values of 6.8±0.2, 12.4±0.2, and 18.5±0.2. In some embodiments, the compound of Formula (I) comprises a mixture of a non-stoichiometric or stoichiometric hydrate of Form 1 having between 1% and about 20% by weight water.

In some embodiments of the process provided herein, the slurry comprises an excipient. In some embodiments, the excipient comprises a surfactant. In some embodiments, the surfactant is a polysorbate. In some embodiments, the slurry comprises about 0.01 g/kg to about 5 g/kg; 0.01 g/kg to about 2.5 g/kg; about 0.01 g/kg to about 1 g/kg; about 0.01 g/kg to about 0.75 g/kg; about 0.01 g/kg to about 0.5 g/kg; about 0.01 g/kg to about 0.25 g/kg; about 0.025 g/kg to about 5 g/kg; about 0.05 g/kg to about 5 g/kg; about 1 g/kg to about 5 g/kg; about 0.1 g/kg to about 5 g/kg; 0.1 g/kg to about 2.5 g/kg; about 0.1 g/kg to about 1 g/kg; about 0.1 g/kg to about 0.75 g/kg; about 0.1 g/kg to about 0.5 g/kg; about 0.1 g/kg to about 0.25 g/kg; about 0.25 g/kg to about 5 g/kg; about 0.25 g/kg to about 2.5 g/kg; about 0.25 g/kg to about 0.75 g/kg; about 0.5 g/kg to about 5 g/kg; about 0.5 g/kg to about 2.5 g/kg; about 0.5 g/kg to about 1 g/kg; about 1 g/kg to about 5 g/kg; about 2.5 g/kg to about 5 g/kg; or about 1 g/kg to about 2 g/kg of a surfactant. In some embodiments, the slurry comprises about 0.5 g/kg of a surfactant.

In some embodiments of the process provided herein, the slurry comprises about 0.15 g/kg of polymorph Form 1 or a non-stoichiometric or stoichiometric hydrate of Form 1 having between 1% and about 20% by weight water and about 0.5 g/kg of polysorbate 80. In some embodiments, the slurry comprises no more than 5% by weight of other Forms. For example, not more than 1% or less than 0.1% of another Form, including amorphous. In some embodiments, the slurry comprises about 0.35 g/kg of polymorph Form 1 or a non-stoichiometric or stoichiometric hydrate of Form 1 having between 1% and about 20% by weight water and about 0.5 g/kg of polysorbate 80. In some embodiments, the slurry comprises about 1.15 g/kg of polymorph Form 1 or a non-stoichiometric or stoichiometric hydrate of Form 1 having between 1% and about 20% by weight water and about 0.5 g/kg of polysorbate 80.

In some embodiments of the process provided herein, the aqueous solution is a filtered mixture. In some embodiments, the filtered mixture comprises water. In some embodiments, the filtered mixture comprises water and an excipient. In some embodiments, the excipient comprises a surfactant, a viscosity enhancer, or a mixture thereof. In some embodiments, the aqueous solution is a sterile filtered mixture. In some embodiments, the aqueous solution is a heat-sterilized mixture.

In some embodiments of the process provided herein, the aqueous solution comprises a sterile diluent.

In some embodiments of the process provided herein, the aqueous solution is a first sterilized mixture; the slurry is a second sterilized mixture; and the process comprises mixing the first sterilized mixture and the second sterilized mixture.

Provided herein is a process comprising mixing the aqueous solution and the slurry to form a suspension. In some embodiments of the process provided herein, the aqueous solution and slurry are mixed to form a suspension comprising about 0.005 mg/mL to about 2.5 mg/mL, about 0.01 mg/mL to about 2.0 mg/mL, about 0.01 mg/mL to about 1 mg/mL, about 0.01 mg/mL to about 0.5 mg/mL, about 0.01 mg/mL to about 0.2 mg/mL, or about 0.015 mg/mL to about 0.115 mg/mL of the compound of Formula (I) or a salt or amorphous or polymorph form thereof.

Provided herein is a process comprising filling a container with the suspension to prepare a single-dose, ready-to-use formulation. In some embodiments of the process provided herein, the container comprises a suspension comprising about 0.005 mg/mL to about 2.5 mg/mL, about 0.005 mg/mL to about 2 mg/mL, about 0.001 mg/mL to about 2 mg/mL, about 0.01 mg/mL to about 1.8 mg/mL, about 0.015 mg/mL to about 0.115, about 0.025 mg/mL to about 1.6 mg/mL, about 0.05 mg/mL to about 1.5 mg/mL, about 0.075 mg/mL to about 1.25 mg/mL, about 0.1 mg/mL to about 1 mg/mL, or about 0.25 mg/mL to about 0.75 mg/mL of the compound of Formula (I) or a salt or amorphous or polymorph form thereof. In some embodiments, the container is selected from the group consisting of a vial, a bottle, an ampule, and a syringe. In some embodiments, the vial is a glass vial or a plastic vial made of polyethylene, polypropylene, polyolefins, polyethylene terephthalate, polyethylene terephthalate G, poly(vinyl chloride), and mixtures thereof. In some embodiments, the container has a volume of 1 mL, 2 mL, 3 mL, 4 mL, or 5 mL, 6 mL, 7 mL, 8 mL, 9 mL, or 10 mL. In some embodiments, the container is a 3 mL polypropylene vial.

In some embodiments of the process provided herein, the mixing is done aseptically.

In some embodiments of the process provided herein, the filling is done aseptically.

In some embodiments, the process further comprises terminally sterilizing the filled container containing the suspension. In some embodiments, the container is terminally sterilized when the suspension comprises about 0.05 mg/mL to about 10 mg/mL of the compound of Formula (I) or a salt or amorphous or polymorph form thereof. For example, the suspension comprises about 0.05 mg/mL to about 5 mg/mL, about 0.05 mg/mL to about 2.5 mg/mL, about 0.05 mg/mL to about 1 mg/mL, about 0.05 mg/mL to about 0.5 mg/mL, about 0.05 mg/mL to about 0.1 mg/mL, about 0.1 mg/mL to about 10 mg/mL, about 0.1 mg/mL to about 5 mg/mL, about 0.1 mg/mL to about 2.5 mg/mL, about 0.1 mg/mL to about 1 mg/mL, about 0.1 mg/mL to about 0.5 mg/mL, about 0.1 mg/mL to about 0.25 mg/mL, about 0.25 mg/mL to about 10 mg/mL, about 0.25 mg/mL to about 5 mg/mL, about 0.25 mg/mL to about 2.5 mg/mL, about 0.25 mg/mL to about 1 mg/mL, about 0.25 mg/mL to about 0.5 mg/mL, bout 0.5 mg/mL to about 10 mg/mL, about 0.5 mg/mL to about 5 mg/mL, about 0.5 mg/mL to about 2.5 mg/mL, about 0.5 mg/mL to about 1 mg/mL, about 1 mg/mL to about 10 mg/mL, about 1 mg/mL to about 5 mg/mL, about 1 mg/mL to about 2.5 mg/mL, about 2.5 mg/mL to about 10 mg/mL, about 2.5 mg/mL to about 5 mg/mL, or about 5 mg/mL to about 10 mg/mL of the compound of Formula (I) or a salt or amorphous or polymorph form thereof.

Also provided herein is a single-dose, ready-to-use formulation comprising a compound of Formula (I)

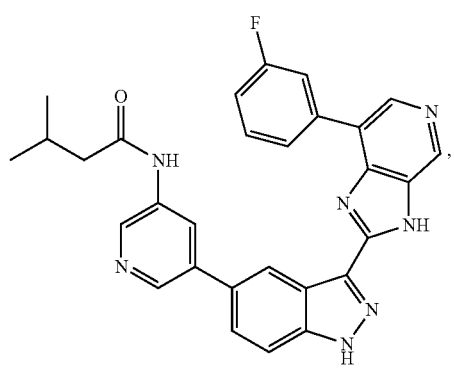

or a pharmaceutically acceptable salt or amorphous or polymorph form thereof, prepared by a process comprising:

(a) providing an aqueous solution comprising water;

(b) providing a slurry comprising a compound of Formula (I), or a pharmaceutically acceptable salt or amorphous or polymorph form thereof;

(c) mixing the aqueous solution and the slurry to form a suspension; and (d) filling a container with the suspension to prepare a single-dose, ready-to-use formulation.

The single-dose, ready-to-use formulation prepared by the process provided herein comprises providing an aqueous solution comprising water. In some embodiments, the aqueous solution comprises a buffer. In some embodiments, the aqueous buffer is a phosphate buffer. In some embodiments, the phosphate buffer is selected from the group consisting of sodium phosphate dibasic, sodium phosphate monobasic, potassium phosphate monobasic, potassium phosphate dibasic, and mixtures thereof. In some embodiments, the phosphate buffer is a mixture of sodium phosphate dibasic heptahydrate and sodium phosphate monobasic monohydrate. In some embodiments, the buffer is phosphate buffered saline.

In some embodiments of the single-dose, ready-to-use formulation prepared by the process provided herein, the aqueous solution comprises an excipient. In some embodiments, the excipient comprises a surfactant, a viscosity enhancer, or a mixture thereof. In some embodiments, the viscosity enhancer is a cellulose derivative. In some embodiments, the cellulose derivative is a water-soluble cellulose derivative. In some embodiments, the cellulose derivative is sodium carboxymethylcellulose. In some embodiments, the aqueous solution comprises about 0.01 g/kg to about 50 g/kg; about 0.5 g/kg to about 50 g/kg; about 1.0 g/kg to about 50 g/kg; about 1 g/kg to about 25 g/kg; about 1 g/kg to about 10 g/kg; about 1 g/kg to about 7.5 g/kg; about 1 g/kg to about 5.5 g/kg; about 1 g/kg to about 2.5 g/kg; about 2.5 g/kg to about 50 g/kg; about 5 g/kg to about 50 g/kg; about 10 g/kg to about 50 g/kg; about 25 g/kg to about 50 g/kg; about 0.1 g/kg to about 5 g/kg; about 2.5 g/kg to about 7.5 g/kg; about 5 g/kg to about 10 g/kg; or about 10 g/kg to about 20 g/kg of a viscosity enhancer. In some embodiments, the aqueous solution comprises about 5.5 g/kg of a cellulose derivative.

In some embodiments of the single-dose, ready-to-use formulation prepared by the process provided herein, the surfactant is a polysorbate. In some embodiments, the aqueous solution comprises about 0.1 g/kg to about 5 g/kg; 0.1 g/kg to about 2.5 g/kg; about 0.1 g/kg to about 1 g/kg; about 0.1 g/kg to about 0.75 g/kg; about 0.1 g/kg to about 0.5 g/kg; about 0.1 g/kg to about 0.25 g/kg; about 0.25 g/kg to about 5 g/kg; about 0.5 g/kg to about 5 g/kg; about 1 g/kg to about 5 g/kg; about 0.1 g/kg to about 5 g/kg; 0.1 g/kg to about 2.5 g/kg; about 0.1 g/kg to about 1 g/kg; about 0.1 g/kg to about 0.75 g/kg; about 0.1 g/kg to about 0.5 g/kg; about 0.1 g/kg to about 0.25 g/kg; about 0.25 g/kg to about 5 g/kg; about 0.25 g/kg to about 2.5 g/kg; about 0.25 g/kg to about 0.75 g/kg; about 0.5 g/kg to about 2.5 g/kg; about 0.5 g/kg to about 1 g/kg; or about 1 g/kg to about 2 g/kg of a surfactant. In some embodiments, the aqueous solution comprises about 0.5 g/kg of a surfactant. In some embodiments, the aqueous solution comprises about 5.55 g/kg of sodium carboxymethylcellulose and about 0.5 g/kg of polysorbate 80.

The single-dose, ready-to-use formulation prepared by the process provided herein comprises providing a slurry comprising a compound of Formula (I), or a pharmaceutically acceptable salt or amorphous or polymorph form thereof. In some embodiments of the process provided herein, the slurry comprises about 0.001 g/kg to about 5 g/kg; about 0.001 g/kg to about 2.5 g/kg; about 0.001 g/kg to about 1 g/kg; about 0.001 g/kg to about 0.75 g/kg; about 0.001 g/kg to about 0.5 g/kg; about 0.001 g/kg to about 0.25 g/kg; about 0.001 g/kg to about 0.01 g/kg; about 0.01 g/kg to about 5 g/kg; about 0.01 g/kg to about 2.5 g/kg; about 0.01 g/kg to about 1 g/kg; about 0.01 g/kg to about 0.75 g/kg; about 0.01 g/kg to about 0.5 g/kg; about 0.01 g/kg to about 0.25 g/kg; about 0.1 g/kg to about 2.5 g/kg; about 0.1 g/kg to about 1 g/kg; about 0.1 g/kg to about 0.75 g/kg; about 0.1 g/kg to about 0.5 g/kg; about 0.1 g/kg to about 0.25 g/kg; about 0.25 g/kg to about 5 g/kg; about 0.5 g/kg to about 5 g/kg; about 1 g/kg to about 5 g/kg; about 2.5 g/kg to about 5 g/kg; about 0.25 g/kg to about 0.75 g/kg; about 0.5 g/kg to about 1 g/kg; or about 1 g/kg to about 2 g/kg of the compound of Formula (I), or a salt or amorphous or polymorph form thereof. In some embodiments, the slurry comprises about 0.15 g/kg, about 0.35 g/kg, or about 1.15 g/kg of the compound of Formula (I), or a salt or amorphous or polymorph form thereof. In some embodiments, the compound of Formula (I) comprises a polymorph form. In some embodiments, the polymorph is Form 1 and has an X-ray powder diffraction pattern comprising peaks at °2θ values of 6.8±0.2, 12.4±0.2, and 18.5±0.2. In some embodiments, the compound of Formula (I) comprises a mixture of a non-stoichiometric or stoichiometric hydrate of Form 1 having between 1% and about 20% by weight water. In some embodiments, the compound comprises no more than 5% by weight of other Forms. For example, not more than 1% or less than 0.1% of another Form, including amorphous.

In some embodiments of the single-dose, ready-to-use formulation prepared by the process provided herein, the slurry comprises an excipient. In some embodiments, the excipient comprises a surfactant. In some embodiments, the surfactant is a polysorbate. In some embodiments, the slurry comprises about 0.01 g/kg to about 5 g/kg; 0.01 g/kg to about 2.5 g/kg; about 0.01 g/kg to about 1 g/kg; about 0.01 g/kg to about 0.75 g/kg; about 0.01 g/kg to about 0.5 g/kg; about 0.01 g/kg to about 0.25 g/kg; about 0.025 g/kg to about 5 g/kg; about 0.05 g/kg to about 5 g/kg; about 1 g/kg to about 5 g/kg; about 0.1 g/kg to about 5 g/kg; 0.1 g/kg to about 2.5 g/kg; about 0.1 g/kg to about 1 g/kg; about 0.1 g/kg to about 0.75 g/kg; about 0.1 g/kg to about 0.5 g/kg; about 0.1 g/kg to about 0.25 g/kg; about 0.25 g/kg to about 5 g/kg; about 0.25 g/kg to about 2.5 g/kg; about 0.25 g/kg to about 0.75 g/kg; about 0.5 g/kg to about 5 g/kg; about 0.5 g/kg to about 2.5 g/kg; about 0.5 g/kg to about 1 g/kg; about 1 g/kg to about 5 g/kg; about 2.5 g/kg to about 5 g/kg; or about 1 g/kg to about 2 g/kg of a surfactant. In some embodiments, the slurry comprises about 0.5 g/kg of a surfactant.

In some embodiments of the single-dose, ready-to-use formulation prepared by the process provided herein, the slurry comprises about 0.15 g/kg of polymorph Form 1 or a non-stoichiometric or stoichiometric hydrate of Form 1 having between 1% and about 20% by weight water and about 0.5 g/kg of polysorbate 80. In some embodiments, the slurry comprises about 0.35 g/kg of polymorph Form 1 or a non-stoichiometric or stoichiometric hydrate of Form 1 having between 1% and about 20% by weight water and about 0.5 g/kg of polysorbate 80. In some embodiments, the slurry comprises about 1.15 g/kg of polymorph Form 1 or a non-stoichiometric or stoichiometric hydrate of Form 1 having between 1% and about 20% by weight water and about 0.5 g/kg of polysorbate 80.

In some embodiments of the single-dose, ready-to-use formulation prepared by the process provided herein, the aqueous solution is a filtered mixture. In some embodiments, the filtered mixture comprises water. In some embodiments, the filtered mixture comprises water and an excipient. In some embodiments, the excipient comprises a surfactant, a viscosity enhancer, or a mixture thereof.

In some embodiments of the single-dose, ready-to-use formulation prepared by the process provided herein, the aqueous solution comprises a sterile diluent.

In some embodiments of the single-dose, ready-to-use formulation prepared by the process provided herein, the aqueous solution is a sterile-filtered mixture or a first bulk sterilized mixture or both; the slurry is a second bulk sterilized mixture; and the process comprises mixing the first bulk sterilized mixture and the second bulk sterilized mixture.

Provided herein is a single-dose, ready-to-use formulation prepared by a process comprising mixing the aqueous solution and the slurry to form a suspension. In some embodiments, the aqueous solution and slurry are mixed to form a suspension comprising about 0.005 mg/mL to about 2.5 mg/mL, about 0.001 mg/mL to about 2 mg/mL, about 0.01 mg/mL to about 2.0 mg/mL, about 0.01 mg/mL to about 1 mg/mL, about 0.01 mg/mL to about 0.5 mg/mL, about 0.01 mg/mL to about 0.2 mg/mL, or about 0.015 mg/mL to about 0.115 mg/mL of the compound of Formula (I) or a salt or amorphous or polymorph form thereof.

Provided herein is a single-dose, ready-to-use formulation prepared by a process comprising filling a container with the suspension to prepare a single-dose, ready-to-use formulation. In some embodiments, the container comprises a suspension comprising about 0.005 mg/mL to about 2.5 mg/mL, about 0.005 mg/mL to about 2 mg/mL, about 0.01 mg/mL to about 1.8 mg/mL, about 0.015 mg/mL to about 0.115, about 0.025 mg/mL to about 1.6 mg/mL, about 0.05 mg/mL to about 1.5 mg/mL, about 0.075 mg/mL to about 1.25 mg/mL, about 0.1 mg/mL to about 1 mg/mL, or about 0.25 mg/mL to about 0.75 mg/mL of the compound of Formula (I) or a salt or amorphous or polymorph form thereof. In some embodiments, the container is selected from the group consisting of a vial, a bottle, an ampule, and a syringe. In some embodiments, the vial is a glass vial or a plastic vial made of polyethylene, polypropylene, polyolefins, polyethylene terephthalate, polyethylene terephthalate G, poly(vinyl chloride), and mixtures thereof. In some embodiments, the container has a volume of 1 mL, 2 mL, 3 mL, 4 mL, or 5 mL. In some embodiments, the container is a 3 mL polypropylene vial.

In some embodiments of the single-dose, ready-to-use formulation prepared by the process provided herein, the mixing is done aseptically.

In some embodiments of the single-dose, ready-to-use formulation prepared by the process provided herein, the filling is done aseptically.

In some embodiments of the single-dose, ready-to-use formulation prepared by the process provided herein, the container containing the suspension is terminally sterilized. In some embodiments, the container is terminally sterilized when the suspension comprises about 0.05 mg/mL to about 10 mg/mL of the compound of Formula (I) or a salt or amorphous or polymorph form thereof. For example, the suspension comprises about 0.05 mg/mL to about 5 mg/mL, about 0.05 mg/mL to about 2.5 mg/mL, about 0.05 mg/mL to about 1 mg/mL, about 0.05 mg/mL to about 0.5 mg/mL, about 0.05 mg/mL to about 0.1 mg/mL, about 0.1 mg/mL to about 10 mg/mL, about 0.1 mg/mL to about 5 mg/mL, about 0.1 mg/mL to about 2.5 mg/mL, about 0.1 mg/mL to about 1 mg/mL, about 0.1 mg/mL to about 0.5 mg/mL, about 0.1 mg/mL to about 0.25 mg/mL, about 0.25 mg/mL to about 10 mg/mL, about 0.25 mg/mL to about 5 mg/mL, about 0.25 mg/mL to about 2.5 mg/mL, about 0.25 mg/mL to about 1 mg/mL, about 0.25 mg/mL to about 0.5 mg/mL, bout 0.5 mg/mL to about 10 mg/mL, about 0.5 mg/mL to about 5 mg/mL, about 0.5 mg/mL to about 2.5 mg/mL, about 0.5 mg/mL to about 1 mg/mL, about 1 mg/mL to about 10 mg/mL, about 1 mg/mL to about 5 mg/mL, about 1 mg/mL to about 2.5 mg/mL, about 2.5 mg/mL to about 10 mg/mL, about 2.5 mg/mL to about 5 mg/mL, or about 5 mg/mL to about 10 mg/mL of the compound of Formula (I) or a salt or amorphous or polymorph form thereof.

Also provided herein is a method for treating osteoarthritis in a subject in need thereof, comprising administering to the subject a therapeutically effective amount of the single-dose, ready-to-use formulation prepared by the process provided herein that comprises a therapeutically effective amount of a compound of Formula (I), including salt and amorphous and polymorph forms thereof. In some embodiments, administration of the formulation is intra-articular. In some embodiments, the formulation is administered to the subject once. In some embodiments, the formulation is administered more than once with each injection separated by about 3 months to about 60 months. In some embodiments, the formulation is administered once every 2 weeks, every 3 weeks, every 4 weeks, every 6 weeks, every 8 weeks, or every 3 months, 6 months, 9 months, 12 months, 18 months, 24 months, 30 months, or 60 months.

Other features and advantages of the processes, formulations, and uses provided herein will be apparent from the following detailed description and figures, and from the claims.

DESCRIPTION OF DRAWINGS

FIG. 1A is an x-ray powder diffraction scan of fully dried Form 1. FIG. 1B is a differential scanning calorimetry scan of Form 1. FIG. 1C is a thermal gravimetric analysis scan of Form 1. FIG. 1D is a dynamic vapor sorption scan of Form 1.

FIG. 2A is an x-ray powder diffraction scan of fully dried Form 2. FIG. 2B is a differential scanning calorimetry scan of Form 2. FIG. 2C is a thermal gravimetric analysis scan of Form 2. FIG. 2D is an x-ray powder diffraction scan of fully dried Form 2*. FIG. 2E is a differential scanning calorimetry scan of Form 2*. FIG. 2F is a thermal gravimetric analysis scan of Form 2*. FIG. 2G is an x-ray powder diffraction scan of Form 2. FIG. 2H is a differential scanning calorimetry scan of Form 2.

FIG. 3A is an x-ray powder diffraction scan of fully dried Form 3. FIG. 3B is a differential scanning calorimetry scan of Form 3. FIG. 3C is a thermal gravimetric analysis scan of Form 3.

FIG. 4A is an x-ray powder diffraction scan of fully dried Form 4. FIG. 4B is a differential scanning calorimetry scan of Form 4. FIG. 4C is a thermal gravimetric analysis scan of Form 4. FIG. 4D is an x-ray powder diffraction scan of fully dried Form 4*. FIG. 4E is a differential scanning calorimetry scan of Form 4*. FIG. 4F is a thermal gravimetric analysis scan of Form 4*. FIG. 4G is an x-ray powder diffraction scan of Form 4. FIG. 4H is a differential scanning calorimetry scan of Form 4. FIG. 4I is a thermal gravimetric analysis scan of Form 4**.

FIG. 5A is an x-ray powder diffraction scan of fully dried Form 5. FIG. 5B is a differential scanning calorimetry scan of Form 5. FIG. 5C is a thermal gravimetric analysis scan of Form 5. FIG. 5D is an x-ray powder diffraction scan of Form 5*.

FIG. 6A is an x-ray powder diffraction scan of Form 6. FIG. 6B is a differential scanning calorimetry scan of Form 6.

FIG. 7A is an x-ray powder diffraction scan of fully dried Form 7. FIG. 7B is a differential scanning calorimetry scan of Form 7. FIG. 7C is a thermal gravimetric analysis scan of Form 7.

FIG. 8A is an x-ray powder diffraction scan of fully dried Form 8. FIG. 8B is a differential scanning calorimetry scan of Form 8. FIG. 8C is a thermal gravimetric analysis scan of Form 8.

FIG. 9A is an x-ray powder diffraction scan of fully dried Form 9. FIG. 9B is a differential scanning calorimetry scan of Form 9. FIG. 9C is a thermal gravimetric analysis scan of Form 9. FIG. 9D is a dynamic vapor sorption scan of Form 9.

FIG. 10A is an x-ray powder diffraction scan of fully dried Form 10. FIG. 10B is a differential scanning calorimetry scan of Form 10. FIG. 10C is a thermal gravimetric analysis scan of Form 10. FIG. 10D is an x-ray powder diffraction scan of Form 10*. FIG. 10E is a differential scanning calorimetry scan of Form 10*.

FIG. 11A is an x-ray powder diffraction scan of fully dried Form 11. FIG. 11B is a differential scanning calorimetry scan of Form 11. FIG. 11C is a thermal gravimetric analysis scan of Form 11. FIG. 11D is an x-ray powder diffraction scan of fully dried Form 11*. FIG. 11E is a differential scanning calorimetry scan of Form 11*. FIG. 11F is a thermal gravimetric analysis scan of Form 11*.

FIG. 12A is an x-ray powder diffraction scan of Form 12. FIG. 12B is a differential scanning calorimetry scan of Form 12. FIG. 12C is a thermal gravimetric analysis scan of Form 12.

FIG. 13A is an x-ray powder diffraction scan of Form 13. FIG. 13B is a differential scanning calorimetry scan of Form 13. FIG. 13C is a thermal gravimetric analysis scan of Form 13. FIG. 13D is a dynamic vapor sorption scan of Form 13.

FIG. 15A is an x-ray powder diffraction scan of Form 1 exposed to 10% RH as the anhydrous Form 1. FIG. 15B is an x-ray powder diffraction scan of Form 1 exposed to 20% RH as a partial hydrate of Form 1. FIG. 15C is an x-ray powder diffraction scan of Form 1 exposed to 30% RH as a hydrate of Form 1 (≈10-12% water uptake). FIG. 15D is an x-ray powder diffraction scan of Form 1 exposed to 90% RH as a full hydrate of Form 1 (≈17-20% water uptake).

DETAILED DESCRIPTION

1. Definitions

Figure 1A:
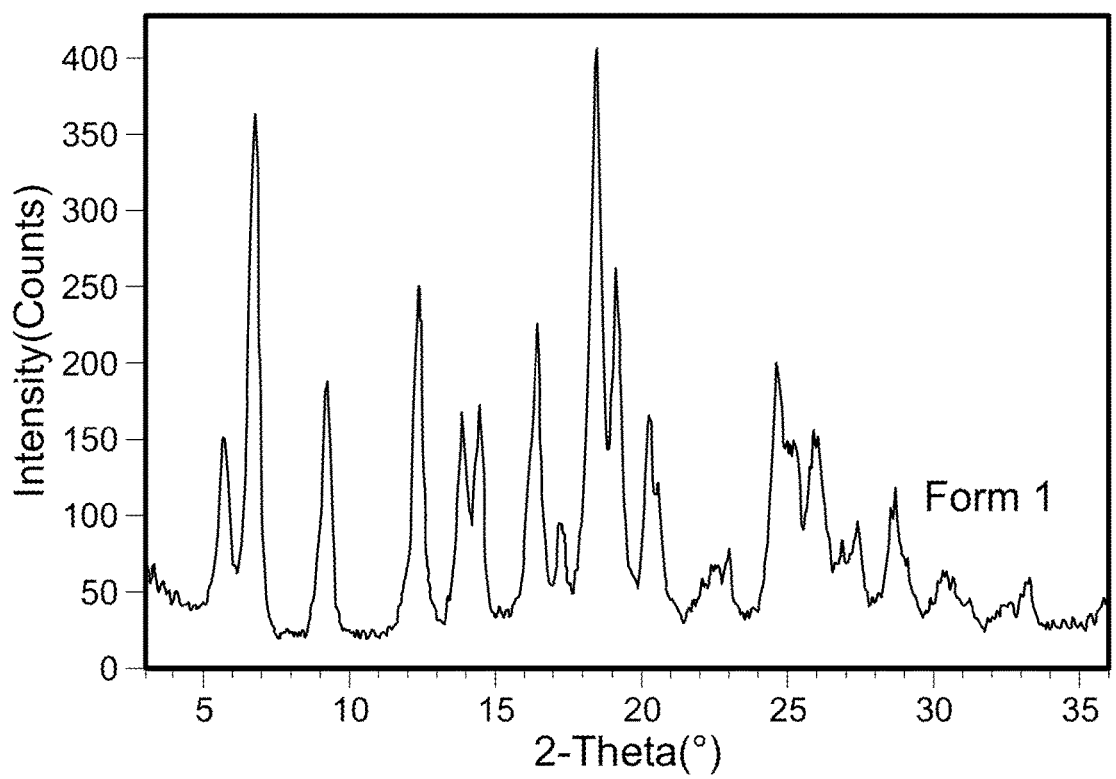
FIGS. 1A-1D are scans of polymorph Form 1 of the compound of Formula (I).

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The term "pharmaceutically acceptable carrier" or "pharmaceutically acceptable excipient" includes any and all solvents, co-solvents, complexing agents, dispersion media, coatings, antibacterial and antifungal agents, isotonic and absorption delaying agents, and the like, which are not biologically or otherwise undesirable. The use of such media and agents for pharmaceutically active substances is well known in the art. Except insofar as any conventional media or agent is incompatible with the active ingredient, its use in the therapeutic formulations is contemplated. Supplementary active ingredients can also be incorporated into the formulations. In addition, various excipients, such as are commonly used in the art, can be included. These and other such compounds are described in the literature, e.g., in the Merck Index, Merck & Company, Rahway, NJ Considerations for the inclusion of various components in pharmaceutical compositions are described, e.g., in Gilman et al. (Eds.) (2010); *Goodman and Gilman's: The Pharmacological Basis of Therapeutics*, 12th Ed., The McGraw-Hill Companies.

As used herein, a "single-dose" refers to a sterile formulation that is packaged in a container for parenteral administration (injection or infusion). A single-dose formulation is designed for use with a single patient as a single injection/infusion. Examples of containers for use with single-dose formulations include vials, ampules, bottles, and syringes.

"Ready-to-use," as used herein, refers to a formulation that does not require constitution or dilution with a prescribed amount of diluent, e.g., water for injection or other suitable diluent, before use by the designated route. For example, a formulation in a vial, of the desired concentration, that only needs to be drawn up into a syringe.

The term "polymorph," as used herein, refers to crystals of the same molecule having different physical properties as a result of the order of the molecules in the crystal lattice. Polymorphs of a single compound have one or more different chemical, physical, mechanical, electrical, thermodynamic, and/or biological properties from each other. Differences in physical properties exhibited by polymorphs can affect pharmaceutical parameters such as storage stability, compressibility, density (important in composition and product manufacturing), dissolution rates (an important factor in determining bio-availability), solubility, melting point, chemical stability, physical stability, powder flowability, water sorption, compaction, and particle morphology. Differences in stability can result from changes in chemical reactivity (e.g. differential oxidation, such that a dosage form discolors more rapidly when comprised of one polymorph than when comprised of another polymorph) or mechanical changes (e.g., crystal changes on storage as a kinetically favored polymorph converts to a thermodynamically more stable polymorph) or both (e.g., one polymorph is more hygroscopic than the other). As a result of solubility/dissolution differences, some transitions affect potency and/or toxicity. In addition, the physical properties of the crystal may be important in processing; for example, one polymorph might be more likely to form solvates or might be difficult to filter and wash free of impurities (i.e., particle shape and size distribution might be different between one polymorph relative to the other). "Polymorph" does not include amorphous forms of the compound. As used herein, "amorphous" refers to a non-crystalline form of a compound which may be a solid state form of the compound or a solubilized form of the compound. For example, "amorphous" refers to a compound without a regularly repeating arrangement of molecules or external face planes.

The term "anhydrous," as used herein, refers to a crystal form of the compound of Formula (I) that has 1% or less by weight water. For example, 0.5% or less, 0.25% or less, or 0.1% or less by weight water.

The term "solvate" as used herein refers to a crystalline form of a compound of Formula (I), such as a polymorph form of the compound, where the crystal lattice comprises one or more solvents of crystallization.

The term "non-stoichiometric hydrate" refers to a crystalline form of a compound of Formula I that comprises water, but wherein variations in the water content do not cause significant changes to the crystal structure. In some embodiments, a non-stoichiometric hydrate can refer to a crystalline form of a compound of Formula I that has channels or networks throughout the crystal structure into which water molecules can diffuse. During drying of non-stoichiometric hydrates, a considerable proportion of water can be removed without significantly disturbing the crystal network, and the crystals can subsequently rehydrate to give the initial non-stoichiometric hydrated crystalline form. Unlike stoichiometric hydrates, the dehydration and rehydration of non-stoichiometric hydrates is not accompanied by a phase transition, and thus all hydration states of a non-stoichiometric hydrate represent the same crystal form. In some embodiments, a non-stoichiometric hydrate can have up to about 20% by weight water, such as, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, or greater than 1% water by weight. In some embodiments, a non-stoichiometric hydrate can have between 1% and about 20% by weight water, such as between 1% and about 5%, 1% and about 10%, 1% and about 15%, about 2% and about 5%, about 2% and about 10%, about 2% and about 15%, about 2% and about 20%, about 5% and about 10%, about 5% and about 15%, about 5% and about 20%, about 10% and about 15%, about 10% and about 20%, or about 15% and about 20% by weight water.

In some embodiments the % water by weight in a crystal form, such as a non-stoichiometric or stoichiometric hydrate, is determined by the Karl Fischer titration method. In some embodiments, the crystal form is dried prior to Karl Fischer titration.

"Purity," when used in reference to a composition including a polymorph of a compound of Formula (I), refers to the percentage of one specific polymorph form relative to another polymorph form or an amorphous form of a compound of Formula (I) in the referenced composition. For example, a composition comprising polymorph Form 1 having a purity of 90% would comprise 90 weight parts Form 1 and 10 weight parts of other polymorph and/or amorphous forms of the compound of Formula (I).

As used herein, a compound or composition is "substantially free of" one or more other components if the compound or composition contains no significant amount of such other components. Such components can include starting materials, residual solvents, or any other impurities that can result from the preparation of and/or isolation of the compounds and compositions provided herein. In some embodiments, a polymorph form provided herein is substantially free of other polymorph forms. In some embodiments, a particular polymorph of the compound of Formula (I) is "substantially free" of other polymorphs if the particular polymorph constitutes at least about 95% by weight of the compound of Formula (I) present. In some embodiments, a particular polymorph of the compound of Formula (I) is "substantially free" of other polymorphs if the particular polymorph constitutes at least about 97%, about 98%, about 99%, or about 99.5% by weight of the compound of Formula (I) present. In certain embodiments, a particular polymorph of the compound of Formula (I) is "substantially free" of water if the amount of water constitutes no more than about 2%, about 1%, or about 0.5% by weight of the polymorph.

As used herein, a compound is "substantially present" as a given polymorph if at least about 50% by weight of the compound is in the form of that polymorph. In some embodiments, at least about 60% by weight of the compound is in the form of that polymorph. In some embodiments, at least about 70% by weight of the compound is in the form of that polymorph. In some embodiments, at least about 80% by weight of the compound is in the form of that polymorph. In some embodiments, at least about 90% by weight of the compound is in the form of that polymorph. In some embodiments, at least about 95% by weight of the compound is in the form of that polymorph. In some embodiments, at least about 96% by weight of the compound is in the form of that polymorph. In some embodiments, at least about 97% by weight of the compound is in the form of that polymorph. In some embodiments, at least about 98% by weight of the compound is in the form of that polymorph. In some embodiments, at least about 99% by weight of the compound is in the form of that polymorph. In some embodiments, at least about 99.5% by weight of the compound is in the form of that polymorph.

"Room temperature" or "RT" refers to the ambient temperature of a typical laboratory, which is typically around 25° C.

The term "administration" or "administering" refers to a method of giving a dosage of a compound or pharmaceutical formulation to a vertebrate or invertebrate, including a mammal, a bird, a fish, or an amphibian. The preferred method of administration can vary depending on various factors, e.g., the components of the pharmaceutical formulation, the site of the disease, and the severity of the disease.

"Subject," as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate. In some embodiments, the subject is a human.

As used herein, "therapeutically effective amount" is an amount of the formulation provided herein comprising a compound of Formula (I), or salt or amorphous or polymorph form thereof, which is sufficient to achieve the desired effect and can vary according to the nature and severity of the disease condition, and the potency of the compound. A therapeutic effect is the relief, to some extent, of one or more of the symptoms of the disease, and can include curing a disease. "Curing" means that the symptoms of active disease are eliminated. However, certain long-term or permanent effects of the disease can exist even after a cure is obtained (such as, e.g., extensive tissue damage).

"Treat," "treatment," or "treating," as used herein, refers to administering a compound or pharmaceutical formulation as provided herein for therapeutic purposes. The term "therapeutic treatment" refers to administering treatment to a patient already suffering from a disease, thus causing a therapeutically beneficial effect, such as ameliorating existing symptoms, preventing additional symptoms, ameliorating the underlying metabolic causes of symptoms, postponing or preventing the further development of a disorder and/or reducing the severity of symptoms that will or are expected to develop.

2. Process for Preparing Single-Dose, Ready-to-Use Formulations

Provided herein is a process for preparing a single-dose, ready-to-use formulation comprising a compound of Formula (I)

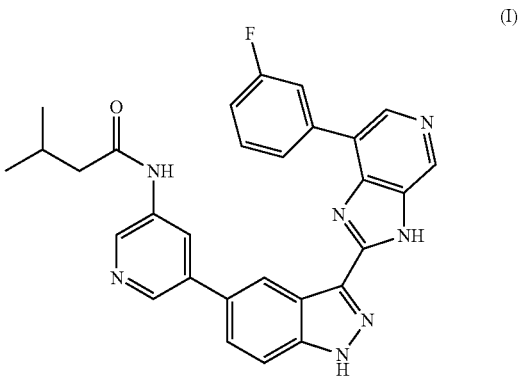 [SMILES: CC(C)CC(=O)Nc1cncc(-c2ccc3[nH]nc(-c4nc5c(-c6cccc(F)c6)cncc5[nH]4)c3c2)c1]

including salts and amorphous and polymorph forms thereof. The process includes:

(a) providing an aqueous solution comprising water;

(b) providing a slurry comprising a compound of Formula (I), including salts and amorphous and polymorph forms thereof;

(c) mixing the aqueous solution and slurry to form a suspension; and (d) aseptically filling a container with the suspension to prepare a single-dose formulation.

In the process provided herein, the process comprises providing an aqueous solution comprising water. Suitable types of water include, but are not limited to, deionized water, distilled water, reverse osmosis filtered water, reagent grade water, water for injection (WFI), USP/EP grade water suitable for use in pharmaceuticals, and aqueous buffer solutions. The water is substantially free of contaminants, such as parasites, pathogens, chemical contaminants, and particulate contamination. In some embodiments, the aqueous solution comprises a buffer. In some embodiments, the aqueous solution comprises an excipient. In some embodiments, the aqueous solution comprises a buffer and an excipient. In some embodiments, the excipient comprises a surfactant. In some embodiments, the excipient comprises a viscosity enhancer. In some embodiments, the excipient comprises a surfactant, a viscosity enhancer, or a mixture thereof. For example, the aqueous solution can include a surfactant and a viscosity enhancer in an aqueous buffer. In some embodiments, the viscosity enhancer is a cellulose derivative. In some embodiments, the aqueous solution comprises about 5.55 g/kg of sodium carboxymethylcellulose and about 0.5 g/kg of polysorbate 80 in phosphate buffered saline.

In some embodiments of the process provided herein, the aqueous solution includes a viscosity enhancer. The viscosity enhancer can be, for example, a cellulose or cellulose derivative or a synthetic polymer. Examples of viscosity enhancers include, but are not limited to, microcrystalline cellulose (Avicel: Asahi Kasei Corp., etc.), microcrystalline cellulose carmellose sodium (Avicel RC: Asahi Kasei Corp., etc.), methyl cellulose (Metolose SM: Shin-Etsu Chemical Co., Ltd., etc.), ethyl cellulose (Ethocel: Dow Chemical Co., etc.), hydroxypropyl cellulose (Nisso HPC: Nippon Soda Co., Ltd., etc.), low-substituted hydroxypropyl cellulose (L-HPC: Shin-Etsu Chemical Co., Ltd., etc.), hydroxypropyl methyl cellulose 2208 (Metolose 90SH: Shin-Etsu Chemical Co., Ltd., etc.), hydroxypropyl methyl cellulose 2906 (Metolose 65SH: Shin-Etsu Chemical Co., Ltd., etc.), hydroxypropyl methyl cellulose 2910 (Metolose 60SH: Shin-Etsu Chemical Co., Ltd., etc.), hydroxypropyl cellulose phthalate 200731 (HPMCP: Shin-Etsu Chemical Co., Ltd., etc.), hydroxypropyl cellulose phthalate 220824 (HPMCP: Shin-Etsu Chemical Co., Ltd., etc.), hydroxypropyl methyl cellulose acetate succinate (Shin-Etsu AQOAT: Shin-Etsu Chemical Co., Ltd., etc.), carmellose (NS-300: Gotoku Chemical Co., Ltd., etc.), carmellose calcium (ECG-505: Gotoku Chemical Co., Ltd., etc.), carmellose sodium (Cellogen: Daiichi Kogyo Seiyaku Co., Ltd., etc.), croscarmellose sodium (Ac-Di-Sol: Asahi Kasei Corp., etc.), carboxymethyl ethyl cellulose (CMEC: Freund Corp., etc.), cellulose acetate phthalate (CAP: Wako Pure Chemical Industries, Ltd., etc.), hydroxyethyl cellulose (NATROSOL: Aqualon Corp., etc.), polyvinyl alcohol, polyvinylpyrrolidone, or mixtures thereof. In some embodiments, the viscosity enhancer is a cellulose derivative. In some embodiments, the cellulose derivative is a water-soluble cellulose or water-soluble cellulose derivative. In some embodiments, the cellulose derivative is a carboxymethylcellulose, or a pharmaceutically acceptable salt thereof. For example, the aqueous solution comprises sodium carboxymethylcellulose.

A viscosity enhancer can be present in the aqueous solution in an amount of about 0.01 g/kg to about 50 g/kg of the aqueous solution. For example, about 0.01 g/kg to about 25 g/kg; about 0.01 g/kg to about 5 g/kg; about 0.1 g/kg to about 50 g/kg; about 0.1 g/kg to about 25 g/kg; about 0.1 g/kg to about 5 g/kg; about 0.5 g/kg to about 50 g/kg; about 0.5 g/kg to about 0.25 g/kg; about 0.5 g/kg to about 10 g/kg; about 0.5 g/kg to about 7.5 g/kg; about 0.5 g/kg to about 5.5 g/kg; about 0.5 g/kg to about 2.5 g/kg; about 1 g/kg to about 50 g/kg; about 1 g/kg to about 25 g/kg; about 1 g/kg to about 10 g/kg; about 1 g/kg to about 7.5 g/kg; about 1 g/kg to about 5.5 g/kg; about 1 g/kg to about 2.5 g/kg; about 2.5 g/kg to about 50 g/kg; about 5 g/kg to about 50 g/kg; about 10 g/kg to about 50 g/kg; about 25 g/kg to about 50 g/kg; about 0.1 g/kg to about 5 g/kg; about 2.5 g/kg to about 7.5 g/kg; about 5 g/kg to about 10 g/kg; and about 10 g/kg to about 20 g/kg of the aqueous solution. In some embodiments, the viscosity enhancer can be present in the aqueous solution at about 5 g/kg of the aqueous solution. In some embodiments, the viscosity enhancer can be present in the aqueous solution at about 5.55 g/kg of the aqueous solution. For example, the aqueous solution comprises about 5.55 g/kg sodium carboxymethylcellulose. In some embodiments, a cellulose derivative is present in the aqueous solution in an amount of about 0.05% to about 5% by weight of the aqueous solution. For example, about 0.05% to about 2.5%; about 0.05% to about 1%; about 0.05% to about 0.75%; about 0.05% to about 0.55%; about 0.05% to about 0.25%; about 0.1% to about 5%; about 0.1% to about 2.5%; about 0.1% to about 1%; about 0.1% to about 0.75%; about 0.1% to about 0.55%; about 0.1% to about 0.25%; about 0.25% to about 5%; about 0.5% to about 5%; about 1% to about 5%; about 2.5% to about 5%; about 0.25% to about 0.75%; about 0.5% to about 1%; and about 1% to about 2% by weight of the aqueous solution. In some embodiments, the viscosity enhancer can be present in the aqueous solution at about 0.55% by weight of the aqueous solution. For example, the aqueous solution comprises about 0.55% sodium carboxymethylcellulose by weight.

In some embodiments of the process provided herein, the aqueous solution includes a surfactant. Examples of surfactants include, but are not limited to, polysorbates such as polysorbate 20, polysorbate 40, polysorbate 60, polysorbate 80, and polysorbate 85; polyoxyethylene hydrogenated castor oils such as polyoxyethylene hydrogenated castor oil 60 and polyoxyl 35 castor oil; sorbitan fatty acid esters; sucrose fatty acid esters; polyoxyethylene polyoxypropylene glycols; polyoxyethylene fatty acid ethers; polyoxyl stearates; phosphatidylcholines; phosphatidylglycerols, including, but not limited to phosphatidylglycerols containing fatty acids, fatty alcohols, or a combination thereof, and carbon chain lengths between 4 and 20 carbons; and other surfactants, including, but not limited to, 1,2-dimyristoyl-sn-glycero-3-(phospho-s-(1-glycerol)), 1,2-dioleoyl-sn-glycero-3-phosphocholine, 1,2-dipalmitoyl-sn-glycero-3-(phospho-rac-(1-glycerol)), 1,2-distearoyl-sn-glycero-3-(phospho-rac-(1-glycerol)), 1,2-distearoyl-sn-glycero-3-phosphocholine, deoxycholic acid, dipalmitoylphosphatidylglycerol (dl), distearoylphosphatidylcholine (dl), docusate sodium, egg phospholipids, glyceryl palmitostearate, glyceryl trioleate, hydrogenated soybean lecithin, hydrolyzed soy protein (enzymatic; 2000 mw), hydroxyethylpiperazine ethane sulfonic acid, lecithin, miripirium chloride, n-(carbonyl-methoxy-polyethylene glycol 2000)-1,2-distearoyl-sn-glycero-3-phiv, oleic acid, palmitic acid, peg vegetable oil, peg-20 sorbitan isostearate, peg-40 castor oil, phospholipid, poloxamer 188, polyethylene glycol 200, polyethylene glycol 300, polyethylene glycol 3350, polyethylene glycol 400, polyethylene glycol 4000, polyethylene glycol 600, polyoxyethylene fatty acid esters, sodium cholesteryl sulfate, sodium deoxycholate, sodium n-(carbonyl-methoxypolyethylene glycol 2000)-1,2-distearoyl-sn-glyc, sodium oleate, sorbitan monolaurate, sorbitan monopalmitate, stearic acid, tricaprylin, or mixtures thereof. In some embodiments, the surfactant is a polysorbate. For example, the aqueous solution comprises polysorbate 80.

A surfactant can be present in the aqueous solution in an amount of about 0.01 g/kg to about 5 g/kg of the aqueous solution. In some embodiments, the concentration of surfactant depends on the critical micelle concentration of the individual surfactant. In some embodiments, the amount of surfactant is enough to be above the critical micelle concentration of the surfactant, enough to coat the surface area of the particles, or both. For example, about 0.01 g/kg to about 2.5 g/kg; about 0.01 g/kg to about 1 g/kg; about 0.01 g/kg to about 0.75 g/kg; about 0.01 g/kg to about 0.5 g/kg; about 0.01 g/kg to about 0.25 g/kg; about 0.025 g/kg to about 5 g/kg; about 0.05 g/kg to about 5 g/kg; about 1 g/kg to about 5 g/kg; about 0.1 g/kg to about 5 g/kg; about 0.1 g/kg to about 2.5 g/kg; about 0.1 g/kg to about 1 g/kg; about 0.1 g/kg to about 0.75 g/kg; about 0.1 g/kg to about 0.5 g/kg; about 0.1 g/kg to about 0.25 g/kg; about 0.25 g/kg to about 5 g/kg; about 0.5 g/kg to about 5 g/kg; about 1 g/kg to about 5 g/kg; about 0.25 g/kg to about 5 g/kg; about 0.25 g/kg to about 2.5 g/kg; about 0.25 g/kg to about 0.75 g/kg; about 0.5 g/kg to about 2.5 g/kg; about 0.5 g/kg to about 1 g/kg; and about 1 g/kg to about 2 g/kg of the aqueous solution. In some embodiments, the surfactant can be present in the aqueous solution at about 0.5 g/kg of the aqueous solution. For example, the aqueous solution comprises about 0.5 g/kg polysorbate 80. In some embodiments, a surfactant can be present in the aqueous solution in an amount of about 0.001% to about 0.5% by weight of the aqueous solution. For example, about 0.001% to about 0.25%; about 0.001% to about 0.1%; about 0.001% to about 0.075%; about 0.001% to about 0.05%; about 0.001% to about 0.025%;

about 0.0025% to about 0.5%; about 0.005% to about 0.5%; about 0.1% to about 0.5%; about 0.01% to about 0.5%; about 0.01% to about 0.25%; about 0.01% to about 0.1%; about 0.01% to about 0.075%; about 0.01% to about 0.05%; about 0.01% to about 0.025%; about 0.025% to about 0.5%; about 0.05% to about 0.5%; about 0.1% to about 0.5%; about 0.025% to about 0.5%; about 0.025% to about 2.5%; about 0.025% to about 0.075%; about 0.05% to about 2.5%; about 0.05% to about 0.1%; and about 0.1% to about 0.2% by weight of the aqueous solution. In some embodiments, the surfactant can be present in the aqueous solution at about 0.05% by weight of the aqueous solution. For example, the aqueous solution comprises about 0.05% polysorbate 80 by weight.

In the process provided herein, the process comprises providing a slurry comprising a compound of Formula (I), including salts and amorphous and polymorph forms thereof. In some embodiments, the compound of Formula (I) is polymorph Form 1. In some embodiments, the compound of Formula (I) is a non-stoichiometric or stoichiometric hydrate of Form 1 having between 1% and about 20% by weight water. In some embodiments, the slurry comprises a surfactant. In some embodiments, the slurry comprises water. For example, the slurry can include a compound of Formula (I), including salts and amorphous and polymorph forms thereof and a surfactant in water.

The compound of Formula (I), including salts and amorphous and polymorph forms thereof can be present in the slurry in an amount of about 0.001 g/kg to about 5 g/kg of the slurry. For example, about 0.001 g/kg to about 5 g/kg; about 0.001 g/kg to about 2.5 g/kg; about 0.001 g/kg to about 1 g/kg; about 0.001 g/kg to about 0.75 g/kg; about 0.001 g/kg to about 0.5 g/kg; about 0.001 g/kg to about 0.25 g/kg; about 0.001 g/kg to about 0.01 g/kg; about 0.01 g/kg to about 2.5 g/kg; about 0.01 g/kg to about 1 g/kg; about 0.01 g/kg to about 0.75 g/kg; about 0.01 g/kg to about 0.5 g/kg; about 0.01 g/kg to about 0.25 g/kg; about 0.1 g/kg to about 2.5 g/kg; about 0.1 g/kg to about 1 g/kg; about 0.1 g/kg to about 0.75 g/kg; about 0.1 g/kg to about 0.5 g/kg; about 0.1 g/kg to about 0.25 g/kg; about 0.25 g/kg to about 5 g/kg; about 0.5 g/kg to about 5 g/kg; about 1 g/kg to about 5 g/kg; about 2.5 g/kg to about 5 g/kg; about 0.25 g/kg to about 0.75 g/kg; about 0.5 g/kg to about 1 g/kg; and about 1 g/kg to about 2 g/kg of the slurry. In some embodiments, the compound of Formula (I), including salts and amorphous and polymorph forms thereof, can be present in the slurry at about 0.15 g/kg of the slurry. In some embodiments, the compound of Formula (I), including salts and amorphous and polymorph forms thereof, can be present in the slurry at about 0.35 g/kg of the slurry. In some embodiments, the compound of Formula (I), including salts and amorphous and polymorph forms thereof, can be present in the slurry at about 1.15 g/kg of the slurry. In some embodiments, the slurry comprises about 0.15 g/kg polymorph Form 1 or a non-stoichiometric or stoichiometric hydrate of Form 1 having between 1% and about 20% by weight water. In some embodiments, the slurry comprises about 0.35 g/kg polymorph Form 1 or a non-stoichiometric or stoichiometric hydrate of Form 1 having between 1% and about 20% by weight water. In some embodiments, the slurry comprises about 1.15 g/kg polymorph Form 1 or a non-stoichiometric or stoichiometric hydrate of Form 1 having between 1% and about 20% by weight water.

In some embodiments, the compound of Formula (I), including salts and amorphous and polymorph forms thereof, can be present in the slurry in an amount of about 0.0001% to about 0.5% by weight of the slurry. For example, about 0.0001% to about 0.5%; about 0.0001% to about 0.25%; about 0.0001% to about 0.1%; about 0.0001% to about 0.075%; about 0.0001% to about 0.05%; about 0.0001% to about 0.025%; about 0.0001% to about 0.001%; about 0.001% to about 0.5%; about 0.001% to about 0.25%; about 0.001% to about 0.1%; about 0.001% to about 0.075%; about 0.001% to about 0.05%; about 0.001% to about 0.025%; about 0.01% to about 0.25%; about 0.01% to about 0.1%; about 0.01% to about 0.075%; about 0.01% to about 0.05%; about 0.01% to about 0.025%; about 0.025% to about 0.5%; about 0.05% to about 0.5%; about 0.1% to about 0.5%; about 0.25% to about 0.5%; about 0.025% to about 0.075%; about 0.05% to about 0.1%; and about 0.1% to about 0.2% by weight of the slurry. In some embodiments, the compound of Formula (I), including salts and amorphous and polymorph forms thereof, can be present in the slurry at about 0.015% by weight of the slurry. For example, the slurry comprises about 0.015% by weight of polymorph Form 1 or a non-stoichiometric or stoichiometric hydrate of Form 1 having between 1% and about 20% by weight water. In some embodiments, the compound of Formula (I), including salts and amorphous and polymorph forms thereof, can be present in the slurry at about 0.035% by weight of the slurry. For example, the slurry comprises about 0.035% by weight of polymorph Form 1 or a non-stoichiometric or stoichiometric hydrate of Form 1 having between 1% and about 20% by weight water. In some embodiments, the compound of Formula (I), including salts and amorphous and polymorph forms thereof, can be present in the slurry at about 0.115% by weight of the slurry. For example, the slurry comprises about 0.115% by weight of polymorph Form 1 or a non-stoichiometric or stoichiometric hydrate of Form 1 having between 1% and about 20% by weight water.

In some embodiments, the slurry comprises about 0.15 g/kg of a compound of Formula (I), e.g., Form 1 or a non-stoichiometric or stoichiometric hydrate of Form 1 having between 1% and about 20% by weight water and about 0.5 g/kg of polysorbate 80 in water. In some embodiments, the compounds has no more than 5% by weight of other Forms. For example, not more than 1% or less than 0.1% of any additional Form, including amorphous. In some embodiments, the slurry comprises about 0.35 g/kg of a compound of Formula (I), e.g., Form 1 or a non-stoichiometric or stoichiometric hydrate of Form 1 having between 1% and about 20% by weight water, and about 0.5 g/kg of polysorbate 80 in water. In some embodiments, the slurry comprises about 1.15 g/kg of a compound of Formula (I), e.g., Form 1 or a non-stoichiometric or stoichiometric hydrate of Form 1 having between 1% and about 20% by weight water, and about 0.5 g/kg of polysorbate 80 in water.

In some embodiments, the slurry comprises water. Suitable types of water include, but are not limited to, deionized water, distilled water, reverse osmosis filtered water, reagent grade water, water for injection (WFI), USP grade water suitable for use in pharmaceuticals, and aqueous buffer solutions. The water is substantially free of contaminants, such as parasites, pathogens, chemical contaminants, and particulate contamination. In some embodiments, the slurry comprises water for injection.

In the process provided herein, the process comprises mixing the aqueous solution and slurry to form a suspension. In some embodiments, the aqueous solution is added to the slurry. In some embodiments, the slurry is added to the aqueous solution. In some embodiments, the aqueous solution and the slurry are added to a container substantially at the same time.

In some embodiments, the aqueous solution is a filtered mixture. In some embodiments, the filtered mixture comprises water. In some embodiments, the filtered mixture comprises water and an excipient. In some embodiments, the excipient comprises a surfactant, a viscosity enhancer, or a mixture thereof. In some embodiments, the filtered mixture is prepared by filtering the aqueous solution through a 0.2 µm filter. In some embodiments, the filter comprises a membrane comprising cellulose acetate, cellulose nitrate, nylon, a polymer, such as polyethersulfone or polytetrafluoroethylene, regenerated cellulose, or glass. In some embodiments, the filter membrane is a polymeric membrane. In some embodiments, the filter membrane is a polyethersulfone (PES) membrane. In some embodiments, a sterile diluent is mixed with the filtered mixture.

In some embodiments, the aqueous solution, the slurry, or both, are sterilized. In some embodiments, sterilization is by heat. In some embodiments, sterilization is by bulk steam sterilization. In some embodiments, sterilization is by dry heat sterilization. In some embodiments, sterilization is by irradiation. In some embodiments, sterilization is by filtration. In some embodiments, sterilization is by bulk steam sterilization, dry heat sterilization, irradiation, or combinations thereof. In some embodiments, the aqueous solution is sterilized by filtration or by heat or by a combination of filtration and heat. In some embodiments, the aqueous solution is sterilized to form a first sterilized mixture prior to mixing with the slurry. In some embodiments, the filtered mixture is sterilized prior to mixing with the slurry. In some embodiments, the filtered mixture is aseptically mixed with sterile diluent and sterilized prior to mixing with the slurry. In some embodiments, the slurry is sterilized to form a second sterilized mixture prior to mixing with the aqueous solution. In some embodiments, the slurry is sterilized by heat. In some embodiments, the aqueous solution is sterilized to form a first sterilized mixture and the slurry is sterilized to form a second sterilized mixture prior to mixing.

In some embodiments, the aqueous solution and the slurry are mixed aseptically to form a suspension. The mixing can be done with any sterile diluent or solution for injection. For example, any commercially available sterile diluent or solution for injection can be used. In some embodiments, the sterile solution for injection includes, but is not limited to, saline, with or without potassium chloride, e.g., a 0.9% saline solution, dextrose, e.g., a 5% dextrose solution, phosphate buffer, Lactated Ringer's solution, and combinations thereof. In some embodiments, the sterile solution for injection is a commercially available solution containing hyaluronic acid or hyaluronic acid derivatives. In some embodiments, the sterile diluent is aseptically added in an amount sufficient to result in a suspension comprising 0.015 mg/mL of the compound of Formula (I) including salts and amorphous and polymorph forms thereof. In some embodiments, the sterile diluent is aseptically added in an amount sufficient to result in a suspension comprising 0.035 mg/mL of the compound of Formula (I) including salts and amorphous and polymorph forms thereof. In some embodiments, the sterile diluent is aseptically added in an amount sufficient to result in a suspension comprising 0.115 mg/mL of the compound of Formula (I) including salts and amorphous and polymorph forms thereof.

In the process provided herein, the aqueous solution and slurry are mixed to form a suspension. For example, in some embodiments, the compound of Formula (I), including salts and amorphous and polymorph forms thereof, is not completely dissolved in the aqueous phase of the suspension. In the process provided herein, the suspension comprises about 0.005 mg/mL to about 2.5 mg/mL, about 0.01 mg/mL to about 2.0 mg/mL, about 0.01 mg/mL to about 1 mg/mL, about 0.01 mg/mL to about 0.5 mg/mL, about 0.01 mg/mL to about 0.2 mg/mL, or about 0.015 mg/mL to about 0.115 mg/mL of the compound of Formula (I) or a salt or amorphous or polymorph form thereof. In some embodiments, the suspension comprises 0.015 mg/mL of the compound of Formula (I) including salts and amorphous and polymorph forms thereof. In some embodiments, the suspension comprises 0.035 mg/mL of the compound of Formula (I) including salts and amorphous and polymorph forms thereof. In some embodiments, the suspension comprises 0.115 mg/mL of the compound of Formula (I) including salts and amorphous and polymorph forms thereof.

In some embodiments of the process provided herein, the aqueous solution, the slurry, the suspension, or combination thereof, are prepared in tanks. For example, the tank can be a tank used for manufacturing. In some embodiments, the tank is a stainless steel tank. In some embodiments, the tanks are jacketed for steam. In some embodiments, the tanks are equipped with one or more mixers, for example, a standard mixer and/or homogenizer, which are used to mix the ingredients added to the tank. In some embodiments, the tank is equipped with a heating and/or cooling device. In some embodiments, the tanks comprise ports for addition, recirculation equipment, transfer equipment, mixers, heating and/or cooling equipment, and combinations thereof. In some embodiments, the tanks have a capacity between about 5 L and about 5000 L. In some embodiments, the tanks have a capacity between about 5 L and about 3000 L; about 5 L and about 2000 L; about 5 L and about 1000 L; about 5 L and about 500 L; about 5 L and about 300 L; about 5 L and about 150 L; about 5 L and about 100 L; about 5 L and about 50 L; about 5 L and about 30 L; about 5 L and about 20 L; about 20 L and about 5000 L; about 20 L and about 3000 L; about 20 L and about 2000 L; about 20 L and about 1000 L; about 20 L and about 500 L; about 20 L and about 300 L; about 20 L and about 150 L; about 20 L and about 100 L; about 20 L and about 50 L; about 20 L and about 30 L; about 30 L and about 5000 L; about 30 L and about 3000 L; about 30 L and about 2000 L; about 30 L and about 1000 L; about 30 L and about 500 L; about 30 L and about 300 L; about 30 L and about 150 L; about 30 L and about 100 L; about 30 L and about 50 L; about 50 L and about 5000 L; about 50 L and about 3000 L; about 50 L and about 2000 L; about 50 L and about 1000 L; about 50 L and about 500 L; about 50 L and about 300 L; about 50 L and about 150 L; about 50 L and about 100 L; about 100 L and about 5000 L; about 100 L and about 3000 L; about 100 L and about 2000 L; about 100 L and about 1000 L; about 100 L and about 500 L; about 100 L and about 300 L; about 100 L and about 150 L; about 150 L and about 5000 L; about 150 L and about 3000 L; about 150 L and about 2000 L; about 150 L and about 1000 L; about 150 L and about 500 L; about 150 L and about 300 L; about 300 L and about 5000 L; about 300 L and about 3000 L; about 300 L and about 2000 L; about 300 L and about 1000 L; about 300 L and about 500 L; about 500 L and about 5000 L; about 500 L and about 3000 L; about 500 L and about 2000 L; about 500 L and about 1000 L; about 1000 L and about 5000 L; about 1000 L and about 3000 L; about 1000 L and about 2000 L; about 2000 L and about 5000 L; about 2000 L and about 3000 L; or about 3000 L and about 5000 L. In some embodiments, the tank has a capacity of about 5000 L, about 3000 L, about 2000 L, about 1000 L, about 500 L, about 300 L, about 150 L, about 100

L, about 50 L, about 30 L, about 20 L, or about 5 L. Other size tanks are known and can be used with the provided process.

In some embodiments, the process is performed using a scaled-up manufacturing process. A scaled-up manufacturing process can be used for volumes greater than 1 L or about 1 L or greater than 1 gallon or about 1 gallon, for example, greater than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, 350, 400, 450, 500, 550, 600, 650, 700, 800, 900, 1000, 1500, 2000, 2500, 3000, or more liters.

In the process provided herein, the process comprises aseptically filling a container with the suspension to prepare a single-dose, ready-to-use formulation. Examples of containers include, but are not limited to, vials, bottles, ampules, and syringes. In some embodiments, the suspension is aseptically filled into a single-use vial (i.e., unused portions of each vial are discarded and not saved for later administration). In some embodiments, the vial is a plastic vial. For example, the vial can be made of polyethylene, polypropylene, polyolefins, polyethylene terephthalate, polyethylene terephthalate G, poly(vinyl chloride), and mixtures thereof. In some embodiments, the vial is a polypropylene vial. In some embodiments, the vial is a glass vial. The container can be any size that can fit the desired amount of the formulation. For example, the container can be a 1 mL, 2 mL, 3 mL, 4 mL, 5 mL, 6 mL, 7 mL, 8 mL, 9 mL, or 10 mL container. In some embodiments, the container is a 3 mL vial. In some embodiments, the container is a 5 mL vial. In some embodiments, the container is a 3 mL polypropylene vial. For example, a polypropylene vial that is made using blow-fill-seal technology. In some embodiments, the vial is designed for easy withdrawal of the formulation with a syringe. In some embodiments, the vial has a Luer slip design. In some embodiments, the vial has a Luer lock design.

The resulting single-dose, ready-to-use formulations produced by the process provided herein are filled into containers comprising between about 0.005 mg/mL and about 2.5 mg/mL of the compound of Formula (I), including amorphous and polymorph forms thereof, for example, between about 0.005 mg/mL to about 2 mg/mL, about 0.01 mg/mL to about 1.8 mg/mL, about 0.015 mg/mL to about 0.115, about 0.025 mg/mL to about 1.6 mg/mL, about 0.05 mg/mL to about 1.5 mg/mL, about 0.075 mg/mL to about 1.25 mg/mL, about 0.1 mg/mL to about 1 mg/mL, or about 0.25 mg/mL to about 0.75 mg/mL. In some embodiments, the containers comprise a formulation comprising about 0.015 mg/mL of the compound of Formula (I), including amorphous and polymorph forms thereof. In some embodiments, the containers comprise a formulation comprising about 0.035 mg/mL of the compound of Formula (I), including amorphous and polymorph forms thereof. In some embodiments, the containers comprise a formulation comprising about 0.115 mg/mL of the compound of Formula (I), including amorphous and polymorph forms thereof. In some embodiments, the containers comprise a concentration between about 0.1 mg/mL and 4 mg/mL. In some embodiments, the concentration is 2 mg/mL.

In some embodiments, the process further comprises terminally sterilizing the container containing the suspension. For example, the sterilization can be performed at 121.1° C. (250° F.) or at lower temperatures, for example, between about 70-100° C., to achieve an $F_o$ of NLT 2. In some embodiments, the NLT is greater than 10 or greater than 30. In some embodiments, the container is terminally sterilized when the suspension comprises about 0.05 mg/mL to about 10 mg/mL of the compound of Formula (I) or a salt or amorphous or polymorph form thereof. For example, the suspension comprises about 0.05 mg/mL to about 5 mg/mL, about 0.05 mg/mL to about 2.5 mg/mL, about 0.05 mg/mL to about 1 mg/mL, about 0.05 mg/mL to about 0.5 mg/mL, about 0.05 mg/mL to about 0.1 mg/mL, about 0.1 mg/mL to about 10 mg/mL, about 0.1 mg/mL to about 5 mg/mL, about 0.1 mg/mL to about 2.5 mg/mL, about 0.1 mg/mL to about 1 mg/mL, about 0.1 mg/mL to about 0.5 mg/mL, about 0.1 mg/mL to about 0.25 mg/mL, about 0.25 mg/mL to about 10 mg/mL, about 0.25 mg/mL to about 5 mg/mL, about 0.25 mg/mL to about 2.5 mg/mL, about 0.25 mg/mL to about 1 mg/mL, about 0.25 mg/mL to about 0.5 mg/mL, bout 0.5 mg/mL to about 10 mg/mL, about 0.5 mg/mL to about 5 mg/mL, about 0.5 mg/mL to about 2.5 mg/mL, about 0.5 mg/mL to about 1 mg/mL, about 1 mg/mL to about 10 mg/mL, about 1 mg/mL to about 5 mg/mL, about 1 mg/mL to about 2.5 mg/mL, about 2.5 mg/mL to about 10 mg/mL, about 2.5 mg/mL to about 5 mg/mL, or about 5 mg/mL to about 10 mg/mL of the compound of Formula (I) or a salt or amorphous or polymorph form thereof.

In some embodiments, the process further comprises labeling the containers. In some embodiments, the process further comprises packaging the containers, for example, into boxes, cartons, or pre-formed blisters. In some embodiments, the process further comprises labeling the boxes, cartons, or preformed blisters.

3. Single-Dose, Ready-to-Use Formulations

Provided herein are single-dose, ready-to-use pharmaceutical formulations comprising a compound of Formula (I), including pharmaceutically acceptable salts and amorphous and polymorph forms thereof, prepared by the process described herein. In some embodiments, the formulations are prepared as single-dose formulations. Provided herein are pharmaceutical formulations prepared from a polymorph form of a compound of Formula (I). In some embodiments, the polymorph form is Form 1. In some embodiments, the polymorph form is a mixture of Form 1 and Form 9. In some embodiments, the polymorph is a non-stoichiometric or stoichiometric hydrate of Form 1 having between 1% and about 20% by weight water.

In some embodiments, the single-dose, ready-to-use pharmaceutical formulation comprises a polymorph form of a compound of Formula (I). In some embodiments, the polymorph form is Form 1. In some embodiments, the pharmaceutical formulation comprises a polymorph form of a compound of Formula (I) that is a mixture of forms. In some embodiments, the mixture of forms is a mixture of Forms 1 and 9. In some embodiments, the pharmaceutical formulation comprises a polymorph form of a compound of Formula (I) that is a non-stoichiometric or stoichiometric hydrate of Form 1 having between 1% and about 20% by weight water.

In some embodiments, the single-dose, ready-to-use pharmaceutical formulation prepared by the process provided herein contains polymorph Form 1 that has a purity of at least about 90% (not including water or solvents). In some embodiments, the purity is at least about 95%. In some embodiments, the purity is at least about 98%. For example, the purity is at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the formulation comprising Form 1 is substantially free of other forms of the compound of Formula (I), e.g., Form 9. In some embodiments, the formulation contains less than 15% by weight of other forms of the compound of Formula (I), such as less than 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.05%, 0.01%, or 0.001% by weight of other forms of the compound of Formula (I). In some embodiments, the other forms of the compound of Formula (I) are other anhydrous forms of the compound of Formula (I). In some embodiments, the formulation contains less than about 15% by weight of one or more other compounds of Formula (I). For example, the formulation contains less than 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.05%, 0.01%, or 0.001% by weight of one or more other forms of the compound of Formula (I). For example, the formulation can contain less than about 15% by weight of Form 2, Form 3, Form 4, Form 5, Form 6, Form 7, Form 8, Form 9, Form 10, Form 11, a non-stoichiometric or stoichiometric hydrate of Form 1, or combinations of two or more thereof.

In some embodiments, the single-dose, ready-to-use pharmaceutical formulation prepared by the process provided herein contains a non-stoichiometric or stoichiometric hydrate of polymorph Form 1 having between 1% and about 20% by weight water that has a purity of at least about 90%. In some embodiments, the purity is at least about 95%. In some embodiments, the purity is at least about 98%. For example, the purity is at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the formulation comprising the non-stoichiometric or stoichiometric hydrate of Form 1 having between 1% and about 20% by weight water is substantially free of other forms of the compound of Formula (I), e.g., Form 9. In some embodiments, the formulation contains less than 15% by weight of other forms of the compound of Formula (I), such as less than 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.05%, 0.01%, or 0.001% by weight of other forms of the compound of Formula (I). In some embodiments, the other forms of the compound of Formula (I) are other anhydrous forms of the compound of Formula (I). In some embodiments, the formulation contains less than about 15% by weight of one or more other compounds of Formula (I). For example, the formulation contains less than 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.05%, 0.01%, or 0.001% by weight of one or more other forms of the compound of Formula (I). For example, the formulation can contain less than about 15% by weight of Form 1, Form 2, Form 3, Form 4, Form 5, Form 6, Form 7, Form 8, Form 9, Form 10, Form 11, or combinations of two or more thereof.

In some embodiments, the single-dose, ready-to-use formulation prepared by the process provided herein comprises about 0.001 mg to about 5.0 mg per injection of a compound of Formula (I), including amorphous and polymorph forms thereof. For example, the formulation in some embodiments comprises about 0.001 mg to about 4 mg, about 0.001 mg to about 3 mg, about 0.001 mg to about 2 mg, about 0.001 mg to about 1 mg, about 0.001 mg to about 0.5 mg, 0.001 mg to about 0.4 mg, about 0.001 mg to about 0.3 mg, about 0.001 mg to about 0.25 mg, about 0.001 mg to about 0.2 mg, about 0.001 mg to about 0.15 mg, about 0.001 mg to about 0.1 mg, about 0.001 mg to about 0.075 mg, about 0.001 mg to about 0.055 mg, about 0.001 mg to about 0.05 mg, about 0.001 mg to about 0.035 mg, about 0.001 mg to about 0.025 mg, about 0.001 mg to about 0.01 mg, about 0.001 mg to about 0.005 mg, about 0.005 mg to about 5.0 mg, about 0.0075 mg to about 5.0 mg, about 0.01 mg to about 5.0 mg, about 0.01 mg to about 4.0 mg, about 0.01 mg to about 3.0 mg, about 0.01 mg to about 2.0 mg, about 0.01 mg to about 1.0 mg, about 0.01 mg to about 0.7 mg, about 0.01 mg to about 0.5 mg, about 0.01 mg to about 0.3 mg, about 0.01 mg to about 0.23 mg, about 0.01 mg to about 0.1 mg, about 0.01 mg to about 0.07 mg, about 0.01 mg to about 0.05 mg, about 0.01 mg to about 0.03 mg, about 0.03 mg to about 4.0 mg, about 0.03 mg to about 3.0 mg, about 0.03 mg to about 2.0 mg, about 0.03 mg to about 1.0 mg, about 0.03 mg to about 0.7 mg, about 0.03 mg to about 0.5 mg, about 0.03 mg to about 0.3 mg, about 0.03 mg to about 0.23 mg, about 0.03 mg to about 0.1 mg, about 0.03 mg to about 0.07 mg, about 0.03 mg to about 0.05 mg, about 0.07 mg to about 4.0 mg, about 0.07 mg to about 3.0 mg, about 0.07 mg to about 2.0 mg, about 0.07 mg to about 1.0 mg, about 0.07 mg to about 0.7 mg, about 0.07 mg to about 0.5 mg, about 0.07 mg to about 0.3 mg, about 0.07 mg to about 0.23 mg, about 0.07 mg to about 0.1 mg, about 0.025 mg to about 5.0 mg, about 0.045 mg to about 5.0 mg, about 0.05 mg to about 5.0 mg, about 0.075 mg to about 5.0 mg, about 0.1 mg to about 5.0 mg, about 0.25 mg to about 5.0 mg, about 0.01 mg to about 3.0 mg, about 0.025 mg to about 2.0 mg, about 0.01 mg to about 0.1 mg, and about 0.15 mg to about 0.25 mg of the compound of Formula (I), including amorphous and polymorph forms thereof. In some embodiments, the formulation comprises about 0.001 mg, 0.005 mg, 0.01 mg, 0.03 mg, 0.05 mg, 0.07 mg, 0.1 mg, 0.23 mg, 0.25 mg, 0.5 mg, 0.75 mg, 1.0 mg, 1.2 mg, 1.5 mg, 1.7 mg, 2.0 mg, 2.2 mg, 2.5 mg, 2.7 mg, 3.0 mg, 3.2 mg, 3.5 mg, 3.7 mg, 4.0 mg, 4.2 mg, 4.5 mg, 4.7 mg, or 5.0 mg of the compound of Formula (I), including amorphous and polymorph forms thereof. In some embodiments, the single-dose, ready-to-use formulation comprises 0.03 mg of the compound of Formula (I), including amorphous and polymorph forms thereof. In some embodiments, the single-dose, ready-to-use formulation comprises 0.07 mg of the compound of Formula (I), including amorphous and polymorph forms thereof. In some embodiments, the single-dose, ready-to-use formulation comprises 0.115 mg of the compound of Formula (I), including amorphous and polymorph forms thereof.

The single-dose, ready-to-use formulations prepared by the process provided herein comprising a compound of Formula (I), including salts and amorphous and polymorph forms thereof, can comprise a conventional pharmaceutical carrier, excipient, or the like. In some embodiments, the compounds of Formula (I), including salts and amorphous and polymorph forms thereof, are formulated as a suspension. For example, the compound of Formula (I) is not completely dissolved in the pharmaceutically acceptable carrier, i.e., the compound of Formula (I) is suspended in the pharmaceutically acceptable carrier. In some embodiments, the formulation comprises the compound of Formula (I) suspended in a pharmaceutically acceptable carrier. In some embodiments, the formulation comprises a polymorph form of Formula (I) suspended in a pharmaceutically acceptable carrier. In some embodiments, the formulation comprises Form 1 suspended in a pharmaceutically acceptable carrier. In some embodiments, the formulation comprises a non-stoichiometric or stoichiometric hydrate of Form 1 having between 1% and about 20% by weight water suspended in a pharmaceutically acceptable carrier. In some embodiments, the pharmaceutical formulation is a solution, i.e., the compound of Formula (I) is completely dissolved in the pharmaceutically acceptable carrier.

In some embodiments, the polymorph form is dried prior to mixing with the pharmaceutically acceptable carrier.

In some embodiments, the single-dose, ready-to-use pharmaceutically administrable formulations comprising a compound of Formula (I), including amorphous and polymorph forms thereof, can optionally comprise pharmaceutical excipients in a carrier, e.g., water, saline, buffer, aqueous dextrose, mannitol, glycerol, glycols, ethanol or the like, to form a suspension. If desired, the pharmaceutical formulation can also contain minor amounts of nontoxic auxiliary substances such as wetting agents, emulsifying agents, co-solvents, solubilizing agents, pH buffering agents, and the like.

In some embodiments, a single-dose, ready-to-use pharmaceutical formulation prepared by the process provided herein comprises water. Suitable types of water include, but are not limited to, deionized water, distilled water, reverse osmosis filtered water, reagent grade water, water for injection (WFI), USP/EP grade water suitable for use in pharmaceuticals, and aqueous buffer solutions. The water is substantially free of contaminants, such as parasites, pathogens, chemical contaminants, and particulate contamination. For example, the pharmaceutical formulation can include an aqueous buffer solution. Examples of buffer agents include, but are not limited to, acetic acid, acetic anhydride, adipic acid, alanine, albumin, alcohol, alfadex, ammonia, ammonium acetate, ammonium sulfate, anhydrous citric acid, anhydrous dextrose, anhydrous lactose, anhydrous trisodium citrate, arginine, ascorbic acid, aspartic acid, benzenesulfonic acid, benzoic acid, calcium chloride, calcium gluceptate, calcium hydroxide, calcium, caprylic acid, carbon dioxide, citric acid monohydrate, dibasic potassium phosphate, diethanolamine, disodium citrate sesquihydrate, disodium hydrogen citrate, edetate calcium disodium, edetate disodium, edetate sodium, edetic acid, ethanolamine hydrochloride, ferric chloride, gluceptate sodium, glycine hydrochloride, glycine, guanidine hydrochloride, histidine, hydrochloric acid, isoleucine, lactic acid, lactobionic acid, leucine, lysine acetate, lysine, lysine monohydrate, magnesium chloride, magnesium stearate, maleic acid, metaphosphoric acid, methanesulfonic acid, nitric acid, phosphate ion, phosphoric acid, potassium chloride, potassium hydroxide, potassium phosphate (monobasic), sodium acetate, sodium ascorbate, sodium benzoate, sodium bicarbonate, sodium bisulfate, sodium carbonate, sodium citrate, sodium hydroxide, sodium hypochlorite, sodium phosphate dihydrate, sodium phosphate, sodium phosphate p-32, sodium phosphate dibasic dihydrate, sodium phosphate dibasic dodecahydrate, sodium phosphate dibasic, sodium phosphate dibasic (anhydrous), sodium phosphate dibasic heptahydrate, sodium phosphate monobasic (anhydrous), sodium phosphate monobasic dihydrate, sodium phosphate monobasic monohydrate, sodium phosphate monobasic, sodium sulfate (anhydrous), sodium sulfate, sodium thioglycolate, sodium thiomalate, sodium thiosulfate, succinic acid, sulfuric acid, tartaric acid, tartaric acid (dl), trifluoroacetic acid, tromantadine, and tromethamine. In some embodiments, the pharmaceutical formulation comprises phosphate buffered saline.

In some embodiments, a single-dose, ready-to-use pharmaceutical formulation prepared by the process provided herein comprises a viscosity enhancer. The viscosity enhancer can be, for example, a cellulose or cellulose derivative or a synthetic polymer. Examples of viscosity enhancers include, but are not limited to, microcrystalline cellulose (Avicel: Asahi Kasei Corp., etc.), microcrystalline cellulose carmellose sodium (Avicel RC: Asahi Kasei Corp., etc.), methyl cellulose (Metolose SM: Shin-Etsu Chemical Co., Ltd., etc.), ethyl cellulose (Ethocel: Dow Chemical Co., etc.), hydroxypropyl cellulose (Nisso HPC: Nippon Soda Co., Ltd., etc.), low-substituted hydroxypropyl cellulose (L-HPC: Shin-Etsu Chemical Co., Ltd., etc.), hydroxypropyl methyl cellulose 2208 (Metolose 90SH: Shin-Etsu Chemical Co., Ltd., etc.), hydroxypropyl methyl cellulose 2906 (Metolose 65SH: Shin-Etsu Chemical Co., Ltd., etc.), hydroxypropyl methyl cellulose 2910 (Metolose 60SH: Shin-Etsu Chemical Co., Ltd., etc.), hydroxypropyl cellulose phthalate 200731 (HPMCP: Shin-Etsu Chemical Co., Ltd., etc.), hydroxypropyl cellulose phthalate 220824 (HPMCP: Shin-Etsu Chemical Co., Ltd., etc.), hydroxypropyl methyl cellulose acetate succinate (Shin-Etsu AQOAT: Shin-Etsu Chemical Co., Ltd., etc.), carmellose (NS-300: Gotoku Chemical Co., Ltd., etc.), carmellose calcium (ECG-505: Gotoku Chemical Co., Ltd., etc.), carmellose sodium (Cellogen: Daiichi Kogyo Seiyaku Co., Ltd., etc.), croscarmellose sodium (Ac-Di-Sol: Asahi Kasei Corp., etc.), carboxymethyl ethyl cellulose (CMEC: Freund Corp., etc.), cellulose acetate phthalate (CAP: Wako Pure Chemical Industries, Ltd., etc.), hydroxyethyl cellulose (NATROSOL: Aqualon Corp., etc.), polyvinyl alcohol, polyvinylpyrrolidone, or mixtures thereof. In some embodiments, the viscosity enhancer is a cellulose derivative. In some embodiments, the cellulose derivative is a water-soluble cellulose or water-soluble cellulose derivative. In some embodiments, a cellulose derivative is a carboxymethylcellulose, or a pharmaceutically acceptable salt thereof. For example, a cellulose derivative is sodium carboxymethylcellulose. A viscosity enhancer can be present in the formulation in an amount of about 0.1% to about 5% by weight of the formulation. For example, about 0.1% to about 2.5%; about 0.1% to about 1%; about 0.1% to about 0.75%; about 0.1% to about 0.5%; about 0.1% to about 0.25%; about 0.25% to about 5%; about 0.5% to about 5%; about 1% to about 5%; about 2.5% to about 5%; about 0.25% to about 0.75%; about 0.5% to about 1%; and about 1% to about 2% by weight of the formulation. In some embodiments, the viscosity enhancer can be present in the formulation at about 0.5% by weight of the formulation. In some embodiments, the viscosity enhancer is a cellulose derivative and is present in the formulation at about 0.5% by weight of the formulation.

In some embodiments, a single-dose, ready-to-use pharmaceutical formulation prepared by the process provided herein comprises a surfactant. Non-limiting examples of surfactants include polysorbates such as polysorbate 20, polysorbate 40, polysorbate 60, polysorbate 80, and polysorbate 85; polyoxyethylene hydrogenated castor oils such as polyoxyethylene hydrogenated castor oil 60 and polyoxyl 35 castor oil; sorbitan fatty acid esters; sucrose fatty acid esters; polyoxyethylene polyoxypropylene glycols; polyoxyethylene fatty acid ethers; polyoxyl stearates; phosphatidylcholines; phosphatidylglycerols, including, but not limited to phosphatidylglycerols containing fatty acids, fatty alcohols, or a combination thereof, and carbon chain lengths between 4 and 20 carbons; and other surfactants, including, but not limited to, 1,2-dimyristoyl-sn-glycero-3-(phosphos-(1-glycerol)), 1,2-dioleoyl-sn-glycero-3-phosphocholine, 1,2-dipalmitoyl-sn-glycero-3-(phospho-rac-(1-glycerol)), 1,2-distearoyl-sn-glycero-3-(phospho-rac-(1-glycerol)), 1,2-di stearoyl-sn-glycero-3-phosphocholine, deoxycholic acid, dipalmitoylphosphatidylglycerol (dl), distearoylphosphatidylcholine (dl), docusate sodium, egg phospholipids, glyceryl palmitostearate, glyceryl trioleate, hydrogenated soybean lecithin, hydrolyzed soy protein (enzymatic; 2000 mw), hydroxyethylpiperazine ethane sulfonic acid, lecithin, miripirium chloride, n-(carbonyl-methoxypolyethylene glycol 2000)-1,2-distearoyl-sn-glycero-3-phiv, oleic acid, palmitic acid, peg vegetable oil, peg-20 sorbitan isostearate, peg-40 castor oil, phospholipid, poloxamer 188, polyethylene glycol 200, polyethylene glycol 300, polyethylene glycol 3350, polyethylene glycol 400, polyethylene glycol 4000, polyethylene glycol 600, polyoxyethylene fatty acid esters, sodium cholesteryl sulfate, sodium deoxycholate, sodium n-(carbonyl-methoxypolyethylene glycol 2000)-1,2-distearoyl-sn-glyc, sodium oleate, sorbitan monolaurate, sorbitan monopalmitate, stearic acid, tricaprylin, or mixtures thereof. In some embodiments, the surfactant is a polysorbate. For example, the pharmaceutical formulation comprises polysorbate 80. A surfactant can be present in the formulation in an amount of about 0.001% to about 0.5% by weight of the formulation. In some embodiments, the concentration of surfactant depends on the critical micelle concentration of the individual surfactant. In some embodiments, the amount of surfactant is enough to be above the critical micelle concentration of the surfactant, enough to coat the surface area of the particles, or both. For example, about 0.001% to about 0.25%; about 0.001% to about 0.1%; about 0.001% to about 0.075%; about 0.001% to about 0.05%; about 0.001% to about 0.025%; about 0.0025% to about 0.5%; about 0.005% to about 0.5%; about 0.1% to about 0.5%; about 0.01% to about 0.5%; about 0.01% to about 0.25%; about 0.01% to about 0.1%; about 0.01% to about 0.075%; about 0.01% to about 0.05%; about 0.01% to about 0.025%; about 0.025% to about 0.5%; about 0.05% to about 0.5%; about 0.1% to about 0.5%; about 0.025% to about 0.5%; about 0.025% to about 2.5%; about 0.025% to about 0.075%; about 0.05% to about 2.5%; about 0.05% to about 0.1%; and about 0.1% to about 0.2% by weight of the formulation. In some embodiments, the surfactant can be present in the formulation at about 0.05% by weight of the formulation.

In some embodiments, a single-dose, ready-to-use pharmaceutical formulation prepared by the process provided herein comprises a compound of Formula (I), including amorphous and polymorph forms thereof, and a pharmaceutically acceptable carrier. For example, the formulation comprises a compound of Formula (I) and saline, e.g., phosphate buffered saline. In some embodiments, the pharmaceutical formulation comprises a compound of Formula (I), a pharmaceutically acceptable carrier, and one or more excipients. For example, the formulation comprises a compound of Formula (I), a pharmaceutically acceptable carrier, e.g., phosphate buffered saline, and one or more excipients, e.g., a surfactant and a cellulose derivative. In some embodiments, the surfactant is a polysorbate, e.g., polysorbate 80. In some embodiments, the cellulose derivative is sodium carboxymethylcellulose. In some embodiments, the pharmaceutical formulation comprises a compound of Formula (I), e.g., a polymorph form of Formula (I), e.g., Form 1, a pharmaceutically acceptable carrier, e.g., phosphate buffered saline, and one or more excipients, e.g., sodium carboxymethylcellulose and a polysorbate, e.g., polysorbate 80.

In some embodiments, the single-dose, ready-to-use pharmaceutical formulation prepared by the process provided herein comprises a compound of Formula (I), e.g., a polymorph form of Formula (I), about 0.01% to about 5% by weight of a cellulose derivative, and about 0.01% to about 0.5% by weight of a surfactant in an aqueous buffer. For example, a pharmaceutical formulation provided herein can include a compound of Formula (I), e.g., Form 1 or a non-stoichiometric or stoichiometric hydrate of Form 1 having between 1% and about 20% by weight water, about 0.5% by weight sodium carboxymethylcellulose and about 0.05% by weight polysorbate 80 in phosphate buffered saline.

In some embodiments, a single-dose, ready-to-use pharmaceutical formulation prepared by the process provided herein has a pH of about 6.0 to about 8.0. For example, a pharmaceutical formulation can have a pH of about 7.3 or 7.4. In some embodiments a pharmaceutical formulation provided herein has a pH of about 3.0 to about 5.0. For example, a pharmaceutical formulation can have a pH of about 3.8.

The single-dose, ready-to-use pharmaceutical formulations prepared by the process provided herein can contain an excipient. The term "excipient" is used herein to describe any ingredient other than the compound(s) provided herein, e.g., compound of Formula (I), including polymorph and amorphous forms thereof. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat, solubilizers, tonicity agents, stabilizers, preservatives, salt formation substances, chelators/chelating agents, viscosity enhancers, contrast agent, antifoam agents, control release agents, lubricants, adhesives, analgesics, antiheparins, antivirals, colorants, emollients, propellants, and other excipients, including, but not limited to activated charcoal, barium sulfate, bibapcitide, brocrinat, calcobutrol, glutathione, zinc, zinc acetate, zinc carbonate, zinc chloride, and zinc oxide. Cyclodextrins such as α-, β-, and γ-cyclodextrin, or chemically modified derivatives such as hydroxyalkylcyclodextrins, including 2- and 3-hydroxypropyl-b-cyclodextrins, or other solubilized derivatives can also be advantageously used to enhance delivery of compounds described herein. Dosage forms or formulations containing a compound as described herein in the range of 0.005% to 100% with the balance made up from non-toxic carrier may be prepared. The contemplated formulations can contain 0.001%-100% active ingredient, in one embodiment 0.1-95%, in another embodiment 75-85%, in a further embodiment 20-80%. Actual methods of preparing such dosage forms are known, or will be apparent, to those skilled in the art; for example, see *Remington: The Science and Practice of Pharmacy*, 22$^{nd}$ Edition (Pharmaceutical Press, London, U K. 2012).

In some embodiments, the single-dose, ready-to-use pharmaceutical formulations prepared by the process provided herein contain a solubilizer. Examples of solubilizers include, but are not limited to, acetyltryptophan (dl), alanine, albumin (aggregated), alcohol, alfadex intracavitary powder, ammonia, anhydrous dextrose, anhydrous lactose, anhydrous trisodium citrate, arginine, ascorbic acid, aspartic acid, benzenesulfonic acid, benzyl alcohol, benzyl benzoate, benzyl chloride, betadex sulfobutyl ether sodium, butanol (mixed isomers), caprylic acid, carboxymethylcellulose, carboxymethylcellulose sodium, castor oil, cholesterol, corn oil, cottonseed oil, creatine, creatinine, croscarmellose sodium, crospovidone, cysteine hydrochloride, cysteine, cysteine (dl), dextran 40, dextran, diacetylated monoglycerides, diethanolamine, dimethyl sulfoxide, ethanolamine hydrochloride, ethyl acetate, ethylene-vinyl acetate copolymer (15% vinyl acetate), gamma cyclodextrin, gelatin, gentisic acid ethanolamide, gentisic acid, gluconolactone, glucuronic acid, glycerin, hetastarch, human albumin microspheres, hyaluronate sodium, hydroxypropyl betadex intramuscular injection, hypromellose, isopropyl alcohol, methylcellulose, methylpyrrolidone, microcrystalline cellulose, N,N-dimethylacetamide, niacinamide, oleic acid, palmitic acid, peanut oil, peg vegetable oil, peg-20 sorbitan isostearate, peg-40 castor oil, phenylethyl alcohol, polyethylene glycol 200, polyethylene glycol 300, polyethylene glycol 3350, polyethylene glycol 400, polyethylene glycol 4000, polyethylene glycol 600, polypropylene glycol, polyvinyl alcohol, poppy seed oil, povidone k12, povidone k17, povidone, proline, propyl gallate, propylene glycol, sesame oil, soybean oil, starch, stearic acid, trimethylsilyl treated dimethiconol/trimethylsiloxysilicate crosspolymer, and yellow wax, and combinations thereof.

In some embodiments, the single-dose, ready-to-use pharmaceutical formulations prepared by the process provided herein contain a tonicity agent. Examples of tonicity agents include, but are not limited to, dextrose monohydrate, dextrose solution, dextrose, dimethyl sulfoxide, fructose, gluconolactone, glucuronic acid, glycerin, glycine hydrochloride, glycine, guanidine hydrochloride, histidine, hydrochloric acid, hypertonic sodium chloride solution, isoleucine, isopropyl alcohol, isotonic sodium chloride solution, lactic acid (dl), lactobionic acid, lactose monohydrate, lactose, leucine, lysine acetate, lysine, lysine monohydrate, magnesium chloride, magnesium stearate, maleic acid, mannitol, meglumine, methionine, methylboronic acid, polypropylene glycol, potassium chloride, potassium hydroxide, potassium phosphate (monobasic), proline, propyl gallate, propylene glycol, saccharin sodium, serine, sodium acetate, sodium ascorbate, sodium benzoate, sodium bicarbonate, sodium bisulfate, sodium carbonate, sodium chloride, sodium citrate, sodium gluconate, sodium hydroxide, sodium hypochlorite, sodium lactate, sodium phosphate dihydrate, sodium phosphate, sodium phosphate p-32, sodium phosphate dibasic dihydrate, sodium phosphate dibasic dodecahydrate, sodium phosphate dibasic, sodium phosphate dibasic (anhydrous), sodium phosphate dibasic heptahydrate, sodium phosphate monobasic (anhydrous), sodium phosphate monobasic dihydrate, sodium phosphate monobasic monohydrate, sodium phosphate monobasic, sodium sulfate (anhydrous), sodium sulfate, sodium thioglycolate, sodium thiomalate, sodium thiosulfate, sorbitol, succinic acid, sucrose, sulfuric acid, tartaric acid, tartaric acid (dl), threonine, trehalose, trifluoroacetic acid, trisodium citrate dihydrate, tromethamine, tryptophan, tyrosine, urea, urethane, and valine and combinations thereof.

In some embodiments, the single-dose, ready-to-use pharmaceutical formulations prepared by the process provided herein contain a stabilizer. Examples of stabilizers include, but are not limited to, acetyltryptophan (dl), alanine, albumin (aggregated), alcohol, alfadex intracavitary powder, ammonia, anhydrous dextrose, anhydrous lactose, anhydrous trisodium citrate, arginine, ascorbic acid, aspartic acid, benzenesulfonic acid, benzyl alcohol, benzyl benzoate, benzyl chloride, betadex sulfobutyl ether sodium, boric acid, butanol (mixed isomers), caprylic acid, carboxymethylcellulose, carboxymethylcellulose sodium, castor oil, cholesterol, creatine, creatinine, croscarmellose sodium, crospovidone, cysteine hydrochloride, cysteine, cysteine (dl), dextran 40, dextran, ethylene-vinyl acetate copolymer (15% vinyl acetate), gelatin, gentisic acid ethanolamide, gentisic acid, hetastarch, human albumin microspheres, hyaluronate sodium, hypromellose, meglumine, methionine, methylboronic acid, methylcellulose, methylpyrrolidone, microcrystalline cellulose, miripirium chloride, n-(carbonyl-methoxypolyethylene glycol 2000)-1,2-di stearoyl-sn-glycero-3-phiv, N,N-dimethylacetamide, niacinamide, phenylalanine, polyvinyl alcohol, povidone K12, povidone K17, povidone, serine, sodium citrate, sodium gluconate, sodium lactate, starch, threonine, trehalose, tricaprylin, trimethylsilyl treated dimethiconol/trimethylsiloxysilicate crosspolymer, trisodium citrate dihydrate, tryptophan, tyrosine, urea, and valine and combinations thereof.

In some embodiments, the single-dose, ready-to-use pharmaceutical formulations prepared by the process provided herein contain a preservative. Examples of preservatives include, but are not limited to, acetone sodium bisulfite, alpha-tocopherol, benzalkonium chloride, benzyl alcohol, benzyl benzoate, benzyl chloride, boric acid, butylated hydroxyanisole, butylated hydroxytoluene, butylparaben, chlorobutanol, chlorobutanol hemihydrate, cresol, diethyl pyrocarbonate, edetate calcium disodium, edetate disodium, edetate sodium, edetic acid, hexylresorcinol, metacresol, methylparaben, miripirium chloride, monothioglycerol, nitrogen, phenol, phenylethyl alcohol, phenylmercuric nitrate, potassium bisulfite, potassium metabisulfite, propylparaben, sodium ascorbate, sodium benzoate, sodium bisulfate, sodium chlorate, sodium dithionite, sodium formaldehyde sulfoxylate, sodium iodide, sodium metabisulfite, sodium sulfite, sodium tartrate, sulfur dioxide, sulfurous acid, and thimerosal and combinations thereof.

In some embodiments, the single-dose, ready-to-use pharmaceutical formulations prepared by the process provided herein contain a salt formation agent. Examples of salt formation agents include, but are not limited to, acetic acid, acetic anhydride, adipic acid, ammonium acetate, ammonium sulfate, anhydrous citric acid, benzoic acid, calcium chloride, calcium gluceptate, calcium hydroxide, calcium, carbon dioxide, citric acid monohydrate, dibasic potassium phosphate, diethanolamine, disodium citrate sesquihydrate, disodium hydrogen citrate, hydrochloric acid, isoleucine, lactic acid (dl), lactobionic acid, magnesium chloride, magnesium stearate, maleic acid, metaphosphoric acid, methanesulfonic acid, nitric acid, phosphate ion, phosphoric acid, sodium hydroxide, sodium hypochlorite, sodium phosphate dihydrate, sodium phosphate, sodium phosphate p-32, sodium phosphate dibasic dihydrate, sodium phosphate dibasic dodecahydrate, sodium phosphate dibasic, sodium phosphate dibasic (anhydrous), sodium phosphate dibasic heptahydrate, sodium phosphate monobasic (anhydrous), sodium phosphate monobasic dihydrate, sodium phosphate monobasic monohydrate, sodium phosphate monobasic, and trifluoroacetic acid and combinations thereof.

In some embodiments, the single-dose, ready-to-use pharmaceutical formulations prepared by the process provided herein contain a chelator or chelating agent. Examples of chelators or chelating agents include, but are not limited to, caldiamide sodium, caloxetate trisodium, calteridol calcium, edetate calcium disodium, edetate disodium, edetate sodium, edetic acid, ferric chloride, gluceptate sodium, methylboronic acid, nioxime, oxidronate disodium, peg-60 hydrogenated castor oil, pentasodium pentetate, pentetate calcium trisodium, pentetic acid, sodium phosphite, sodium pyrophosphate, sodium succinate hexahydrate, sodium trimetaphosphate, succimer, and versetamide and combinations thereof.

In some embodiments, the single-dose, ready-to-use pharmaceutical formulations prepared by the process provided herein contain a viscosity enhancer. Examples of viscosity enhancers include, but are not limited to, carboxymethylcellulose, carboxymethylcellulose sodium, croscarmellose sodium, crospovidone, ethylene-vinyl acetate copolymer (15% vinyl acetate), gelatin, hetastarch, human albumin microspheres, hyaluronate sodium, hypromellose, methylcellulose, methylpyrrolidone, microcrystalline cellulose, polyvinyl alcohol, povidone K12, povidone K17, povidone, starch, and trimethylsilyl treated dimethiconol/trimethylsiloxysilicate crosspolymer and combinations thereof.

In some embodiments, the single-dose, ready-to-use pharmaceutical formulations prepared by the process provided herein contain a contrast agent. Examples of contrast agents include, but are not limited to, diatrizoic acid, perflutren, stannous chloride, stannous fluoride, stannous tartrate, tetrakis(2-methoxyisobutylisocyanide)copper(I) tetrafluoroborate, and tetrofosmin and combinations thereof.

In some embodiments, the single-dose, ready-to-use pharmaceutical formulations prepared by the process provided herein contain an anti-foam agent. Examples of anti-foam agents include, but are not limited to, dimethicone, polysiloxane, silicone, and simethicone and combinations thereof.

In some embodiments, the single-dose, ready-to-use pharmaceutical formulations prepared by the process provided herein contain a control release agent. Examples of control release agents include, but are not limited to, poly(dl-lactic-co-glycolic acid), (50:50; 12000 mw), polyglactin, and polylactide and combinations thereof.

In some embodiments, the single-dose, ready-to-use pharmaceutical formulations prepared by the process provided herein contain a lubricant. Examples of lubricants include, but are not limited to, silicone and simethicone and combinations thereof.

In some embodiments, the single-dose, ready-to-use pharmaceutical formulations prepared by the process provided herein contain an adhesive. An example of an adhesive includes, but is not limited to, Duro-Tak 87-2287.

In some embodiments, the single-dose, ready-to-use pharmaceutical formulations prepared by the process provided herein contain an analgesic. An example of an analgesic includes, but is not limited to, disodium sulfosalicylate.

In some embodiments, the single-dose, ready-to-use pharmaceutical formulations prepared by the process provided herein contain an anti-heparin agent. An example of an anti-heparin agent includes, but is not limited to, protamine sulfate.

In some embodiments, the single-dose, ready-to-use pharmaceutical formulations prepared by the process provided herein contain an antiviral agent. An example of an antiviral agent includes, but is not limited to, tromantadine.

In some embodiments, the single-dose, ready-to-use pharmaceutical formulations prepared by the process provided herein contain a colorant. An example of a colorant includes, but is not limited to, methylene blue.

In some embodiments, the single-dose, ready-to-use pharmaceutical formulations prepared by the process provided herein contain an emollient. An example of an emollient includes, but is not limited to, urethane.

In some embodiments, the single-dose, ready-to-use pharmaceutical formulations prepared by the process provided herein contain a propellant. An example of a propellant includes, but is not limited to, dichlorodifluoromethane.

The formulations prepared by the process provided herein are single-dose, ready-to-use pharmaceutical formulations packaged in a container for parenteral administration (injection or infusion). For example, the pharmaceutical formulation is prepared to contain the therapeutically effective amount of the compound of Formula (I), including amorphous and polymorph forms thereof, and is intended to be used in a single subject for a single fusion or injection. The formulations provided herein are not designed for multiple-dose administration or for multiple use. The formulations provided herein are "ready-to-use," i.e., formulations that do not require constitution or dilution with a prescribed amount of diluent, e.g., water for injection or other suitable diluent, before use by the designated route. For example, a formulation in a vial, of the desired concentration, that only needs to be drawn up into a syringe.

In some embodiments, the single-dose, ready-to-use pharmaceutical formulation prepared by the process provided herein comprises a volume of about 0.1 mL to about 10 mL per container (i.e., per injection). For example, about 0.1 mL to about 10 mL, about 0.1 mL to about 5 mL, about 0.1 mL to about 4 mL, about 0.1 mL to about 3 mL, about 0.1 mL to about 2 mL, about 0.1 mL to about 1 mL, about 0.1 mL to about 0.5 mL, about 0.1 mL to about 0.25 mL, about 2 mL to about 10 mL, about 2 mL to about 5 mL, about 2 mL to about 4 mL, about 2 mL to about 3 mL, about 3 mL to about 5 mL, about 3 mL to about 10 mL, about 0.5 mL to about 1 mL, about 0.25 mL to about 2 mL. In some embodiments, the single-dose, ready-to-use pharmaceutical formulation prepared by the process provided herein comprises a volume of about 1 mL to about 10 mL per container (i.e., per injection). For example, about 1 mL to about 10 mL, about 1 mL to about 5 mL, about 1 mL to about 4 mL, about 1 mL to about 3 mL, about 1 mL to about 2 mL, about 2 mL to about 10 mL, about 2 mL to about 5 mL, about 2 mL to about 4 mL, about 2 mL to about 3 mL, about 3 mL to about 5 mL, about 3 mL to about 10 mL. In some embodiments, the formulation comprises a volume of about 2 mL per container (i.e., injection).

In some embodiments, the unit dosage of the compound of Formula (I), including amorphous and polymorph forms thereof, is about 0.1 µg/kg to about 10 µg/kg of body weight in humans.

In some embodiments, the unit dosage of compound of Formula (I), including amorphous and polymorph forms thereof, is about 0.1 µg/kg to about 5 µg/kg of body weight in humans.

In some embodiments, the unit dosage of compound of Formula (I), including amorphous and polymorph forms thereof, is about 0.2 µg/kg to about 9 µg/kg of body weight in humans.

In some embodiments, the unit dosage of compound of Formula (I), including amorphous and polymorph forms thereof, is about 0.25 µg/kg to about 8 µg/kg of body weight in humans.

In some embodiments, the unit dosage of compound of Formula (I), including amorphous and polymorph forms thereof, is about 0.3 µg/kg to about 7 µg/kg of body weight in humans.

In some embodiments, the unit dosage of compound of Formula (I), including amorphous and polymorph forms thereof, is about 0.4 µg/kg to about 6 µg/kg of body weight in humans.

In some embodiments, the unit dosage of compound of Formula (I), including amorphous and polymorph forms thereof, is about 0.5 µg/kg to about 5 µg/kg of body weight in humans.

In some embodiments, the unit dosage of compound of Formula (I), including amorphous and polymorph forms thereof, is about 0.6 µg/kg to about 5 µg/kg of body weight in humans.

In some embodiments, the unit dosage of compound of Formula (I), including amorphous and polymorph forms thereof, is about 1.0 µg/kg to about 4 µg/kg of body weight in humans.

In some embodiments, the unit dosage of compound of Formula (I), including amorphous and polymorph forms thereof, is about 2.0 µg/kg to about 4 µg/kg of body weight in humans.

In some embodiments, the unit dosage of compound of Formula (I), including amorphous and polymorph forms thereof, is about 3.0 µg/kg to about 5 µg/kg of body weight in humans.

In some embodiments, the unit dosage of compound of Formula (I), including amorphous and polymorph forms thereof, is about 4.0 µg/kg to about 6 µg/kg of body weight in humans.

In some embodiments, the unit dosage of compound of Formula (I), including amorphous and polymorph forms thereof, is about 5.0 µg/kg to about 10 µg/kg of body weight in humans.

In some embodiments, the unit dosage of compound of Formula (I), including amorphous and polymorph forms thereof, is 0.001 mg to 1 mg of body weight in humans.

In some embodiments, the unit dosage of compound of Formula (I), including amorphous and polymorph forms thereof, is 0.001 mg to 0.5 mg of body weight in humans.

In some embodiments, the unit dosage of compound of Formula (I), including amorphous and polymorph forms thereof, is 0.001 mg to 0.3 mg in humans.

In some embodiments, the unit dosage of compound of Formula (I), including amorphous and polymorph forms thereof, is 0.01 mg to 1 mg of body weight in humans.

In some embodiments, the unit dosage of compound of Formula (I), including amorphous and polymorph forms thereof, is 0.01 mg to 0.5 mg of body weight in humans.

In some embodiments, the unit dosage of compound of Formula (I), including amorphous and polymorph forms thereof, is 0.01 mg to 0.3 mg in humans.

In some embodiments, the unit dosage of compound of Formula (I), including amorphous and polymorph forms thereof, is 0.03 mg to 0.9 mg of body weight in humans.

In some embodiments, the unit dosage of compound of Formula (I), including amorphous and polymorph forms thereof, is 0.03 mg to 0.23 mg of body weight in humans.

In some embodiments, the unit dosage of compound of Formula (I), including amorphous and polymorph forms thereof, is 0.05 mg to 0.8 mg of body weight in humans.

In some embodiments, the unit dosage of compound of Formula (I), including amorphous and polymorph forms thereof, is 0.07 mg to 0.7 mg of body weight in humans.

In some embodiments, the unit dosage of compounds of Formula (I), including amorphous and polymorph forms thereof, is 0.08 mg to 0.7 mg of body weight in humans. In some embodiments, the unit dosage of compound of Formula (I), including amorphous and polymorph forms thereof, is 0.1 mg to 0.6 mg of body weight in humans.

In some embodiments, the unit dosage of compound of Formula (I), including amorphous and polymorph forms thereof, is 0.12 mg to 0.6 mg of body weight in humans.

In some embodiments, the unit dosage of compound of Formula (I), including amorphous and polymorph forms thereof, is 0.14 mg to 0.5 mg of body weight in humans.

In some embodiments, the unit dosage of compound of Formula (I), including amorphous and polymorph forms thereof, is 0.16 mg to 0.5 mg of body weight in humans.

In some embodiments, the unit dosage of compound of Formula (I), including amorphous and polymorph forms thereof, is 0.18 mg to 0.4 mg of body weight in humans.

In some embodiments, the unit dosage of compound of Formula (I), including amorphous and polymorph forms thereof, is 0.2 mg to 0.4 mg of body weight in humans.

In some embodiments, the single-dose, ready-to-use pharmaceutical formulations prepared by the process provided herein are stable for at least 3 months. For example, the formulations do not exhibit a change (e.g., greater than 5%) in one or more of polymorph forms (e.g., an increase or decrease of a certain form), appearance, pH, percent impurities, activity (as measured by in vitro assays), or osmolarity over time, e.g., at least 3 months as compared to the original formulation after manufacturing. In some embodiments, the single-dose, ready-to-use pharmaceutical formulations prepared by the process provided herein are stable for at least 6 months. For example, the formulations do not exhibit a significant change (e.g., greater than 5%) in one or more of polymorph form (e.g., an increase or decrease of a certain form), appearance, pH, percent impurities, activity (as measured by in vitro assays), or osmolarity over time, e.g., at least 6 months as compared to the original formulation after manufacturing. In some embodiments, the single-dose, ready-to-use pharmaceutical formulations prepared by the process provided herein are stable for at least 9 months. For example, the formulations do not exhibit a significant change (e.g., greater than 5%) in one or more of polymorph form (e.g., an increase or decrease of a certain form), appearance, pH, percent impurities, activity (as measured by in vitro assays), or osmolarity over time, e.g., at least 9 months as compared to the original formulation after manufacturing. In some embodiments, the single-dose, ready-to-use pharmaceutical formulations prepared by the process provided herein are stable for at least 12 months. For example, the formulations do not exhibit a significant change, as defined by the International Conference on Harmonisation of Technical Requirements for Registration of Pharmaceuticals for Human Use (ICH), in one or more of polymorph form (e.g., an increase or decrease of a certain form), appearance, pH, percent impurities, activity (as measured by in vitro assays), or osmolarity over time, e.g., at least 12 months as compared to the original formulation after manufacturing.

In some such embodiments, the single-dose, ready-to-use pharmaceutical formulation prepared by the process provided herein comprises between about 0.005 mg/mL and 2.5 mg/mL of the compound of Formula (I), including amorphous and polymorph forms thereof, for example, between about 0.005 mg/mL to about 2 mg/mL, about 0.01 mg/mL to about 1.8 mg/mL, about 0.025 mg/mL to about 1.6 mg/mL, about 0.05 mg/mL to about 1.5 mg/mL, about 0.075 mg/mL to about 1.25 mg/mL, about 0.1 mg/mL to about 1 mg/mL, or about 0.25 mg/mL to about 0.75 mg/mL. In some such embodiments, the pharmaceutical formulation comprises about 0.015 mg/mL to about 0.115 mg/mL of the compound of Formula (I), including amorphous and polymorph forms thereof. In some such embodiments, the pharmaceutical formulation comprises about 0.015 mg/mL of the compound of Formula (I), including amorphous and polymorph forms thereof. In some such embodiments, the pharmaceutical formulation comprises about 0.035 mg/mL of the compound of Formula (I), including amorphous and polymorph forms thereof. In some such embodiments, the pharmaceutical formulation comprises about 0.115 mg/mL of the compound of Formula (I), including amorphous and polymorph forms thereof. In some embodiments, the injection volume comprises between about 0.1 mg/mL and 4 mg/mL. In some embodiments, the injection volume is 2 mg/mL.

The single-dose, ready-to-use formulations prepared by the process provided herein comprising a compound of Formula (I), including amorphous and polymorph forms thereof, can be formulated as a plurality of particles. For example, particles of a compound of Formula (I), including amorphous and polymorph forms thereof, can have a median particle size of less than 20 µm (e.g., less than about 15 µm; less than about 10 µm; less than about 7.5 µm; less than about 5 µm; less than about 2.5 µm; less than about 1 µm; and less than about 0.5 µm). For example, the median particle size can be between about 0.1 µm and 20 µm, such as between about 0.5-20, 0.5-15, 0.5-10, 0.5-7.5, 0.5-5, 0.5-2.5, 0.5-1, 2.5-15, 5-10, 7.5-20, or 1-5 µm. In some embodiments, the particles also comprise a polymer. Examples of suitable polymers include biocompatible and biodegradable polymers like poly(lactic acid), a poly(glycolic acid), a poly(lactic-co-glycolic acid), a poly(lactide-co-glycolide), and mixtures thereof. In some embodiments, the particles comprise poly(lactic-co-glycolic acid) (PLGA).

In some embodiments, the compound of Formula (I), including amorphous and polymorph forms thereof, e.g., a polymorph form of Formula (I), e.g., Form 1, has a particle size distribution (D value), e.g., a D50, of between about 1 and about 6 µm, such as between about 1.5 and about 5 µm, or about 2.4 to about 2.55 µm. For example, the D50 can be about 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 4, 4.5, or 5 µm. In some embodiments, the D50 value is about 2.55 µm. In some embodiments, the D50 value is about 2.45 µm. In some embodiments, the D50 value is about 2.1 µm. In some embodiments, the D50 value is about 2 µm. In some embodiments, the D50 value is about 1.6 µm. The D50 can be measured by conventional particle size measuring techniques well known to those skilled in the art. Such techniques include, for example, sedimentation field flow fractionation, photon correlation spectroscopy, light scattering, laser diffraction and disc centrifugation.

In some embodiments, the single-dose, ready-to-use formulations prepared by the process provided herein comprising a compound of Formula (I), including amorphous and polymorph forms thereof, are administered parenterally, including intramuscularly, intra-articularly, periarticularly, intraspinally, intradiscal, intrasynovially, and epidurally. In some embodiments, the formulation is administered to a patient with disc degeneration. In some embodiments, the formulation is administered to a patient with osteoarthritis. In some embodiments, the formulation can be a bursa injection, a caudal injection (e.g., a caudal epidural steroid injection (ESI)), a facet injection, a facet synovial injection, a hip joint injection, an intradiscal injection, an occipital nerve injection, a sciatic/piriformis injection, a sacroiliac (SI) joint injection, or combinations thereof. In some embodiments, the formulation can be injected locally, for example, in a patient with osteoarthritis, at the site of osteoarthritis (e.g., knee, hip, shoulder, etc.). Injections can occur at one or more locations surrounding the joint. In some embodiments, the injection is guided using an imaging method such as ultrasound. In some embodiments, administration (e.g., injection) of the formulation is preceded or combined with a local anesthetic.

The single-dose, ready-to-use formulations prepared by the process provided herein comprising a compound of Formula (I), including amorphous and polymorph forms thereof, can also be administered in combination (administered together or sequentially) with other known agents.

In some embodiments, the single-dose, ready-to-use formulations prepared by the process provided herein comprising a compound of Formula (I), including amorphous and polymorph forms thereof, can be administered in combination with one or more of the following: (a) Nonsteroidal anti-inflammatory drugs (NSAIDs), including, but not limited to, ibuprofen, naproxen, aspirin, acetaminophen, indomethacin (e.g., INDOCIN® and TIVORBEX®), diclofenac by mouth or to the affected area (e.g., VOLTAREN®, ZIPSOR®, PENNSAID®, FLECTOR®, and CATAFLAM®), meloxicam (e.g., MOBIC), celecoxib (e.g., CELEBREX®), piroxicam (e.g., FELDENE®), etodolac (e.g., LODINE®), nabumetone (e.g., RELAFEN®), lumiracoxib, valdecoxib (e.g., BEXTRA), etoricoxib, parecoxib, fenoprofen (e.g., NALFON®), oxaprozin (e.g., DAYPRO®), mefanamic acid (e.g. PONSTEL®), diflunisal (e.g., DOLOBID®), fenoprofen (e.g., NALFON®), flurbirofen (e.g., ANSAID®), ketoprofen (e.g., ORUVAIL®), ketorolac (e.g., TORADOL®), sulindac (e.g., CLINORIL®), meclofenamate, choline salicylate-magnesium salicylate, salsalate (e.g., DISALCID®), and tolmetin (e.g., TOLECTIN®); (b) physical therapy; (c) injections of corticosteroid medications such as, e.g., prednisone, dexamethasone, hydrocortisone, and methylprenisolone; (d) injections of hyaluronic acid derivatives (e.g., HYALGAN®, SYNVISC®, EUFLEXXA®, GEL-ONE®, MONOVISC®, ORTHOVISC®, and SUPARTZ®); (e) injections or topical application of Capsaicin (e.g., CAPSAGELL®); (f) narcotics, such as, e.g., codeine, fentanyl, hydrocodone, hydromorphone, morphine, meperidine, oxycodone, and tramadol (e.g., ULTRAM®, CONZIP®, and RYZOLTL®); (g) antidepressants such as dulozetine (e.g., CYMBALTA®); (h) braces and/or shoe inserts or any device that can immobilize or support the joints to help keep pressure off it (e.g., splints, braces, shoe inserts or other medical devices); (i) realigning bones (osteotomy); (j) joint replacement (arthroplasty); and (k) chronic pain class.

In some embodiments, the single-dose, ready-to-use formulations prepared by the process provided herein comprising a compound of Formula (I), including amorphous and polymorph forms thereof, can be used to treat osteoarthritis. In some embodiments, the formulations can be used to treat osteoarthritis in combination with one or more of the following drugs or methods: prednisone, methylprednisolone, SYNVISC® (hylan G-F 20), ABT-981 [*MAbs* (2015) 7(3): 605-619], stem cell injection, JNJ-42160443 (fulranumab), platelet rich plasma (PRGF) injection, tanezumab, venlafaxine, PH-797804, PG-530742 (the dihydrated sodium salt PG-116800), Sprifermin (AS902330, rhFGF-18), epicutaneous ketoprofen in transfersome (IDEA-033) [*Annals of the Rheumatic Diseases* (2007) 66(9):1178-1183], FX005 and FX006 (both by Flexion Therapeutics, Inc.), JNJ-39439335 (Mavatrep) [*J. Med. Chem.* (2015) 58(9):3859-3874], polmacoxib (Acelex, CG100649), balicatib (AAE581), GSK3196165, cebranopadol (GRT6005), fasinumab (REGN475), TPX-100 (by OrthoTrophix), PRX167700 (by Proximagen), EP 104IAR (extended release fluticasone propionate composition), LY2951742 and LY545694 (both by Eli Lilly & Co), Adalimumab (Humira®), GW842166 (by GSK), YY1201 (by Yooyoung Pharmaceutical Co., Ltd.), CF101 (IB-MECA) and CF602 (both by Can-Fite Bio-Pharma), PLA-695 (by Pfizer), VX-150 (by Vertex), ADL5859 and ADL5747 (both by Adolor Corporation now Cubist Pharmaceuticals), funapide (INN) (TV-45070, XEN402), AGG-523 (by Pfizer) [*Osteoarthritis Cartilage* (2011) 19(3):315-323], CNTX-4975 (capsaicin for injection by Centrexion Corporation), CR845 (by Cara Therapeutics), ASP7962 (by Astellas Pharma), DA-5202 (by Dong-A ST Co., Ltd.), GZ389988 (by Sanofi-Genzyme), and MEDI 7352 (by AstraZeneca), LNA043 (by Novartis).

4. Kits

Also provided herein are kits. Typically, a kit includes one or more formulations as described herein, e.g., a single-dose, ready-to-use formulation prepared by the process provided herein comprising a compound of Formula (I), including amorphous and polymorph forms thereof. In certain embodiments, a kit can include one or more delivery systems, e.g., for delivering or administering the formulation as provided herein, and directions for use of the kit (e.g., instructions for treating a patient). In some embodiments, the kit can include a formulation as described herein and a label that indicates that the contents are to be administered to a patient with bone or cartilage diseases or osteoarthritis. The actual dose of the compound of Formula (I) provided herein depends on the specific compound, and on the condition to be treated; the selection of the appropriate dose is well within the knowledge of the skilled artisan.

5. Methods for Treating Osteoarthritis

Provided are methods for the treatment of osteoarthritis in a subject. The methods comprise administering to the subject a therapeutically effective amount of a single-dose, ready-to-use formulation provided herein comprising a compound of Formula (I), including salt and amorphous or polymorph forms thereof. In some embodiments, the formulation is prepared by the process provided herein. In some embodiments, the methods provided herein include intra-articular administration of a single-dose, ready-to-use pharmaceutical formulation comprising a therapeutically effective amount of a compound of Formula (I), including salt and amorphous and polymorph forms thereof. In some embodiments, the methods provided herein include intra-articular administration of a single-dose, ready-to-use pharmaceutical formulation prepared by a process provided herein. In some embodiments, the polymorph form is Form 1. In some embodiments, the polymorph form is a non-stoichiometric or stoichiometric hydrate of Form 1 having between 1% and about 20% by weight water.

In some embodiments, provided herein are methods for treating osteoarthritis in a subject comprising intra-articular administration to the subject a single-dose, ready-to-use pharmaceutical formulation comprising a therapeutically effective amount of a compound of Formula (I). In some embodiments, the compound of Formula (I) in the formulation comprises Form 1. In some embodiments, the compound of Formula (I) in the formulation comprises a non-stoichiometric or stoichiometric hydrate of Form 1 having between 1% and about 20% by weight water. In some embodiments, the compound of Formula (I) in the formulation is substantially present as a non-stoichiometric or stoichiometric hydrate of Form 1 having between 1% and 20% by weight water.

In some embodiments of the method provided herein, the single-dose, ready-to-use formulations prepared by the process provided herein comprising a compound of Formula (I), including amorphous and polymorph forms thereof, are administered parenterally, including intramuscularly, intra-articularly, periarticularly, intradiscal, intraspinally, intra-synovially, and epidurally. In some embodiments, the formulation is administered to a patient with disc degeneration. In some embodiments, the formulation is administered to a patient with osteoarthritis. In some embodiments, the formulation can be a bursa injection, a caudal injection (e.g., a caudal epidural steroid injection (ESI)), a facet injection, a facet synovial injection, a hip joint injection, an intradiscal injection, an occipital nerve injection, a sciatic/piriformis injection, a sacroiliac (SI) joint injection, or combinations thereof. In some embodiments, the formulation can be injected locally, for example, in a patient with osteoarthritis, at the site of osteoarthritis (e.g., knee, hip, shoulder, etc.). Injections can occur at one or more locations surrounding the joint. In some embodiments, the formulation is administered intra-articularly. In some embodiments, the injection is guided using an imaging method such as ultrasound. In some embodiments, administration (e.g., injection) of the formulation is preceded or combined with a local anesthetic.

In some embodiments of the methods provided herein, the formulation comprising a compound of Formula (I), including salt and amorphous and polymorph forms thereof, is administered once. In some embodiments, the formulation comprising a compound of Formula (I), including salt and amorphous and polymorph forms thereof, is administered more than once. For example, the formulation is administered by injections spaced at least 7 days apart. In some embodiments, the formulation is administered once every two weeks. In some embodiments, the formulation is administered once every three weeks. In some embodiments, the formulation is administered once every four weeks. In some embodiments, the formulation is administered once every six weeks. In some embodiments, the formulation is administered once every eight weeks. In some embodiments, the formulation is administered once every twelve weeks (three months).

6. Polymorphs

Provided herein are formulations comprising a compound of Formula (I):

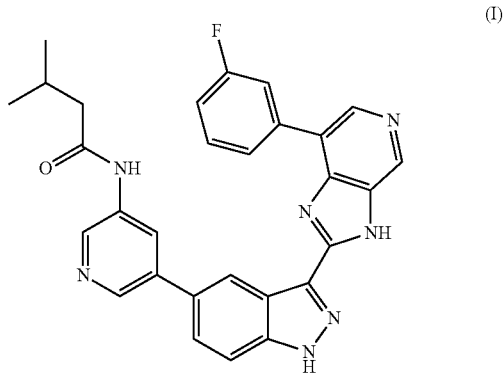 [SMILES: CC(C)CC(=O)Nc1cncc(-c2ccc3[nH]nc(-c4nc5c(-c6cccc(F)c6)cncc5[nH]4)c3c2)c1]

(I)

including pharmaceutically acceptable salts and amorphous and polymorph forms thereof.

The compound of Formula (I) provided herein can be prepared using methods known and understood by those of ordinary skill in the art. For example, synthetic methods such as those described in PCT/US2013/031055 can be used, and this application is herein incorporated by reference in its entirety.

The formulations provided herein can contain a polymorph form of the compound of Formula (I). The forms include, e.g., solvates, hydrates, non-stoichiometric or stoichiometric hydrates, and non-solvated forms of the compound of Formula (I), including, for example, polymorph Forms 1, 2, 3, 4, 5, 6, 7, 8, 9, 10, 11, 12, and 13.

One such polymorph is a polymorph known as Form 1. Form 1 is an anhydrous polymorph of the compound of Formula (I). In one embodiment, Form 1 has an X-ray powder diffraction (XRPD or XRD) pattern, obtained with CuKα1-radiation, with at least peaks at ° 2θ values of 6.8±0.2, 12.4±0.2, and 18.5±0.2. In some embodiments, Form 1 has an XRPD pattern with at least peaks at ° 2θ values of 6.8±0.2, 12.4±0.2, 16.5±0.2, 18.5±0.2, and 19.2±0.2. In some embodiments, Form 1 has an XRPD pattern with at least peaks at ° 2θ values of 6.8±0.2, 9.3±0.2, 12.4±0.2, 13.9±0.2, 16.5±0.2, 18.5±0.2, 19.2±0.2, and 24.6±0.2. For example, in some embodiments, Form 1 has an XRPD pattern with at least peaks at ° 2θ values of 6.8±0.2, 9.3±0.2, 12.4±0.2, 13.9±0.2, 14.5±0.2, 16.5±0.2, 18.5±0.2, 19.2±0.2, 20.3±0.2, and 24.6±0.2.

In some embodiments, the formulations provided herein comprise a composition comprising polymorph Form 1. In some embodiments, the composition can be substantially pure. For example, the composition has a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than about 15% by weight of other forms of the compound of Formula (I). For example, the composition can contain less than 14%, 13%, 12%, 11%, 10%, 9%, 8%, 7%, 6%, 5%, 4%, 3%, 2%, 1% or less by weight of other anhydrous forms of the compound of Formula (I). In some embodiments, the composition contains less than about 15% by weight of the polymorph Form 9. For example, the composition can contain less than 14%, 13%, 12%, 11%, 10%, 9%, 8%, 7%, 6%, 5%, 4%, 3%, 2%, 1% or less by weight of the polymorph of Form 9. In some embodiments, the composition contains less than about 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 2, Form 3, Form 4, Form 5, Form 6, Form 7, Form 8, Form 9, Form 10, and Form 11, a non-stoichiometric or stoichiometric hydrate of Form 1 having between 1% and about 20% by weight water, or a combination of two or more thereof.

In some embodiments, provided herein is a formulation comprising polymorph Form 1 that exhibits an endotherm between about 50-100° C. as measured by differential scanning calorimetry (DSC) related to sorbed water. In some embodiments, polymorph Form 1 exhibits a recrystallization event that is observed between about 270-290° C., e.g., around 280° C. In some embodiments, the endotherm and exotherm are observed when using a scan rate of 10° C. per minute.

In some embodiments, provided herein is a formulation comprising polymorph Form 1 that recrystallizes into Form 9 with a melting point of around 363° C. In some embodiments, polymorph Form 1 undergoes a total mass loss of about 0.33% before around 100° C., e.g., from about 39° C. to about 100° C., as measured by thermal gravimetric analysis (TGA).

In some embodiments, polymorph Form 1 is prepared by a method comprising drying a composition comprising the compound of Formula (I), including amorphous and polymorph forms thereof, to generate polymorph Form 1. In some embodiments, the composition comprises a non-stoichiometric or stoichiometric hydrate of Form 1 having between 1% and about 20% by weight water. In some embodiments, polymorph Form 1 is prepared by a method comprising reslurrying a composition comprising the compound of Formula (I), including amorphous and polymorph forms thereof, in a solvent or mixture of solvents to generate polymorph Form 1 as a residual solid. In some embodiments, the reslurrying takes place at room temperature (RT). In some embodiments, the reslurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, polymorph Form 1 is prepared by a method comprising reslurrying a composition comprising the compound of Formula (I), including amorphous and polymorph forms thereof in a solvent or mixture of solvents to generate polymorph Form 1 as a residual solid. In some embodiments, the compound of Formula (I) is a non-stoichiometric or stoichiometric hydrate of Form 1 having between 1% and about 20% by weight water. In some embodiments, the solvent is methanol. In some embodiments, the solvent is toluene. In some embodiments, the solvent is heptane. In some embodiments, the solvent is dichloromethane (DCM). In some embodiments, the solvent is water. In some embodiments, the solvent is in a mixture with water, for example the solvent can be a mixture of water and acetonitrile, methanol, ethyl acetate (EA), methyl tert-butyl ether (MtBE), isopropyl alcohol (IPAc), methyl acetate (MA), methyl isobutyl ketone (MIBK), DCM, n-butyl acetate, heptane, toluene, or n-butanol. In some embodiments, the water is present in an amount of about 5% by weight. In some embodiments, the reslurrying takes place at room temperature. In some embodiments, the reslurrying takes place at around 50° C. In some embodiments, polymorph Form 1 is prepared by a method further comprising drying the residual solid, for example, under vacuum. In some embodiments, the drying is at a temperature of between about 60° C. and 90° C., such as, e.g., around 75° C.

Provided herein are formulations comprising a non-stoichiometric or stoichiometric hydrate of Form 1 having between 1% and about 20% by weight water. In some embodiments, for example, above 30% relative humidity (RH), Form 1 readily sorbs water and shows a distinctive shift in Form 1 peaks from 6.8±0.2 to 6.2±0.2 and 12.6±0.2 to 11±0.2. In some embodiments, a non-stoichiometric or stoichiometric hydrate of Form 1 comprises up to about 20% by weight water. For example, up to about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, or greater than 1% water by weight. In some embodiments, a non-stoichiometric or stoichiometric hydrate of Form 1 has between 1 to about 20% water by weight, e.g., between 1% and about 10%, about 5% and about 15%, about 10% and about 20%, 1% and about 5%, about 5% and about 10%, about 10% and about 15%, about 15% and about 20%, or about 17% and about 20% water by weight.

In some embodiments, provided herein is a formulation comprising a composition comprising a non-stoichiometric or stoichiometric hydrate of Form 1 having between 1% and about 20% by weight water. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I) (e.g., anhydrous forms of the compound of Formula (I)). In some embodiments, the composition contains less than 20% by weight of polymorph Form 9 having X-ray powder diffraction pattern comprising peaks at ° 2θ values of 4.9±0.2, 18.6±0.2, and 21.1±0.2. For example, the composition contains less than 15% by weight of Form 9, such as less than 14%, 13%, 12%, 11%, 10%, 9%, 8%, 7%, 6%, 5%, 4%, 3%, 2%, 1% or less by weight of other forms of the compound of Form 9. In some embodiments, the composition contains less than 15% of one or more other forms of the compound of Formula (I), such as less than 14%, 13%, 12%, 11%, 10%, 9%, 8%, 7%, 6%, 5%, 4%, 3%, 2%, 1% or less of one or more other forms of the compound of Formula (I). For example, the composition can contain less than about 15% of Form 1, Form 2, Form 3, Form 4, Form 5, Form 6, Form 7, Form 8, Form 9, Form 10, Form 11, or a combination of two or more thereof.

Another example of a non-stoichiometric hydrate of polymorph Form 1 is referred to as Form 12.

In one embodiment, provided herein is a formulation comprising polymorph Form 12. In some embodiments, Form 12 has an XRPD pattern, obtained with CuKα1-radiation, with at least peaks at ° 2θ positions 6.4±0.2, 11.0±0.2, and 18.4±0.2. In some embodiments, Form 12 has an XRPD pattern with at least peaks at ° 2θ positions 6.4±0.2, 9.2±0.2, 11.0±0.2, 18.4±0.2, and 19.7±0.2. In some embodiments, Form 12 has an XRPD pattern with at least peaks at ° 2θ positions 6.4±0.2, 9.2±0.2, 11.0±0.2, 15.6±0.2, 18.4±0.2, 19.7±0.2, 24.4±0.2, and 25.2±0.2. For example, in some embodiments, Form 12 has an XRPD pattern with at least peaks at ° 2θ positions 6.4±0.2, 9.2±0.2, 11.0±0.2, 15.6±0.2, 16.1±0.2, 18.4±0.2, 19.7±0.2, 20.8±0.2, 24.4±0.2, and 25.2±0.2.

In some embodiments, provided herein is polymorph Form 12 that exhibits an endotherm between about 50-100° C. as measured by DSC. In some embodiments, polymorph Form 12 exhibits an exotherm at around 283° C. In some embodiments, the endotherms and exotherms are observed when using a scan rate of 10° C. per minute.

In some embodiments, provided herein is polymorph Form 12 that has a melting point of around 364° C. In some embodiments, polymorph Form 12 undergoes a weight loss of about 1.4% before around 100° C., e.g., from about 30° C. to about 100° C., as measured by TGA.

One example of a non-stoichiometric hydrate of polymorph Form 1 is referred to as Form 13.

In one embodiment, provided herein is a formulation comprising polymorph Form 13. In some embodiments, polymorph Form 13 has an XRPD pattern, obtained with CuKα1-radiation, with at least peaks at ° 2θ values of 6.8±0.2, 12.4±0.2, and 18.5±0.2. In some embodiments, Form 13 has an XRPD pattern with at least peaks at ° 2θ values of 6.8±0.2, 12.4±0.2, 16.5±0.2, 18.5±0.2, and 19.2±0.2. In some embodiments, Form 13 has an XRPD pattern with at least peaks at ° 2θ values of 6.8±0.2, 9.3±0.2, 12.4±0.2, 13.9±0.2, 16.5±0.2, 18.5±0.2, 19.2±0.2, and 24.6±0.2. For example, in some embodiments, Form 13 has an XRPD pattern with at least peaks at ° 2θ values of 6.8±0.2, 9.3±0.2, 12.4±0.2, 13.9±0.2, 14.5±0.2, 16.5±0.2, 18.5±0.2, 19.2±0.2, 20.3±0.2, and 24.6±0.2.

In some embodiments, polymorph Form 13 exhibits an endotherm between about 50-100° C. as measured by DSC. In some embodiments, polymorph Form 13 exhibits an exotherm at between about 265-285° C., e.g., around 278° C. For example, in some embodiments, the endotherms and exotherms are observed when using a scan rate of 10° C. per minute.

In some embodiments, polymorph Form 13 has a melting point of around 363° C. In some embodiments, polymorph Form 13 undergoes a weight loss of about 1.9% before around 100° C. as measured by TGA.

Provided herein are methods of preparing a non-stoichiometric or stoichiometric hydrate of polymorph Form 1. In some embodiments, the method comprises reslurrying a composition comprising the compound of Formula (I), including amorphous and polymorph forms thereof, in a solvent or mixture of solvents to generate a non-stoichiometric or stoichiometric hydrate of polymorph Form 1 as a residual solid. In some embodiments, the composition comprising the compound of Formula (I) is a mixture of a non-stoichiometric or stoichiometric hydrate of polymorph Form 1 and Form 1. In some embodiments, the reslurrying takes place at RT. In some embodiments, the reslurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, the method comprises reslurrying a composition comprising a mixture of a non-stoichiometric or stoichiometric hydrate of polymorph Form 1 and Form 1 in a solvent or mixture of solvents to generate a non-stoichiometric or stoichiometric hydrate of polymorph Form 1 as a residual solid. In some embodiments, the solvent is in a mixture with water, for example the solvent can be a mixture of water and acetonitrile, methanol, MtBE, MA, MIBK, DCM, IPAc, n-butyl acetate, heptane, toluene, or n-butanol. In some embodiments, the water is present in an amount of about 5% by weight. In some embodiments, the reslurrying takes place at RT. In some embodiments, the reslurrying takes place at around 50° C.

Provided herein is a formulation comprising a polymorph known as Form 2. Form 2 is an anhydrous polymorph of the compound of Formula (I). In one embodiment, polymorph Form 2 has an XRPD pattern, obtained with CuKα1-radiation, with at least peaks at ° 2θ values of 7.0±0.2, 21.5±0.2, and 22.0±0.2. In some embodiments, Form 2 has an XRPD pattern with at least peaks at ° 2θ values of 7.0±0.2, 18.9±0.2, 21.5±0.2, 22.0±0.2, and 24.2±0.2. In some embodiments, Form 2 has an XRPD pattern with at least peaks at ° 2θ values of 7.0±0.2, 14.1±0.2, 18.9±0.2, 19.2±0.2, 21.5±0.2, 22.0±0.2, 24.2±0.2, and 26.4±0.2. For example, in some embodiments, Form 2 has an XRPD pattern with at least peaks at ° 2θ values of 7.0±0.2, 10.4±0.2, 14.1±0.2, 17.6±0.2, 18.9±0.2, 19.2±0.2, 21.5±0.2, 22.0±0.2, 24.2±0.2, and 26.4±0.2.

In some embodiments, provided herein is a formulation comprising a composition comprising polymorph Form 2. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I). In some embodiments, the composition contains less than 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 1, Form 3, Form 4, Form 5, Form 6, Form 7, Form 8, Form 9, Form 10, Form 11, a non-stoichiometric or stoichiometric hydrate of Form 1, or a combination of two or more thereof.

In some embodiments, polymorph Form 2 exhibits an endotherm between about 50-100° C. as measured by DSC. In some embodiments, polymorph Form 2 exhibits an endotherm between about 220-230° C. In some embodiments, polymorph Form 2 exhibits an exotherm between about 233-238° C. In some embodiments, polymorph Form 2 exhibits an exotherm between about 290-295° C. In some embodiments, the endotherms and exotherms are observed when using a scan rate of 10° C. per minute.

In some embodiments, polymorph Form 2 has a melting point of around 363° C. In some embodiments, polymorph Form 2 undergoes a weight loss of about 2.7% before around 116° C., e.g., from about 36° C. to about 116° C., as measured by TGA.

In some embodiments, polymorph Form 2 is prepared by a method comprising reslurrying a composition comprising the compound of Formula (I), including amorphous and polymorph forms thereof, in a solvent or mixture of solvents to generate Form 2 as a residual solid. In some embodiments, the composition comprising the compound of Formula (I) comprises a non-stoichiometric or stoichiometric hydrate of Form 1 having between 1% and about 20% by weight water. In some embodiments, the reslurrying takes place at RT. In some embodiments, the slurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, polymorph Form 2 is prepared by a method comprising reslurrying a composition comprising a non-stoichiometric or stoichiometric hydrate of Form 1 having between 1% and about 20% by weight water in a solvent or mixture of solvents to generate polymorph Form 2 as a residual solid. In some embodiments, the solvent is acetonitrile. In some embodiments, the solvent is ethanol. In some embodiments, the solvent is in a mixture with water, for example the solvent can be a mixture of water and ethanol or water and n-propanol. In some embodiments, the water is present in an amount of about 5% by weight. In some embodiments, the reslurrying takes place at RT. In some embodiments, the reslurrying takes place at around 50° C.

Provided herein is a formulation comprising a polymorph known as Form 3. Form 3 is an anhydrous polymorph of the compound of Formula (I). In one embodiment, polymorph Form 3 has an XRPD pattern, obtained with CuKα1-radiation, with at least peaks at ° 2θ values of 7.2±0.2, 22.2±0.2, and 24.4±0.2. In some embodiments, Form 3 has an XRPD pattern with at least peaks at ° 2θ values of 6.3±0.2, 7.2±0.2, 21.6±0.2, 22.2±0.2, and 24.4±0.2. In some embodiments, Form 3 has an XRPD pattern with at least peaks at ° 2θ values of 6.3±0.2, 7.2±0.2, 11.0±0.2, 18.4±0.2, 19.0±0.2, 21.6±0.2, 22.2±0.2, and 24.4±0.2. For example, in some embodiments, Form 3 has an XRPD pattern with at least peaks at ° 2θ values of 6.3±0.2, 7.2±0.2, 11.0±0.2, 14.2±0.2, 17.8±0.2, 18.4±0.2, 19.0±0.2, 21.6±0.2, 22.2±0.2, and 24.4±0.2.

In some embodiments, provided herein is a formulation comprising a composition comprising polymorph Form 3. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I). In some embodiments, the composition contains less than 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 1, Form 2, Form 4, Form 5, Form 6, Form 7, Form 8, Form 9, Form 10, Form 11, a non-stoichiometric or stoichiometric hydrate of Form 1, or a combination of two or more thereof.

In some embodiments, polymorph Form 3 exhibits an exotherm between about 190-220° C., as measured by DSC. In some embodiments, polymorph Form 3 exhibits an exotherm at between about 225-235° C., e.g., around 230° C., as measured by DSC. In some embodiments, polymorph Form 3 exhibits an exotherm at between about 292-300° C., e.g., around 297° C., as measured by DSC. For example, in some embodiments, the endotherms and exotherms are observed when using a scan rate of 10° C. per minute.

In some embodiments, polymorph Form 3 has a melting point of around 365° C. In some embodiments, polymorph Form 3 undergoes a weight loss of about 1.6% before around 81° C. and a weight loss of about 1.7% between about 81-169° C. as measured by TGA.

In some embodiments, polymorph Form 3 is prepared by a method comprising reslurrying a composition comprising the compound of Formula (I), including amorphous and polymorph forms thereof, in a solvent or mixture of solvents to generate Form 3 as a residual solid. In some embodiments, the composition comprising the compound of Formula (I) comprises a non-stoichiometric or stoichiometric hydrate of Form 1 having between 1% and about 20% by weight water. In some embodiments, the reslurrying takes place at RT. In some embodiments, the slurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, polymorph Form 3 is prepared by a method comprising reslurrying a composition comprising a non-stoichiometric or stoichiometric hydrate of Form 1 having between 1% and about 20% by weight water in a solvent or mixture of solvents to generate polymorph Form 3 as a residual solid. In some embodiments, the solvent is IPAc. In some embodiments, the solvent is n-butyl acetate. In some embodiments, the reslurrying takes place at RT. In some embodiments, the reslurrying takes place at around 50° C.

Provided herein is a formulation comprising a polymorph known as Form 4. Form 4 is an anhydrous polymorph of the compound of Formula (I). In one embodiment, polymorph Form 4 has an XRPD pattern, obtained with CuKα1-radiation, with at least peaks at ° 2θ values of 7.0±0.2, 21.8±0.2, and 25.1±0.2. In some embodiments, Form 4 has an XRPD pattern with at least peaks at ° 2θ values of 7.0±0.2, 19.5±0.2, 21.8±0.2, 23.2±0.2, and 25.1±0.2. In some embodiments, Form 4 has an XRPD pattern with at least peaks at ° 2θ values of 7.0±0.2, 17.6±0.2, 18.3±0.2, 19.5±0.2, 21.8±0.2, 23.2±0.2, 25.1±0.2, and 25.8±0.2. For example, in some embodiments, Form 4 has an XRPD pattern with at least peaks at ° 2θ values of 7.0±0.2, 9.6±0.2, 17.6±0.2, 18.3±0.2, 19.5±0.2, 21.8±0.2, 23.2±0.2, 25.1±0.2, 25.8±0.2, and 29.3±0.2.

In some embodiments, provided herein is a formulation comprising a composition comprising polymorph Form 4. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I). In some embodiments, the composition contains less than 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 1, Form 2, Form 3, Form 5, Form 6, Form 7, Form 8, Form 9, Form 10, Form 11, a non-stoichiometric or stoichiometric hydrate of Form 1, or a combination of two or more thereof.

In some embodiments, polymorph Form 4 exhibits an endotherm between about 50-100° C. as measured by DSC. In some embodiments, polymorph Form 4 exhibits an endotherm at between about 180-215° C. In some embodiments, polymorph Form 4 exhibits an endotherm between about 220-230° C. In some embodiments, polymorph Form 4 exhibits an exotherm at between about 230-240° C., e.g., around 235° C. In some embodiments, polymorph Form 4 exhibits an exotherm at between about 300-310° C. For example, in some embodiments, the endotherms and exotherms are observed when using a scan rate of 10° C. per minute.

In some embodiments, polymorph Form 4 has a melting point of between about 366-369° C., e.g., around 367° C. In some embodiments, polymorph Form 4 undergoes a weight loss of about 8.3% before around 200° C., e.g., from about 42° C. to about 200° C., as measured by TGA.

In some embodiments, polymorph Form 4 is prepared by a method comprising reslurrying a composition comprising the compound of Formula (I), including amorphous and polymorph forms thereof, in a solvent or mixture of solvents to generate Form 4 as a residual solid. In some embodiments, the composition comprising the compound of Formula (I) comprises a non-stoichiometric or stoichiometric hydrate of Form 1 having between 1% and about 20% by weight water. In some embodiments, the reslurrying takes place at RT. In some embodiments, the slurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, polymorph Form 4 is prepared by a method comprising reslurrying a composition comprising a non-stoichiometric or stoichiometric hydrate of Form 1 having between 1% and about 20% by weight water in a solvent or mixture of solvents to generate polymorph Form 4 as a residual solid. In some embodiments, the solvent is EA. In some embodiments, the solvent is MA. In some embodiments, the solvent is MtBE. In some embodiments, the solvent is n-propanol. In some embodiments, the solvent is acetone. In some embodiments, the solvent is in a mixture with water, for example the solvent can be a mixture of water and MA, EA, or acetone. In some embodiments, the water is present in an amount of about 5% by weight. In some embodiments, the reslurrying takes place at RT. In some embodiments, the reslurrying takes place at around 50° C.

Provided herein is a formulation comprising a polymorph known as Form 5. Form 5 is an anhydrous polymorph of the compound of Formula (I). In one embodiment, polymorph Form 5 has an XRPD pattern, obtained with CuKα1-radiation, with at least peaks at ° 2θ values of 7.3±0.2, 22.3±0.2, and 24.5±0.2. In some embodiments, Form 5 has an XRPD pattern with at least peaks at ° 2θ values of 6.3±0.2, 7.3±0.2, 21.7±0.2, 22.3±0.2, and 24.5±0.2. In some embodiments, Form 5 has an XRPD pattern with at least peaks at ° 2θ values of 6.3±0.2, 7.3±0.2, 11.0±0.2, 19.1±0.2, 19.5±0.2, 21.7±0.2, 22.3±0.2, and 24.5±0.2. For example, in some embodiments, Form 5 has an XRPD pattern with at least peaks at ° 2θ values of 6.3±0.2, 7.3±0.2, 11.0±0.2, 14.3±0.2, 19.1±0.2, 19.5±0.2, 21.7±0.2, 22.3±0.2, 24.5±0.2, and 26.5±0.2.

In some embodiments, provided herein is a formulation comprising a composition comprising polymorph Form 5. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I). In some embodiments, the composition contains less than 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 1, Form 2, Form 3, Form 4, Form 6, Form 7, Form 8, Form 9, Form 10, Form 11, a non-stoichiometric or stoichiometric hydrate of Form 1, or a combination of two or more thereof.

In some embodiments, polymorph Form 5 exhibits an endotherm between about 50-100° C. as measured by DSC. In some embodiments, polymorph Form 5 exhibits an endotherm at between about 210-235° C., e.g., around 222° C. In some embodiments, polymorph Form 5 exhibits an exotherm at between about 227-240° C., e.g., around 235° C. In some embodiments, polymorph Form 5 exhibits an exotherm at between about 280-300° C., e.g., around 293° C. For example, in some embodiments, the endotherms and exotherms are observed when using a scan rate of 10° C. per minute.

In some embodiments, polymorph Form 5 has a melting point of around 363° C. In some embodiments, polymorph Form 5 undergoes a weight loss of about 3.1% before around 100° C. and about 1.7% between about 100-250° C. as measured by TGA.

In some embodiments, polymorph Form 5 is prepared by a method comprising reslurrying a composition comprising the compound of Formula (I), including amorphous and polymorph forms thereof, in a solvent or mixture of solvents to generate Form 5 as a residual solid. In some embodiments, the composition comprising the compound of Formula (I) comprises a non-stoichiometric or stoichiometric hydrate of Form 1 having between 1% and about 20% by weight water. In some embodiments, the reslurrying takes place at RT. In some embodiments, the slurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, polymorph Form 5 is prepared by a method comprising reslurrying a composition comprising a non-stoichiometric or stoichiometric hydrate of Form 1 having between 1% and about 20% by weight water in a solvent or mixture of solvents to generate polymorph Form 5 as a residual solid. In some embodiments, the solvent is MtBE. In some embodiments, the reslurrying takes place at RT. In some embodiments, the reslurrying takes place at around 50° C.

Provided herein is a formulation comprising a polymorph known as Form 6. Form 6 is an anhydrous polymorph of the compound of Formula (I).

In some embodiments, provided herein is a formulation comprising a composition comprising polymorph Form 6. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I). In some embodiments, the composition contains less than 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 1, Form 2, Form 3, Form 4, Form 5, Form 7, Form 8, Form 9, Form 10, Form 11, a non-stoichiometric or stoichiometric hydrate of Form 1, or a combination of two or more thereof.

In some embodiments, polymorph Form 6 exhibits an exotherm between about 245-260° C. as measured by DSC. For example, in some embodiments, the endotherms and exotherms are observed when using a scan rate of 10° C. per minute. In some embodiments, polymorph Form 6 has a melting point of around 364° C.

In some embodiments, polymorph Form 6 is prepared by a method comprising reslurrying a composition comprising the compound of Formula (I), including amorphous and polymorph forms thereof, in a solvent or mixture of solvents to generate Form 6 as a residual solid. In some embodiments, the composition comprising the compound of Formula (I) is a non-stoichiometric or stoichiometric hydrate of Form 1 having between 1% and about 20% by weight water. In some embodiments, the reslurrying takes place at RT. In some embodiments, the slurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, polymorph Form 6 is prepared by a method comprising reslurrying a composition comprising a non-stoichiometric or stoichiometric hydrate of Form 1 having between 1% and about 20% by weight water in a solvent or mixture of solvents to generate polymorph Form 6 as a residual solid. In some embodiments, the solvent is IPAc. In some embodiments, the solvent is in a mixture with water, for example the solvent can be a mixture of water and IPAc. In some embodiments, the water is present in an amount of about 5% by weight. In some embodiments, the reslurrying takes place at RT. In some embodiments, the reslurrying takes place at around 50° C.

Provided herein is a formulation comprising a polymorph known as Form 7. Form 7 is an anhydrous polymorph of the compound of Formula (I). In one embodiment, polymorph Form 7 has an XRPD pattern, obtained with CuKα1-radiation, with at least peaks at ° 2θ values of 7.1±0.2, 21.6±0.2, and 23.2±0.2. In some embodiments, Form 7 has an XRPD pattern with at least peaks at ° 2θ values of 4.9±0.2, 7.1±0.2, 18.5±0.2, 21.6±0.2, and 23.2±0.2. In some embodiments, Form 7 has an XRPD pattern with at least peaks at ° 2θ values of 4.9±0.2, 7.1±0.2, 10.9±0.2, 18.5±0.2, 19.4±0.2, 21.6±0.2, 23.2±0.2, and 30.3±0.2. For example, in some embodiments, Form 7 has an XRPD pattern with at least peaks at ° 2θ values of 4.9±0.2, 7.1±0.2, 8.8±0.2, 10.9±0.2, 18.5±0.2, 19.4±0.2, 21.6±0.2, 22.1±0.2, 23.2±0.2, and 30.3±0.2.

In some embodiments, provided herein is a formulation comprising a composition comprising polymorph Form 7. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I). In some embodiments, the composition contains less than 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 1, Form 2, Form 3, Form 4, Form 5, Form 6, Form 8, Form 9, Form 10, Form 11, a non-stoichiometric or stoichiometric hydrate of Form 1, or a combination of two or more thereof.

In some embodiments, polymorph Form 7 exhibits an exotherm between about 227-235° C., e.g., around 232° C., as measured by DSC. In some embodiments, polymorph Form 7 exhibits an exotherm between about 299-305° C., e.g., around 303° C. For example, in some embodiments, the endotherms and exotherms are observed when using a scan rate of 10° C. per minute.

In some embodiments, polymorph Form 7 has a melting point of around 365° C. In some embodiments, polymorph Form 7 undergoes a weight loss of about 12% before around 200° C., e.g., from about 36° C. to about 200° C., as measured by TGA.

In some embodiments, polymorph Form 7 is prepared by a method comprising reslurrying a composition comprising the compound of Formula (I), including amorphous and polymorph forms thereof, in a solvent or mixture of solvents to generate Form 7 as a residual solid. In some embodiments, the composition comprising the compound of Formula (I) is a non-stoichiometric or stoichiometric hydrate of Form 1 having between 1% and about 20% by weight water. In some embodiments, the reslurrying takes place at RT. In some embodiments, the slurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, polymorph Form 7 is prepared by a method comprising reslurrying a composition comprising a non-stoichiometric or stoichiometric hydrate of Form 1 having between 1% and about 20% by weight water in a solvent or mixture of solvents to generate polymorph Form 7 as a residual solid. In some embodiments, the solvent is methyl ethyl ketone (MEK). In some embodiments, the solvent is in a mixture with water, for example the solvent can be a mixture of water and MEK. In some embodiments, the water is present in an amount of about 5% by weight. In some embodiments, the reslurrying takes place at RT. In some embodiments, the reslurrying takes place at around 50° C.

Provided herein is a formulation comprising a polymorph known as Form 8. Form 8 is an anhydrous polymorph of the compound of Formula (I). In one embodiment, polymorph Form 8 has an XRPD pattern, obtained with CuKα1-radiation, with at least peaks at ° 2θ values of 6.9±0.2, 17.7±0.2, and 21.5±0.2. In some embodiments, Form 8 has an XRPD pattern with at least peaks at ° 2θ values of 6.9±0.2, 11.5±0.2, 17.7±0.2, 21.5±0.2, and 27.6±0.2. In some embodiments, Form 8 has an XRPD pattern with at least peaks at ° 2θ values of 6.9±0.2, 11.5±0.2, 15.3±0.2, 16.9±0.2, 17.7±0.2, 21.5±0.2, 27.6±0.2, and 28.9±0.2. For example, in some embodiments, Form 8 has an XRPD pattern with at least peaks at ° 2θ values of 6.9±0.2, 11.5±0.2, 12.7±0.2, 14.2±0.2, 15.3±0.2, 16.9±0.2, 17.7±0.2, 21.5±0.2, 27.6±0.2, and 28.9±0.2.

In some embodiments, provided herein is a formulation comprising a composition comprising polymorph Form 8. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I). In some embodiments, the composition contains less than 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 1, Form 2, Form 3, Form 4, Form 5, Form 6, Form 7, Form 9, Form 10, Form 11, a non-stoichiometric or stoichiometric hydrate of Form 1, or a combination of two or more thereof.

In some embodiments, polymorph Form 8 exhibits an endotherm between about 41-60° C. as measured by DSC. In some embodiments, polymorph Form 8 exhibits an exotherm at between about 221-235° C., e.g., around 231° C. In some embodiments, polymorph Form 8 exhibits an endotherm between about 279-290° C., e.g., around 285° C. For example, in some embodiments, the endotherms and exotherms are observed when using a scan rate of 10° C. per minute.

In some embodiments, polymorph Form 8 has a melting point of around 364° C. In some embodiments, polymorph Form 8 undergoes a weight loss of about 4.2% before around 190° C. and about 3.9% between about 190-261° C. as measured by TGA.

In some embodiments, polymorph Form 8 is prepared by a method comprising reslurrying a composition comprising the compound of Formula (I), including amorphous and polymorph forms thereof, in a solvent or mixture of solvents to generate Form 8 as a residual solid. In some embodiments, the composition comprising the compound of Formula (I) a non-stoichiometric or stoichiometric hydrate of Form 1 having between 1% and about 20% by weight water. In some embodiments, the reslurrying takes place at RT. In some embodiments, the slurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, polymorph Form 8 is prepared by a method comprising reslurrying a composition comprising a non-stoichiometric or stoichiometric hydrate of Form 1 having between 1% and about 20% by weight water in a solvent or mixture of solvents to generate polymorph Form 8 as a residual solid. In some embodiments, the solvent is MIBK. In some embodiments, the reslurrying takes place at RT. In some embodiments, the reslurrying takes place at around 50° C.

Provided herein is a formulation comprising a polymorph known as Form 9. Form 9 is an anhydrous polymorph of the compound of Formula (I). In one embodiment, polymorph Form 9 has an XRPD pattern, obtained with CuKα1-radiation, with at least peaks at ° 2θ values of 4.9±0.2, 18.6±0.2, and 21.1±0.2. In some embodiments, Form 9 has an XRPD pattern with at least peaks at ° 2θ values of 4.9±0.2, 18.6±0.2, 21.1±0.2, 24.1±0.2, and 25.2±0.2. In some embodiments, Form 9 has an XRPD pattern with at least peaks at ° 2θ values of 4.9±0.2, 15.3±0.2, 16.5±0.2, 18.6±0.2, 21.1±0.2, 22.4±0.2, 24.1±0.2, and 25.2±0.2. For example, in some embodiments, Form 9 has an XRPD pattern with at least peaks at ° 2θ values of 4.9±0.2, 10.1±0.2, 15.3±0.2, 16.5±0.2, 18.6±0.2, 21.1±0.2, 22.4±0.2, 24.1±0.2, 25.2±0.2, and 28.6±0.2.

In some embodiments, provided herein is a formulation comprising a composition comprising polymorph Form 9. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I). In some embodiments, the composition contains less than 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 1, Form 2, Form 3, Form 4, Form 5, Form 6, Form 7, Form 8, Form 10, Form 11, a non-stoichiometric or stoichiometric hydrate of Form 1, or a combination of two or more thereof.

In some embodiments, polymorph Form 9 exhibits a single melting endotherm at around 364° C. as measured by DSC. For example, in some embodiments, the endotherm is observed when using a scan rate of 10° C. per minute. In some embodiments, other polymorph forms provided herein, such as, e.g., Form 1 and Form 2, can convert to Form 9 when heated to just before melting (i.e., around 364° C.).

In some embodiments, polymorph Form 9 has a melting point of around 364° C. In some embodiments, polymorph Form 9 undergoes a weight loss of about 0.28% before around 100° C., e.g., from about 30.5° C. to about 100° C., as measured by TGA.

In some embodiments, polymorph Form 9 is prepared by a method comprising reslurrying a composition comprising the compound of Formula (I), including amorphous and polymorph forms thereof, in a solvent or mixture of solvents to generate Form 9 as a residual solid. In some embodiments, the composition comprising the compound of Formula (I) is a non-stoichiometric or stoichiometric hydrate of Form 1 having between 1% and about 20% by weight water. In some embodiments, the reslurrying takes place at RT. In some embodiments, the slurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, polymorph Form 9 is prepared by a method comprising reslurrying a composition comprising a non-stoichiometric or stoichiometric hydrate of Form 1 having between 1% and about 20% by weight water in a solvent or mixture of solvents to generate polymorph Form 9 as a residual solid. In some embodiments, the solvent is n-butanol. In some embodiments, the solvent is IPAc. In some embodiments, the solvent is n-butyl acetate. In some embodiments, the solvent is in a mixture with water, for example the solvent can be a mixture of water and ethanol or water and n-propanol. In some embodiments, the water is present in an amount of about 5% by weight. In some embodiments, the reslurrying takes place at RT. In some embodiments, the reslurrying takes place at around 50° C.

Provided herein is a formulation comprising a polymorph known as Form 10. Polymorph Form 10 is a polymorph of the compound of Formula (I) comprising DMSO. For example, DMSO is on the surface of the polymorph. In one embodiment, polymorph Form 10 has an XRPD pattern, obtained with CuKα1-radiation, with at least peaks at ° 2θ values of 20.7±0.2, 21.7±0.2, and 24.2±0.2. In some embodiments, Form 10 has an XRPD pattern with at least peaks at ° 2θ values of 18.2±0.2, 19.0±0.2, 20.7±0.2, 21.7±0.2, and 24.2±0.2. In some embodiments, Form 10 has an XRPD pattern with at least peaks at ° 2θ values of 17.8±0.2, 18.2±0.2, 19.0±0.2, 20.7±0.2, 21.7±0.2, 23.4±0.2, 24.2±0.2, and 27.9±0.2. For example, in some embodiments, Form 10 has an XRPD pattern with at least peaks at ° 2θ values of 6.7±0.2, 17.8±0.2, 18.2±0.2, 19.0±0.2, 19.9±0.2, 20.7±0.2, 21.7±0.2, 23.4±0.2, 24.2±0.2, and 27.9±0.2.

In some embodiments, provided herein is a formulation comprising a composition comprising polymorph Form 10. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I). In some embodiments, the composition contains less than 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 1, Form 2, Form 3, Form 4, Form 5, Form 6, Form 7, Form 8, Form 9, Form 11, a non-stoichiometric or stoichiometric hydrate of Form 1, or a combination of two or more thereof.

In some embodiments, polymorph Form 10 exhibits an endotherm between about 212-237° C. as measured by DSC. In some embodiments, polymorph Form 10 exhibits an endotherm at between about 234-245° C., e.g., around 237° C. In some embodiments, polymorph Form 10 exhibits an exotherm between about 300-325° C., e.g., around 308° C. For example, in some embodiments, the endotherms and exotherms are observed when using a scan rate of 10° C. per minute.

In some embodiments, polymorph Form 10 has a melting point of between about 364-372° C., such as, e.g., around 369° C. In some embodiments, polymorph Form 10 undergoes a weight loss of about 0.6% before around 100° C., a weight loss of about 3.8% between about 100-170° C., and a weight loss of about 7.1% between about 170-260° C. as measured by TGA.

In some embodiments, polymorph Form 10 is prepared by a method comprising reslurrying a composition comprising the compound of Formula (I), including amorphous and polymorph forms thereof, in a solvent or mixture of solvents to generate Form 10 as a residual solid. In some embodiments, the composition comprising the compound of Formula (I) is a non-stoichiometric or stoichiometric hydrate of Form 1 having between 1% and about 20% by weight water. In some embodiments, the reslurrying takes place at RT. In some embodiments, the slurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, polymorph Form 10 is prepared by a method comprising reslurrying a composition comprising a non-stoichiometric or stoichiometric hydrate of Form 1 having between 1% and about 20% by weight water in a solvent or mixture of solvents to generate polymorph Form 10 as a residual solid. In some embodiments, the solvent is DMSO. In some embodiments, the solvent is in a mixture with water, for example the solvent can be a mixture of water and DMSO. In some embodiments, the water is present in an amount of about 5% by weight. In some embodiments, the reslurrying takes place at RT. In some embodiments, the reslurrying takes place at around 50° C.

Provided herein is a formulation comprising a polymorph known as Form 11. Form 11 is an anhydrous polymorph of the compound of Formula (I). In one embodiment, polymorph Form 11 has an XRPD pattern, obtained with CuKα1-radiation, with at least peaks at ° 2θ values of 6.4±0.2, 18.5±0.2, and 22.4±0.2. In some embodiments, Form 11 has an XRPD pattern with at least peaks at ° 2θ values of 6.4±0.2, 17.8±0.2, 18.5±0.2, 19.9±0.2, and 22.4±0.2. In some embodiments, Form 11 has an XRPD pattern with at least peaks at ° 2θ values of 6.4±0.2, 8.4±0.2, 17.8±0.2, 18.5±0.2, 19.9±0.2, 22.4±0.2, 24.5±0.2, and 26.8±0.2. For example, in some embodiments, Form 11 has an XRPD pattern with at least peaks at ° 2θ values of 6.4±0.2, 8.4±0.2, 17.8±0.2, 18.5±0.2, 19.9±0.2, 20.3±0.2, 22.4±0.2, 22.9±0.2, 24.5±0.2, and 26.8±0.2.

In some embodiments, provided herein is a formulation comprising a composition comprising polymorph Form 11. In some embodiments, the composition is substantially pure. For example, the composition can have a purity of at least about 90%. In some embodiments, the composition has a purity of at least about 95%. In some embodiments, the composition has a purity of at least about 98%. For example, the composition can have a purity of at least 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In some embodiments, the composition is substantially free of other forms of the compound of Formula (I). For example, in some embodiments, the composition is substantially free of other anhydrous forms of the compound of Formula (I). In some embodiments, the composition contains less than 15% by weight of other forms of the compound of Formula (I), such as less than 14%, 13%, 12%, 11%, 10%, 9%, 8%, 7%, 6%, 5%, 4%, 3%, 2%, 1% or less by weight of other forms of the compound of Formula (I). In some embodiments, the composition contains less than 15% by weight of one or more other forms of the compound of Formula (I), such as less than 14%, 13%, 12%, 11%, 10%, 9%, 8%, 7%, 6%, 5%, 4%, 3%, 2%, 1% or less by weight of one or more other forms of the compound of Formula (I). For example, the composition can contain less than about 15% of Form 1, Form 2, Form 3, Form 4, Form 5, Form 6, Form 7, Form 8, Form 9, Form 10, a non-stoichiometric or stoichiometric hydrate of Form 1, or a combination of two or more thereof.

In some embodiments, polymorph Form 11 exhibits an endotherm between about 215-230° C. as measured by DSC. In some embodiments, polymorph Form 11 exhibits an exotherm at between about 230-240° C., e.g., around 235° C. In some embodiments, polymorph Form 11 exhibits an exotherm between about 300-315° C., e.g., around 310° C. For example, in some embodiments, the endotherms and exotherms are observed when using a scan rate of 10° C. per minute.

In some embodiments, polymorph Form 11 has a melting point of around 368° C. In some embodiments, polymorph Form 11 undergoes a weight loss of about 0.8% before around 100° C. and a weight loss of about 7.0% between about 100-249° C., as measured by TGA.

In some embodiments, polymorph Form 11 is prepared by a method comprising reslurrying a composition comprising the compound of Formula (I), including amorphous and polymorph forms thereof, in a solvent or mixture of solvents to generate Form 11 as a residual solid. In some embodiments, the composition comprising the compound of Formula (I) is a non-stoichiometric or stoichiometric hydrate of Form 1 having between 1% and about 20% by weight water. In some embodiments, the reslurrying takes place at RT. In some embodiments, the slurrying takes place at around 50° C. In some embodiments, the method further comprises drying the residual solid, for example, under vacuum. In some embodiments, the drying is at a temperature of between about 60° C. and 90° C., such as, e.g., around 75° C.

In some embodiments, polymorph Form 11 is prepared by a method comprising reslurrying a composition comprising a non-stoichiometric or stoichiometric hydrate of Form 1 having between 1% and about 20% by weight water in a solvent or mixture of solvents to generate polymorph Form 11 as a residual solid. In some embodiments, the solvent is dimethylformamide (DMF). In some embodiments, the solvent is in a mixture with water, for example the solvent can be a mixture of water and DMF. In some embodiments, the water is present in an amount of about 5% by weight. In some embodiments, the reslurrying takes place at RT. In some embodiments, the reslurrying takes place at around 50° C.

EXAMPLES

Example 1: Preparation of Single-Dose, Ready-to-Use Formulations

Single-dose, ready-to-use formulations containing either 0.015 mg/mL, 0.025 mg/mL or 0.115 mg/mL of polymorph Form 1 of the compound of Formula (I) were prepared. The compound of Formula (I) was prepared according to the process provided in US 2013/0267495, incorporated herein by reference in its entirety. The polymorph of Form 1 was prepared as described herein.

For a 0.015 mg/mL Formulation:

Water, sodium carboxymethylcellulose (CMC) (5.55 g/kg), polysorbate 80 (0.50 g/kg), sodium phosphate monobasic monohydrate (0.268 g/kg), sodium phosphate dibasic heptahydrate (2.44 g/kg), and sodium chloride (9.11 g/kg) were added to a 300 L first tank. The aqueous solution in the first tank was then filtered through a 0.2 μm polyethersulfone (PES) filter into a second tank, where it was bulk sterilized. 0.15 g/kg of polymorph Form 1 of the compound of Formula (I), water for injection, and 0.5 g/kg polysorbate 80 were added to a 30 L third tank to form a slurry containing 15 μg/mL of the compound of Formula (I). The slurry was sterilized by overhead steam pressure, then added to the second tank containing the aqueous solution. The slurry was homogenized at 30 Hz and manufactured using principles of overkill cycle ($F_0 \geq 30$). The mixture was aseptically mixed with sterile diluent to form a suspension with a concentration of 0.015 mg/mL of the compound of Formula (I). The bulk solution temperature was maintained at 250° F. as monitored by bottom TC and overhead pressure was maintained greater than the steam pressure introduced in the tank jacket (~>5 psi). To maintain overhead pressure during bleeding of the top valve next to the mixer to monitor TC above the tank, steam was introduced via the air filter into the tank to maintain pressure and high temperature. The steam pressure was monitored and bulk sterilization performed. The suspension was then aseptically filled using a Weiler 624 BFS machine into 3 mL polypropylene vials, with a target volume of 2.5 mL and a final concentration of 0.015 mg/mL of the compound of Formula (I). Each vial contained 0.03 mg of Form 1 of the compound of Formula (I) in 2 mL phosphate buffered saline. The vials were labeled and packaged.

For a 0.035 mg/mL Formulation:

Water, sodium carboxymethylcellulose (CMC) (5.55 g/kg), polysorbate 80 (0.50 g/kg), sodium phosphate monobasic monohydrate (0.268 g/kg), sodium phosphate dibasic heptahydrate (2.44 g/kg), and sodium chloride (9.11 g/kg) were added to a 300 L first tank. The aqueous solution in the first tank was then filtered through a 0.2 μm polyethersulfone (PES) filter into a second tank, where it was bulk sterilized. 0.35 g/kg of polymorph Form 1 of the compound of Formula (I), water for injection, and 0.5 g/kg polysorbate 80 were added to a 30 L third tank to form a slurry containing 35 μg/mL of the compound of Formula (I). The slurry was sterilized by overhead steam pressure, then added to the second tank containing the aqueous solution. The slurry was homogenized at 30 Hz and manufactured using principles of overkill cycle ($F_0 \geq 30$). The mixture was aseptically mixed with sterile diluent to form a suspension with a concentration of 0.035 mg/mL of the compound of Formula (I). The bulk solution temperature was maintained at 250° F. as monitored by bottom TC and overhead pressure was maintained greater than the steam pressure introduced in the tank jacket (~>5 psi). To maintain overhead pressure during bleeding of the top valve next to the mixer to monitor TC above the tank, steam was introduced via the air filter into the tank to maintain pressure and high temperature. The steam pressure was monitored and bulk sterilization performed. The suspension was then aseptically filled using a Weiler 624 BFS machine into 3 mL polypropylene vials, with a target volume of 2.5 mL and a final concentration of 0.035 mg/mL of the compound of Formula (I). Each vial contained 0.07 mg of Form 1 of the compound of Formula (I) in 2 mL phosphate buffered saline. The vials were labeled and packaged.

For a 0.075 mg/mL Formulation:

Water, sodium carboxymethylcellulose (CMC) (5.55 g/kg), polysorbate 80 (0.50 g/kg), sodium phosphate monobasic monohydrate (0.268 g/kg), sodium phosphate dibasic heptahydrate (2.44 g/kg), and sodium chloride (9.11 g/kg) were added to a 300 L first tank. The aqueous solution in the first tank was then filtered through a 0.2 μm polyethersulfone (PES) filter into a second tank, where it was bulk sterilized. 0.75 g/kg of polymorph Form 1 of the compound of Formula (I), water for injection, and 0.5 g/kg polysorbate 80 were added to a 30 L third tank to form a slurry containing 75 μg/mL of the compound of Formula (I). The slurry was sterilized by overhead steam pressure, then added to the second tank containing the aqueous solution. The slurry was homogenized at 30 Hz and manufactured using principles of overkill cycle ($F_0 \geq 30$). The mixture was aseptically mixed with sterile diluent to form a suspension with a concentration of 0.075 mg/mL of the compound of Formula (I). The bulk solution temperature was maintained at 250° F. as monitored by bottom TC and overhead pressure was maintained greater than the steam pressure introduced in the tank jacket (~>5 psi). To maintain overhead pressure during bleeding of the top valve next to the mixer to monitor TC above the tank, steam was introduced via the air filter into the tank to maintain pressure and high temperature. The steam pressure was monitored and bulk sterilization performed. The suspension was then aseptically filled using a Weiler 624 BFS machine into 3 mL polypropylene vials, with a target volume of 2.5 mL and a final concentration of 0.075 mg/mL of the compound of Formula (I). Each vial contained 0.15 mg of Form 1 of the compound of Formula (I) in 2 mL phosphate buffered saline. The vials were labeled and packaged.

For a 0.115 mg/mL Formulation:

Water, sodium carboxymethylcellulose (CMC) (5.55 g/kg), polysorbate 80 (0.50 g/kg), sodium phosphate monobasic monohydrate (0.268 g/kg), sodium phosphate dibasic heptahydrate (2.44 g/kg), and sodium chloride (9.11 g/kg) were added to a 300 L first tank. The aqueous solution in the first tank was then filtered through a 0.2 µm polyethersulfone (PES) filter into a second tank, where it was bulk sterilized. 0.15 g/kg of polymorph Form 1 of the compound of Formula (I), water for injection, and 0.5 g/kg polysorbate 80 were added to a 30 L third tank to form a slurry containing 115 µg/mL of the compound of Formula (I). The slurry was sterilized by overhead steam pressure, then added to the second tank containing the aqueous solution. The slurry was homogenized at 30 Hz and manufactured using principles of overkill cycle ($F_0 \geq 30$). The mixture was aseptically mixed with sterile diluent to form a suspension with a concentration of 0.115 mg/mL of the compound of Formula (I). The bulk solution temperature was maintained at 250° F. as monitored by bottom TC and overhead pressure was maintained greater than the steam pressure introduced in the tank jacket (~>5 psi). To maintain overhead pressure during bleeding of the top valve next to the mixer to monitor TC above the tank, steam was introduced via the air filter into the tank to maintain pressure and high temperature. The steam pressure was monitored and bulk sterilization performed. The suspension was then aseptically filled using a Weiler 624 BFS machine into 3 mL polypropylene vials, with a target volume of 2.5 mL and a final concentration of 0.035 mg/mL of the compound of Formula (I). Each vial contained 0.23 mg of Form 1 of the compound of Formula (I) in 2 mL phosphate buffered saline. The vials were labeled and packaged.

Example 2: Polymorph Screen

A polymorph form of the compound of Formula (I) was used in the ready-to-use formulations described in Example 1, above. A polymorph screen was performed on the compound of Formula (I) to determine solubility, polymorphism, and thermodynamic stability.

A. Analysis of the Starting Solid

X-ray powder diffraction (XRD), differential scanning calorimetry (DSC), and thermal gravimetric analysis (TGA) scans of the starting solid compound of Formula (I) indicated that the starting solid was a crystalline material and was a mixture of Form 1 and a non-stoichiometric or stoichiometric hydrate of Form 1 having between 1% and about 20% by weight water. According to the DSC scan (FIG. 12B), the solid showed a wide endotherm between 50° C.-100° C.; it also showed a sharp exotherm at 284° C.; and the solid eventually melted at 364° C. According to the TGA scan (FIG. 12C), a 1.4% weight loss was observed before 100° C.

The solubility of the starting solid was measured by the gravimetric method and indicated that the compound had low solubility at RT and at 50° C. in all solvents tested except DMF and DMSO. Results from the solubility data test at RT and at 50° C. are shown in Table 3.

TABLE 3

Solubility data of the starting solid (a non-stoichiometric or stoichiometric hydrate of Form 1)

| Solvents | Solubility at RT (mg/mL) | Solubility at 50° C. (mg/mL) |
| --- | --- | --- |
| Acetone | 1 | 1 |
| Acetonitrile | ~0 | 0 |
| MeOH | 1 | 1 |
| Toluene | 1 | 1 |
| EtOH | 2 | 2 |
| IPAc | ~0 | ~0 |
| EA | 1 | 1 |
| MtBE | ~0 | ~0 |
| IPA | 2 | 5 |
| MEK | 1 | 1 |
| MA | ~0 | ~0 |
| n-Propanol | 1 | 2 |
| MIBK | 1 | 1 |
| n-Butyl acetate | ~0 | ~0 |
| water | 1 | 1 |
| Heptane | ~0 | ~0 |
| n-Butanol | 1 | 2 |
| DMSO | n/a | n/a |
| DMF | 12 | 16 |
| DCM | 2 | 2 |
| Acetic acid | ~0 | 3 |

Reslurry experiments in various solvents were performed. Approximately 30-80 mg of the starting solid (a non-stoichiometric or stoichiometric hydrate of Form 1 having between 1% and about 20% by weight water) was slurried in 39 different solvents (pure and binary solvents; the ratio of organic solvent/water (V/V) was 95%/5%) at RT and 50° C. for 5 days. Three solvates, one hydrate, and eleven non-solvated forms were identified. A "*" after a particular Form, e.g., Form 2*, indicates that the forms had similar XRD scans with minor differences and were considered to belong to the same class. Generally, the identified forms showed multiple endotherms/exotherms on differential scanning calorimetry (DSC) scans; Form 9 showed a single endotherm. XRD of both wet and dry samples were scanned (FIG. 12A (dry sample)). The data is shown in Tables 4 and 5 below.

TABLE 4

Results of slurry experiments at RT

| Solvent | Crystalline Form (wet/dry) | | Solvent | Crystalline Form (wet/dry) | |
| --- | --- | --- | --- | --- | --- |
| Acetone | Solvate 1 | Form 2 | Acetone/water | Solvate 2 | Form 4** |
| Acetonitrile | Form 2 | Form 1 | Acetonitrile/water | Form 12 | Form 1 |
| MeOH | Form 13 | Form 1 | | | |
| Toluene | Form 1 | Form 2* | MeOH/water | Form 12 | Form 1 |
| EtOH | Form 2* | Form 3 | Toluene/water | Form 13 | Form 1 |
| IPAc | Form 3 | Form 4 | EtOH/water | Solvate 3 | Form 2 |
| EA | Form 4* | Form 5 | IPAc/water | Form 12 | Form 1 |
| MtBE | Form 5* | Form 6 | EA/water | Form 12 | Form 1 |
| IPA | Form 6 | Form 7 | MtBE/water | Form 12 | Form 1 |
| MEK | Form 7 | Form 4 | IPA/water | Form 6 | Form 6 |
| MA | Form 4 | Form 4* | MEK/water | Form 7 | Form 7 |
| n-Propanol | Form 4* | Form 8 | MA/water | Form 13 | Form 1 |
| MIBK | Form 8 | Form 3 | n-Propanol/water | Form 2** | Form 2** |
| n-Butyl acetate | Form 3* | Form 1 | | | |
| | | | MIBK/water | Form 12 | Form 1 |
| Water | Form 13 | Form 1 | n-Butyl acetate/water | Form 13 | Form 12 |
| Heptane | Form 1 | Form 9 | | | |
| n-Butanol | Form 9 | Form 10 | Heptane/water | Form 13 | Form 12 |
| DMSO | amorphous | Form 11 | n-Butanol/water | Form 13 | Form 13 |
| DMF | Form 11 | Form 1 | DMSO/water | amorphous | Form 10 |
| DCM | Form 1 | Form 2 | DMF/water | Form 11 | Form 11 |
| | | | DCM/water | Form 13 | Form 1 |

TABLE 5

Results of slurry experiments at 50° C.

| Solvent | Crystalline Form (wet/dry) | | Solvent | Crystalline Form (wet/dry) | |
|---|---|---|---|---|---|
| Acetone | Solvate 2 | Form 4** | Acetone/water | Form 4** | Form 4** |
| Acetonitrile | Form 2* | Form 2 | Acetonitrile/water | Form 13 | Form 13 |
| MeOH | Form 1 | Form 1 | MeOH/water | Form 13 | Form 13 |
| Toluene | Form 1 | Form 1 | Toluene/water | Form 13 | Form 13 |
| EtOH | Form 2* | Form 2* | EtOH/water | Form 9 | Form 9 |
| IPAc | Form 9 | Form 9 | IPAc/water | Form 13 | Form 13 |
| EA | Form 4* | Form 4 | EA/water | Form 4* | Form 4* |
| MtBE | Form 5* | Form 4 | MtBE/water | Form 13 | Form 13 |
| IPA | Form 6 | Form 6 | IPA/water | Form 6 | Form 6 |
| MEK | Form 7 | Form 7 | MEK/water | Form 7 | Form 7 |
| MA | Form 4 | Form 4 | MA/water | Form 12 | Form 4 |
| n-Propanol | Form 4 | Form 4** | n-Propanol/water | Form 9 | Form 9 |
| MIBK | Form 8 | Form 8 | MIBK/water | Form 13 | Form 1 |
| n-Butyl acetate | Form 9 | Form 9 | n-Butyl acetate/water | Form 13 | Form 1 |
| water | Form 13 | Form 13 | Heptane/water | Form 13 | Form 1 |
| Heptane | Form 13 | Form 13 | n-Butanol/water | Form 13 | Form 1 |
| n-Butanol | Form 9 | Form 9 | DMSO/water | Amorphous | Form 10 |
| DMSO | Amorphous | Form 10* | DMF/water | Form 11 | Form 11 |
| DMF | Form 11 | Form 11* | DCM/water | Form 13 | Form 1 |
| DCM | Form 13 | Form 13 | | | |

The slurry experiments identified 3 solvated forms from wet samples (Solvates 1, 2, and 3); 2 non-stoichiometric hydrates of Form 1 (Forms 12 and 13); and 11 non-solvated forms (Forms 1-11). In some instances, similar XRD scans with minor differences were obtained. These were considered to be part of the same class (e.g., the same form). For example, XRD scans of Form 2 and Form 2* were similar and were considered to belong to the same class. The solvated forms were obtained from wet sample analysis; after drying, the sample indicated a different XRD.

Solvate 1 was obtained from acetone at RT, and after drying, a low crystallinity solid was generated. Solvate 2 was obtained from acetone (at RT) and acetone/water (at RT), and after drying, Form 4** was generated. Solvate 3 was obtained from EtOH/water at RT, and after drying, Form 2 was generated.

B. Form 1

The experiments that generated Form 1 are shown in Table 6, below. Form 1 was generally obtained from drying of Form 13 or Form 12. Form 1 may be considered as a dehydrated hydrate. Reslurry in many binary solvents (with 5% water) generated Form 1. Purity of the residual solid was 98.9%. KF of Form 1 (one sample) solid was 5.8%; residual MeOH of Form 1 solid was 0.01%. A TGA scan of fully dried Form 1 solid was performed (FIG. 1C). A 0.33% weight loss was observed before 100° C.

Figure 1B:
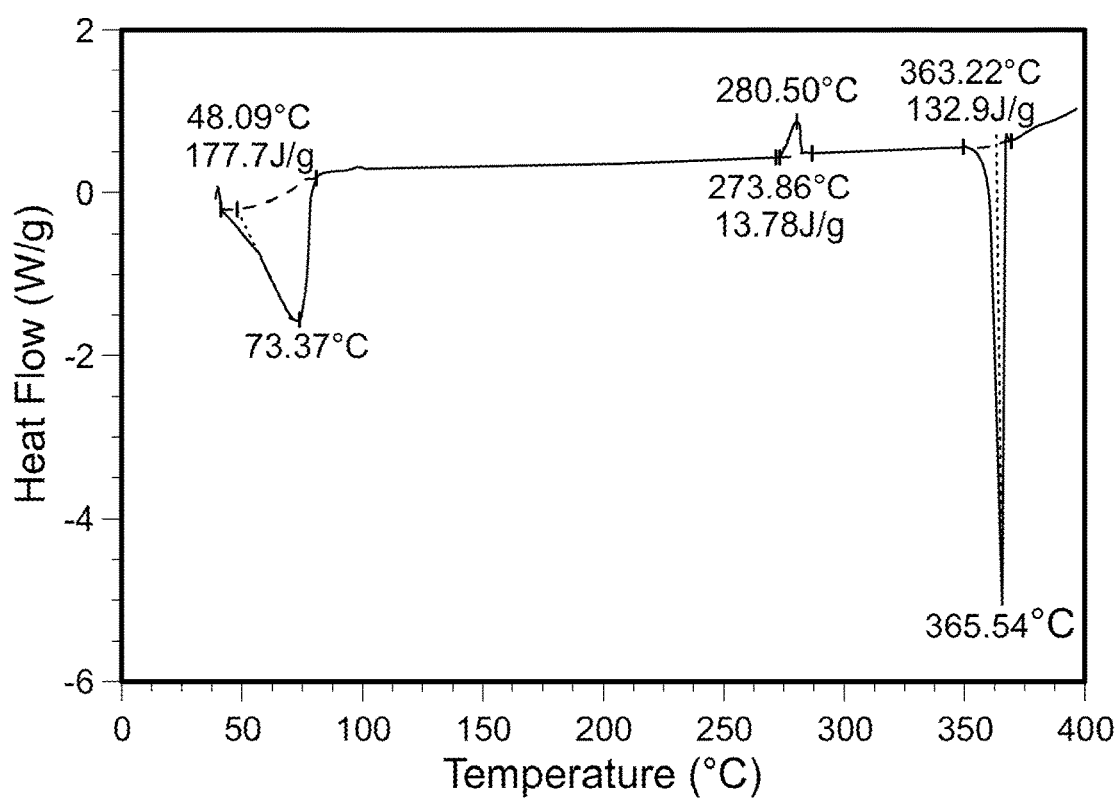
Figure 1C:
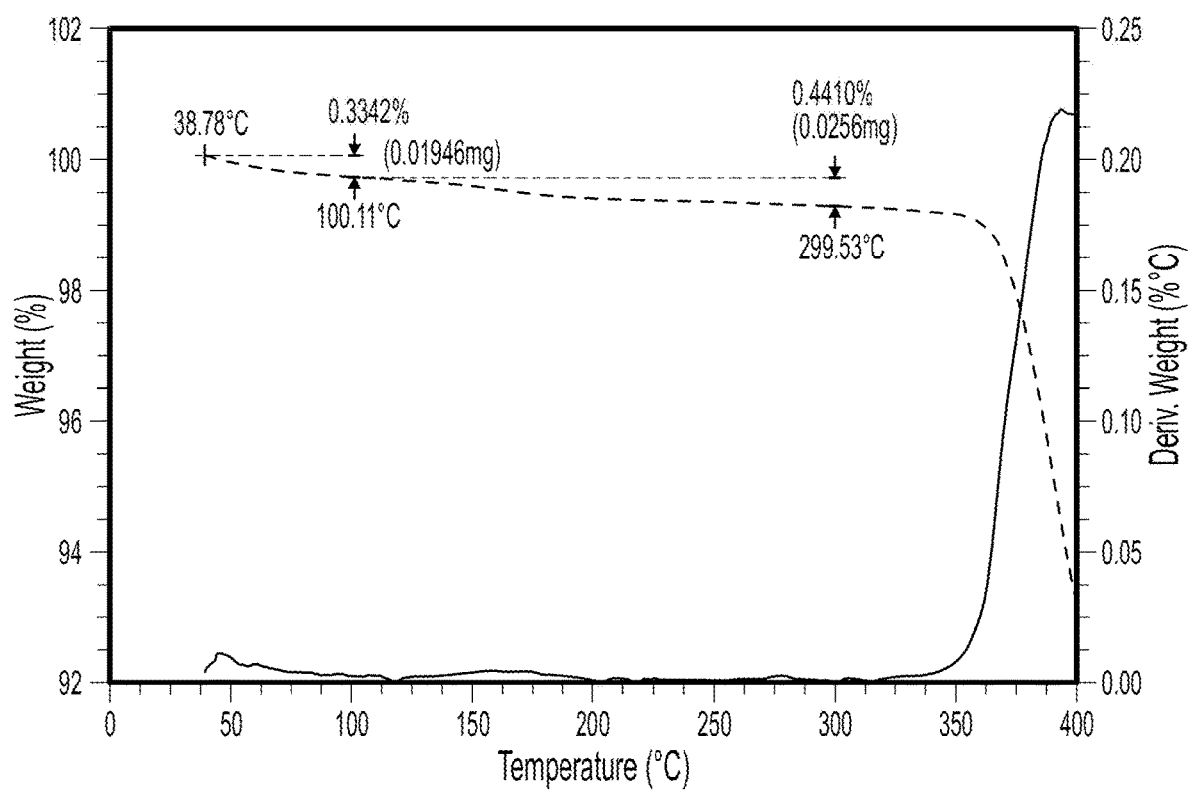

Form 1 showed sharp crystalline peaks on the XRD scan (FIG. 1A). The XRD peaks of Form 1 are shown in Table 7, below. According to the DSC scan (FIG. 1B), the solid showed a wide endotherm between 50-100° C.; it showed a sharp exotherm at 281° C.; and the melting point was 363° C. Form 1 has a primitive orthorhombic crystal structure with the approximate dimensions: a [Å]=29.062, b [Å]=23.945, c [Å]=7.245 and an approximate volume cell of [Å$^3$/cell]=5,041.7 and a space group defined as Pbca (61).

The Form 1 solid was dried at 75° C. under vacuum overnight, and XRD, DSC, and TGA scans were performed. Comparison of the first and the second XRD scans (after drying at 75° C. under vacuum overnight), showed no change. However, the DSC scans indicated the absence of endotherm. The loss of the early peak on the DSC scan had no effect on the XRD trace, showing that the wide endotherm between 50-100° C. on DSC scan was due to the free solvent.

The Form 1 solid was heated in a DSC chamber to 305° C. (past the endotherm/exotherm around 280° C.), and then scanned by XRD. Comparison of the first and the third XRD and DSC scans shows that after heating to 305° C., Form 1 converted to Form 9. It can be concluded that the endotherm/exotherm around 280° C. might be due to melting/crystallization events.

Form 1 tended to convert to a non-stoichiometric or stoichiometric hydrate of Form 1 having between 1% and about 20% by weight water (Form 13) at RH above 4050%. The hydrate lost its water below 30% RH. Form 1 converts to Form 13 when exposed to air.

Figure 1D:
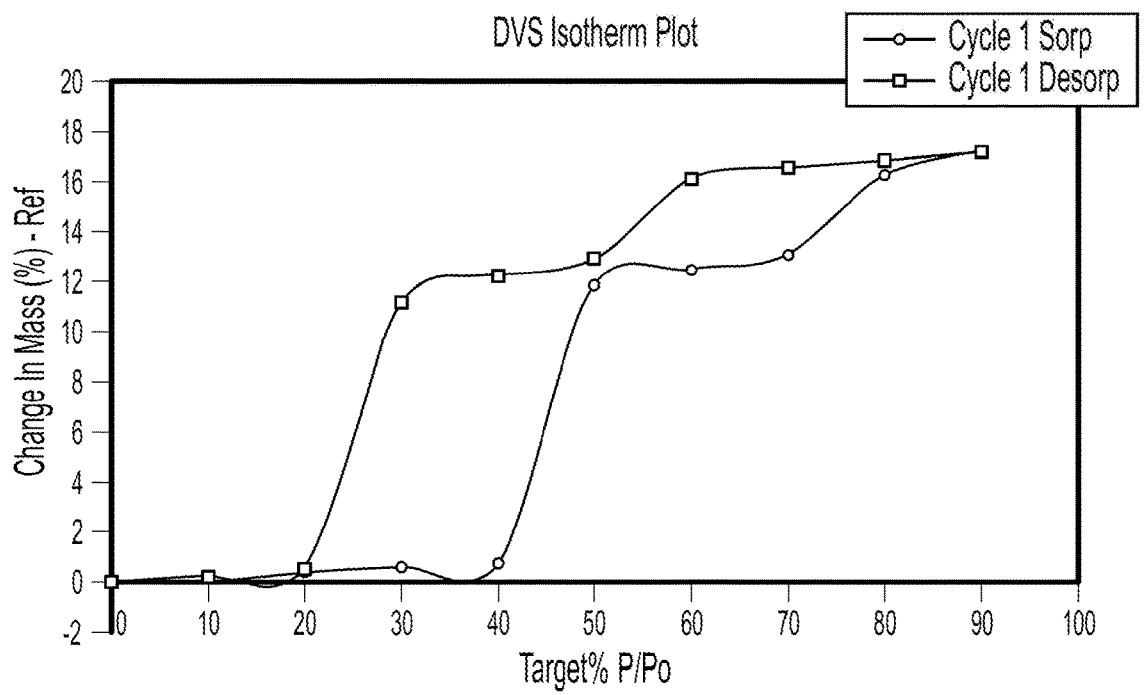

The dynamic vapor sorption (DVS) scan of Form 1 solid showed a 17% water absorption at 90% RH (FIG. 1D). The XRD data indicated that the solid used in the DVS test converted to the hydrate form before the start of the DVS test. However, at 0% RH, water was lost, perhaps indicating that the solid was Form 1.

TABLE 6

Summary of experiments that generated Form 1

| Form | Solvent | Temperature | Wet | Dry |
|---|---|---|---|---|
| Form 1 | MeOH | RT | Form 13 | Form 1 |
| | MeOH | 50° C. | Form 1 | Form 1 |
| | Toluene | RT | Form 1 | Form 1 |
| | Toluene | 50° C. | Form 1 | Form 1 |
| | water | RT | Form 13 | Form 1 |
| | Heptane | RT | Form 1 | Form 1 |
| | DCM | RT | Form 1 | Form 1 |
| | Acetonitrile/water | RT | Form 12 | Form 1 |
| | MeOH/water | RT | Form 12 | Form 1 |
| | Toluene/water | RT | Form 13 | Form 1 |
| | IPAc/water | RT | Form 13 | Form 1 |
| | EA/water | RT | Form 12 | Form 1 |
| | MtBE/water | RT | Form 12 | Form 1 |
| | MA/water | RT | Form 13 | Form 1 |
| | MIBK/water | RT | Form 12 | Form 1 |
| | MIBK/water | 50° C. | Form 13 | Form 1 |
| | DCM/water | RT | Form 13 | Form 1 |

TABLE 6-continued

Summary of experiments that generated Form 1

| Form | Solvent | Temperature | Wet | Dry |
|---|---|---|---|---|
| | DCM/water | 50° C. | Form 13 | Form 1 |
| | n-Butyl acetate/water | 50° C. | Form 13 | Form 1 |
| | Heptane/water | 50° C. | Form 13 | Form 1 |
| | n-Butanol/water | 50° C. | Form 13 | Form 1 |

*Amount of water in binary solvents is 5%

TABLE 7

XRD peaks of Form 1

| 2-Theta | d(A) | BG | Height | I % | Area | I % | FWHM |
|---|---|---|---|---|---|---|---|
| 5.778 | 15.2835 | 57 | 97 | 28.3 | 1765 | 18.5 | 0.309 |
| 6.801 | 12.9871 | 19 | 343 | 100 | 8306 | 87.1 | 0.412 |
| 9.26 | 9.5427 | 20 | 178 | 51.9 | 3884 | 40.7 | 0.371 |
| 12.421 | 7.1203 | 30 | 231 | 67.3 | 4862 | 51 | 0.358 |
| 13.919 | 6.357 | 35 | 147 | 42.9 | 3668 | 38.5 | 0.424 |
| 14.501 | 6.1033 | 40 | 133 | 38.8 | 3439 | 36.1 | 0.44 |
| 16.5 | 5.3681 | 47 | 196 | 57.1 | 4286 | 44.9 | 0.372 |
| 17.26 | 5.1333 | 53 | 46 | 13.4 | 560 | 5.9 | 0.207 |
| 18.52 | 4.7868 | 68 | 342 | 99.7 | 9539 | 100 | 0.474 |
| 19.161 | 4.6282 | 54 | 215 | 62.7 | 4130 | 43.3 | 0.327 |
| 20.302 | 4.3706 | 49 | 133 | 38.8 | 2823 | 29.6 | 0.361 |
| 20.619 | 4.304 | 43 | 80 | 23.3 | 2047 | 21.5 | 0.435 |
| 23.056 | 3.8543 | 41 | 38 | 11.1 | 765 | 8 | 0.342 |
| 24.642 | 3.6098 | 33 | 175 | 51 | 7235 | 75.8 | 0.703 |
| 25.302 | 3.5171 | 86 | 80 | 23.3 | 2345 | 24.6 | 0.498 |
| 26.1 | 3.4113 | 83 | 69 | 20.1 | 1545 | 16.2 | 0.381 |
| 27.46 | 3.2453 | 52 | 46 | 13.4 | 872 | 9.1 | 0.322 |
| 28.739 | 3.1038 | 39 | 84 | 24.5 | 2146 | 22.5 | 0.434 |
| 30.444 | 2.9337 | 34 | 32 | 9.3 | 1080 | 11.3 | 0.54 |
| 33.302 | 2.6882 | 30 | 27 | 7.9 | 683 | 7.2 | 0.405 |

C. Forms 2, 2*, and 2***

Figure 2A:
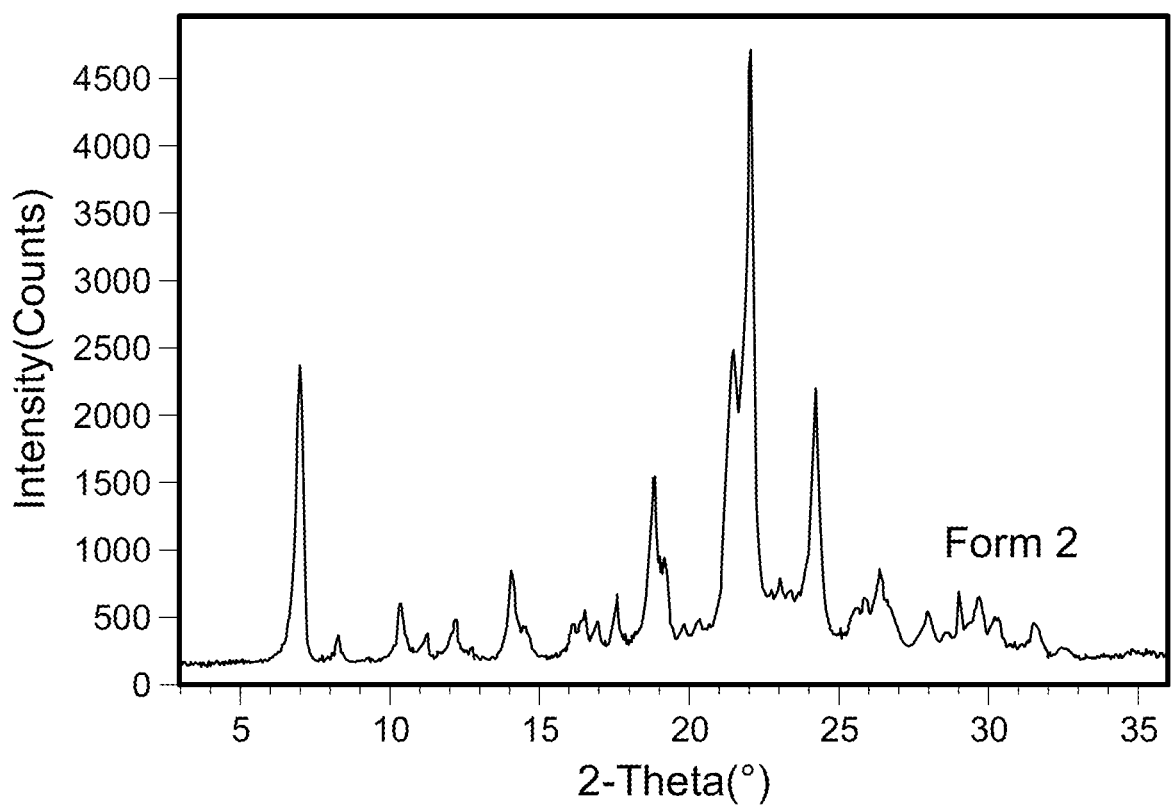
FIGS. 2A-2H are scans of polymorph Forms 2, 2*, and 2** of the compound of Formula (I).
Figure 2B:
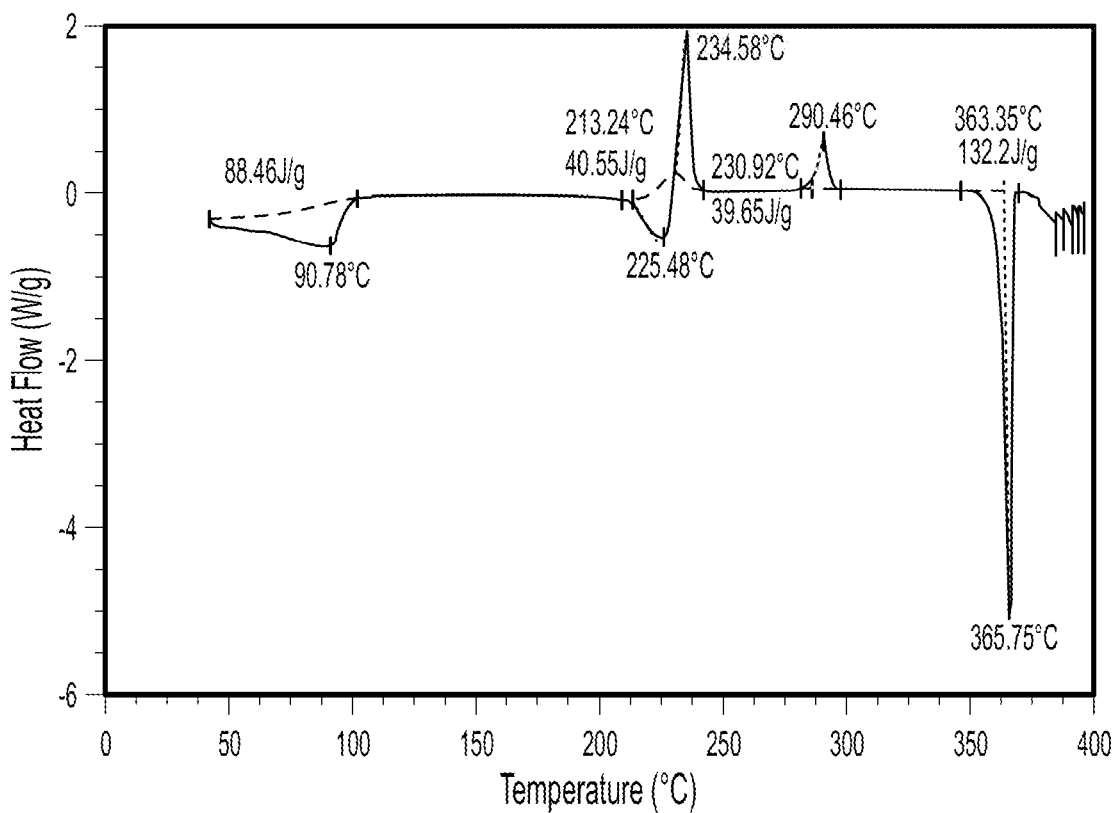
Figure 2C:
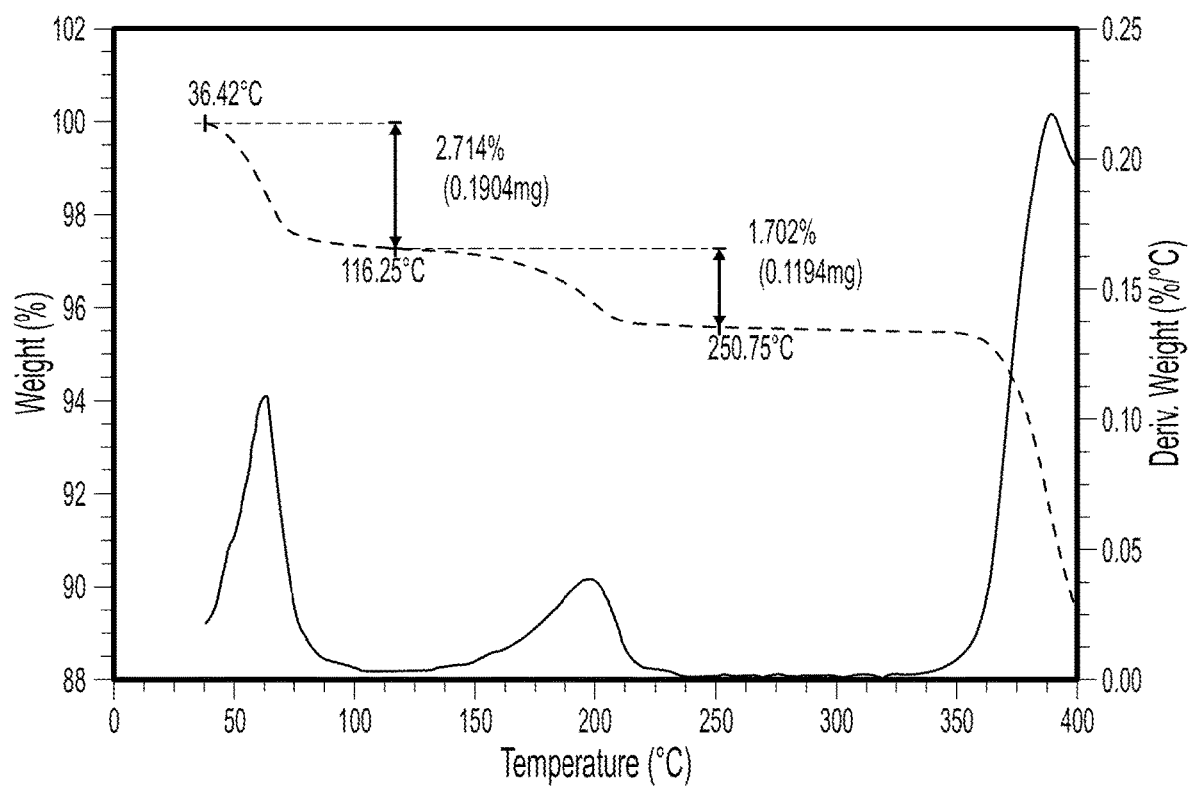
Figure 2D:
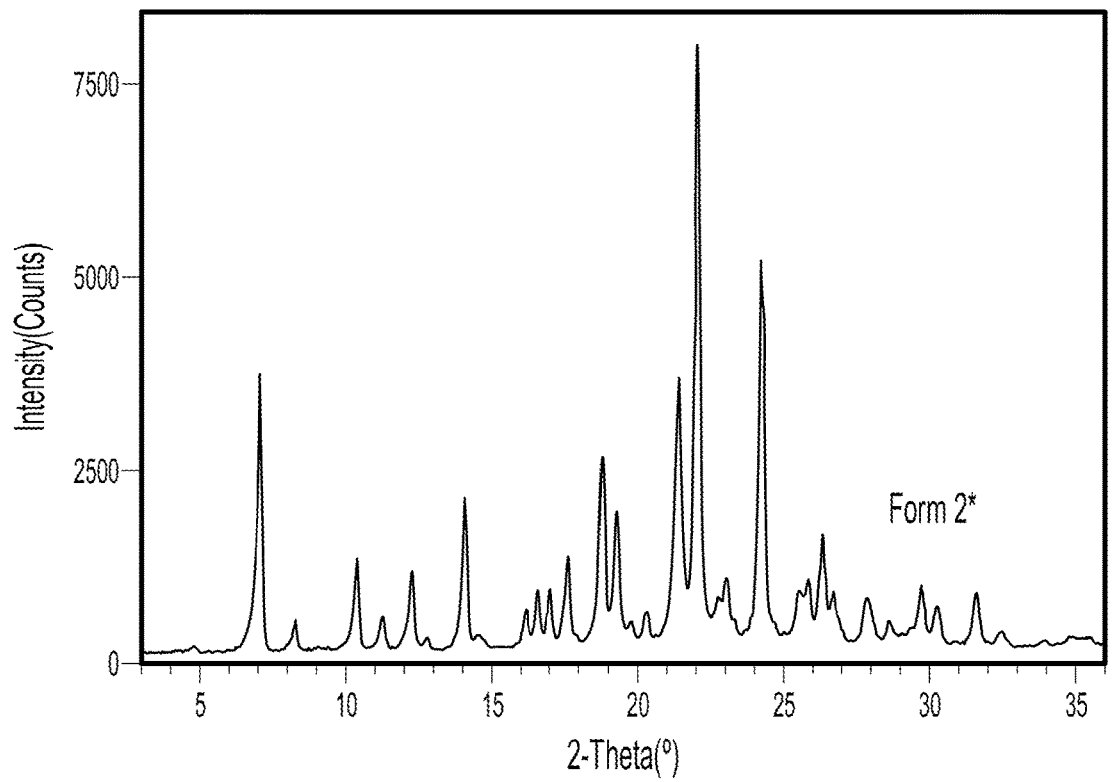
Figure 2E:
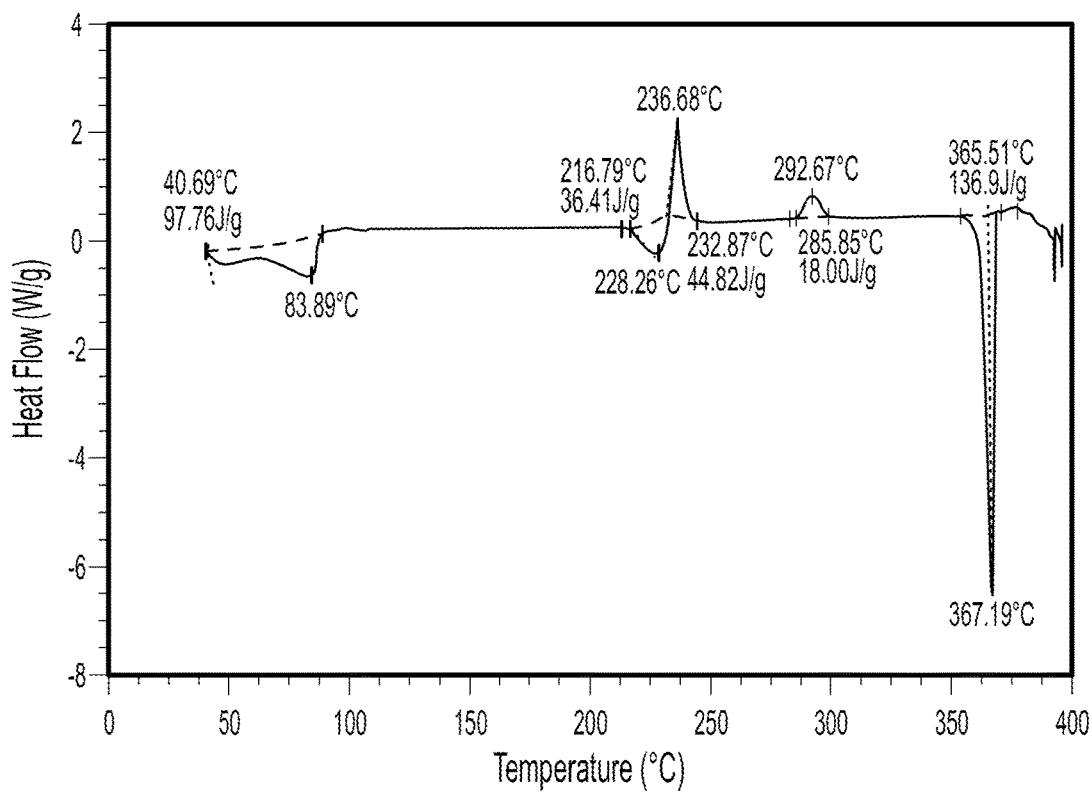
Figure 2F:
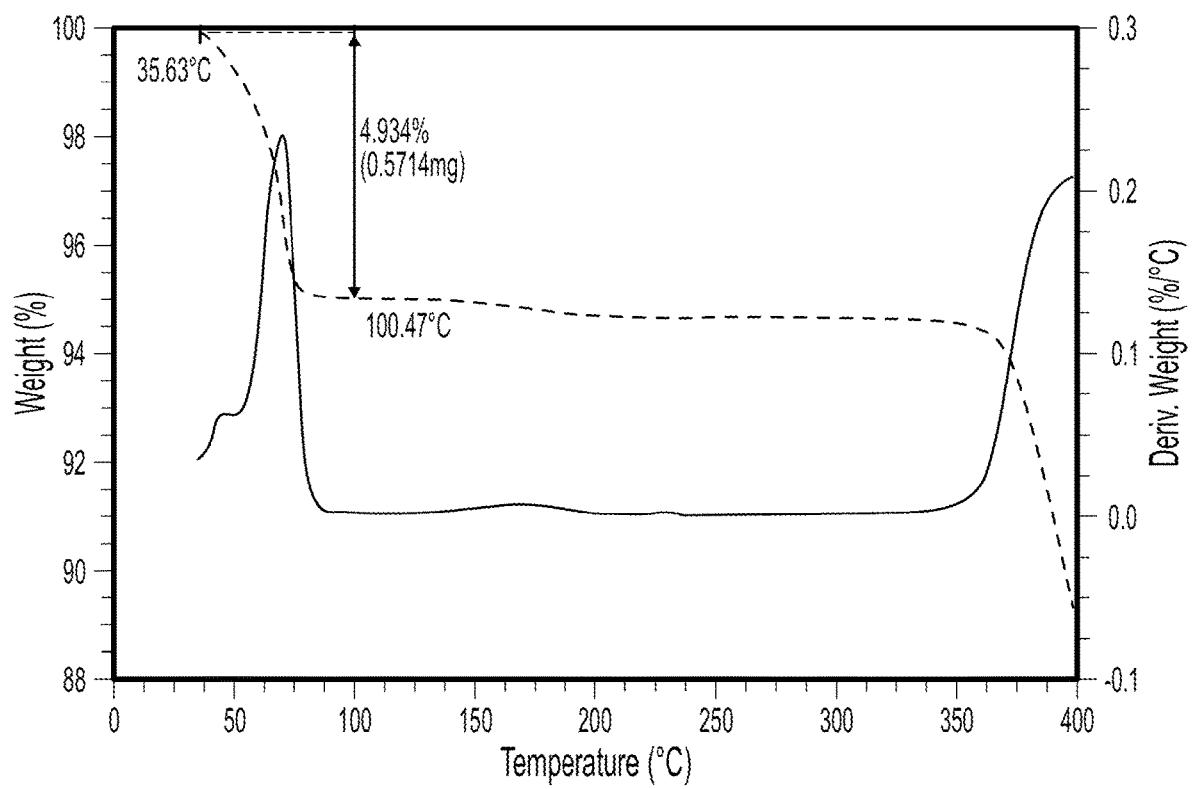
Figure 2G:
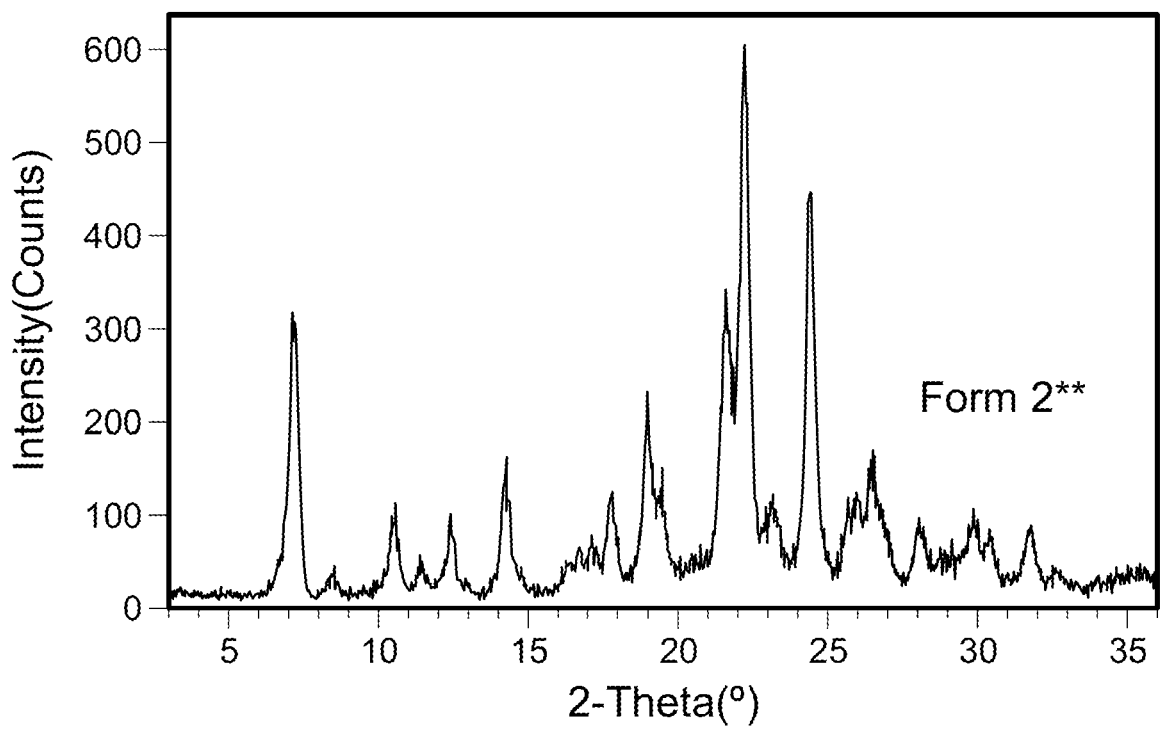
Figure 2H:
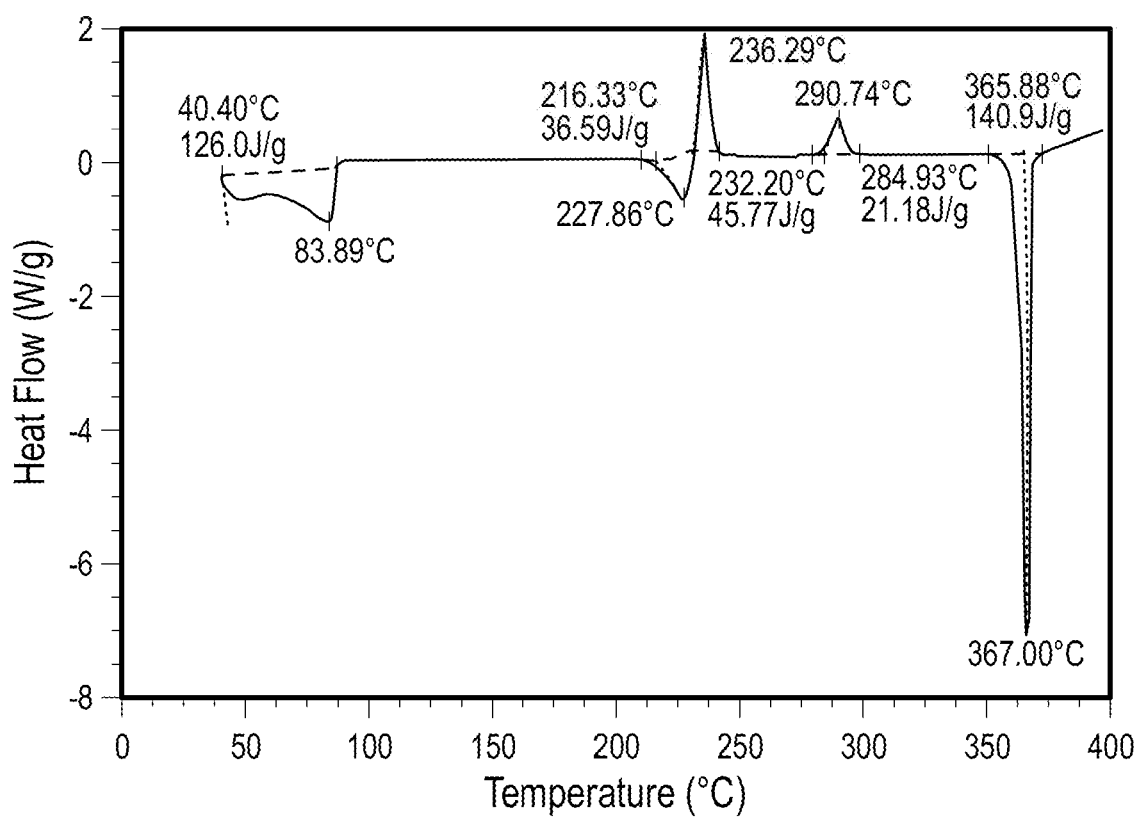

The experiments that generated Forms 2, 2*, and 2** are shown in Table 8, below. XRD scans of Forms 2, 2* and 2** were performed (FIGS. 2A, 2D, and 2G show the XRD scans of Forms 2, 2*, and 2**, respectively). The XRD peaks of Forms 2 and 2* are shown in Tables 9 and 10, below, respectively. DSC scans were also performed (FIGS. 2B, 2E, and 2H show the DSC scans of Forms 2, 2*, and 2**, respectively). According to the DSC scans, Forms 2, 2* and 2** each showed a wide endotherm between 50° C.-100° C., and multiple endotherms and exotherms before melting at 363° C. The wide endotherm before 100° C. may be due to the containment of water/solvent in the solid. Form 2 was obtained from acetonitrile; Form 2* from ethanol; Form 2** from n-propanol/5% water.

A TGA scan of Form 2 (FIG. 2C) showed a 2.7% weight loss before 116° C. FIG. 2F shows the TGA scan of Form 2*

A PLM photo of Form 2 was taken, indicating that the particle size of this solid was around 50 um.

The Form 2 solid was heated in a DSC machine to 90° C. (past the wide endotherm between 50-100° C.); to 270° C. (past the endotherm/exotherm around 240° C.); and finally to 330° C. (past the exotherm around 330° C.). The residual solid was analyzed by XRD. According to the first and second XRD and DSC scans, the form did not change before and after heating to 90° C. The wide endotherm between 50-100° C. might be free solvent or hydrate. According to the first and third XRD and DSC scans, after heating a Form 2 sample to 270° C., the solid converted to low crystalline solids. According to the first and fourth XRD and DSC scans, after heating the sample to 330° C., the solid converted to Form 9. Thus, the exotherm around 290° C. was a re-crystallization event. According to an XRD and DSC overlay, the behavior of Form 2* was similar to Form 2.

Residual acetonitrile and EtOH in Form 2 and 2* was not detected.

TABLE 8

Summary of experiments that generated Forms 2, 2*, and 2**

| Form | Solvent | Temperature | Wet | Dry |
|---|---|---|---|---|
| Form 2 | Acetonitrile | RT | Form 2 | Form 2 |
| | Acetonitrile | 50° C. | Form 2* | Form 2 |
| | EtOH/water | RT | Solvate 3 | Form 2 |
| Form 2* | EtOH | RT | Form 2* | Form 2* |
| | EtOH | 50° C. | Form 2* | Form 2* |
| | Acetonitrile | 50° C. | Form 2* | Form 2 |
| Form 2** | n-Propanol/water | RT | Form 2** | Form 2** |

*Amount of water in binary solvents is 5%

TABLE 9

XRD peaks of Form 2

| 2-Theta | d(A) | BG | Height | I % | Area | I % | FWHM |
|---|---|---|---|---|---|---|---|
| 7.021 | 12.5802 | 164 | 2202 | 54.1 | 36151 | 38.2 | 0.279 |
| 8.298 | 10.6462 | 156 | 194 | 4.8 | 2332 | 2.5 | 0.204 |
| 10.399 | 8.5 | 193 | 397 | 9.8 | 6246 | 6.6 | 0.267 |
| 11.258 | 7.8531 | 206 | 151 | 3.7 | 1407 | 1.5 | 0.158 |
| 12.239 | 7.2259 | 181 | 287 | 7 | 5980 | 6.3 | 0.354 |
| 14.1 | 6.2759 | 186 | 648 | 15.9 | 14147 | 15 | 0.371 |
| 14.597 | 6.0632 | 195 | 182 | 4.5 | 7983 | 8.4 | 0.746 |
| 16.18 | 5.4734 | 235 | 201 | 4.9 | 4033 | 4.3 | 0.341 |
| 16.561 | 5.3484 | 251 | 280 | 6.9 | 8382 | 8.9 | 0.509 |
| 17.033 | 5.2013 | 288 | 160 | 3.9 | 1810 | 1.9 | 0.192 |
| 17.639 | 5.0238 | 295 | 366 | 9 | 3542 | 3.7 | 0.165 |
| 18.878 | 4.6968 | 316 | 1210 | 29.7 | 29303 | 31 | 0.412 |
| 19.22 | 4.614 | 333 | 585 | 14.4 | 21169 | 22.4 | 0.615 |
| 19.863 | 4.4662 | 340 | 95 | 2.3 | 437 | 0.5 | 0.078 |
| 20.411 | 4.3474 | 385 | 86 | 2.1 | 671 | 0.7 | 0.133 |
| 21.48 | 4.1335 | 532 | 1944 | 47.8 | 61345 | 64.8 | 0.536 |
| 22.04 | 4.0297 | 647 | 4071 | 100 | 94605 | 100 | 0.395 |
| 23.036 | 3.8576 | 634 | 142 | 3.5 | 1478 | 1.6 | 0.177 |
| 24.24 | 3.6686 | 497 | 1688 | 41.5 | 28976 | 30.6 | 0.292 |
| 25.561 | 3.482 | 422 | 120 | 2.9 | 2545 | 2.7 | 0.361 |
| 25.918 | 3.4349 | 365 | 271 | 6.7 | 11426 | 12.1 | 0.717 |
| 26.379 | 3.3759 | 349 | 497 | 12.2 | 15133 | 16 | 0.518 |
| 26.739 | 3.3313 | 387 | 181 | 4.4 | 2845 | 3 | 0.267 |
| 27.979 | 3.1863 | 297 | 235 | 5.8 | 4050 | 4.3 | 0.293 |
| 29.043 | 3.072 | 338 | 347 | 8.5 | 4584 | 4.8 | 0.225 |
| 29.661 | 3.0094 | 321 | 310 | 7.6 | 7879 | 8.3 | 0.432 |
| 30.204 | 2.9565 | 355 | 135 | 3.3 | 1501 | 1.6 | 0.189 |
| 31.58 | 2.8308 | 232 | 206 | 5.1 | 3991 | 4.2 | 0.329 |
| 32.602 | 2.7443 | 193 | 63 | 1.5 | 1129 | 1.2 | 0.305 |

TABLE 10

XRD peaks of Form 2*

| 2-Theta | d(A) | BG | Height | I % | Area | I % | FWHM |
|---|---|---|---|---|---|---|---|
| 4.859 | 18.1701 | 127 | 87 | 1.2 | 1714 | 1.9 | 0.335 |
| 7.119 | 12.4067 | 148 | 3587 | 48.4 | 44853 | 50.4 | 0.213 |
| 8.321 | 10.6166 | 149 | 407 | 5.5 | 4871 | 5.5 | 0.203 |
| 10.439 | 8.4669 | 186 | 1184 | 16 | 13629 | 15.3 | 0.196 |
| 11.319 | 7.8109 | 190 | 413 | 5.6 | 4673 | 5.3 | 0.192 |
| 12.3 | 7.1899 | 179 | 1010 | 13.6 | 13220 | 14.9 | 0.223 |
| 12.803 | 6.9089 | 182 | 140 | 1.9 | 1587 | 1.8 | 0.193 |
| 14.121 | 6.2667 | 179 | 1966 | 26.5 | 27290 | 30.7 | 0.236 |
| 14.559 | 6.0791 | 199 | 169 | 2.3 | 4381 | 4.9 | 0.441 |
| 16.236 | 5.4546 | 244 | 436 | 5.9 | 5696 | 6.4 | 0.222 |
| 16.62 | 5.3297 | 271 | 674 | 9.1 | 7919 | 8.9 | 0.2 |
| 17.059 | 5.1935 | 313 | 629 | 8.5 | 6279 | 7.1 | 0.17 |
| 17.699 | 5.0071 | 303 | 1094 | 14.7 | 12619 | 14.2 | 0.196 |

TABLE 10-continued

XRD peaks of Form 2*

| 2-Theta | d(A) | BG | Height | I % | Area | I % | FWHM |
|---|---|---|---|---|---|---|---|
| 18.858 | 4.7018 | 359 | 2334 | 31.5 | 31734 | 35.7 | 0.231 |
| 19.321 | 4.5903 | 325 | 1650 | 22.2 | 28313 | 31.8 | 0.292 |
| 19.823 | 4.4751 | 412 | 127 | 1.7 | 582 | 0.7 | 0.078 |
| 20.321 | 4.3665 | 327 | 333 | 4.5 | 3361 | 3.8 | 0.172 |
| 21.479 | 4.1336 | 451 | 3245 | 43.8 | 56365 | 63.3 | 0.295 |
| 22.119 | 4.0154 | 612 | 7417 | 100 | 89000 | 100 | 0.204 |
| 22.782 | 3.9 | 536 | 327 | 4.4 | 11890 | 13.4 | 0.618 |
| 23.098 | 3.8475 | 466 | 638 | 8.6 | 11127 | 12.5 | 0.296 |
| 24.3 | 3.6597 | 361 | 4873 | 65.7 | 61170 | 68.7 | 0.213 |
| 25.599 | 3.4769 | 487 | 475 | 6.4 | 7278 | 8.2 | 0.26 |
| 25.88 | 3.4399 | 541 | 562 | 7.6 | 10968 | 12.3 | 0.332 |
| 26.361 | 3.3782 | 372 | 1289 | 17.4 | 20859 | 23.4 | 0.275 |
| 26.739 | 3.3312 | 266 | 660 | 8.9 | 13196 | 14.8 | 0.34 |
| 27.938 | 3.1909 | 284 | 560 | 7.6 | 9888 | 11.1 | 0.3 |
| 28.641 | 3.1142 | 319 | 210 | 2.8 | 2324 | 2.6 | 0.188 |
| 29.398 | 3.0357 | 357 | 100 | 1.3 | 2376 | 2.7 | 0.404 |
| 29.779 | 2.9977 | 295 | 708 | 9.5 | 13168 | 14.8 | 0.316 |
| 30.3 | 2.9473 | 283 | 451 | 6.1 | 6600 | 7.4 | 0.249 |
| 31.658 | 2.8239 | 239 | 667 | 9 | 9228 | 10.4 | 0.235 |
| 32.519 | 2.7511 | 221 | 191 | 2.6 | 2896 | 3.3 | 0.258 |
| 33.903 | 2.6419 | 213 | 72 | 1 | 876 | 1 | 0.207 |
| 34.82 | 2.5744 | 229 | 110 | 1.5 | 3822 | 4.3 | 0.591 |
| 35.504 | 2.5264 | 230 | 97 | 1.3 | 3876 | 4.4 | 0.679 |

D. Form 3

Figure 3A:
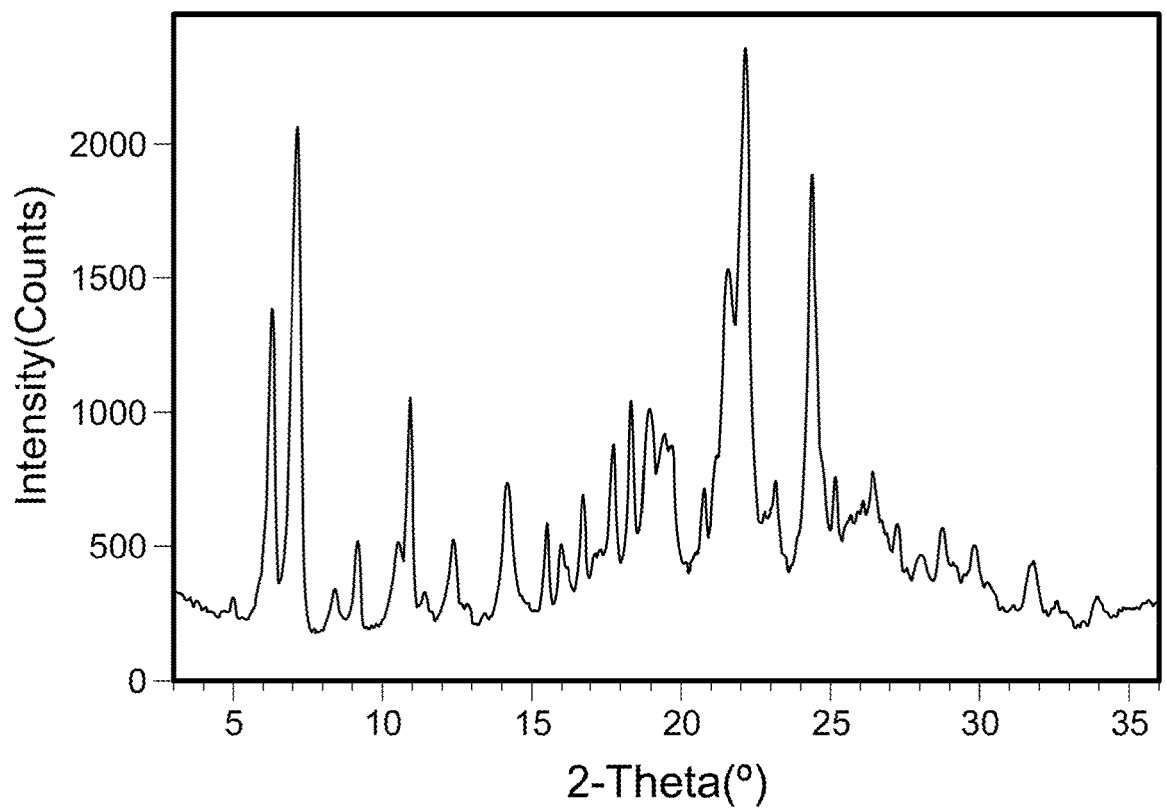
FIGS. 3A-3C are scans of polymorph Form 3 of the compound of Formula (I).
Figure 3B:
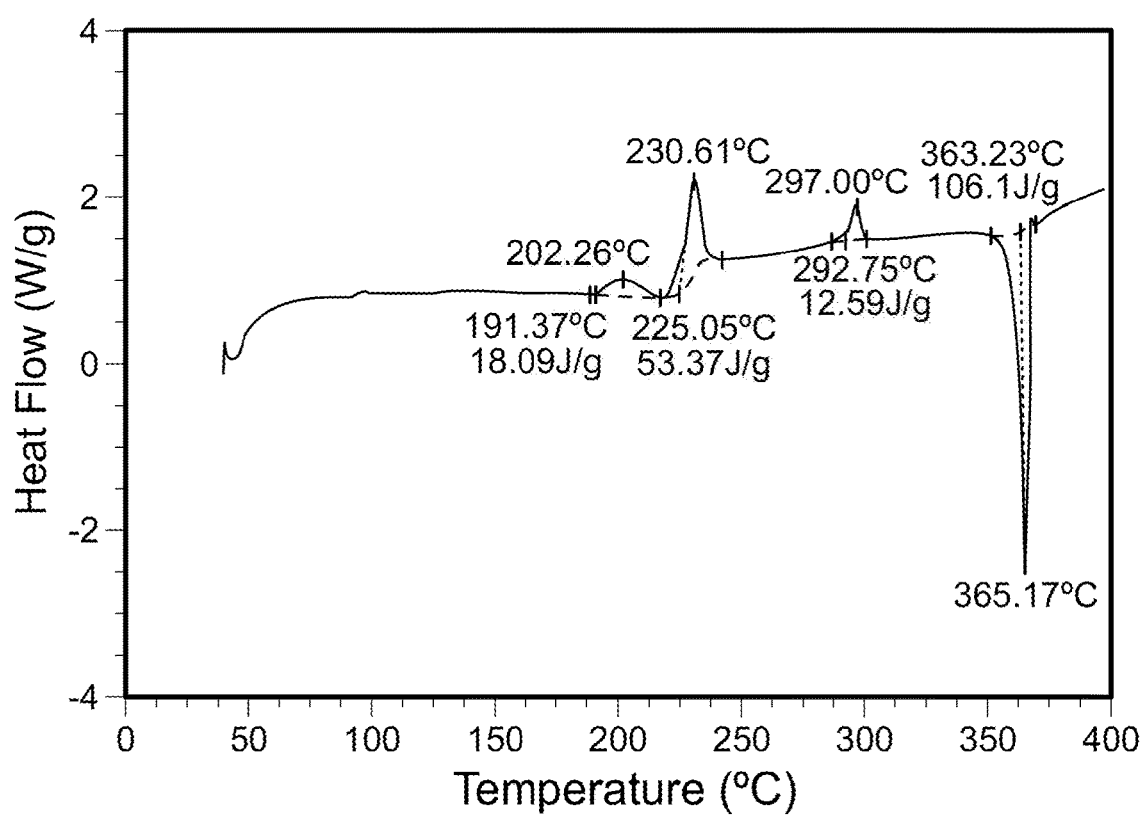

The experiments that generated Form 3 are shown in Table 11, below. XRD and DSC scans of Form 3 were taken (FIGS. 3A and 3B, respectively). Table 12, below, shows the XRD peaks of Form 3. Multiple exotherms and endotherms were observed from the DSC scan of Form 3.

Figure 3C:
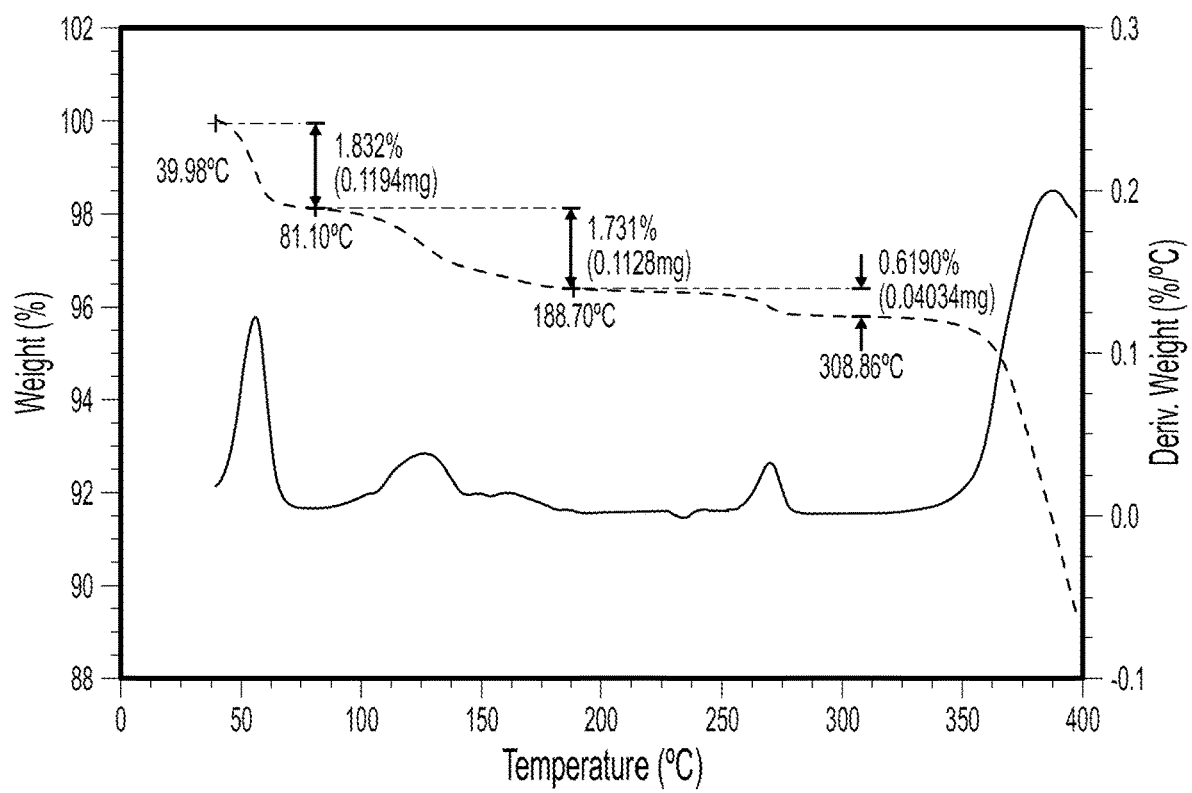

A TGA scan of Form 3 was taken (FIG. 3C) and showed a 1.6% weight loss of the solid before 81° C., followed by a 1.7% weight loss between 81° C. and 169° C.

Form 3 was obtained from IPAc at RT, while Form 3* was obtained from reslurry in n-butyl acetate.

TABLE 11

Summary of experiments that generated Form 3 and Form 3*

| Form | Solvent | Temperature | Wet | Dry |
|---|---|---|---|---|
| Form 3 | IPAc | RT | Form 3 | Form 3 |
|  | n-Butyl acetate | RT | Form 3* | Form 3 |
| Form 3* | n-Butyl acetate | RT | Form 3* | Form 3 |

TABLE 12

XRD peaks of Form 3

| 2-Theta | d(A) | BG | Height | I % | Area | I % | FWHM |
|---|---|---|---|---|---|---|---|
| 5.024 | 17.5739 | 231 | 87 | 4.4 | 845 | 1.9 | 0.165 |
| 6.34 | 13.9294 | 368 | 1030 | 52.5 | 12361 | 27.5 | 0.204 |
| 7.219 | 12.2357 | 182 | 1962 | 100 | 36491 | 81.1 | 0.316 |
| 8.441 | 10.4665 | 188 | 159 | 8.1 | 3261 | 7.2 | 0.349 |
| 9.237 | 9.5659 | 207 | 320 | 16.3 | 3365 | 7.5 | 0.179 |
| 10.561 | 8.37 | 240 | 278 | 14.2 | 6270 | 13.9 | 0.383 |
| 10.998 | 8.0381 | 217 | 849 | 43.3 | 17119 | 38.1 | 0.343 |
| 11.46 | 7.715 | 256 | 87 | 4.4 | 662 | 1.5 | 0.129 |
| 12.439 | 7.11 | 215 | 311 | 15.9 | 6502 | 14.5 | 0.355 |
| 12.865 | 6.8756 | 209 | 92 | 4.7 | 1599 | 3.6 | 0.295 |
| 14.22 | 6.2233 | 231 | 522 | 26.6 | 12265 | 27.3 | 0.399 |
| 15.524 | 5.7034 | 273 | 311 | 15.9 | 2957 | 6.6 | 0.162 |
| 16.021 | 5.5276 | 309 | 218 | 11.1 | 2669 | 5.9 | 0.208 |
| 16.78 | 5.2792 | 368 | 330 | 16.8 | 3780 | 8.4 | 0.195 |
| 17.181 | 5.1567 | 384 | 99 | 5 | 2614 | 5.8 | 0.449 |
| 17.782 | 4.9837 | 428 | 496 | 25.3 | 6264 | 13.9 | 0.215 |
| 18.381 | 4.8227 | 509 | 551 | 28.1 | 5102 | 11.3 | 0.157 |
| 19.02 | 4.6622 | 447 | 589 | 30 | 20513 | 45.6 | 0.592 |

TABLE 12-continued

XRD peaks of Form 3

| 2-Theta | d(A) | BG | Height | I % | Area | I % | FWHM |
|---|---|---|---|---|---|---|---|
| 19.758 | 4.4896 | 487 | 423 | 21.6 | 14362 | 31.9 | 0.577 |
| 20.8 | 4.267 | 520 | 214 | 10.9 | 1518 | 3.4 | 0.121 |
| 21.19 | 4.1893 | 408 | 418 | 21.3 | 4581 | 10.2 | 0.186 |
| 21.6 | 4.1107 | 553 | 1017 | 51.8 | 41986 | 93.3 | 0.702 |
| 22.181 | 4.0044 | 662 | 1736 | 88.5 | 44981 | 100 | 0.44 |
| 23.185 | 3.8333 | 508 | 259 | 13.2 | 3327 | 7.4 | 0.218 |
| 24.44 | 3.6392 | 467 | 1441 | 73.4 | 29510 | 65.6 | 0.348 |
| 25.198 | 3.5313 | 551 | 232 | 11.8 | 1362 | 3 | 0.1 |
| 25.618 | 3.4745 | 557 | 79 | 4 | 365 | 0.8 | 0.079 |
| 26.103 | 3.4109 | 512 | 180 | 9.2 | 7374 | 16.4 | 0.696 |
| 26.479 | 3.3634 | 475 | 306 | 15.6 | 11652 | 25.9 | 0.647 |
| 27.3 | 3.264 | 455 | 133 | 6.8 | 1016 | 2.3 | 0.13 |
| 28.04 | 3.1796 | 378 | 93 | 4.7 | 1485 | 3.3 | 0.271 |
| 28.82 | 3.0953 | 372 | 201 | 10.2 | 3455 | 7.7 | 0.292 |
| 29.258 | 3.0499 | 362 | 76 | 3.9 | 2580 | 5.7 | 0.577 |
| 29.88 | 2.9878 | 334 | 191 | 9.7 | 4011 | 8.9 | 0.357 |
| 31.802 | 2.8115 | 251 | 205 | 10.4 | 4094 | 9.1 | 0.34 |
| 32.62 | 2.7429 | 231 | 87 | 4.4 | 1109 | 2.5 | 0.217 |
| 32.943 | 2.7167 | 215 | 52 | 2.7 | 1107 | 2.5 | 0.362 |
| 33.961 | 2.6375 | 217 | 101 | 5.1 | 1686 | 3.7 | 0.284 |

E. Form 4

Figure 4A:
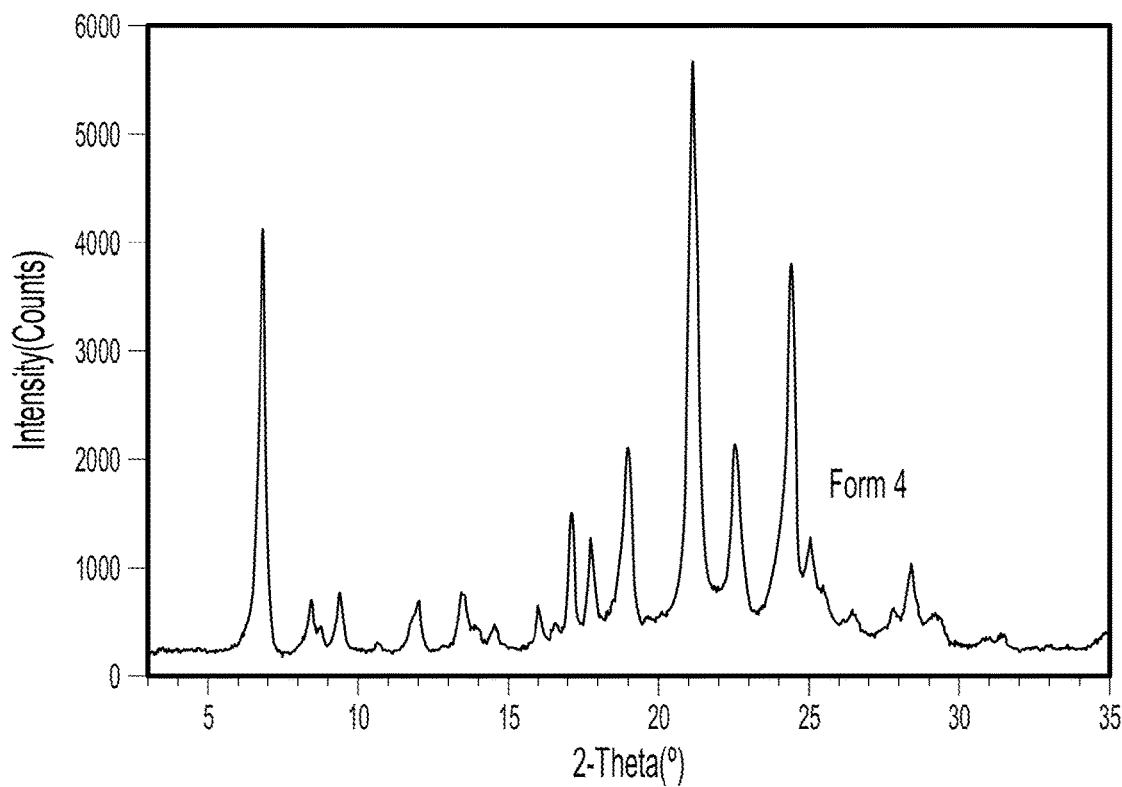
FIGS. 4A-4I are scans of polymorph Forms 4, 4*, and 4** of the compound of Formula (I).
Figure 4B:
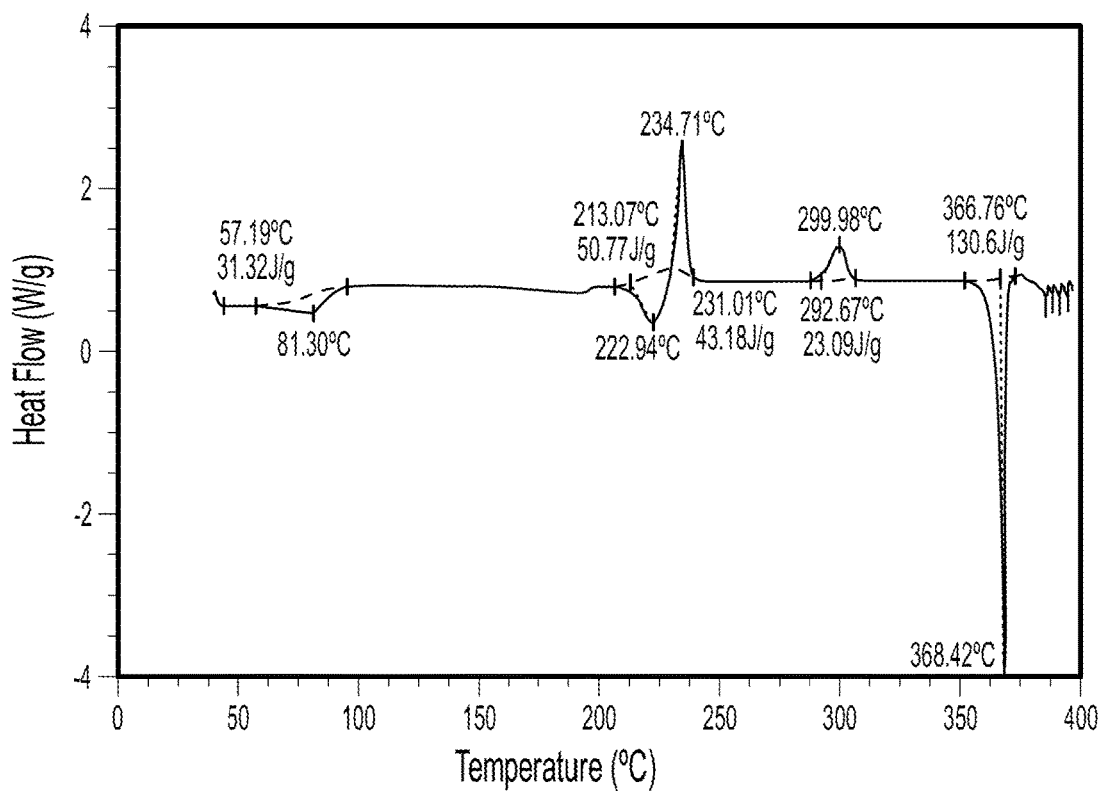

The experiments that generated Forms 4, 4*, and 4** are shown in Table 13, below. XRD of Forms 4, 4*, and 4** were taken (FIGS. 4A, 4D, and 4G, respectively). Tables 14 and 15, below, show the XRD peaks of Form 4 and Form 4*, respectively. DSC scans of Forms 4, 4*, and 4** were also performed (FIGS. 4B, 4E, and 4H, respectively). According to the DSC scans, Form 4 showed a wide endotherm between 50° C.-100° C., followed by multiple endotherms/exotherms, and then melted at around 367° C. Forms 4* and 4** showed similar DSC patterns as Form 4.

Figure 4C:
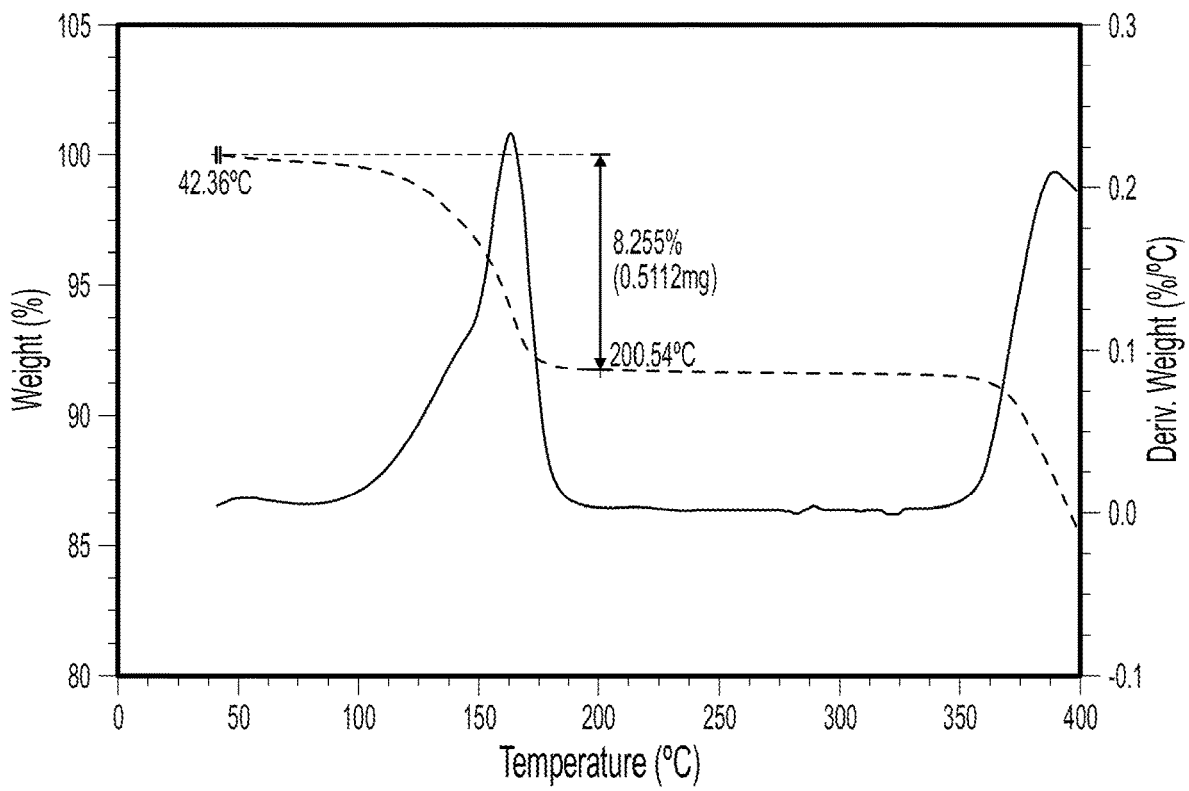
Figure 4D:
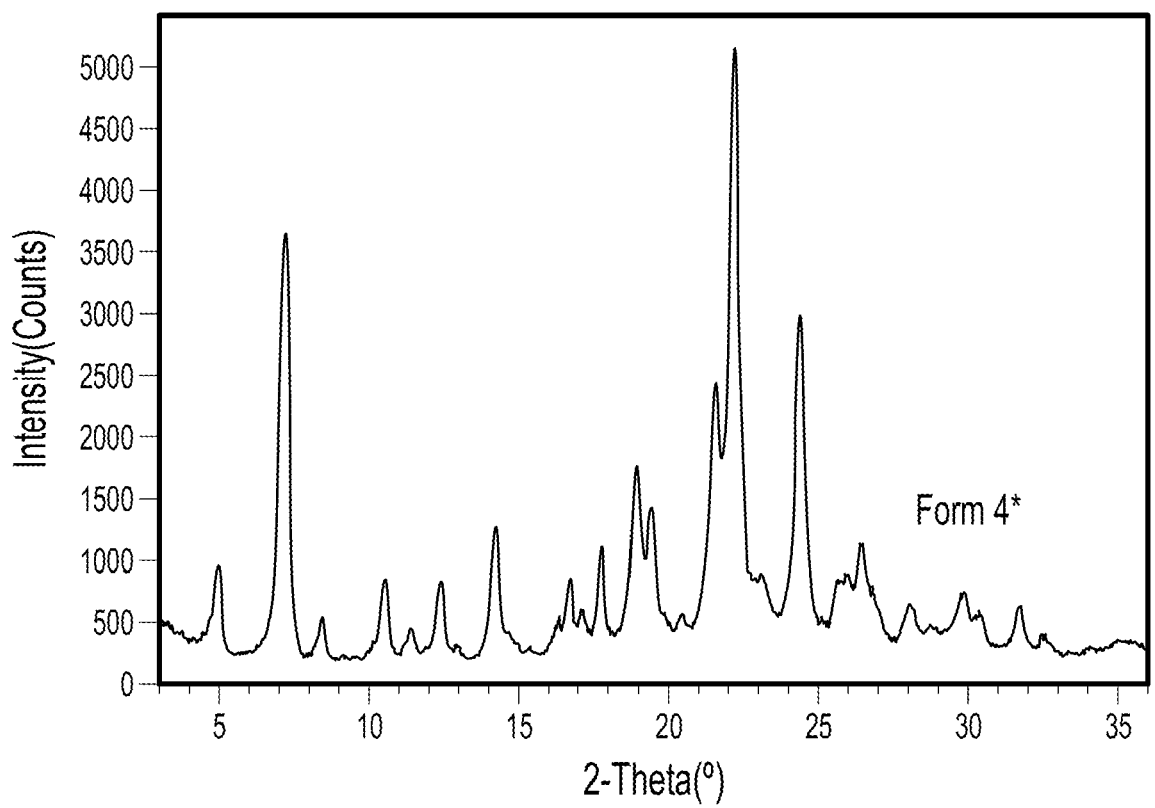
Figure 4E:
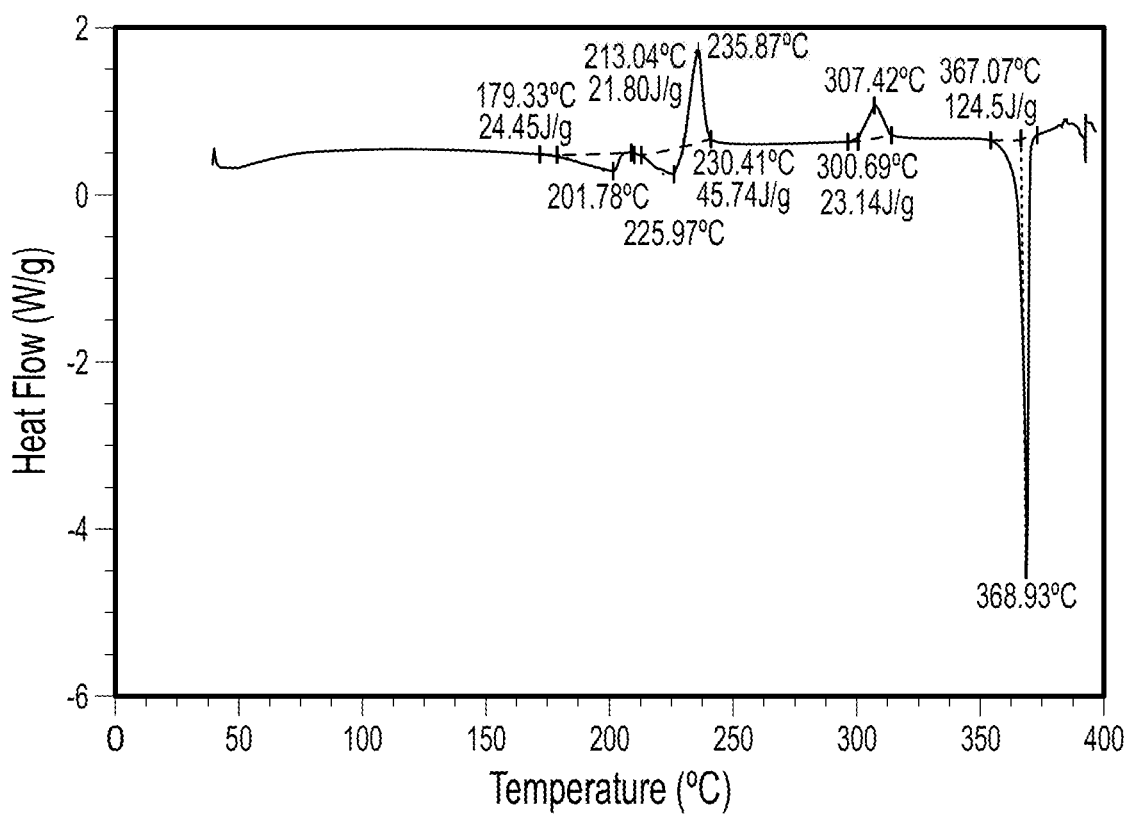
Figure 4F:
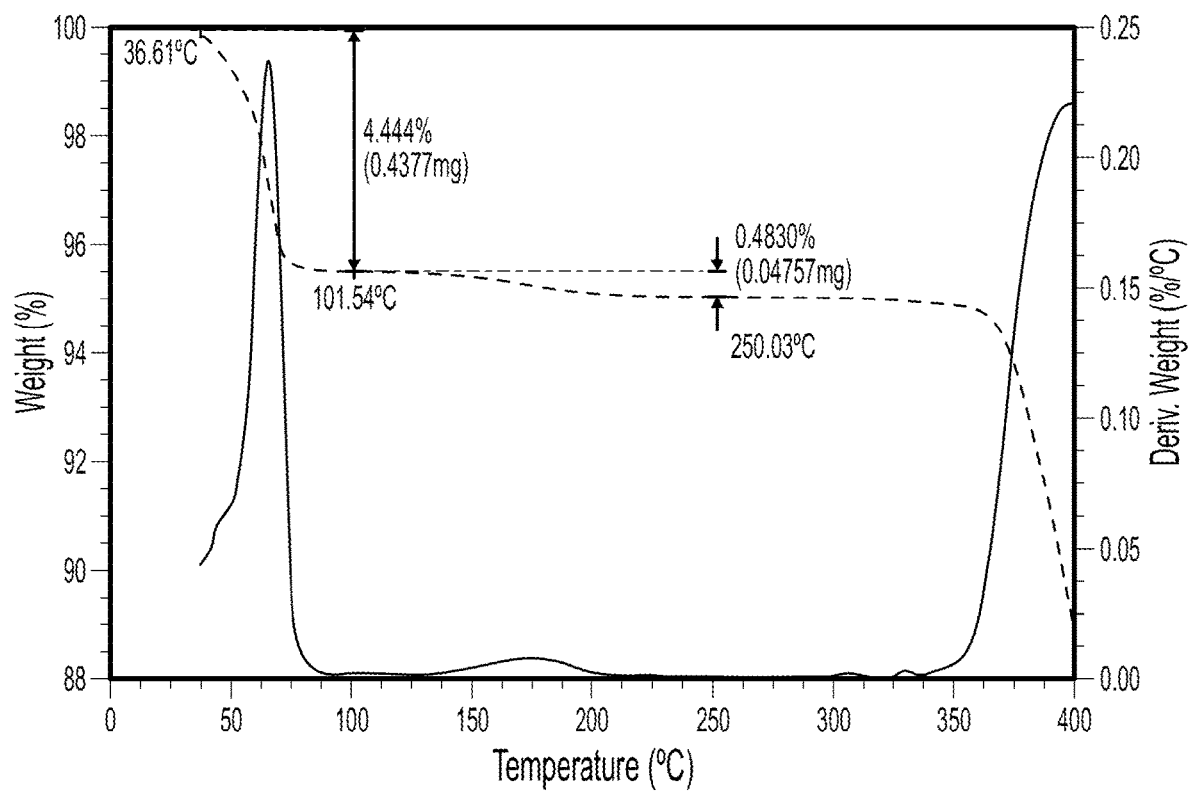
Figure 4G:
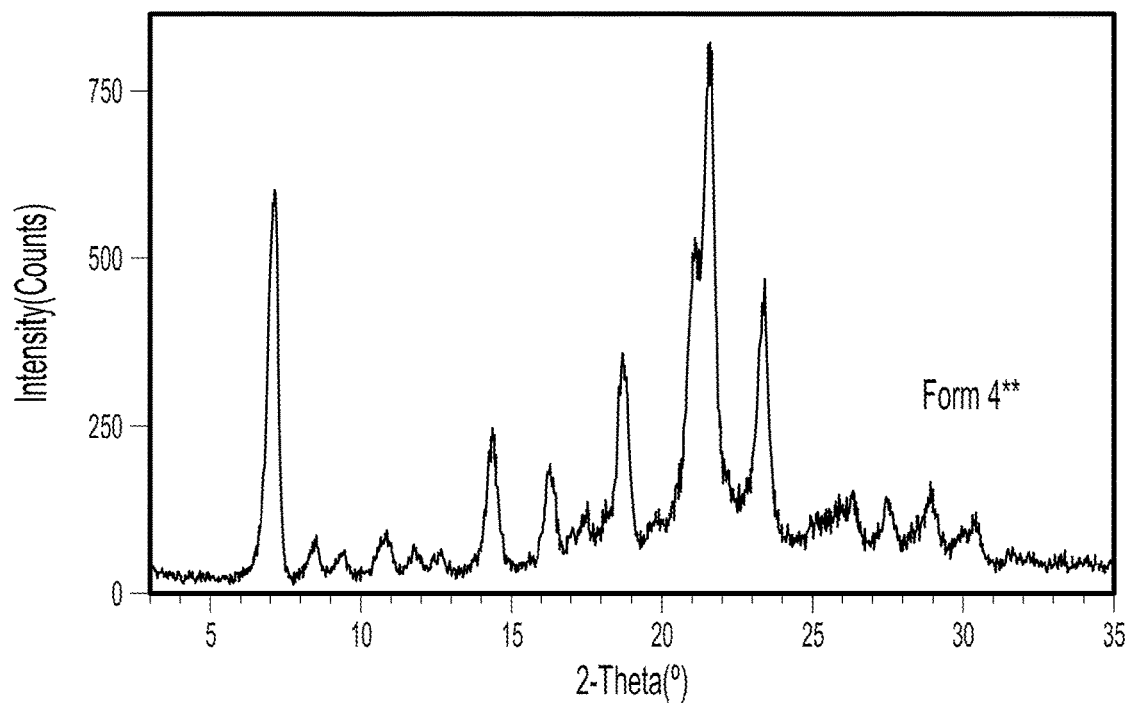
Figure 4H:
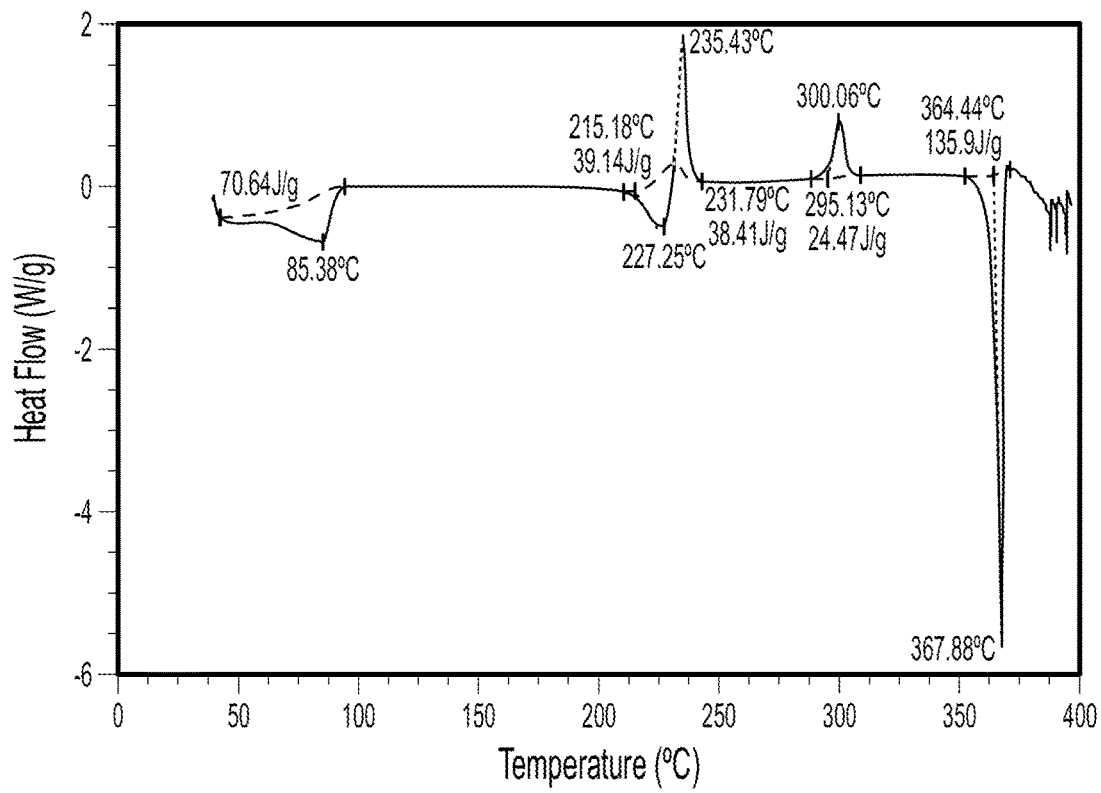
Figure 4I:
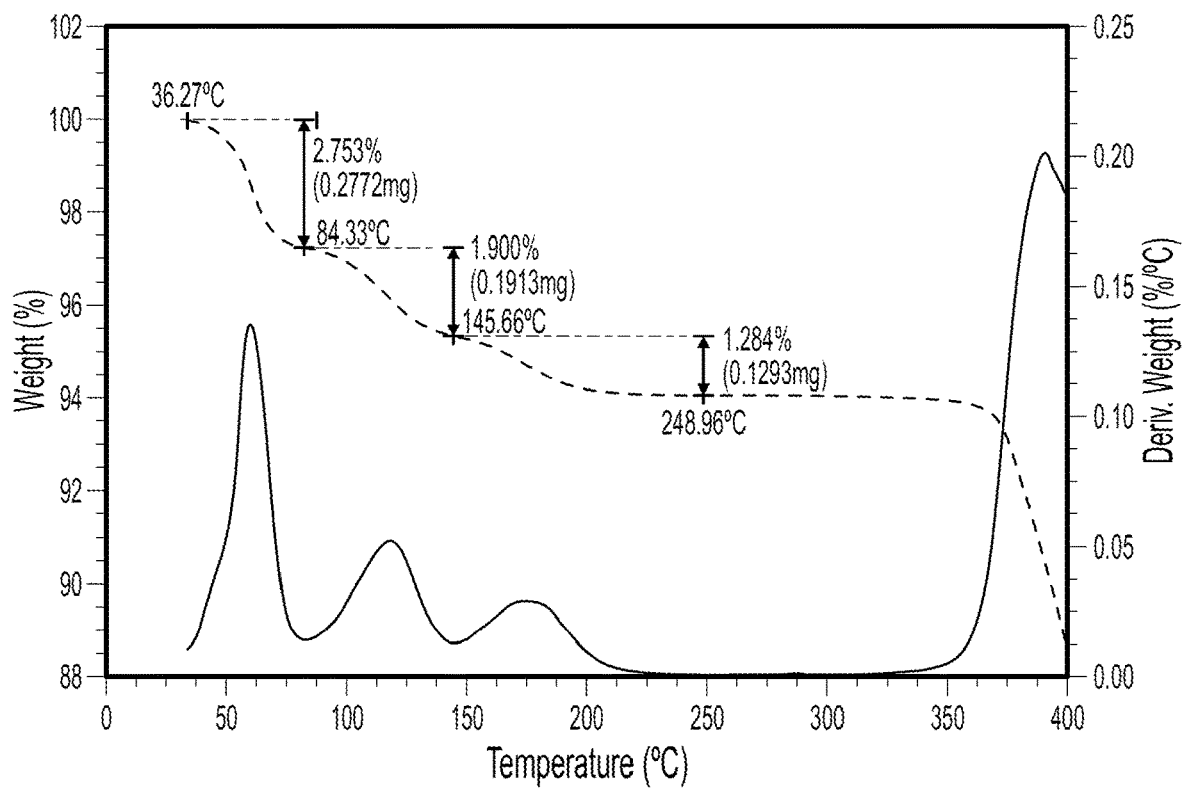

TGA scans of Form 4, Form 4*, and Form 4** were taken (FIGS. 4C, 4F, and 4I, respectively). For Form 4, there was an 8.3% weight loss before 200° C.; for Form 4*, there was a 4.4% weight loss before 102° C., followed by a 0.5% weight loss between 102° C. and 250° C.; and for Form 4**, there were three stages of weight loss, which were 2.8%, 1.9%, and 1.3%, respectively.

These solid forms were obtained from methyl acetate, n-propanol, MIBK, MtBE, ethyl acetate, acetone/water, and ethyl acetate/water.

TABLE 13

Summary of experiments that generated Forms 4, 4*, and 4**

| Form | Solvent | Temperature | Wet | Dry |
|---|---|---|---|---|
| Form 4 | EA | RT | Form 4* | Form 4 |
|  | EA | 50° C. | Form 4* | Form 4 |
|  | MA | RT | Form 4 | Form 4 |
|  | MA | 50° C. | Form 4 | Form 4 |
|  | MA/water | 50° C. | Form 12 | Form 4 |
|  | MtBE | 50° C. | Form 5* | Form 4 |
|  | n-Propanol | RT | Form 4 | Form 4* |
| Form 4* | EA | RT | Form 4* | Form 4* |
|  | EA | 50° C. | Form 4* | Form 4 |
|  | EA/water | 50° C. | Form 4* | Form 4* |
|  | n-Propanol | RT | Form 4 | Form 4* |
| Form 4** | Acetone/water | RT | Solvate 2 | Form 4** |
|  | Acetone | 50° C. | Solvate 2 | Form 4** |
|  | n-Propanol | 50° C. | Form 4 | Form 4** |
|  | Acetone/water | 50° C. | Form 4** | Form 4** |

*Amount of water in binary solvents is 5%

TABLE 14

XRD peaks of Form 4

| 2-Theta | d(A) | BG | Height | I % | Area | I % | FWHM |
|---|---|---|---|---|---|---|---|
| 3.433 | 25.7129 | 197 | 48 | 1 | 697 | 0.7 | 0.247 |
| 7.019 | 12.5829 | 222 | 3897 | 77.3 | 66968 | 69.4 | 0.292 |
| 8.659 | 10.203 | 242 | 448 | 8.9 | 8198 | 8.5 | 0.311 |
| 8.98 | 9.8395 | 223 | 219 | 4.3 | 7649 | 7.9 | 0.594 |
| 9.64 | 9.1672 | 251 | 516 | 10.2 | 6969 | 7.2 | 0.23 |
| 10.917 | 8.0978 | 210 | 77 | 1.5 | 1041 | 1.1 | 0.23 |
| 12.339 | 7.1673 | 220 | 465 | 9.2 | 9572 | 9.9 | 0.35 |
| 13.82 | 6.4023 | 268 | 501 | 9.9 | 11493 | 11.9 | 0.39 |
| 14.278 | 6.1981 | 271 | 192 | 3.8 | 7288 | 7.6 | 0.645 |
| 14.923 | 5.9314 | 288 | 172 | 3.4 | 1636 | 1.7 | 0.162 |
| 16.462 | 5.3804 | 310 | 329 | 6.5 | 3066 | 3.2 | 0.158 |
| 17.041 | 5.199 | 375 | 105 | 2.1 | 942 | 1 | 0.153 |
| 17.638 | 5.0241 | 435 | 1073 | 21.3 | 13511 | 14 | 0.214 |
| 18.281 | 4.8488 | 487 | 772 | 15.3 | 9782 | 10.1 | 0.215 |
| 19.52 | 4.5437 | 504 | 1590 | 31.5 | 31949 | 33.1 | 0.342 |
| 21.759 | 4.081 | 677 | 5040 | 100 | 96504 | 100 | 0.326 |
| 23.22 | 3.8275 | 693 | 1457 | 28.9 | 28109 | 29.1 | 0.328 |
| 25.12 | 3.5421 | 710 | 3091 | 61.3 | 69330 | 71.8 | 0.381 |
| 25.76 | 3.4556 | 455 | 827 | 16.4 | 22029 | 22.8 | 0.453 |
| 27.221 | 3.2733 | 419 | 180 | 3.6 | 2915 | 3 | 0.275 |
| 28.638 | 3.1145 | 409 | 210 | 4.2 | 4338 | 4.5 | 0.351 |
| 29.259 | 3.0498 | 461 | 568 | 11.3 | 11998 | 12.4 | 0.359 |
| 30.137 | 2.9629 | 409 | 149 | 3 | 1946 | 2 | 0.222 |
| 31.817 | 2.8102 | 253 | 110 | 2.2 | 4034 | 4.2 | 0.623 |
| 32.319 | 2.7677 | 245 | 137 | 2.7 | 3829 | 4 | 0.475 |

TABLE 15

XRD peaks of Form 4*

| 2-Theta | d(A) | BG | Height | I % | Area | I % | FWHM |
|---|---|---|---|---|---|---|---|
| 4.981 | 17.7282 | 270 | 684 | 15.8 | 12231 | 12.6 | 0.304 |
| 7.22 | 12.2329 | 244 | 3416 | 79 | 65744 | 67.8 | 0.327 |
| 8.459 | 10.4447 | 202 | 335 | 7.7 | 4814 | 5 | 0.244 |
| 10.56 | 8.3707 | 219 | 629 | 14.5 | 10739 | 11.1 | 0.29 |
| 11.42 | 7.7419 | 240 | 203 | 4.7 | 2908 | 3 | 0.244 |
| 12.42 | 7.1209 | 221 | 614 | 14.2 | 11445 | 11.8 | 0.317 |
| 13.019 | 6.7947 | 238 | 59 | 1.4 | 423 | 0.4 | 0.122 |
| 14.26 | 6.2057 | 227 | 1052 | 24.3 | 20787 | 21.4 | 0.336 |
| 16.318 | 5.4274 | 409 | 85 | 2 | 665 | 0.7 | 0.133 |
| 16.722 | 5.2973 | 332 | 496 | 11.5 | 8980 | 9.3 | 0.308 |
| 17.199 | 5.1515 | 393 | 226 | 5.2 | 3448 | 3.6 | 0.259 |
| 17.82 | 4.9733 | 402 | 725 | 16.8 | 8502 | 8.8 | 0.199 |
| 18.98 | 4.672 | 432 | 1352 | 31.3 | 36895 | 38.1 | 0.464 |
| 19.44 | 4.5623 | 439 | 990 | 22.9 | 28546 | 29.4 | 0.49 |
| 20.46 | 4.3371 | 444 | 119 | 2.8 | 1163 | 1.2 | 0.166 |
| 21.58 | 4.1144 | 458 | 1982 | 45.8 | 71568 | 73.8 | 0.614 |
| 22.22 | 3.9974 | 837 | 4325 | 100 | 96937 | 100 | 0.381 |
| 23.16 | 3.8373 | 758 | 114 | 2.6 | 1085 | 1.1 | 0.162 |
| 24.42 | 3.6421 | 522 | 2466 | 57 | 48977 | 50.5 | 0.338 |
| 25.679 | 3.4663 | 590 | 252 | 5.8 | 5211 | 5.4 | 0.352 |
| 26.5 | 3.3607 | 470 | 671 | 15.5 | 23177 | 23.9 | 0.587 |
| 26.95 | 3.3056 | 356 | 313 | 7.2 | 3645 | 3.8 | 0.198 |
| 28.118 | 3.1709 | 385 | 255 | 5.9 | 5045 | 5.2 | 0.336 |
| 29.9 | 2.9858 | 360 | 383 | 8.9 | 13112 | 13.5 | 0.582 |
| 30.421 | 2.9359 | 346 | 239 | 5.5 | 5602 | 5.8 | 0.398 |
| 31.779 | 2.8134 | 293 | 336 | 7.8 | 5905 | 6.1 | 0.299 |
| 32.618 | 2.743 | 267 | 124 | 2.9 | 1934 | 2 | 0.265 |

F. Forms 5 and 5*

Figure 5A:
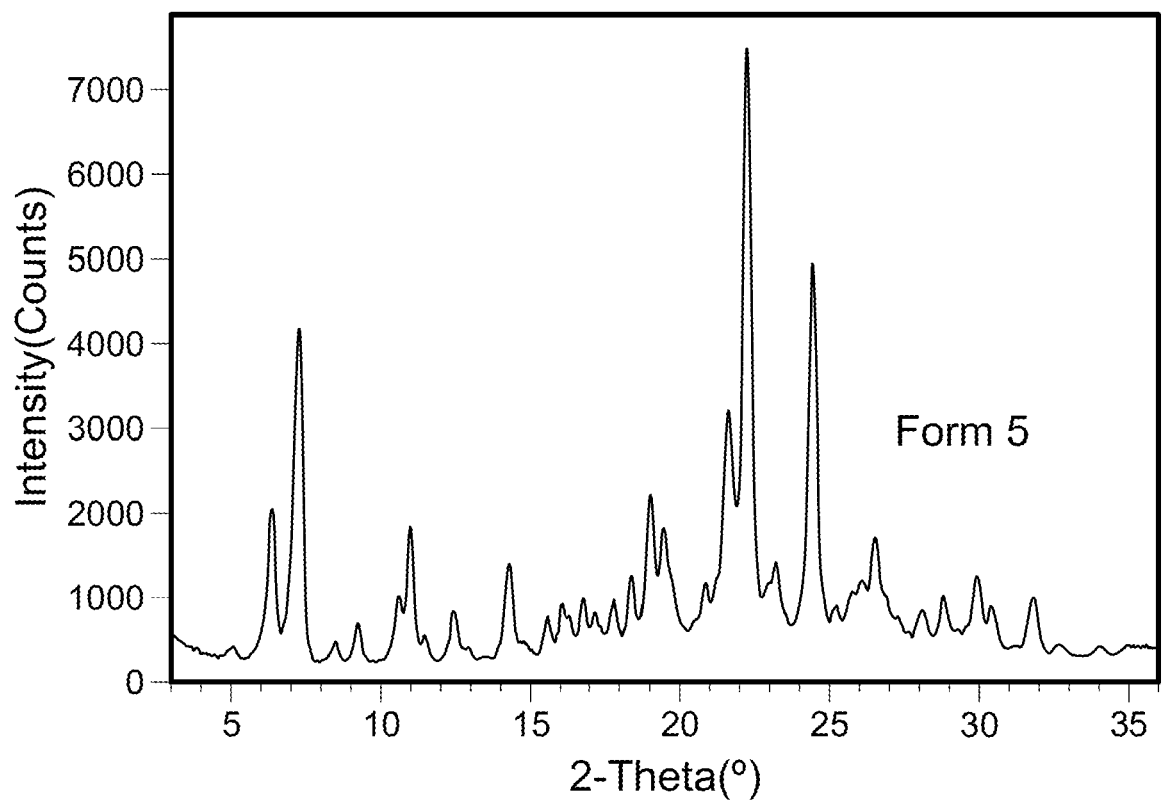
FIGS. 5A-5D are scans of polymorph Forms 5 and 5* of the compound of Formula (I).
Figure 5B:
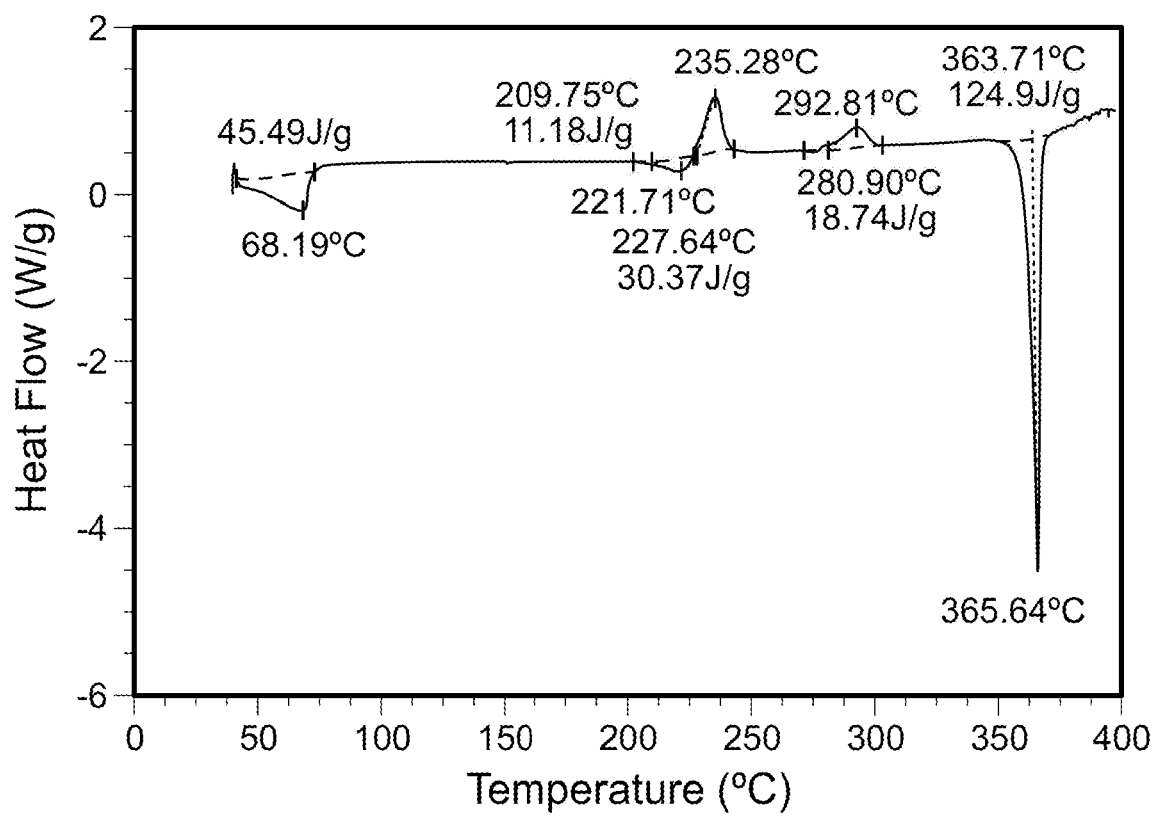
Figure 5C:
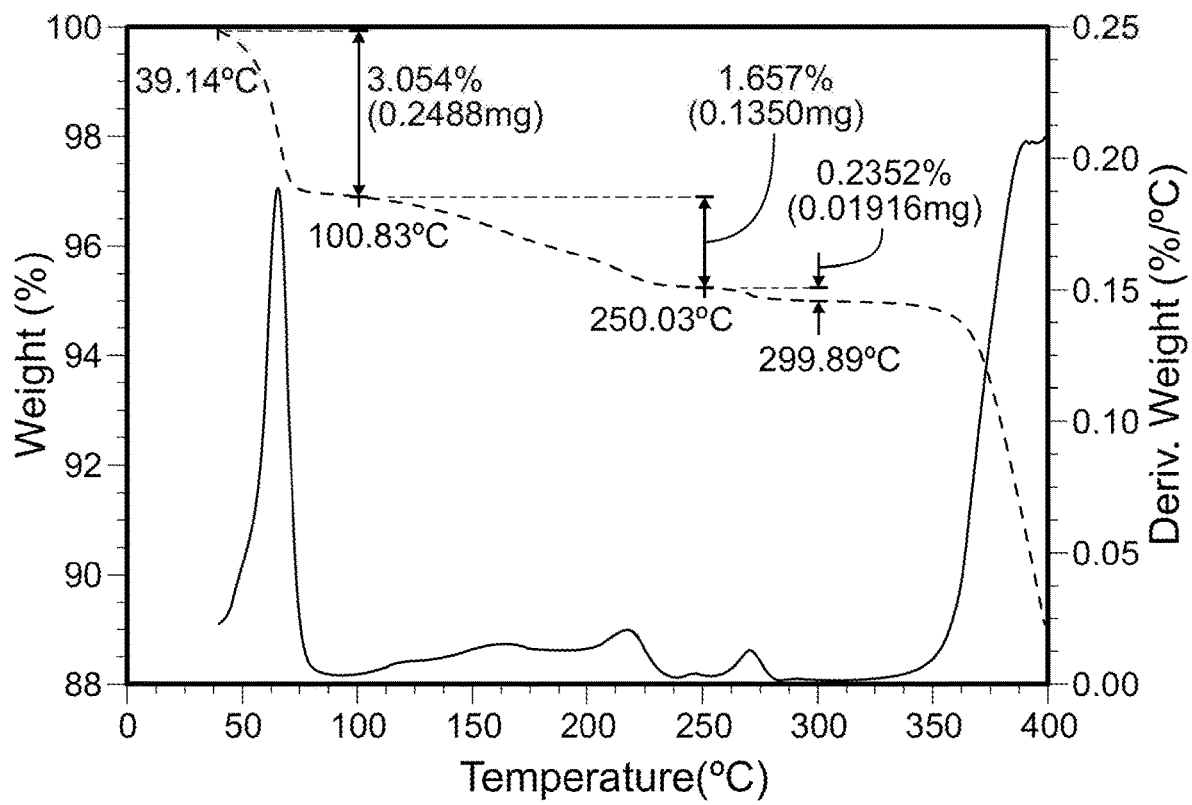
Figure 5D:
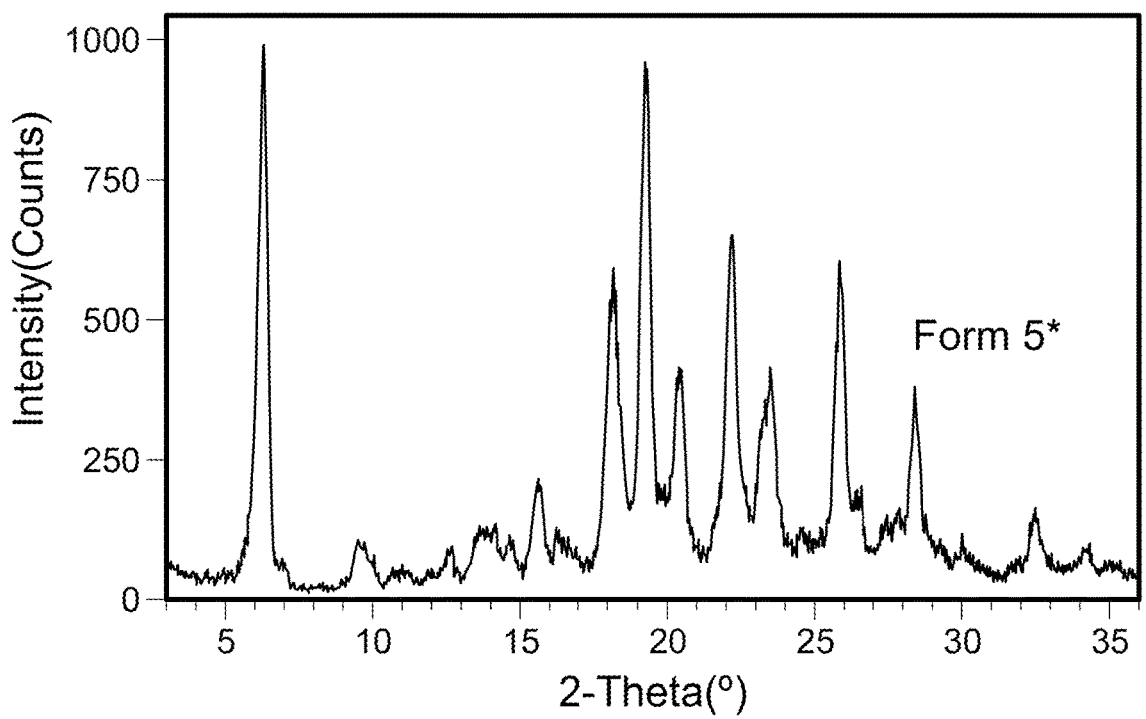

The experiments that generated Forms 5 and 5* are shown in Table 16, below. XRD scans of Forms 5 and 5* were taken (FIGS. 5A and 5D, respectively). The XRD peaks of Form 5 are shown in Table 17, below. A DSC scan of Form 5 was also performed and showed a wide endotherm between 50° C.-100° C., and multiple endotherms and exotherms before melting at 363° C. (FIG. 5B).

A TGA scan of Form 5 solid showed a 3.1% weight loss before 100° C., followed by a 1.7% weight loss between 100° C. and 250° C. (FIG. 5C).

Forms 5 and 5* were obtained from slurrying Form 12 in MtBE at RT and 50° C. Wet solid showed Form 5*, while dry solid indicated Form 5.

TABLE 16

Summary of experiments that generated Forms 5 and 5*

| Form | Solvent | Temperature | Wet | Dry |
|---|---|---|---|---|
| Form 5 | MtBE | RT | Form 5* | Form 5 |
| Form 5* | MtBE | RT | Form 5* | Form 5 |
|  | MtBE | 50° C. | Form 5* | Form 4 |

TABLE 17

XRD peaks of Form 5

| 2-Theta | d(A) | BG | Height | I % | Area | I % | FWHM |
|---|---|---|---|---|---|---|---|
| 5.098 | 17.3185 | 260 | 155 | 2.4 | 2464 | 2.1 | 0.27 |
| 6.38 | 13.8428 | 256 | 1778 | 27.7 | 34733 | 29.6 | 0.332 |
| 7.28 | 12.1332 | 214 | 3964 | 61.6 | 78158 | 66.5 | 0.335 |
| 8.518 | 10.3715 | 234 | 241 | 3.7 | 3170 | 2.7 | 0.224 |
| 9.24 | 9.5627 | 227 | 472 | 7.3 | 6614 | 5.6 | 0.238 |
| 10.639 | 8.3083 | 266 | 765 | 11.9 | 20508 | 17.5 | 0.456 |
| 11.019 | 8.0226 | 242 | 1596 | 24.8 | 37620 | 32 | 0.401 |
| 11.483 | 7.6998 | 398 | 133 | 2.1 | 949 | 0.8 | 0.121 |
| 12.44 | 7.1091 | 246 | 584 | 9.1 | 11910 | 10.1 | 0.347 |
| 12.94 | 6.8358 | 249 | 152 | 2.4 | 4189 | 3.6 | 0.469 |
| 14.301 | 6.1883 | 279 | 1114 | 17.3 | 22226 | 18.9 | 0.339 |
| 14.839 | 5.9648 | 300 | 167 | 2.6 | 5989 | 5.1 | 0.61 |
| 15.581 | 5.6827 | 404 | 376 | 5.8 | 4045 | 3.4 | 0.183 |
| 16.08 | 5.5073 | 452 | 459 | 7.1 | 9013 | 7.7 | 0.334 |
| 16.357 | 5.4146 | 509 | 260 | 4 | 11967 | 10.2 | 0.782 |
| 16.839 | 5.2606 | 521 | 473 | 7.4 | 7195 | 6.1 | 0.259 |
| 17.254 | 5.1351 | 550 | 258 | 4 | 4373 | 3.7 | 0.288 |
| 17.839 | 4.968 | 562 | 414 | 6.4 | 4207 | 3.6 | 0.173 |
| 18.439 | 4.8078 | 667 | 590 | 9.2 | 5946 | 5.1 | 0.171 |
| 19.059 | 4.6527 | 616 | 1603 | 24.9 | 35964 | 30.6 | 0.381 |
| 19.5 | 4.5486 | 671 | 1163 | 18.1 | 30384 | 25.9 | 0.444 |
| 20.882 | 4.2506 | 850 | 305 | 4.7 | 2860 | 2.4 | 0.159 |
| 21.679 | 4.0959 | 935 | 2272 | 35.3 | 66194 | 56.4 | 0.495 |
| 22.28 | 3.9867 | 1083 | 6430 | 100 | 117449 | 100 | 0.311 |
| 23.221 | 3.8273 | 856 | 564 | 8.8 | 9429 | 8 | 0.284 |
| 24.461 | 3.6361 | 697 | 4250 | 66.1 | 74709 | 63.6 | 0.299 |
| 25.276 | 3.5206 | 726 | 170 | 2.6 | 1349 | 1.1 | 0.135 |
| 26.081 | 3.4137 | 756 | 442 | 6.9 | 17518 | 14.9 | 0.674 |
| 26.52 | 3.3582 | 689 | 1014 | 15.8 | 34615 | 29.5 | 0.58 |
| 28.139 | 3.1686 | 528 | 306 | 4.8 | 4846 | 4.1 | 0.269 |
| 28.821 | 3.0952 | 533 | 463 | 7.2 | 7067 | 6 | 0.259 |
| 29.94 | 2.9819 | 499 | 755 | 11.7 | 15565 | 13.3 | 0.35 |
| 30.458 | 2.9324 | 435 | 467 | 7.3 | 9861 | 8.4 | 0.359 |
| 31.86 | 2.8065 | 343 | 648 | 10.1 | 13697 | 11.7 | 0.359 |
| 32.642 | 2.741 | 314 | 125 | 1.9 | 2403 | 2 | 0.327 |
| 34.002 | 2.6344 | 298 | 123 | 1.9 | 1956 | 1.7 | 0.27 |

G. Form 6

Figure 6A:
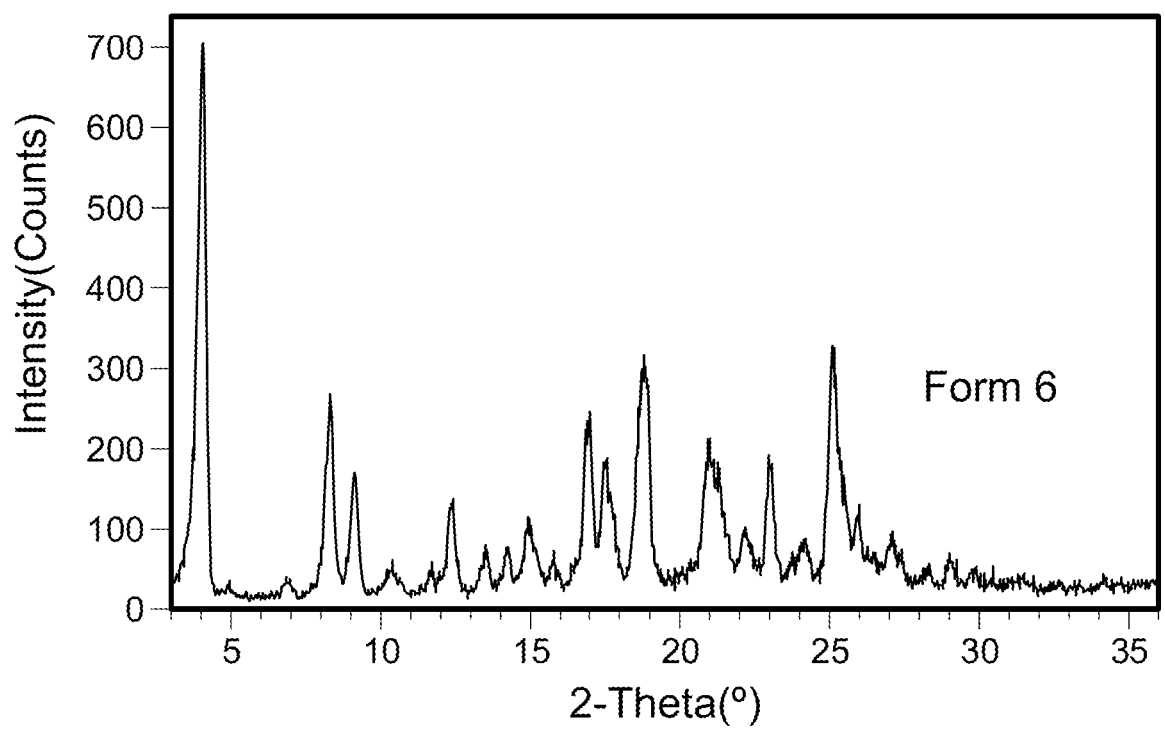
FIGS. 6A and 6B are scans of polymorph Form 6 of the compound of Formula (I).
Figure 6B:
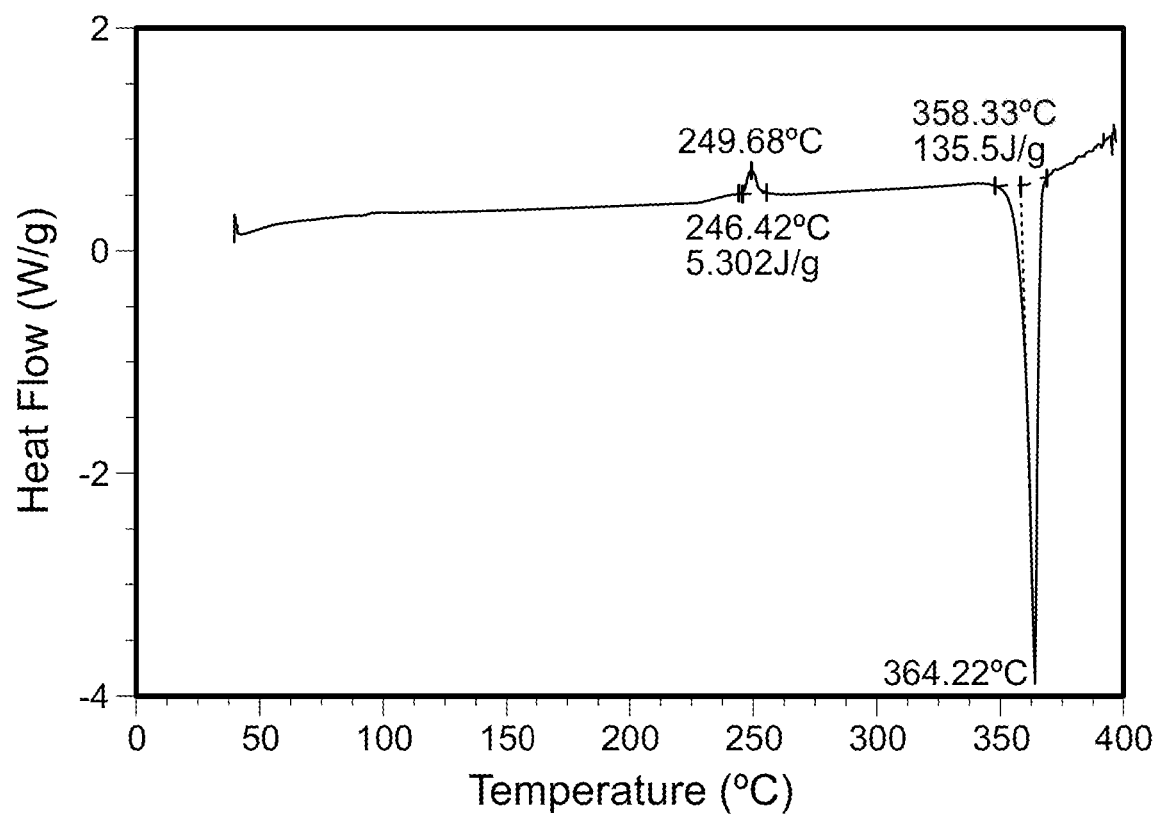

The experiments that generated Form 6 are shown in Table 18, below. XRD and DSC scans of Form 6 were taken (FIGS. 6A and 6B, respectively). According to the DSC scan, the solid showed a small exotherm at 250° C. and a sharp melting endotherm at 358° C.

Form 6 was obtained by slurrying starting material in IPA and IPA/5% water at RT and 50° C.

TABLE 18

Summary of experiments that generated Form 6

| Form | Solvent | Temperature | Wet | Dry |
|---|---|---|---|---|
| Form 6 | IPA | RT | Form 6 | Form 6 |
| | IPA | 50° C. | Form 6 | Form 6 |
| | IPA/water | RT | Form 6 | Form 6 |
| | IPA/water | 50° C. | Form 6 | Form 6 |

*Amount of water in binary solvents is 5%

H. Form 7

Figure 7A:
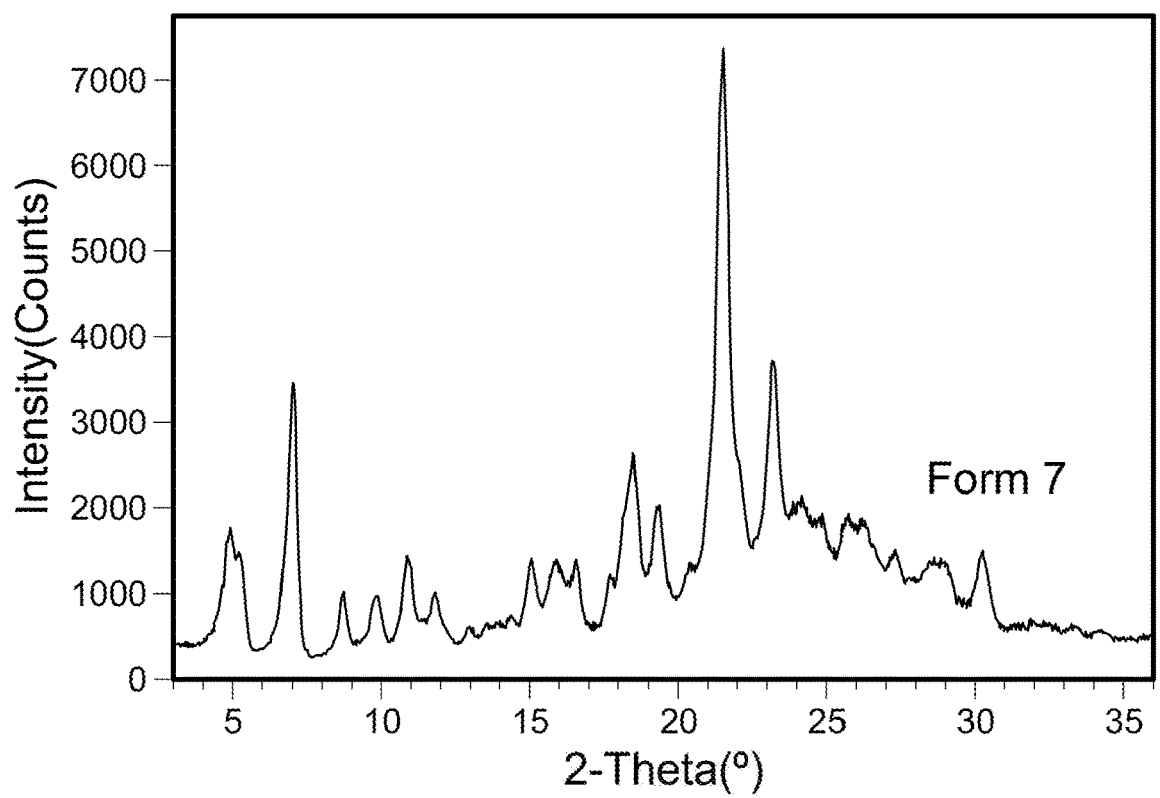
FIGS. 7A-7C are scans of polymorph Form 7 of the compound of Formula (I).
Figure 7B:
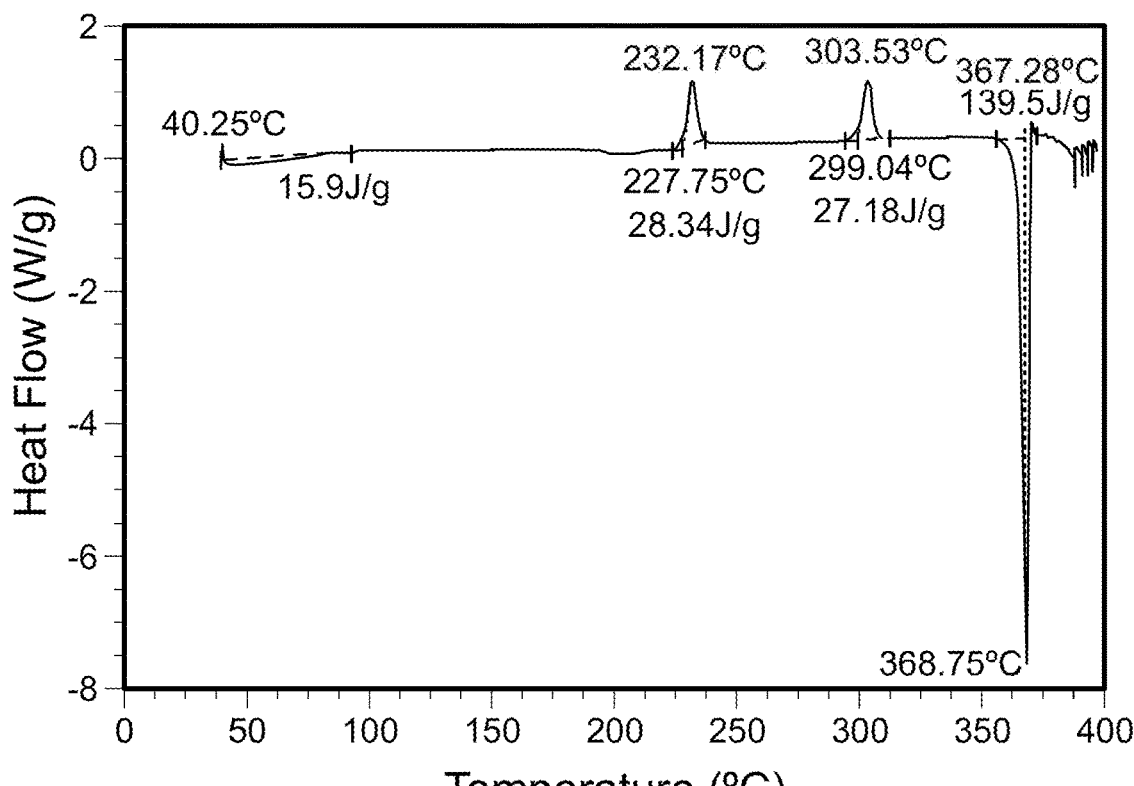

The experiments that generated Form 7 are shown in Table 19, below. XRD and DSC scans of Form 7 were taken (FIGS. 7A and 7B, respectively). The XRD peaks of Form 7 are shown in Table 20, below. According to the DSC scan, the solid showed two exotherms at 227° C. and 299° C., followed by a melting endotherm at 365° C. Form 7 showed low degree of crystallinity on XRD. The double exotherm on the DSC scans may be associated with the low crystallinity observed on the XRD scan.

Figure 7C:
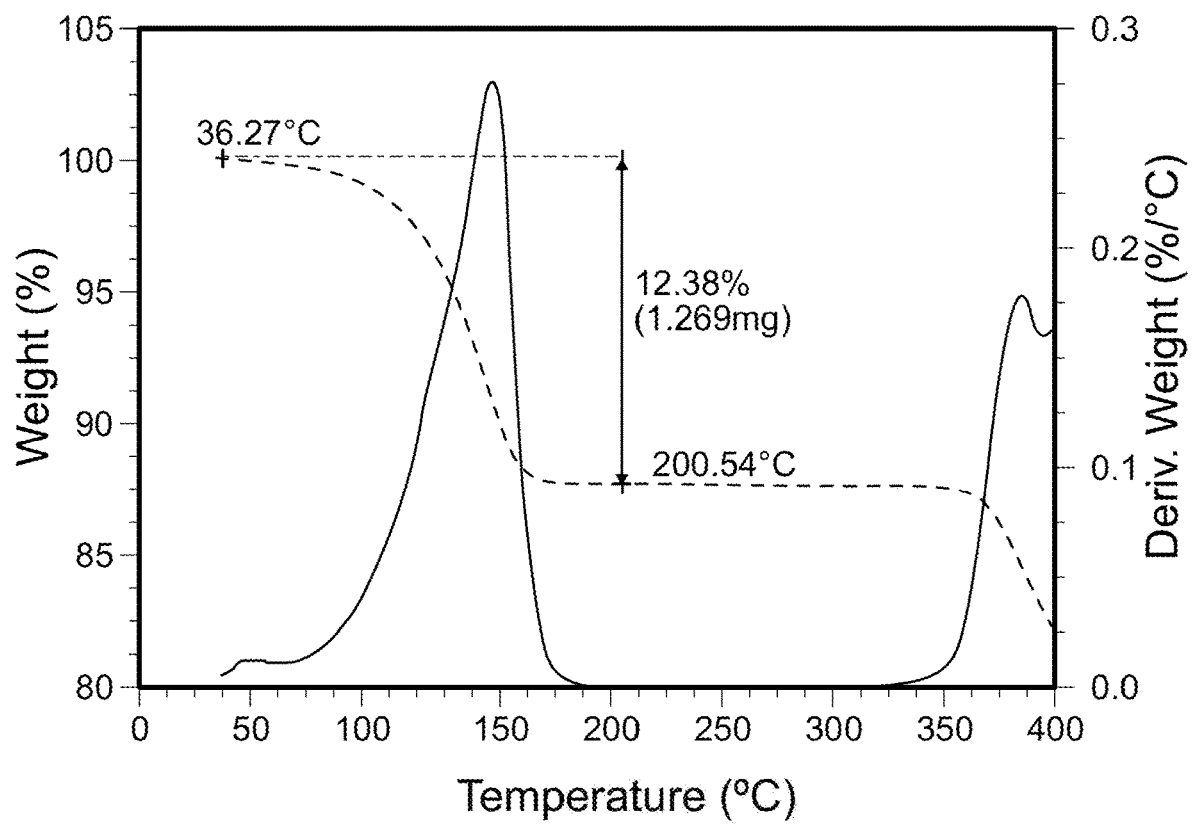

A TGA scan of Form 7 solid showed a 12% weight loss before 200° C. (FIG. 7C).

Form 7 was obtained from MEK and MEK/5% water at RT and 50° C.

TABLE 19

Summary of experiments that generated Form 7

| Form | Solvent | Temperature | Wet | Dry |
|---|---|---|---|---|
| Form 7 | MEK | RT | Form 7 | Form 7 |
| | MEK | 50° C. | Form 7 | Form 7 |
| | MEK/water | RT | Form 7 | Form 7 |
| | MEK/water | 50° C. | Form 7 | Form 7 |

*Amount of water in binary solvents is 5%

TABLE 20

XRD peaks of Form 7

| 2-Theta | d(A) | BG | Height | I % | Area | I % | FWHM |
|---|---|---|---|---|---|---|---|
| 4.94 | 17.8745 | 362 | 1384 | 23.3 | 50829 | 29.2 | 0.624 |
| 7.06 | 12.5111 | 286 | 3171 | 53.3 | 69159 | 39.8 | 0.371 |
| 8.759 | 10.0876 | 370 | 628 | 10.6 | 9606 | 5.5 | 0.26 |
| 9.9 | 8.9272 | 429 | 537 | 9 | 11110 | 6.4 | 0.352 |
| 10.881 | 8.1241 | 546 | 879 | 14.8 | 16425 | 9.4 | 0.318 |
| 11.84 | 7.4681 | 588 | 413 | 6.9 | 7187 | 4.1 | 0.296 |
| 12.997 | 6.8061 | 463 | 135 | 2.3 | 1351 | 0.8 | 0.17 |
| 14.404 | 6.1442 | 604 | 126 | 2.1 | 3331 | 1.9 | 0.449 |
| 15.1 | 5.8626 | 791 | 596 | 10 | 8819 | 5.1 | 0.252 |
| 15.92 | 5.5622 | 792 | 593 | 10 | 24460 | 14.1 | 0.701 |
| 16.581 | 5.3421 | 739 | 641 | 10.8 | 14919 | 8.6 | 0.396 |
| 18.5 | 4.7919 | 1066 | 1555 | 26.1 | 43174 | 24.8 | 0.472 |
| 19.4 | 4.5717 | 1087 | 930 | 15.6 | 17521 | 10.1 | 0.32 |
| 20.382 | 4.3535 | 1178 | 154 | 2.6 | 867 | 0.5 | 0.096 |
| 21.56 | 4.1183 | 1424 | 5949 | 100 | 173972 | 100 | 0.497 |
| 22.098 | 4.0192 | 1830 | 692 | 11.6 | 17678 | 10.2 | 0.434 |
| 23.22 | 3.8275 | 1749 | 1971 | 33.1 | 42151 | 24.2 | 0.364 |
| 24.203 | 3.6743 | 1776 | 351 | 5.9 | 11935 | 6.9 | 0.578 |
| 24.884 | 3.5751 | 1658 | 271 | 4.6 | 2378 | 1.4 | 0.149 |
| 25.759 | 3.4556 | 1416 | 492 | 8.3 | 19894 | 11.4 | 0.687 |
| 26.3 | 3.3858 | 1335 | 499 | 8.4 | 23631 | 13.6 | 0.805 |
| 27.34 | 3.2594 | 1192 | 307 | 5.2 | 4494 | 2.6 | 0.249 |
| 28.641 | 3.1142 | 1004 | 382 | 6.4 | 18030 | 10.4 | 0.802 |
| 29.078 | 3.0684 | 979 | 324 | 5.4 | 14234 | 8.2 | 0.747 |
| 30.28 | 2.9492 | 759 | 711 | 12 | 16004 | 9.2 | 0.383 |
| 31.985 | 2.7959 | 551 | 111 | 1.9 | 4816 | 2.8 | 0.738 |
| 33.402 | 2.6804 | 509 | 102 | 1.7 | 2060 | 1.2 | 0.343 |
| 34.24 | 2.6167 | 474 | 92 | 1.5 | 1901 | 1.1 | 0.351 |

I. Form 8

Figure 8A:
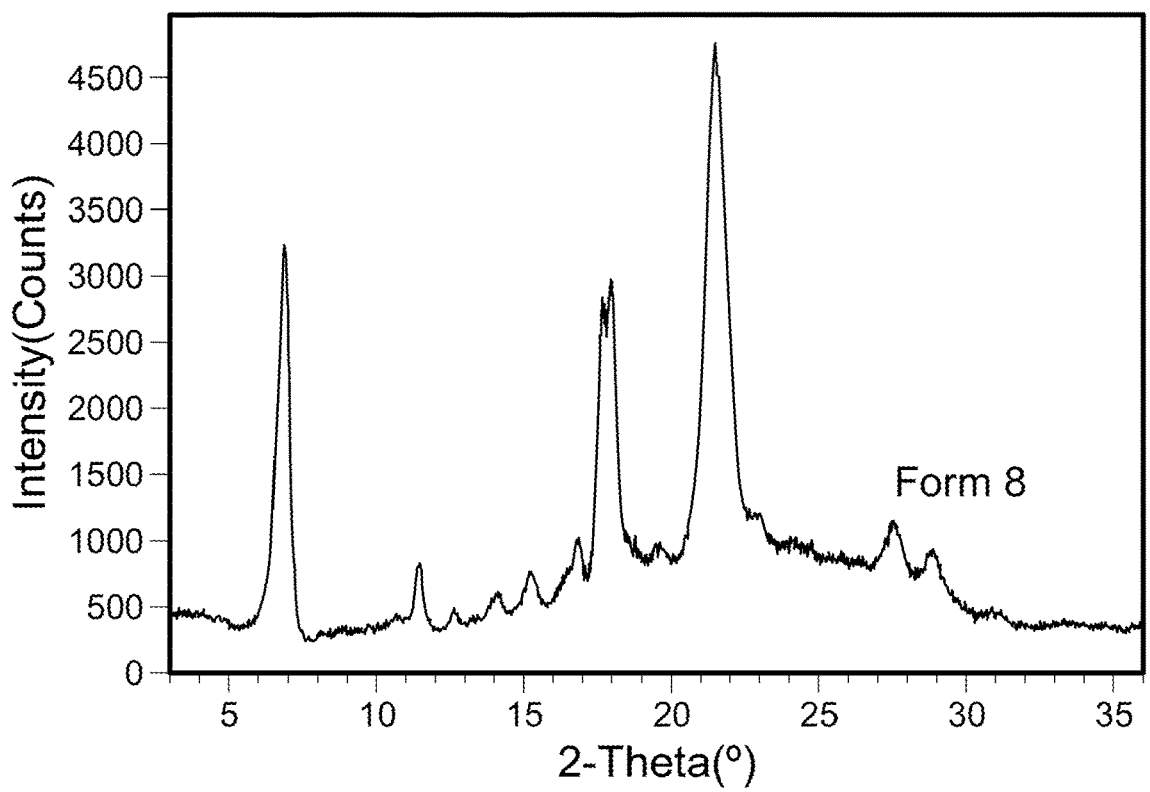
FIGS. 8A-8C are scans of polymorph Form 8 of the compound of Formula (I).
Figure 8B:
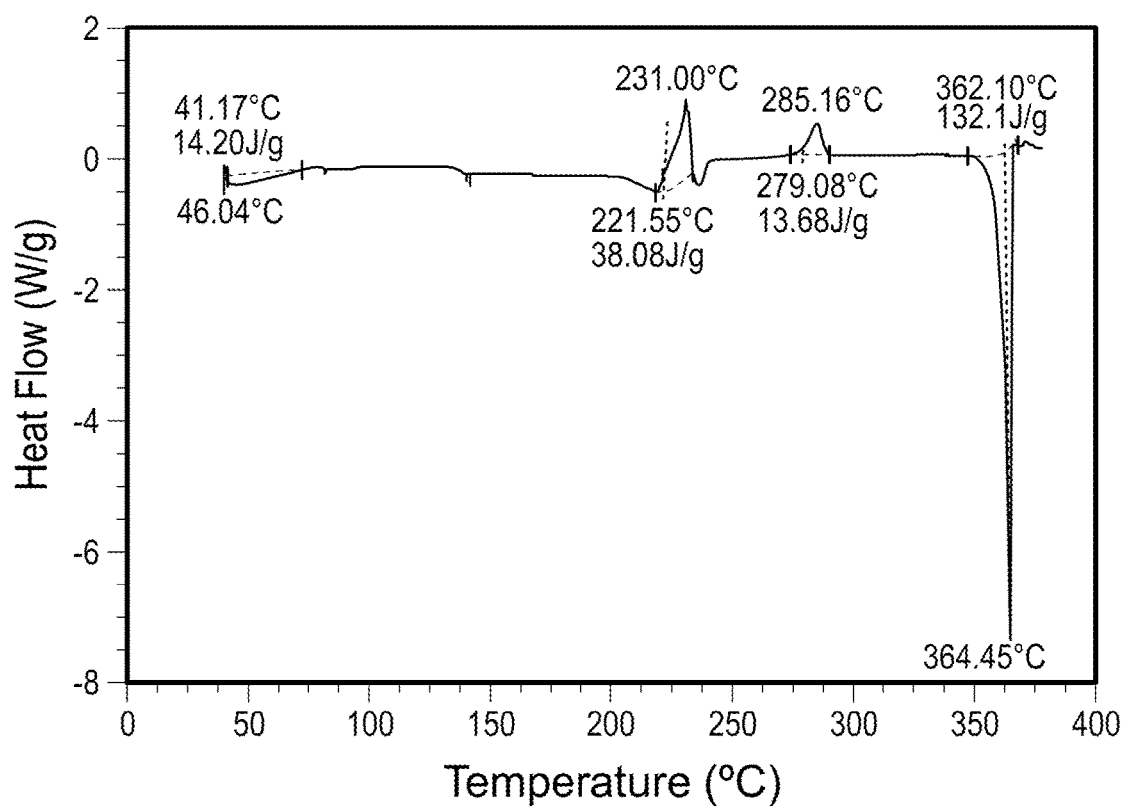

The experiments that generated Form 8 are shown in Table 21, below. XRD and DSC scans of Form 8 were taken (FIGS. 8A and 8B, respectively). The XRD peaks of Form 8 are shown in Table 22, below. According to the DSC scan, the solid showed two endotherms at 205° C. and 231° C., followed by an exotherm at 279° C., followed by a melting endotherm at 362° C. Form 8 showed a low degree of crystallinity on the XRD scan. The double exotherm on the DSC scan may confirm the low crystallinity seen on XRD (low crystalline material convert to higher crystallinity solid).

Figure 8C:
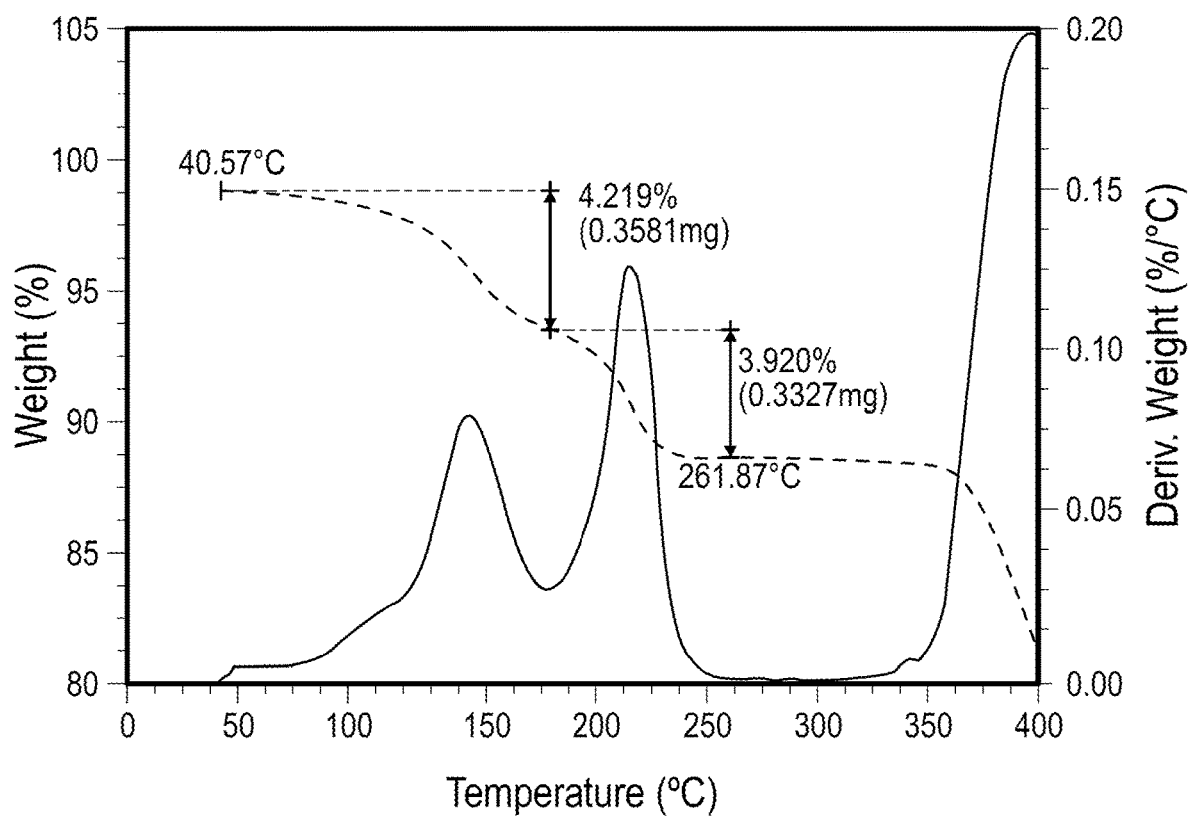

A TGA scan of Form 8 showed a 4.2% weight loss before 190° C., followed by a 3.9% weight loss between 190° C. and 261° C. (FIG. 8C).

Form 8 was obtained from MIBK at RT and 50° C. MIBK/5% water reslurry does not produce the same form.

TABLE 21

Summary of experiments that generated Form 8

| Form | Solvent | Temperature | Wet | Dry |
|---|---|---|---|---|
| Form 8 | MIBK | RT | Form 8 | Form 8 |
| | MIBK | 50° C. | Form 8 | Form 8 |

TABLE 22

XRD peaks of Form 8

| 2-Theta | d(A) | BG | Height | I % | Area | I % | FWHM |
|---|---|---|---|---|---|---|---|
| 6.88 | 12.8368 | 318 | 2815 | 80.8 | 71578 | 51.7 | 0.432 |
| 10.699 | 8.2619 | 380 | 70 | 2 | 722 | 0.5 | 0.175 |
| 11.48 | 7.7016 | 344 | 466 | 13.4 | 9513 | 6.9 | 0.347 |
| 12.66 | 6.9866 | 348 | 136 | 3.9 | 1759 | 1.3 | 0.22 |
| 14.16 | 6.2496 | 435 | 166 | 4.8 | 3298 | 2.4 | 0.338 |
| 15.259 | 5.8017 | 483 | 269 | 7.7 | 6267 | 4.5 | 0.396 |
| 16.879 | 5.2484 | 669 | 333 | 9.6 | 7638 | 5.5 | 0.39 |
| 17.681 | 5.0121 | 780 | 1959 | 56.2 | 76035 | 54.9 | 0.66 |
| 19.618 | 4.5213 | 833 | 134 | 3.8 | 2110 | 1.5 | 0.268 |
| 21.5 | 4.1296 | 1116 | 3484 | 100 | 138450 | 100 | 0.676 |
| 24.244 | 3.6682 | 899 | 99 | 2.8 | 2643 | 1.9 | 0.454 |
| 27.559 | 3.234 | 753 | 366 | 10.5 | 11182 | 8.1 | 0.519 |
| 28.881 | 3.0889 | 636 | 279 | 8 | 8137 | 5.9 | 0.496 |
| 30.878 | 2.8935 | 403 | 87 | 2.5 | 1890 | 1.4 | 0.369 |
| 31.221 | 2.8624 | 386 | 69 | 2 | 1898 | 1.4 | 0.468 |

J. Form 9

Figure 9A:
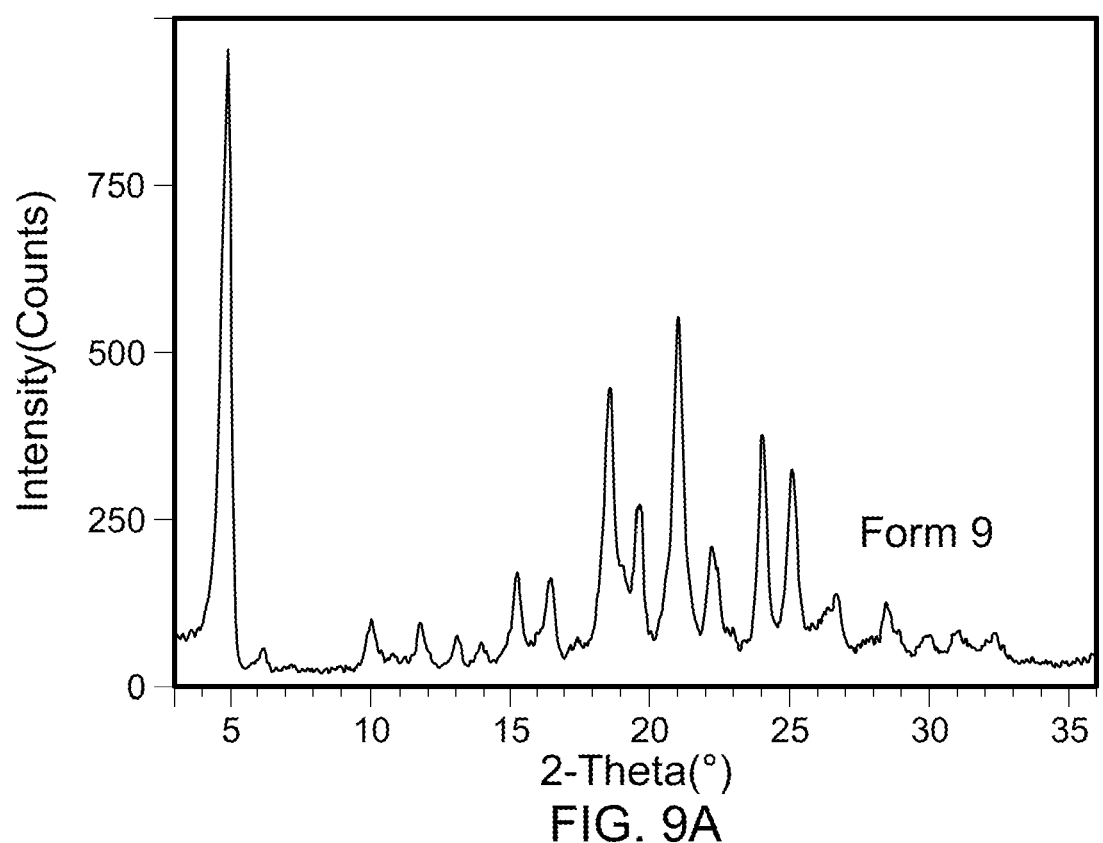
FIGS. 9A-9D are scans of polymorph Form 9 of the compound of Formula (I).
Figure 9B:
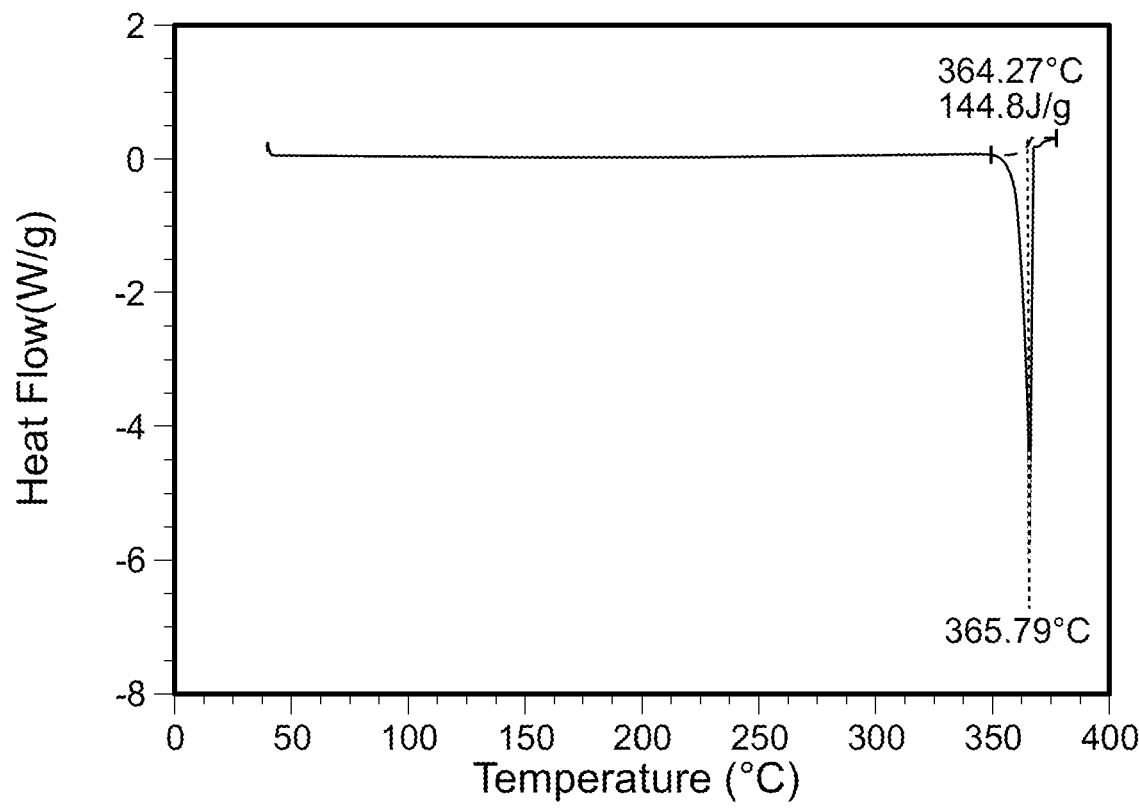

The experiments that generated Form 9 are shown in Table 23, below. XRD and DSC scans of Form 9 were taken (FIGS. 9A and 9B, respectively). The XRD peaks of Form 9 are shown in Table 24, below. According to the DSC scan, the solid showed a single melting endotherm at 364° C. Form 9 has a primitive monoclinic crystal structure with the approximate dimensions: a [Å]=17.135, b [Å]=14.342, c [Å]=10.186; α(deg)=90, β(deg)=95.99, γ(deg)=90 and an approximate volume cell of [Å$^3$/cell]=2,489.5 and a space group defined as P2$_1$/c (14).

Figure 9C:
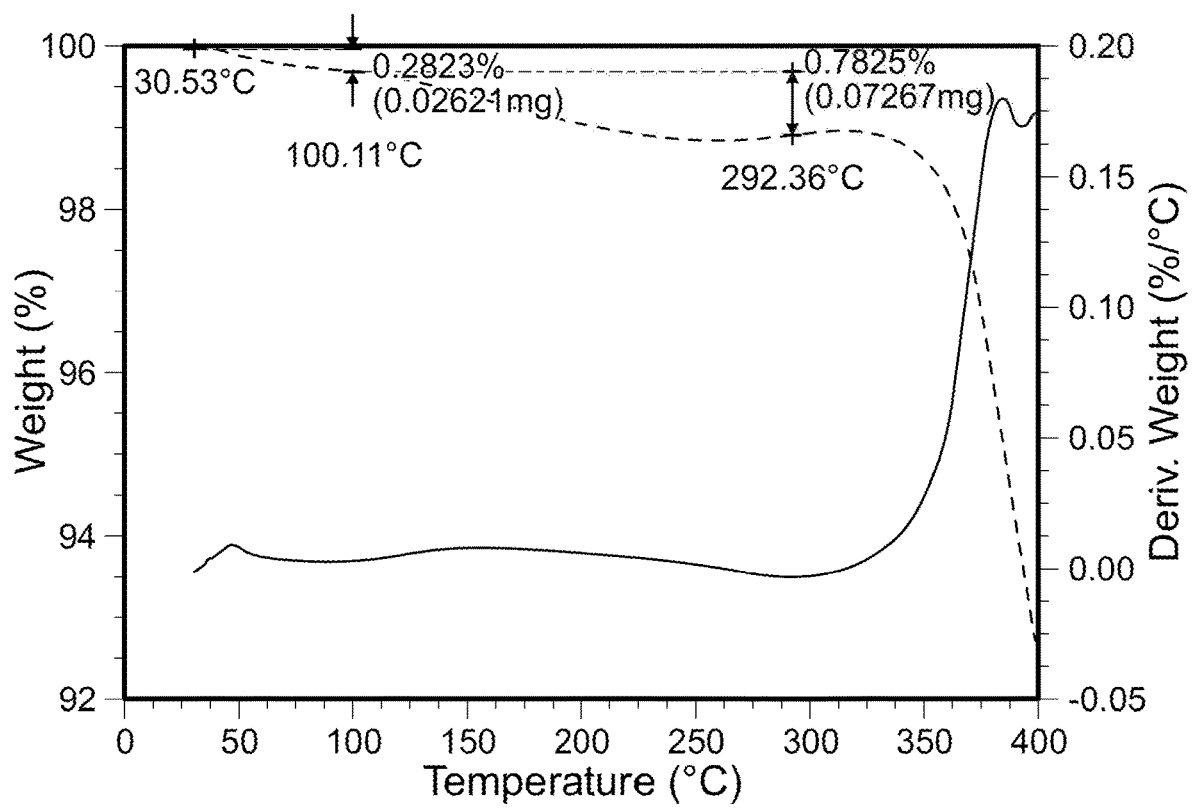

A TGA scan of Form 9 showed a 0.28% weight loss before 100° C. (FIG. 9C).

Other forms, when heated to just before melting at 364° C., seemed to convert to Form 9. This has been confirmed for Forms 1 and 2.

Figure 9D:
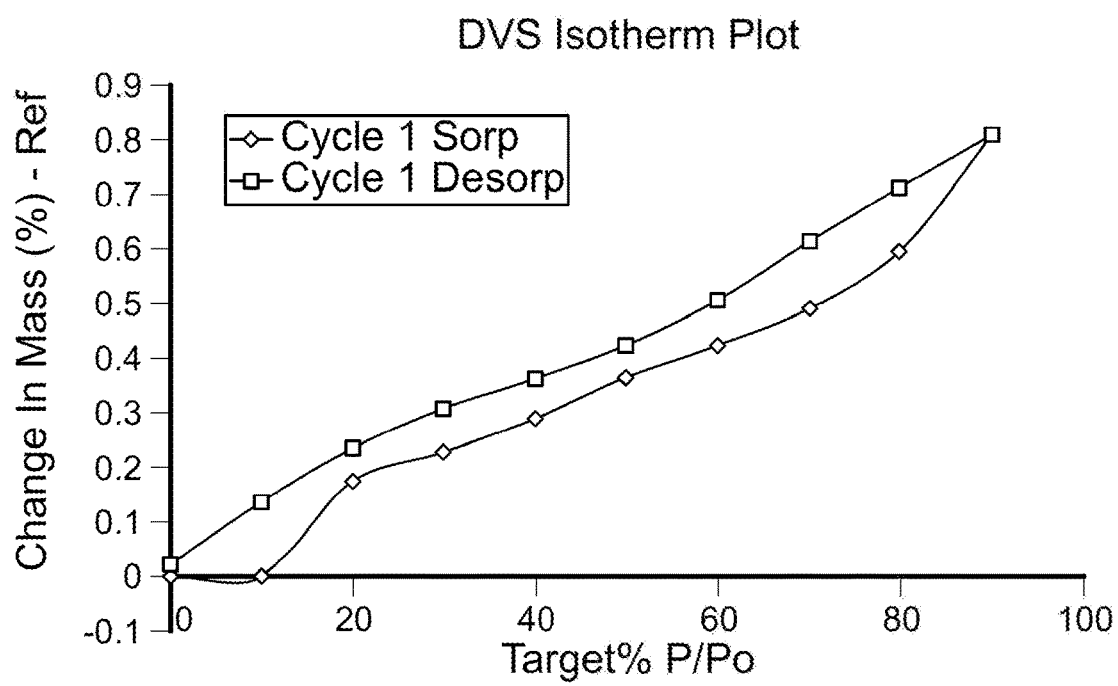

A DVS scan of Form 9 showed a 0.8% water absorption at 90% RH. Form 9 did not change its form before and after the DVS scan (FIG. 9D).

TABLE 23

Summary of experiments that generated Form 9

| Form | Solvent | Temperature | Wet | Dry |
|---|---|---|---|---|
| Form 9 | n-Butanol | RT | Form 9 | Form 9 |
|  | IPAc | 50° C. | Form 9 | Form 9 |
|  | n-Butyl acetate | 50° C. | Form 9 | Form 9 |
|  | n-Butanol | 50° C. | Form 9 | Form 9 |
|  | EtOH/water | 50° C. | Form 9 | Form 9 |
|  | n-Propanol/water | 50° C. | Form 9 | Form 9 |

*Amount of water in binary solvents is 5%

TABLE 24

XRD peaks of Form 9

| 2-Theta | d(A) | BG | Height | I % | Area | I % | FWHM |
|---|---|---|---|---|---|---|---|
| 4.94 | 17.8746 | 21 | 895 | 100 | 23398 | 100 | 0.444 |
| 6.26 | 14.1076 | 21 | 34 | 3.8 | 513 | 2.2 | 0.257 |
| 10.099 | 8.7516 | 28 | 66 | 7.4 | 1172 | 5 | 0.302 |
| 11.883 | 7.4413 | 30 | 46 | 5.1 | 828 | 3.5 | 0.306 |
| 13.16 | 6.7221 | 27 | 37 | 4.1 | 400 | 1.7 | 0.184 |
| 15.341 | 5.771 | 39 | 71 | 7.9 | 1541 | 6.6 | 0.369 |
| 16.518 | 5.3622 | 40 | 93 | 10.4 | 1728 | 7.4 | 0.316 |
| 18.622 | 4.7608 | 46 | 260 | 29.1 | 7069 | 30.2 | 0.462 |
| 19.74 | 4.4938 | 80 | 138 | 15.4 | 1937 | 8.3 | 0.239 |
| 21.101 | 4.2068 | 64 | 342 | 38.2 | 8314 | 35.5 | 0.413 |
| 22.42 | 3.9622 | 56 | 77 | 8.6 | 1721 | 7.4 | 0.38 |
| 24.1 | 3.6897 | 58 | 198 | 22.1 | 3904 | 16.7 | 0.335 |
| 25.2 | 3.5311 | 63 | 157 | 17.5 | 3615 | 15.5 | 0.391 |
| 26.897 | 3.312 | 46 | 44 | 4.9 | 1307 | 5.6 | 0.505 |
| 28.577 | 3.121 | 35 | 54 | 6 | 1754 | 7.5 | 0.552 |
| 29.884 | 2.9874 | 32 | 30 | 3.4 | 477 | 2 | 0.254 |
| 30.926 | 2.8891 | 35 | 32 | 3.6 | 682 | 2.9 | 0.341 |

K. Forms 10 and 10*

Figure 10A:
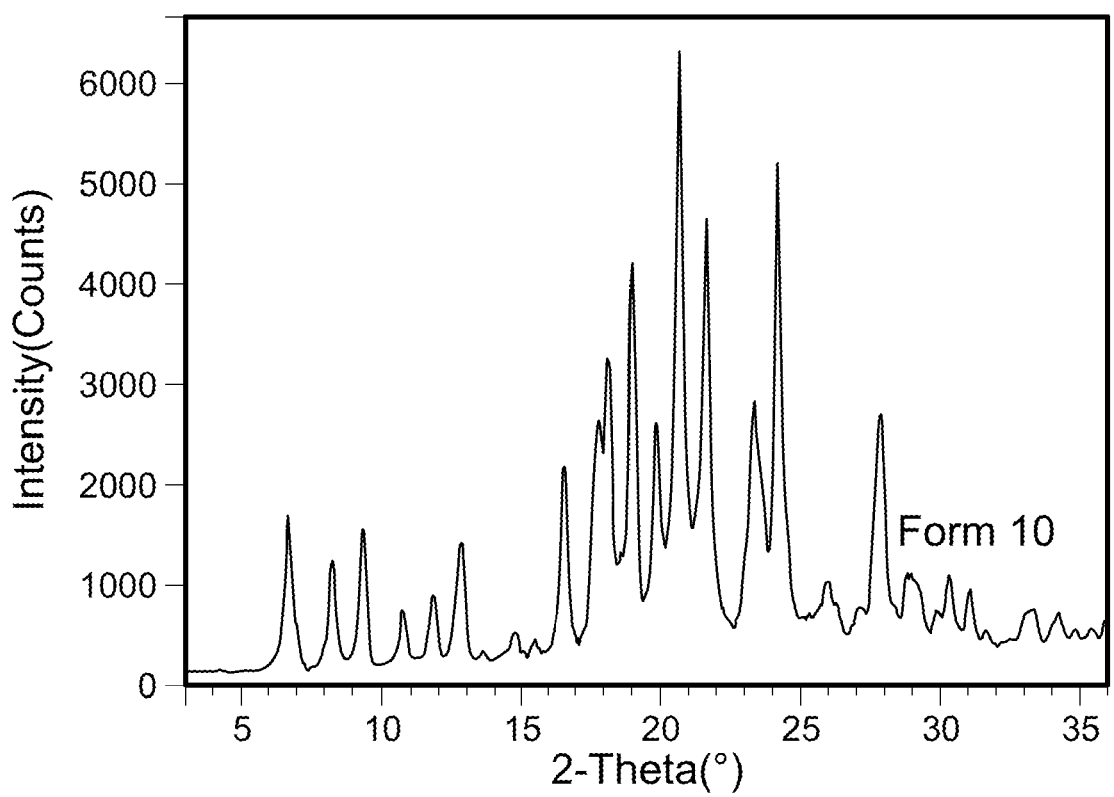
FIGS. 10A-10E are scans of polymorph Forms 10 and 10* of the compound of Formula (I).
Figure 10B:
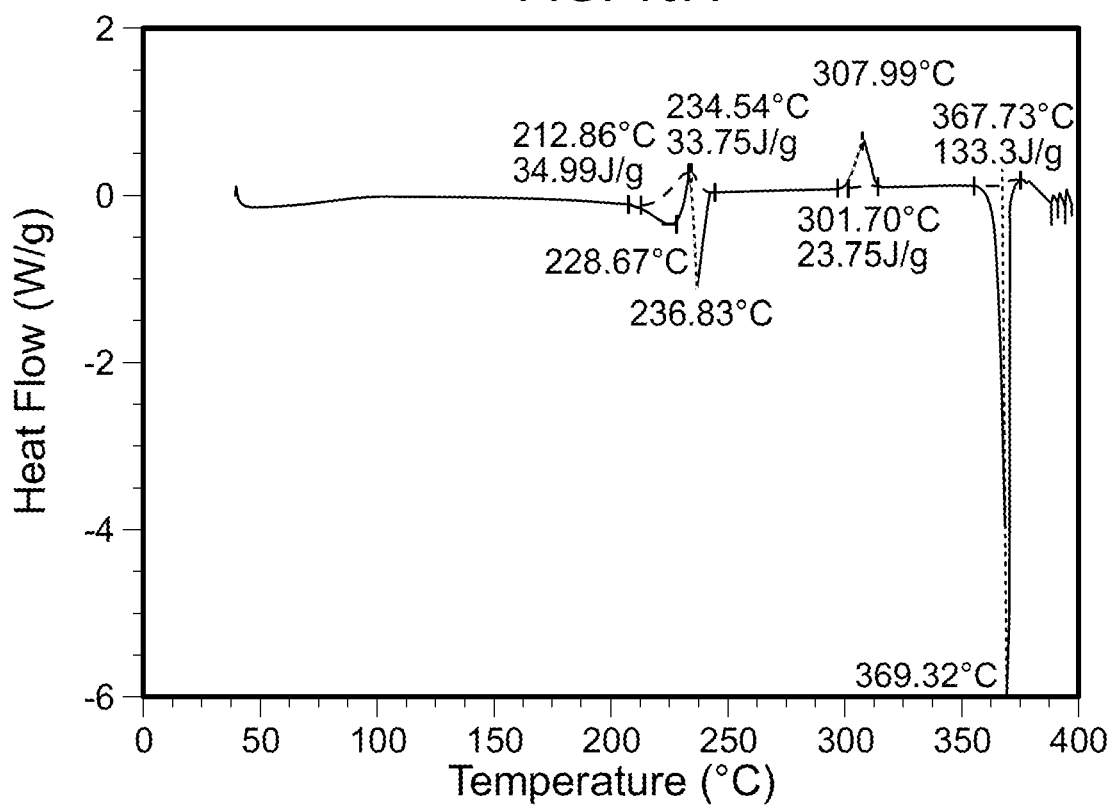
Figure 10C:
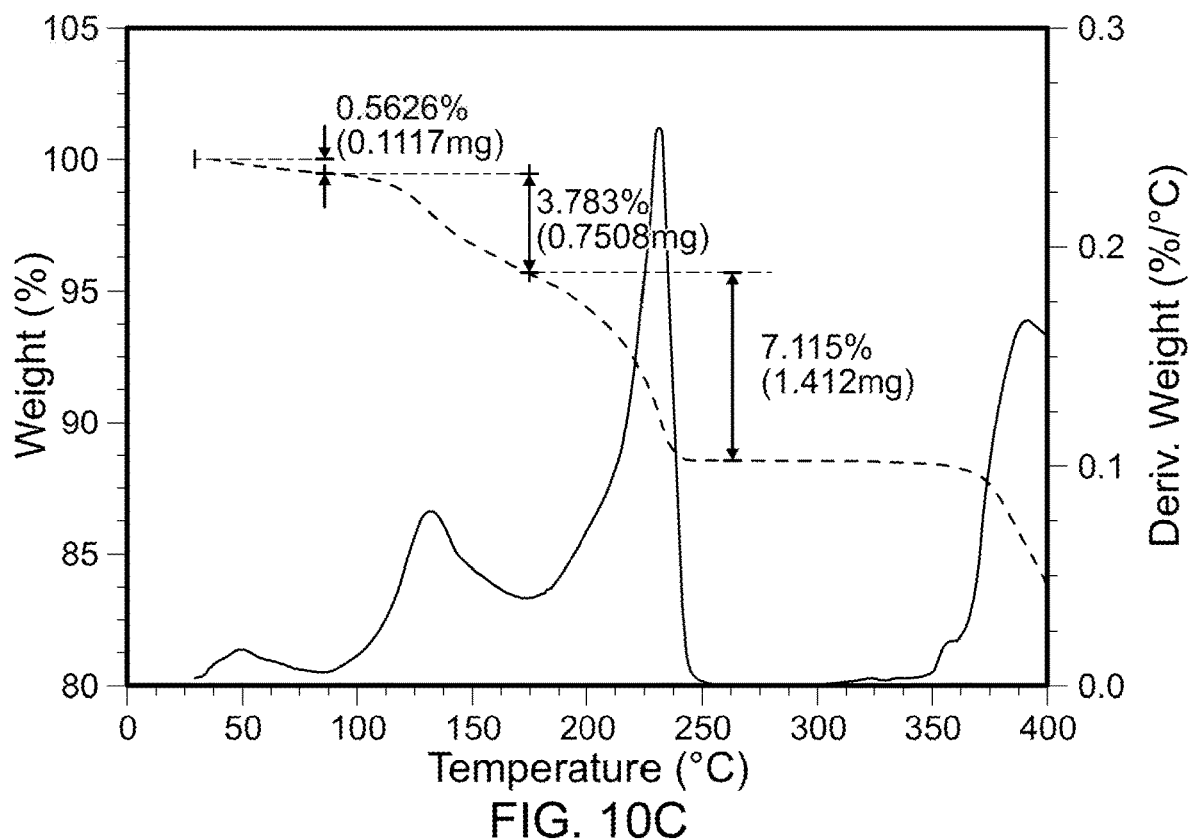
Figure 10D:
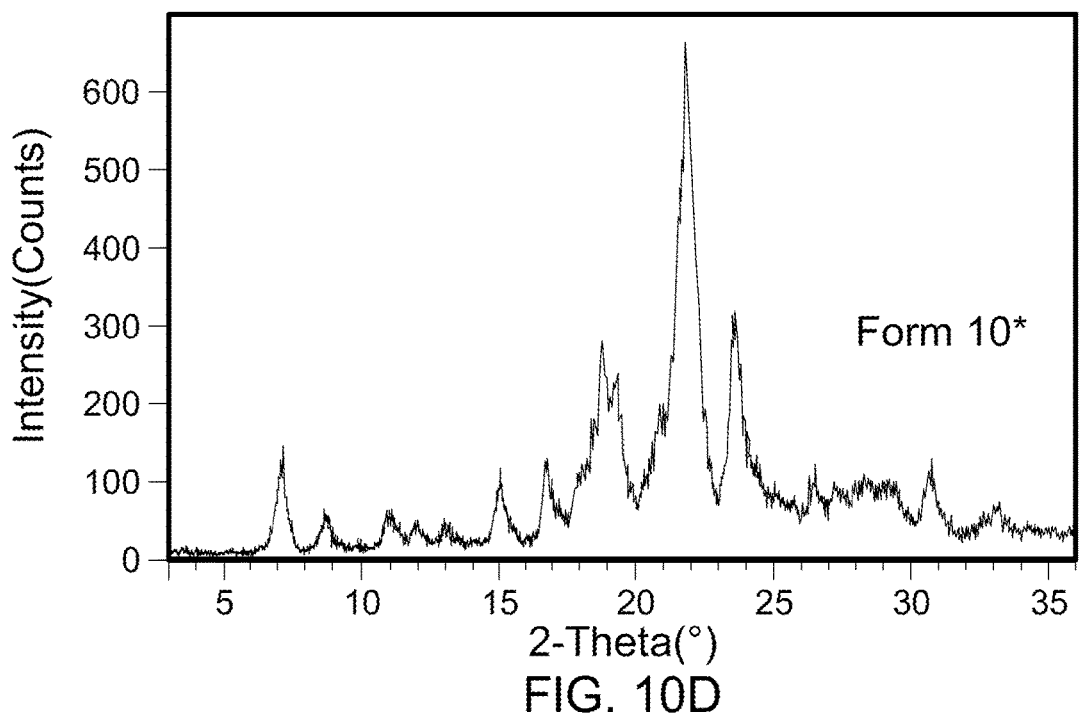
Figure 10E:
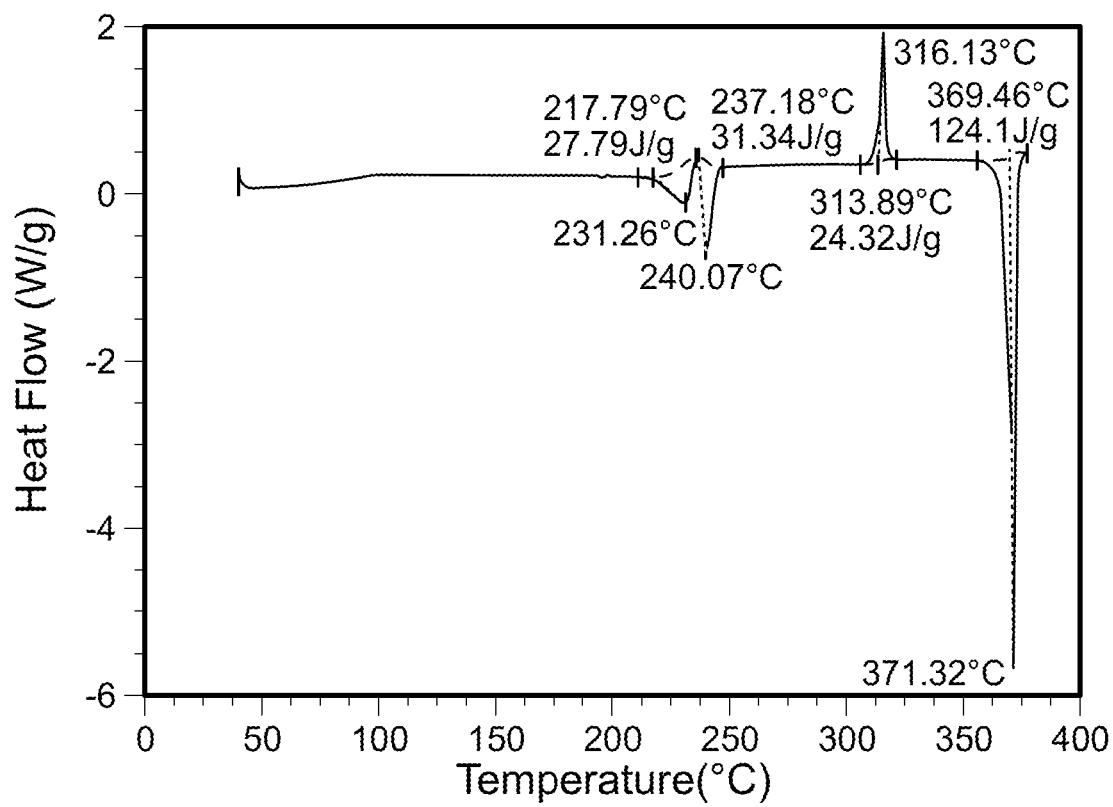

The experiments that generated Forms 10 and 10* are shown in Table 25, below. XRD scans of Forms 10 and 10* were taken (FIGS. 10A and 10D, respectively). The XRD peaks of Form 10 are shown in Table 26, below. DSC scans of Forms 10 and 10* were also taken and indicated multiple endotherms/exotherms, followed by melting at 367° C. (FIGS. 10B and 10E, respectively).

Forms 10 and 10* were produced by drying of amorphous solids (obtained from DMSO and DMSO/water reslurry at RT and 50° C.). Both Form 10 and 10* are associated with DMSO.

A TGA scan of Form 10 solid showed a 0.6% weight loss before 100° C., followed by a 3.8% weight loss between 100° C. and 170° C., followed by a 7.1% weight loss between 170° C. and 260° C. (FIG. 10C).

TABLE 25

Summary of experiments that generated Forms 10 and 10*

| Form | Solvent | Temperature | Wet | Dry |
|---|---|---|---|---|
| Form 10 | DMSO | RT | amorphous | Form 10 |
|  | DMSO/water | RT | amorphous | Form 10 |
|  | DMSO/water | 50° C. | amorphous | Form 10 |
| Form 10* | DMSO | 50° C. | amorphous | Form 10* |

*Amount of water in binary solvents is 5%

TABLE 26

XRD peaks of Form 10

| 2-Theta | d(A) | BG | Height | I % | Area | I % | FWHM |
|---|---|---|---|---|---|---|---|
| 6.701 | 13.1792 | 148 | 1553 | 32.1 | 31364 | 34.4 | 0.343 |
| 8.3 | 10.6444 | 207 | 1026 | 21.2 | 17914 | 19.6 | 0.297 |
| 9.38 | 9.4203 | 212 | 1352 | 27.9 | 21528 | 23.6 | 0.271 |
| 10.819 | 8.1705 | 223 | 514 | 10.6 | 8714 | 9.6 | 0.288 |
| 11.919 | 7.4192 | 271 | 635 | 13.1 | 9435 | 10.3 | 0.253 |
| 12.919 | 6.8469 | 266 | 1160 | 24 | 22094 | 24.2 | 0.324 |
| 13.718 | 6.45 | 242 | 81 | 1.7 | 856 | 0.9 | 0.18 |
| 14.84 | 5.9646 | 271 | 244 | 5 | 4716 | 5.2 | 0.329 |
| 15.536 | 5.6988 | 312 | 147 | 3 | 1304 | 1.4 | 0.151 |
| 16.58 | 5.3424 | 392 | 1813 | 37.5 | 30451 | 33.4 | 0.286 |
| 17.821 | 4.9731 | 434 | 2208 | 45.6 | 58342 | 64 | 0.449 |
| 18.16 | 4.881 | 434 | 2862 | 59.2 | 89029 | 97.6 | 0.529 |
| 19.001 | 4.6667 | 1021 | 3215 | 66.5 | 45840 | 50.2 | 0.242 |
| 19.88 | 4.4623 | 1163 | 1454 | 30.1 | 19014 | 20.8 | 0.222 |
| 20.701 | 4.2873 | 1514 | 4838 | 100 | 78140 | 85.7 | 0.275 |
| 21.66 | 4.0994 | 596 | 4067 | 84.1 | 91229 | 100 | 0.381 |
| 23.38 | 3.8017 | 596 | 2251 | 46.5 | 64928 | 71.2 | 0.49 |
| 24.22 | 3.6717 | 663 | 4578 | 94.6 | 84228 | 92.3 | 0.313 |
| 26 | 3.4242 | 595 | 430 | 8.9 | 11172 | 12.2 | 0.442 |
| 27.12 | 3.2853 | 639 | 146 | 3 | 1986 | 2.2 | 0.231 |
| 27.88 | 3.1974 | 642 | 2073 | 42.8 | 48132 | 52.8 | 0.395 |
| 28.88 | 3.089 | 638 | 477 | 9.9 | 14155 | 15.5 | 0.504 |
| 29.867 | 2.9891 | 544 | 205 | 4.2 | 4572 | 5 | 0.379 |
| 30.32 | 2.9454 | 528 | 568 | 11.7 | 11936 | 13.1 | 0.357 |
| 31.098 | 2.8735 | 517 | 443 | 9.2 | 5841 | 6.4 | 0.224 |
| 31.661 | 2.8236 | 433 | 118 | 2.4 | 953 | 1 | 0.137 |
| 33.379 | 2.6822 | 433 | 311 | 6.4 | 9235 | 10.1 | 0.505 |
| 34.22 | 2.6181 | 444 | 281 | 5.8 | 6059 | 6.6 | 0.367 |
| 34.822 | 2.5743 | 460 | 84 | 1.7 | 2707 | 3 | 0.548 |
| 35.438 | 2.5309 | 465 | 89 | 1.8 | 858 | 0.9 | 0.164 |

L. Forms 11 and 11*

Figure 11A:
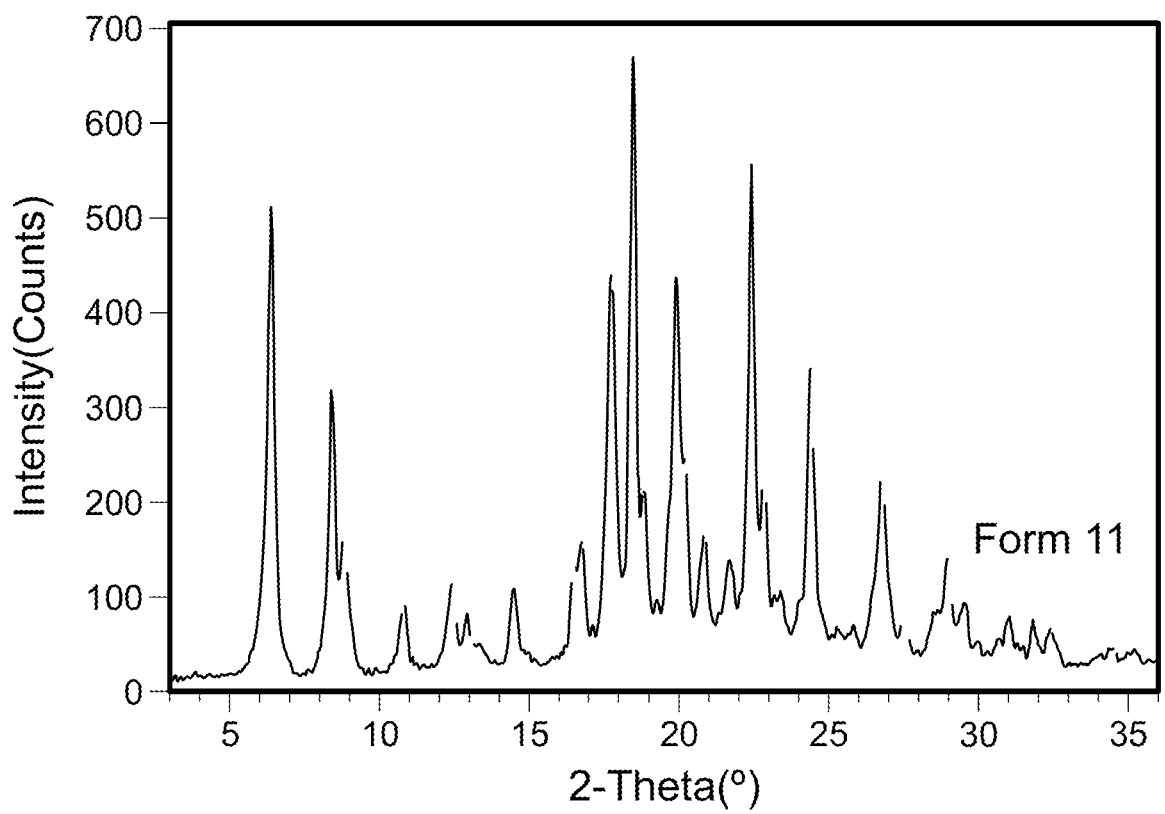
FIGS. 11A-11F are scans of polymorph Forms 11 and 11* of the compound of Formula (I).
Figure 11B:
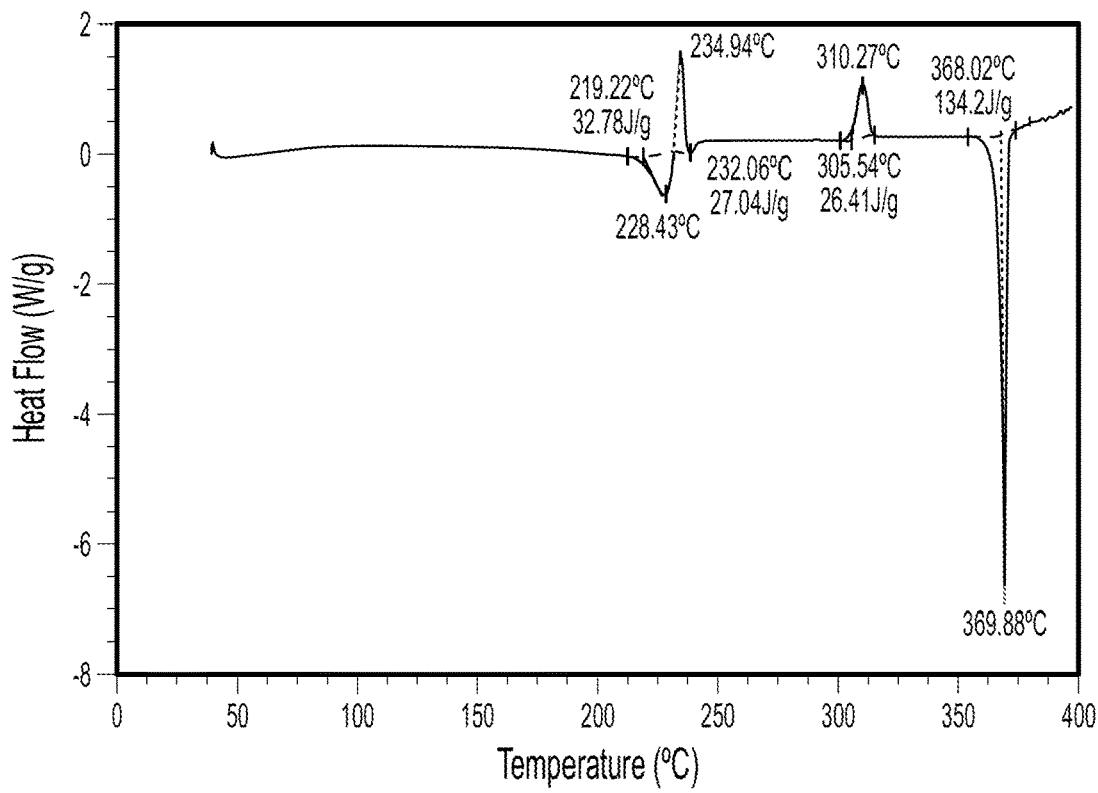

The experiments that generated Forms 11 and 11* are shown in Table 27, below. XRD scans of Forms 11 and 11* were taken (FIGS. 11A and 11D, respectively). The XRD peaks of Form 11 and Form 11* are shown in Tables 28 and 29, below, respectively. DSC scans of Forms 11 and 11* were also taken (FIGS. 11B and 11E, respectively). According to the DSC scans, the solid showed multiple endotherms/exotherms and eventually melted at 368° C. Amorphous halo was observed in the XRD of both Forms. The double exotherm on the DSC of both forms may be also associated with the amorphous halo observed on XRD scans.

Figure 11C:
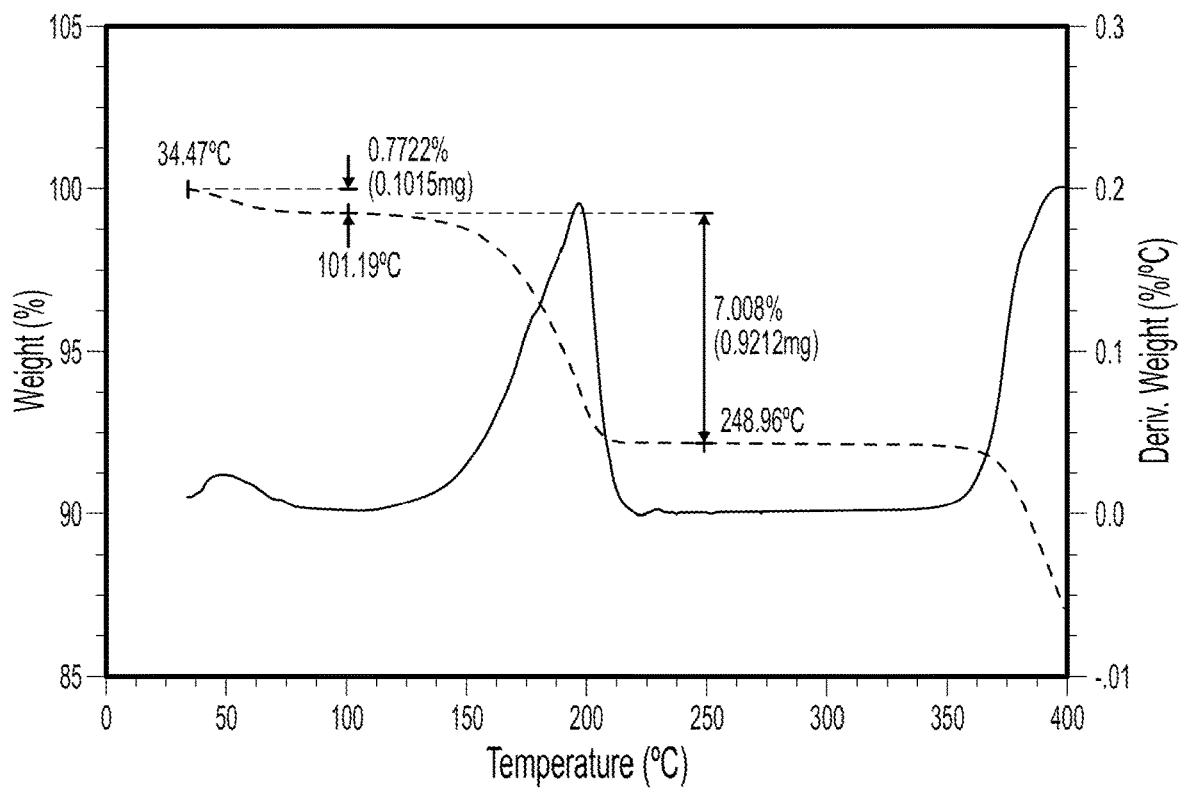
Figure 11D:
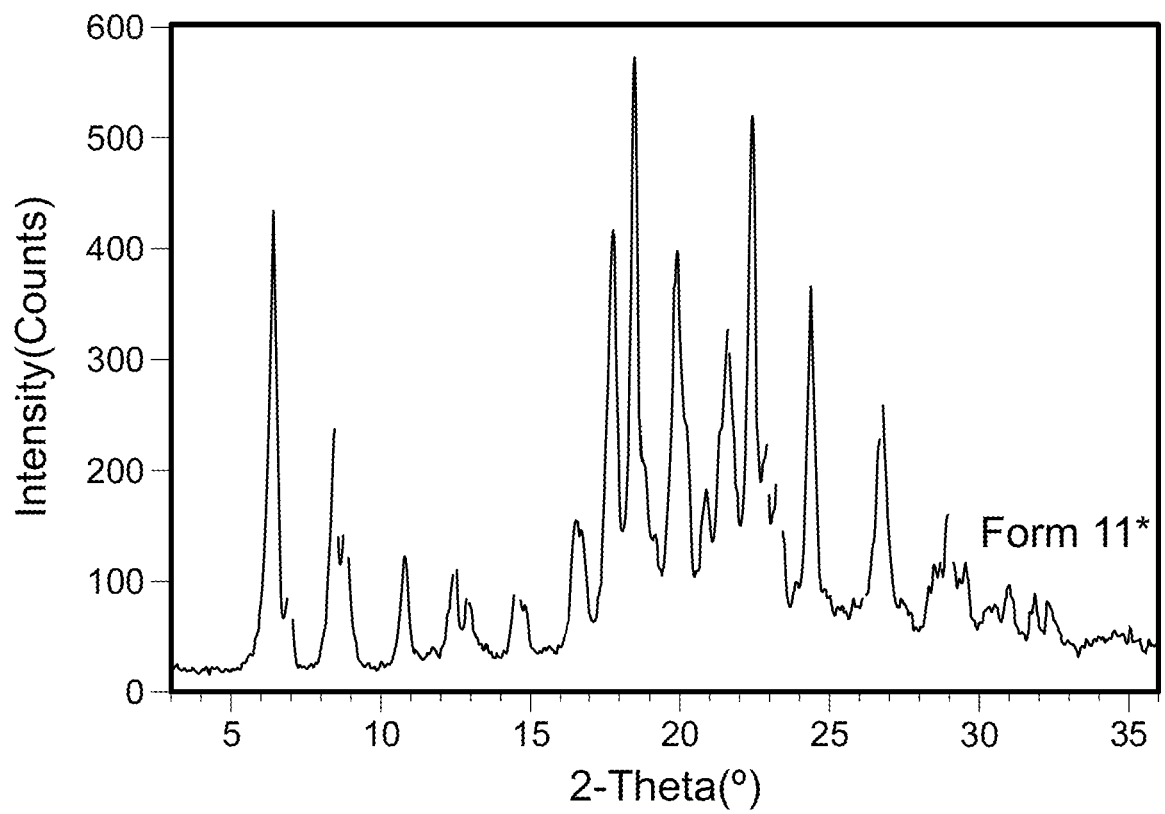
Figure 11E:
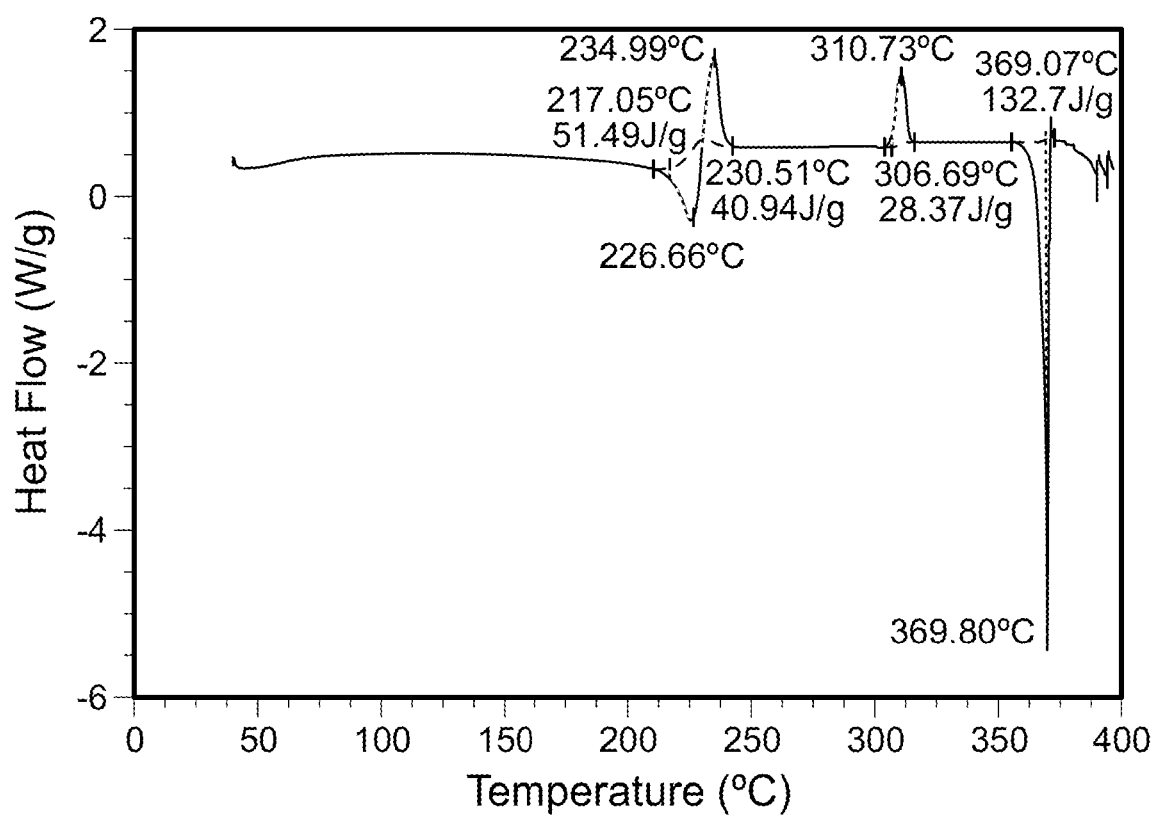
Figure 11F:
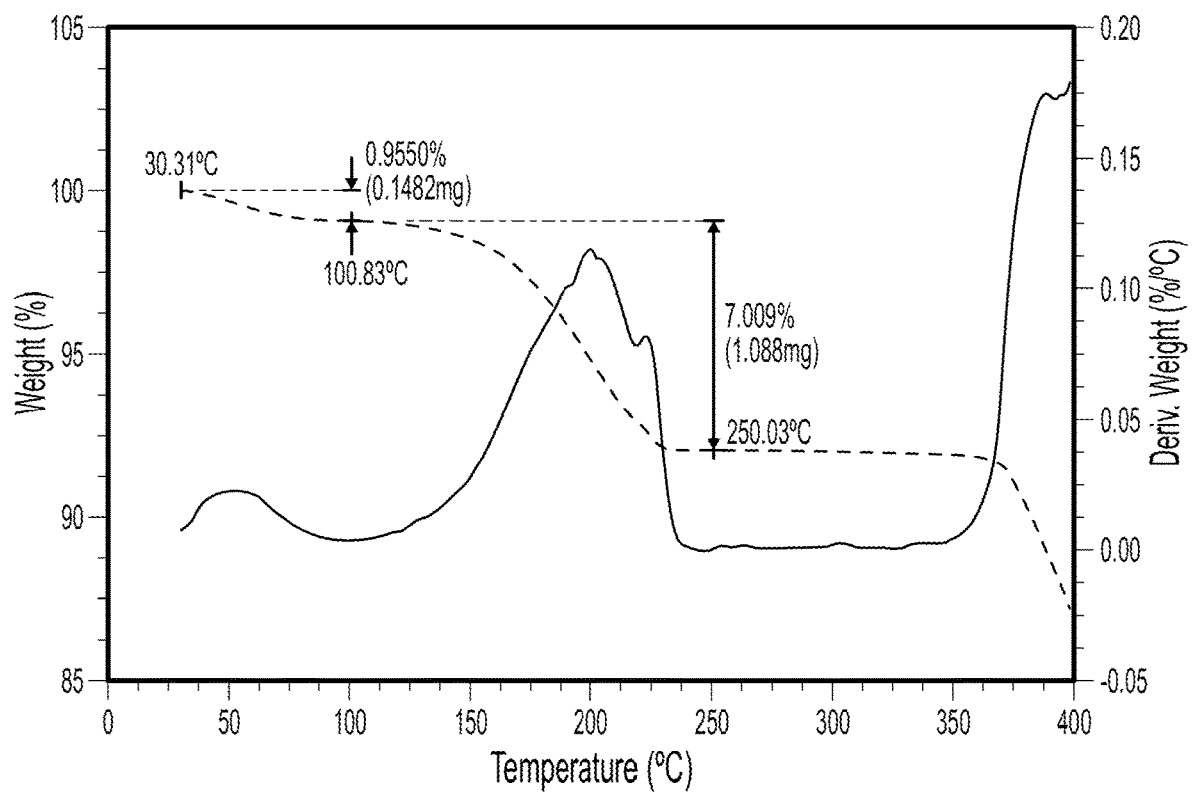

TGA scans of Form 11 and 11* were taken (FIGS. 11C and 11F, respectively). Form 11 solids showed a 0.8% weight loss before 100° C., followed by a 7.0% weight loss between 100° C. and 249° C. Form 11* solids showed a 1.0% weight loss before 100° C., and followed by a 7.0% weight loss before 250° C.

Forms 11 and 11* were obtained from DMF and DMF/5% water at RT and 50° C.

TABLE 27

Summary of experiments that generated Forms 11 and 11*

| Form | Solvent | Temperature | Wet | Dry |
|---|---|---|---|---|
| Form 11 | DMF | RT | Form 11 | Form 11 |
|  | DMF | 50° C. | Form 11 | Form 11* |
|  | DMF/water | RT | Form 11 | Form 11 |
|  | DMF/water | 50° C. | Form 11 | Form 11 |
| Form 11* | DMF | 50° C. | Form 11 | Form 11* |

*Amount of water in binary solvents is 5%

TABLE 28

XRD peaks of Form 11

| 2-Theta | d(A) | BG | Height | I % | Area | I % | FWHM |
|---|---|---|---|---|---|---|---|
| 6.42 | 13.7554 | 19 | 496 | 81.7 | 9502 | 100 | 0.326 |
| 8.421 | 10.4908 | 20 | 335 | 55.2 | 5775 | 60.8 | 0.293 |
| 8.86 | 9.9726 | 24 | 166 | 27.3 | 4268 | 44.9 | 0.437 |
| 10.859 | 8.1404 | 21 | 91 | 15 | 1292 | 13.6 | 0.241 |
| 12.479 | 7.0871 | 44 | 83 | 13.7 | 1004 | 10.6 | 0.206 |
| 12.977 | 6.8165 | 29 | 51 | 8.4 | 1542 | 16.2 | 0.514 |
| 14.519 | 6.0957 | 28 | 91 | 15 | 1421 | 15 | 0.265 |
| 16.801 | 5.2727 | 57 | 104 | 17.1 | 2226 | 23.4 | 0.364 |
| 17.801 | 4.9787 | 103 | 358 | 59 | 5109 | 53.8 | 0.243 |
| 18.519 | 4.7871 | 101 | 607 | 100 | 8460 | 89 | 0.237 |
| 18.861 | 4.7011 | 102 | 125 | 20.6 | 1763 | 18.6 | 0.24 |
| 19.922 | 4.453 | 85 | 383 | 63.1 | 7376 | 77.6 | 0.327 |
| 20.258 | 4.38 | 79 | 180 | 29.7 | 5778 | 60.8 | 0.546 |
| 20.899 | 4.247 | 76 | 105 | 17.3 | 1291 | 13.6 | 0.209 |
| 21.738 | 4.085 | 86 | 55 | 9.1 | 757 | 8 | 0.234 |
| 22.441 | 3.9585 | 94 | 471 | 77.6 | 7125 | 75 | 0.257 |
| 22.859 | 3.8871 | 78 | 167 | 27.5 | 3724 | 39.2 | 0.379 |
| 24.458 | 3.6365 | 60 | 298 | 49.1 | 4544 | 47.8 | 0.259 |
| 26.82 | 3.3213 | 45 | 195 | 32.1 | 4777 | 50.3 | 0.416 |
| 29 | 3.0764 | 43 | 99 | 16.3 | 3112 | 32.8 | 0.534 |
| 29.524 | 3.023 | 63 | 37 | 6.1 | 190 | 2 | 0.087 |
| 31.04 | 2.8788 | 38 | 46 | 7.6 | 826 | 8.7 | 0.305 |
| 31.825 | 2.8095 | 36 | 56 | 9.2 | 737 | 7.8 | 0.224 |
| 32.456 | 2.7563 | 31 | 40 | 6.6 | 857 | 9 | 0.364 |

TABLE 29

XRD peaks of Form 11*

| 2-Theta | d(A) | BG | Height | I % | Area | I % | FWHM |
|---|---|---|---|---|---|---|---|
| 6.441 | 13.7116 | 24 | 424 | 93.4 | 8643 | 100 | 0.347 |
| 6.944 | 12.7196 | 20 | 84 | 18.5 | 2078 | 24 | 0.421 |
| 8.518 | 10.3718 | 22 | 227 | 50 | 4871 | 56.4 | 0.365 |
| 8.86 | 9.9721 | 23 | 147 | 32.4 | 3581 | 41.4 | 0.414 |
| 10.859 | 8.141 | 26 | 107 | 23.6 | 1695 | 19.6 | 0.269 |
| 12.519 | 7.0648 | 34 | 90 | 19.8 | 2165 | 25 | 0.409 |
| 13.021 | 6.7935 | 31 | 54 | 11.9 | 1517 | 17.6 | 0.478 |
| 14.618 | 6.0547 | 32 | 76 | 16.7 | 1605 | 18.6 | 0.359 |
| 16.638 | 5.3238 | 55 | 115 | 25.3 | 2410 | 27.9 | 0.356 |
| 17.838 | 4.9684 | 71 | 368 | 81.1 | 6709 | 77.6 | 0.31 |
| 18.522 | 4.7864 | 130 | 454 | 100 | 7473 | 86.5 | 0.28 |
| 19.96 | 4.4447 | 109 | 315 | 69.4 | 6433 | 74.4 | 0.347 |
| 20.26 | 4.3795 | 109 | 146 | 32.2 | 5359 | 62 | 0.624 |
| 20.904 | 4.2461 | 127 | 58 | 12.8 | 559 | 6.5 | 0.164 |
| 21.639 | 4.1034 | 142 | 194 | 42.7 | 4690 | 54.3 | 0.411 |
| 22.441 | 3.9586 | 161 | 368 | 81.1 | 5409 | 62.6 | 0.25 |
| 22.94 | 3.8735 | 78 | 150 | 33 | 6057 | 70.1 | 0.686 |
| 23.398 | 3.7988 | 78 | 116 | 25.6 | 2330 | 27 | 0.341 |
| 24.44 | 3.6391 | 75 | 305 | 67.2 | 5097 | 59 | 0.284 |
| 26.819 | 3.3215 | 68 | 206 | 45.4 | 4795 | 55.5 | 0.396 |
| 29.018 | 3.0745 | 56 | 109 | 24 | 4093 | 47.4 | 0.638 |
| 29.566 | 3.0188 | 82 | 43 | 9.5 | 341 | 3.9 | 0.135 |
| 31.022 | 2.8804 | 58 | 55 | 12.1 | 509 | 5.9 | 0.157 |
| 31.881 | 2.8047 | 49 | 48 | 10.6 | 482 | 5.6 | 0.171 |
| 32.338 | 2.7661 | 42 | 50 | 11 | 1360 | 15.7 | 0.462 |

Additional experiments with Form 1 of a compound of Formula (I) showed that when Form 1 was exposed to moisture (FIGS. 15A-15D), Form 1 formed non-stoichiometric or stoichiometric hydrates. The crystal lattice of Form 1 expanded when water was sorbed, giving rise to XRD peaks at ~5, ~7 and ~11 degrees while maintaining the main XRD pattern. The hydrates of Form 1 of a compound of Formula (I) (Form 11) were fully reversible, and lost water when exposed to % RH of less than 20%, turning Form 11 to hydrated forms of Form 1 and to the anhydrous Form 1.

M. Form 13 and Form 12

Figure 12A:
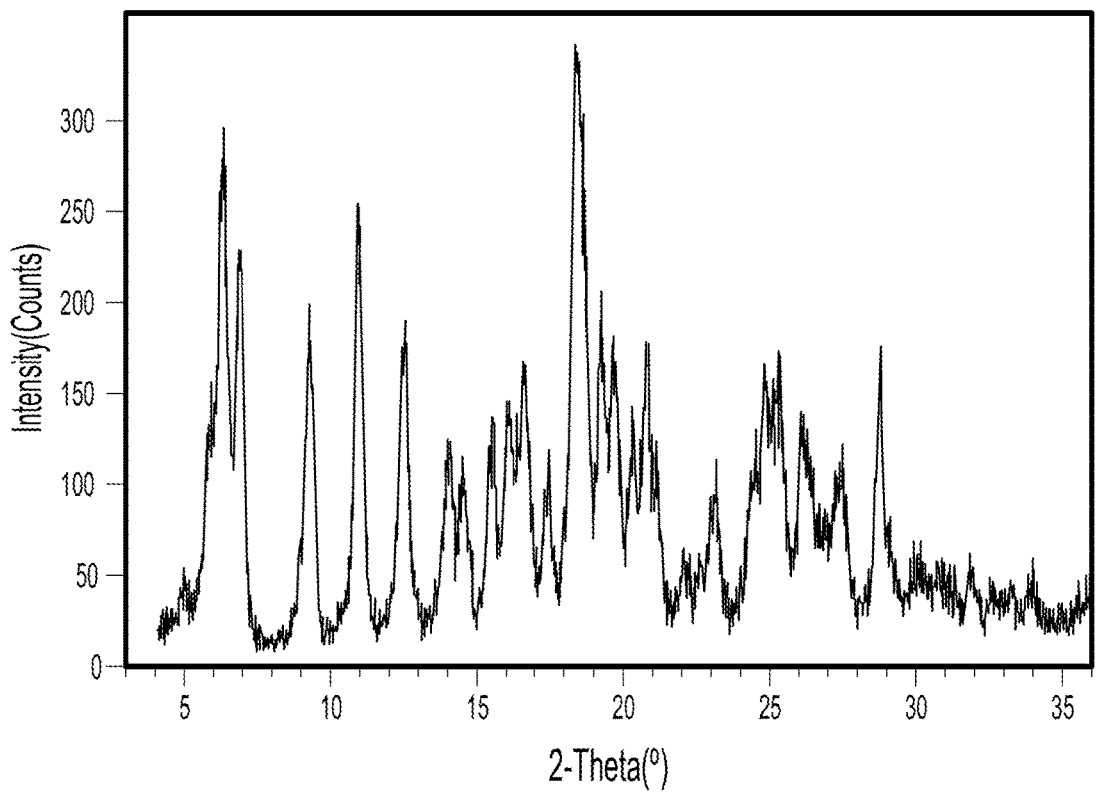
FIGS. 12A-12C are scans of Form 12, an example of a non-stoichiometric hydrate of polymorph Form 1 of the compound of Formula (I).
Figure 12B:
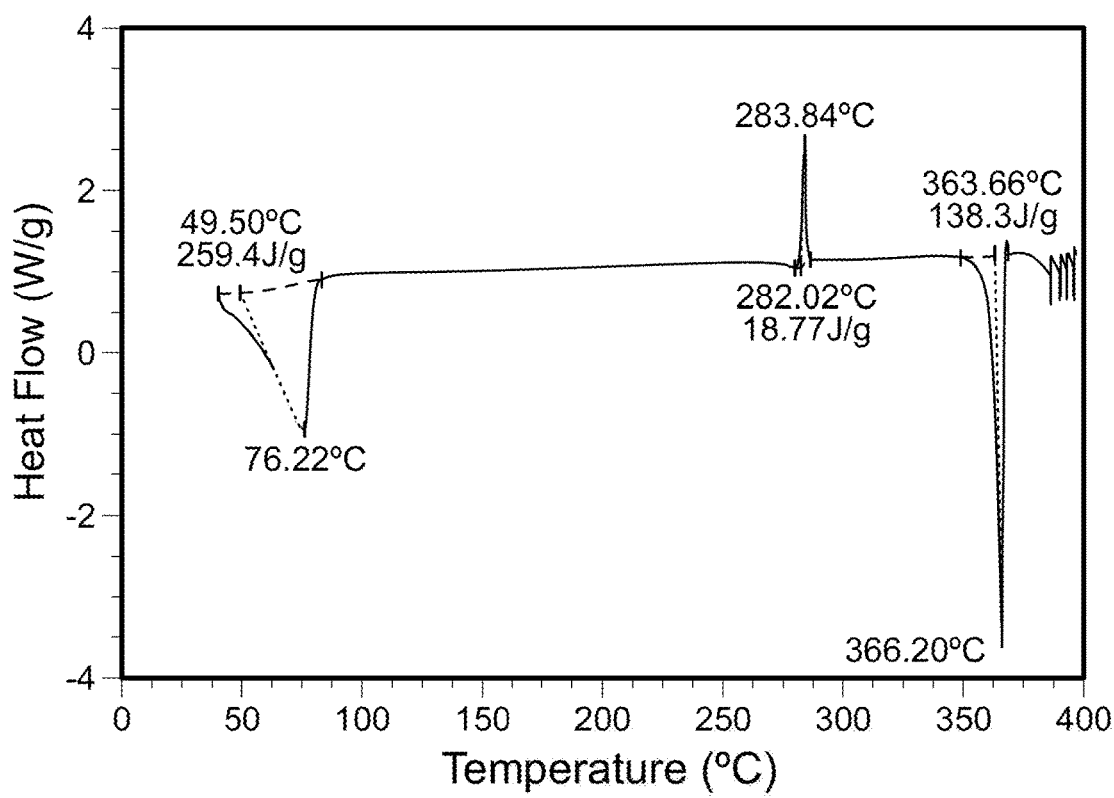
Figure 12C:
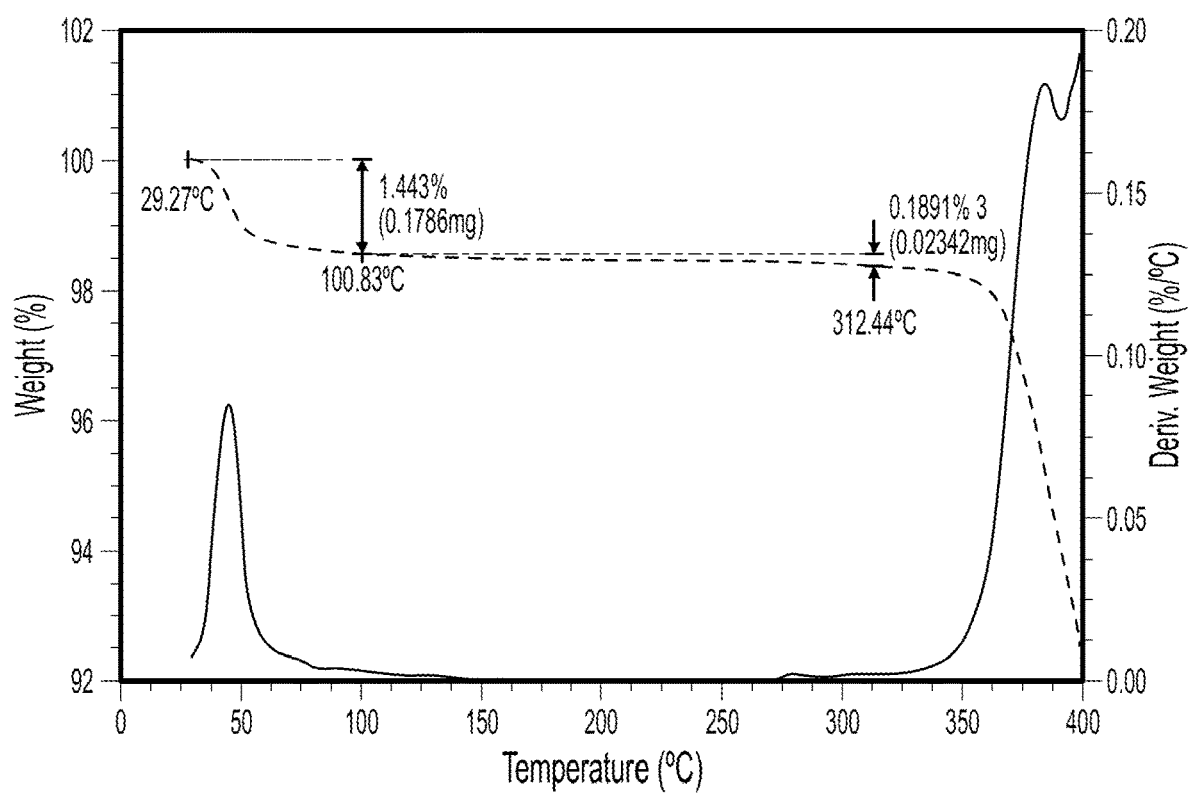
Figure 13A:
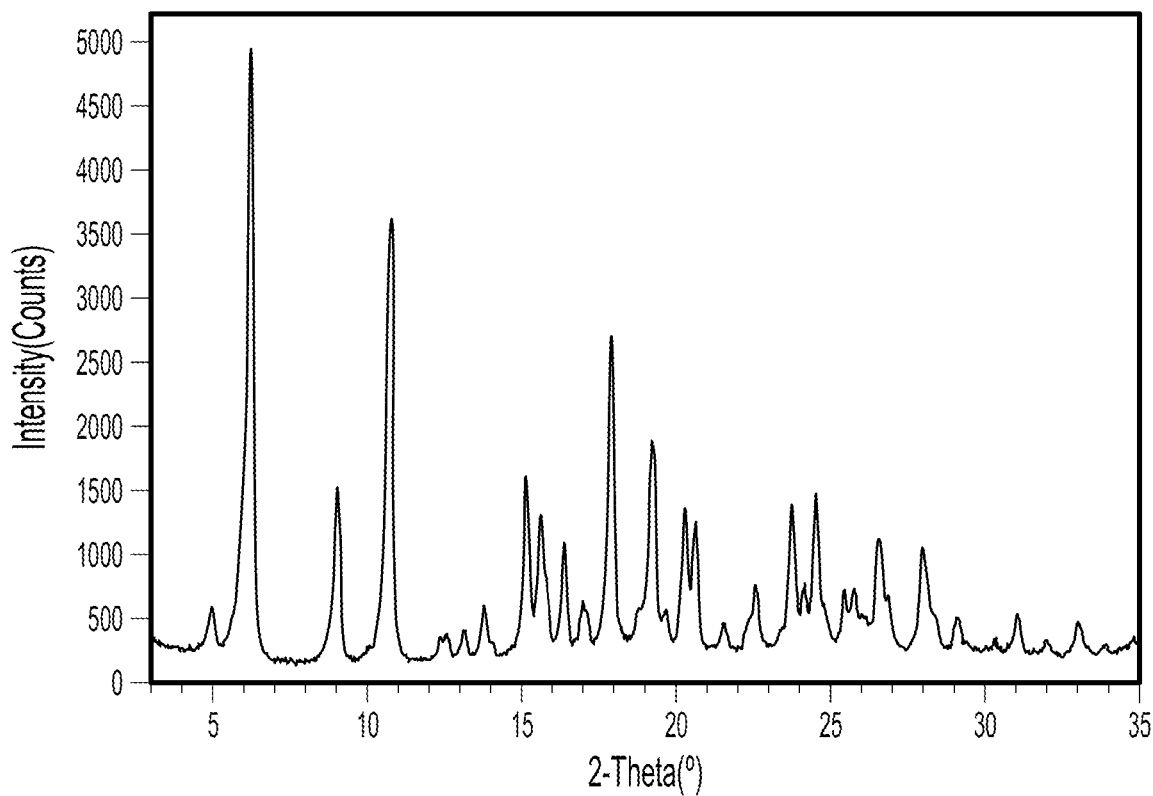
FIGS. 13A-13D are scans of Form 13, an example of a non-stoichiometric hydrate of polymorph Form 1 of the compound of Formula (I).
Figure 13B:
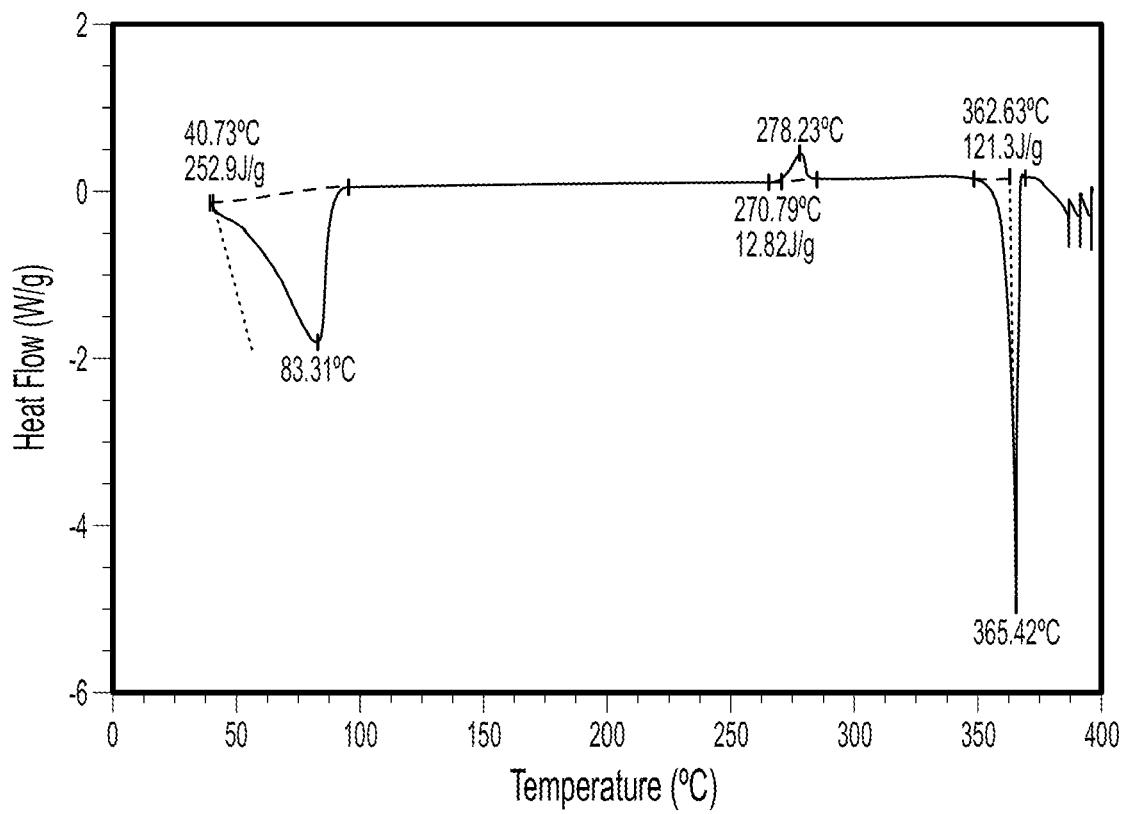

The experiments that generated Form 13 and Form 12 are shown in Tables 30 and 32, below, respectively. Forms 12 and 13 are examples of non-stoichiometric hydrates of Form 1 that have between 1% and about 20% by weight water. XRD scans of Form 13 and Form 12 were taken (FIGS. 13A and 12A, respectively). The XRD peaks of Form 13 are shown in Table 31, below. DSC scans of Form 13 and Form 12 were also taken (FIGS. 13B and 12B, respectively). According to the DSC scan, Form 13 solids showed a wide endotherm between 50° C.-100° C., followed by a small exotherm at 278° C.; and a melting endotherm at 363° C. According to the DSC scan, Form 12 solids showed a wide endotherm between 50° C.-100° C., followed by a sharp exotherm at 283° C.; and a melting endotherm at 364° C.

Figure 13C:
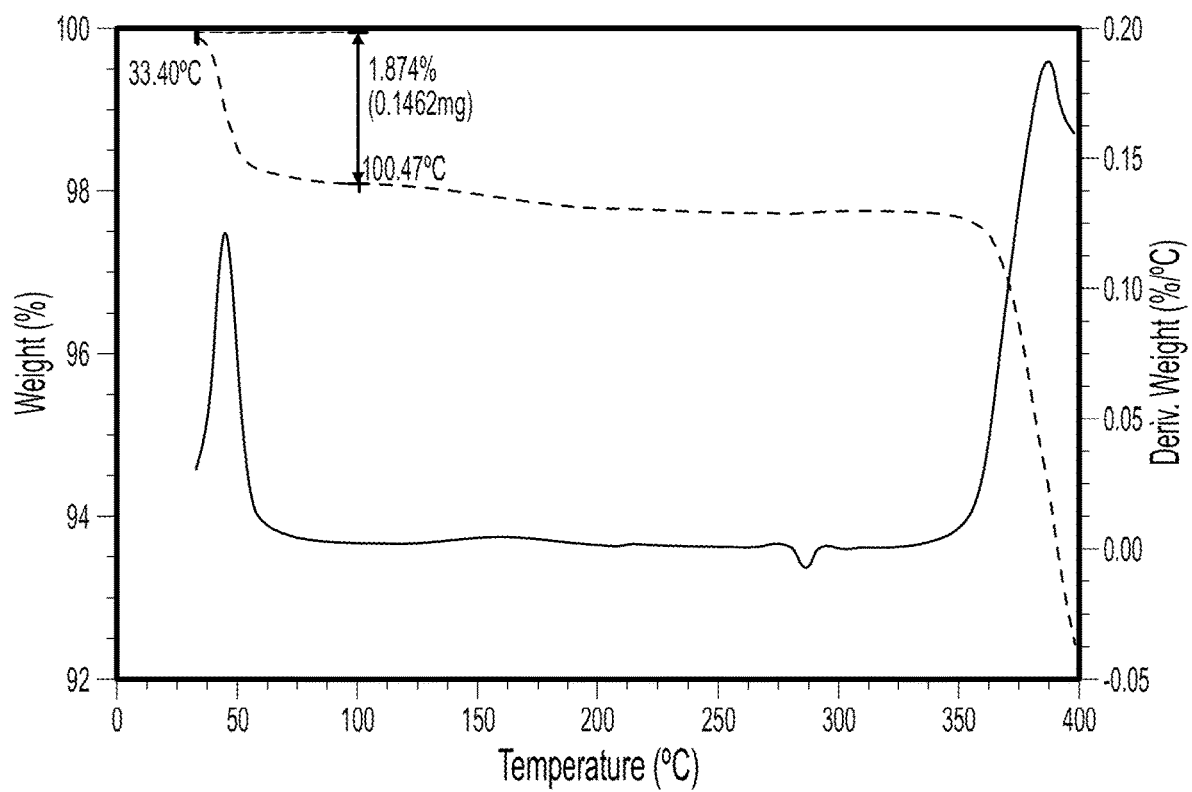
Figure 13D:
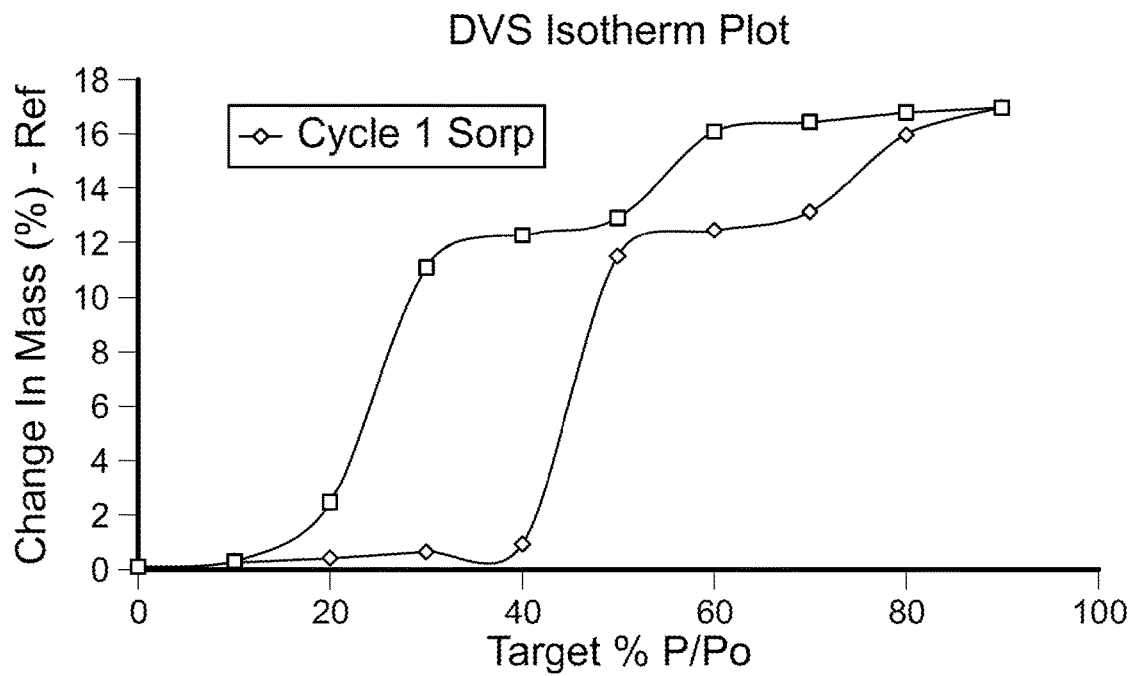
Figure 14:
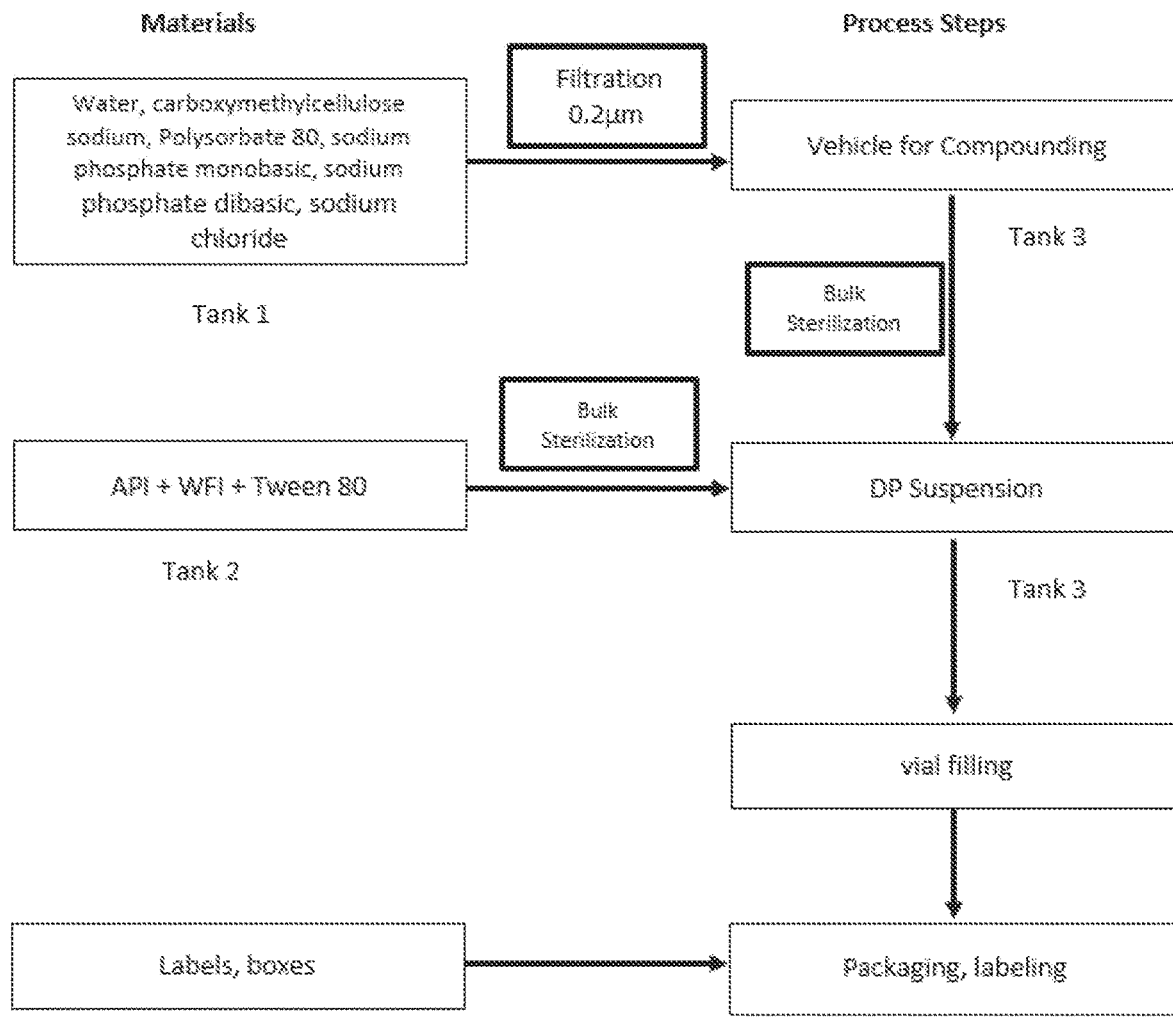
FIG. 14 is a flow chart showing an exemplary process described herein.
Figure 15A:
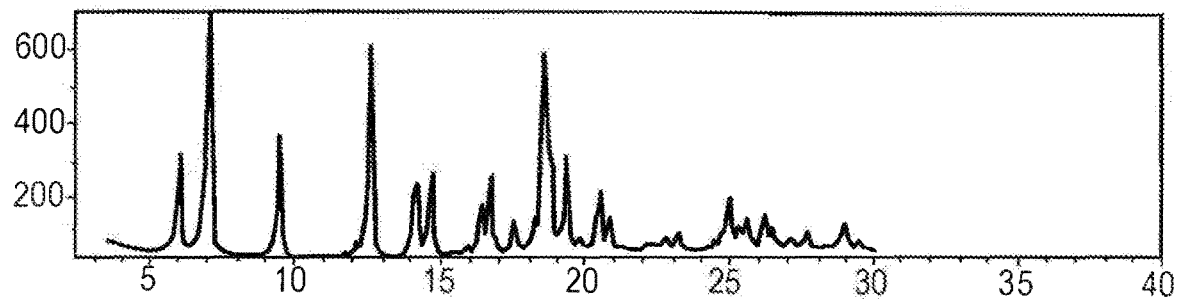
FIGS. 15A-15D are scans of Form 1 in the presence of increasing relative humidity (RH), an example of a non-stoichiometric or stoichiometric hydrate of polymorph Form 1 of the compound of Formula (I).
Figure 15B:
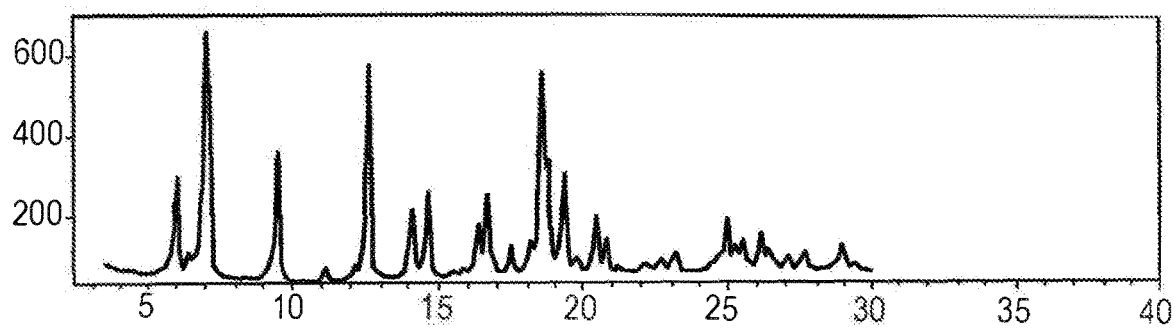
Figure 15C:
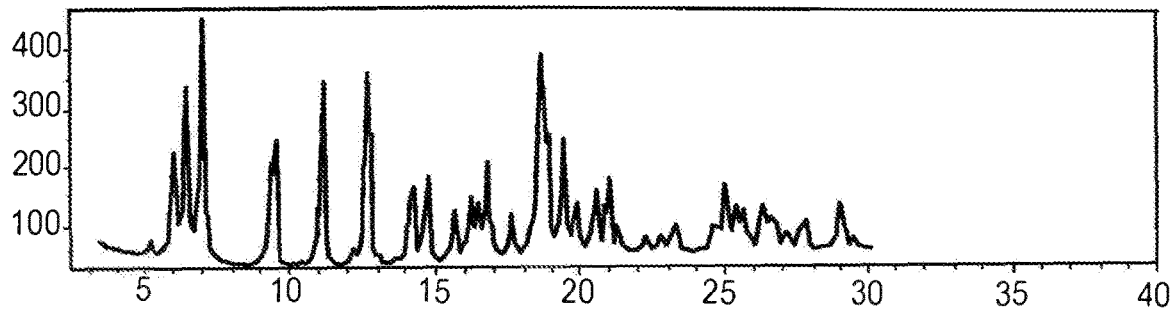
Figure 15D:
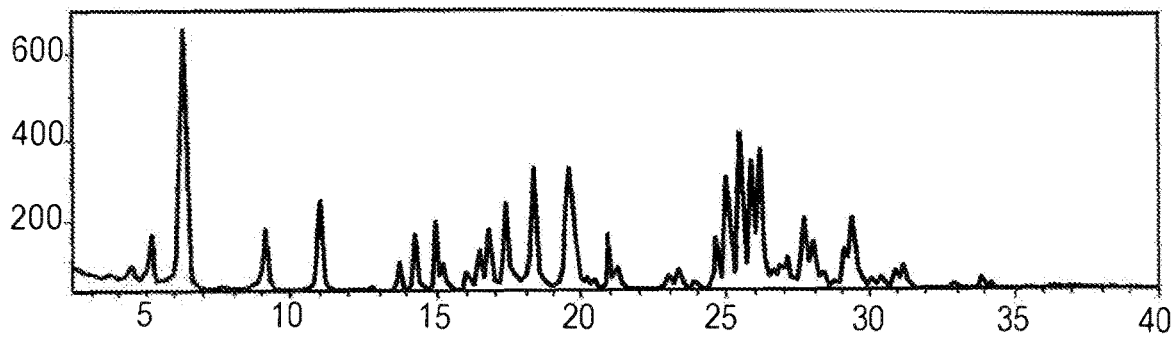

The purity of the Form 13 sample was 98.8%; the KF of an undried Form 13 sample was 35.7%. A DVS scan of Form 13 solid showed a 17% water sorption at 90% RH (FIG. 13D). Form 13 converted to Form 1 upon drying.

A TGA scan of Form 13 solid showed a 1.9% weight loss before 100° C. (FIG. 13C).

Form 13 solid was heated in a DSC chamber to 170° C. (past the endotherm between 50-100° C.), and then scanned by XRD. A comparison of the first and the second XRD and DSC scans, after heating to 170° C., showed that Form 13 converted to Form 1. It can be concluded that the endotherm between 50-100° C. is due to bonded water.

Form 13 has a primitive orthorhombic crystal structure with the approximate dimensions: a [Å]=33.759, b [Å]=22.590, c [Å]=7.386 and an approximate volume cell of [Å$^3$/cell]=5,632.5 and a space group defined as Pbca(61).

Form 13 solid was heated in a DSC chamber to 330° C. (past the endotherm/exotherm around 300° C.), and then scanned by XRD. A comparison of the first and the third XRD and DSC scans, after heating to 170° C., showed that Form 13 converted to Form 9. It can be concluded that the endotherm/exotherm is due to melting/crystallization events.

TABLE 30

Summary of experiments that generated Form 13

| Form | Solvent | Temperature | Wet | Dry |
|---|---|---|---|---|
| Form 13 | MeOH | RT | Form 13 | Form 1 |
| | MeOH/water | 50° C. | Form 13 | Form 13 |
| | water | RT | Form 13 | Form 1 |
| | water | 50° C. | Form 13 | Form 13 |
| | Toluene/water | RT | Form 13 | Form 1 |
| | Toluene/water | 50° C. | Form 13 | Form 13 |
| | MA/water | RT | Form 13 | Form 1 |
| | n-Butyl acetate/water | RT | Form 13 | Form 12 |
| | n-Butyl acetate/water | 50° C. | Form 13 | Form 1 |
| | Heptane | 50° C. | Form 13 | Form 13 |
| | Heptane/water | RT | Form 13 | Form 12 |
| | Heptane/water | 50° C. | Form 13 | Form 1 |
| | n-Butanol/water | RT | Form 13 | Form 13 |
| | n-Butanol/water | 50° C. | Form 13 | Form 1 |
| | DCM | 50° C. | Form 13 | Form 13 |
| | DCM/water | RT | Form 13 | Form 1 |
| | DCM/water | 50° C. | Form 13 | Form 1 |
| | Acetonitrile/water | 50° C. | Form 13 | Form 13 |
| | IPAc/water | 50° C. | Form 13 | Form 13 |
| | MtBE/water | 50° C. | Form 13 | Form 13 |
| | MIBK/water | 50° C. | Form 13 | Form 1 |

*Amount of water in binary solvents is 5%

TABLE 31

XRD peaks of Form 13

| 2-Theta | d(A) | BG | Height | I % | Area | I % | FWHM |
|---|---|---|---|---|---|---|---|
| 5.06 | 17.45 | 278 | 309 | 6.5 | 3685 | 4.8 | 0.203 |
| 6.379 | 13.8451 | 223 | 4743 | 100 | 76110 | 100 | 0.273 |
| 9.24 | 9.5632 | 164 | 1370 | 28.9 | 20018 | 26.3 | 0.248 |
| 11 | 8.0364 | 173 | 3445 | 72.6 | 51777 | 68 | 0.256 |
| 12.899 | 6.8574 | 195 | 173 | 3.6 | 3114 | 4.1 | 0.306 |
| 13.462 | 6.572 | 199 | 204 | 4.3 | 2376 | 3.1 | 0.198 |
| 14.159 | 6.2498 | 202 | 390 | 8.2 | 5424 | 7.1 | 0.236 |
| 15.56 | 5.6901 | 262 | 1335 | 28.1 | 19295 | 25.4 | 0.246 |
| 16.059 | 5.5145 | 302 | 1002 | 21.1 | 17561 | 23.1 | 0.298 |
| 16.841 | 5.26 | 313 | 774 | 16.3 | 7797 | 10.2 | 0.171 |
| 17.46 | 5.075 | 322 | 314 | 6.6 | 3863 | 5.1 | 0.209 |
| 18.419 | 4.8128 | 339 | 2354 | 49.6 | 29374 | 38.6 | 0.212 |
| 19.3 | 4.5951 | 357 | 210 | 4.4 | 8112 | 10.7 | 0.657 |
| 19.741 | 4.4935 | 329 | 1566 | 33 | 30236 | 39.7 | 0.328 |
| 20.202 | 4.3919 | 342 | 210 | 4.4 | 2880 | 3.8 | 0.233 |
| 20.84 | 4.2589 | 300 | 1054 | 22.2 | 18033 | 23.7 | 0.291 |
| 21.201 | 4.1873 | 284 | 964 | 20.3 | 15700 | 20.6 | 0.277 |
| 22.121 | 4.015 | 259 | 197 | 4.2 | 2208 | 2.9 | 0.191 |
| 23.2 | 3.8307 | 268 | 482 | 10.2 | 7844 | 10.3 | 0.277 |
| 24.42 | 3.642 | 280 | 1101 | 23.2 | 16244 | 21.3 | 0.251 |
| 24.839 | 3.5816 | 303 | 468 | 9.9 | 9306 | 12.2 | 0.338 |
| 25.219 | 3.5284 | 385 | 1093 | 23 | 16646 | 21.9 | 0.259 |
| 26.164 | 3.4032 | 359 | 357 | 7.5 | 5064 | 6.7 | 0.241 |
| 26.499 | 3.3609 | 402 | 317 | 6.7 | 7316 | 9.6 | 0.392 |
| 26.798 | 3.324 | 346 | 179 | 3.8 | 8025 | 10.5 | 0.762 |
| 27.339 | 3.2594 | 394 | 720 | 15.2 | 13063 | 17.2 | 0.308 |
| 27.639 | 3.2247 | 341 | 318 | 6.7 | 5673 | 7.5 | 0.303 |
| 28.799 | 3.0974 | 256 | 805 | 17 | 16756 | 22 | 0.354 |
| 29.902 | 2.9857 | 262 | 234 | 4.9 | 3508 | 4.6 | 0.255 |
| 31.234 | 2.8613 | 230 | 106 | 2.2 | 1473 | 1.9 | 0.236 |
| 31.96 | 2.798 | 226 | 308 | 6.5 | 3908 | 5.1 | 0.216 |
| 32.939 | 2.717 | 208 | 117 | 2.5 | 1444 | 1.9 | 0.21 |
| 33.962 | 2.6375 | 199 | 266 | 5.6 | 4617 | 6.1 | 0.295 |
| 34.917 | 2.5675 | 217 | 73 | 1.5 | 736 | 1 | 0.171 |

TABLE 32

Summary of experiments that generated Form 12

| Form | Solvent | Temperature | Wet | Dry |
|---|---|---|---|---|
| Form 12 | Acetonitrile/water | RT | Form 12 | Form 1 |
| | MeOH/water | RT | Form 12 | Form 1 |
| | IPAc/water | RT | Form 12 | Form 1 |
| | EA/water | RT | Form 12 | Form 1 |
| | MtBE/water | RT | Form 12 | Form 1 |
| | MIBK/water | RT | Form 12 | Form 1 |
| | n-Butyl acetate/water | RT | Form 13 | Form 12 |
| | Heptane/water | RT | Form 13 | Form 12 |
| | MA/water | 50° C. | Form 12 | Form 4 |

*Amount of water in binary solvents is 5%

N. Solvates 1-3

The experiments that generated Solvates 1, 2, and 3 are shown in Table 33, below. Solvates 1 and 2 solids were exposed to air overnight, and then analyzed by XRD. After the analysis, the solids were dried at 50° C. under vacuum, and then analyzed by XRD again.

After exposure to air overnight, Solvate 1 converted to low crystallinity; after drying at 50° C., the sample was still low crystallinity solid. After exposure to air overnight, the XRD pattern of Solvate 2 changed a little; after drying at 50° C., the form remained the same as the solid exposed to air overnight.

TABLE 33

Summary of experiments that generated solvates 1-3

| Form | Solvent | Temperature | Wet | Dry |
|---|---|---|---|---|
| Solvate 1 | Acetone | RT | Solvate 1 | Low crystallinity |
| Solvate 2 | Acetone/water | RT | Solvate 2 | Form 4** |
| | Acetone | 50° C. | Solvate 2 | Form 4** |
| Solvate 3 | EtOH/water | RT | Solvate 3 | Form 2 |

*Amount of water in binary solvent is 5%

Example 2: Competitive Slurry Experiments Between Polymorph Forms

In order to find out the thermodynamic stability between the different forms, several competitive slurry experiments were carried out. Form 1, Form 2, Form 2*, Form 3, Form 4, Form 4*, Form 4**, Form 5, Form 7, Form 8, Form 9, Form 10, Form 11, Form 11*, and Form 13 (10 mg for each) was mixed and slurried in 2 mL of solvent at both RT and 50° C. The solids were slurried for 3-5 days and then analyzed by XRD. According to the analytical data, Form 2* was the most stable form in a MeOH, EtOH, and acetone system at both RT and 50° C. Form 4 or 4* was most stable in EA at RT and 50° C. Form 13 was most stable in water at RT and 50° C. Table 34 shows the XRD scan results from the competitive slurry experiments.

TABLE 34

XRD scan results of competitive slurry experiments

| Temperature | Solvent | Form after 3 days; wet/dry | Form after 5 days; wet/dry |
|---|---|---|---|
| RT | MeOH | Form 2*/Form 2* | Form 2*/Form 2* |
| | EtOH | Form 2*/Form 2* | Form 2*/Form 2* |
| | Acetone | Form 2*/Form 2* | Form 2*/Form 2* |
| | EA | Form 4/Form 4 | Form 4/Form 4 |
| | water | Form 13/Form 13 | Form 13/Form 1&Form 13 |
| 50° C. | MeOH | Form 2*/Form 2* | Form 2*/Form 2* |
| | EtOH | Form 2*/Form 2* | Form 2*/Form 2* |
| | Acetone | Form 2*/Form 2* | Form 2*/Form 2* |
| | EA | Form 4/Form 4 | Form 4*/Form 4* |
| | water | Form 13/Form 13 | Form 13/Form 13 |

In order to find out the thermodynamic stability between Form 13 and Form 9, several competitive slurry experiments were carried out. 15 mg of Form 1, Form 9 and Form 13 solid were mixed in 1 mL of toluene, IPAc, and n-butyl acetate, and slurried for 3 days at RT and 50° C.

The residual solid was analyzed by XRD. After a three-day slurry, it was difficult to tell which one was more stable between Form 13 and Form 9. The XRD scan results of the experiment is shown in Table 35, below.

TABLE 35

XRD scan results competitive slurry experiments

| Temperature | Solvent | Form after 3 days; wet/dry |
|---|---|---|
| RT | Toluene | Form 13/Form 1 |
| | IPAc | Form 9 + Form 13/Form 9 + Form 1 |
| | n-Butyl acetate | Form 9 + Form 13/Form 9 + Form 1 |
| 50° C. | Toluene | Form 9 + Form 13/Form 9 + Form 1 |
| | IPAc | Form 9/Form 9 |
| | n-Butyl acetate | Form 9 + Form 13/Form 9 + Form 1 |

OTHER EMBODIMENTS

It is to be understood that the foregoing description is intended to illustrate and not limit the scope of the disclosure, which is defined by the scope of the appended claims. Other aspects, advantages, and modifications are within the scope of the following claims.

What is claimed is:

1. A method of treating osteoarthritis in a subject in need thereof, comprising administering to the subject a therapeutically effective amount of a single-dose, ready-to-use formulation comprising a compound of Formula (I)

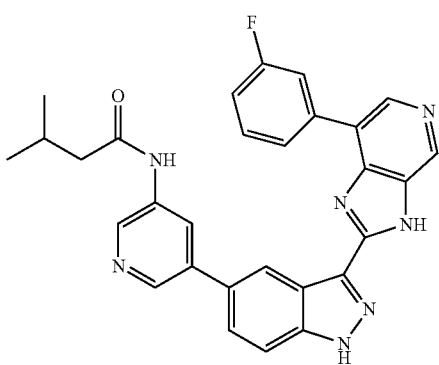

wherein the compound of Formula (I) is present as:
polymorph Form 1 having an X-ray powder diffraction pattern comprising peaks at ° 2θ values of 6.8±0.2, 12.4±0.2, and 18.5±0.2; and
polymorph Form 9 having an X-ray powder diffraction pattern comprising peaks at ° 2θ values of 4.9±0.2, 18.6±0.2, and 21.1±0.2, wherein the compound comprises no more than about 5% by weight of polymorph Form 9;
wherein the compound of Formula (I) is prepared by a process comprising:
(a) providing an aqueous solution comprising water;
(b) providing a slurry comprising a compound of Formula (I);
(c) mixing the aqueous solution and the slurry to form a suspension; and
(d) filling a container with the suspension to prepare the single-dose, ready-to-use formulation.

2. The method of claim 1, wherein the aqueous solution comprises a buffer.

3. The method of claim 2, wherein the buffer is a phosphate buffer.

4. The method of claim 3, wherein the phosphate buffer is selected from the group consisting of sodium phosphate dibasic, sodium phosphate monobasic, potassium phosphate monobasic, potassium phosphate dibasic, and mixtures thereof.

5. The method of claim 4, wherein the phosphate buffer is a mixture of sodium phosphate dibasic heptahydrate and sodium phosphate monobasic monohydrate.

6. The method of claim 3, wherein the buffer is phosphate buffered saline.

7. The method of claim 1, wherein the aqueous solution comprises an excipient.

8. The method of claim 7, wherein the excipient comprises a surfactant, a viscosity enhancer, or a mixture thereof.

9. The method of claim 8, wherein the viscosity enhancer is a water-soluble cellulose derivative.

10. The method of claim 9, wherein the cellulose derivative is sodium carboxymethylcellulose.

11. The method of claim 8, wherein the surfactant is a polysorbate.

12. The method of claim 8, wherein the aqueous solution comprises about 0.01 g/kg to about 50 g/kg; about 1.0 g/kg to about 50 g/kg; about 1 g/kg to about 25 g/kg; about 1 g/kg to about 10 g/kg; about 1 g/kg to about 7.5 g/kg; about 1 g/kg to about 5.5 g/kg; about 1 g/kg to about 2.5 g/kg; about 2.5 g/kg to about 50 g/kg; about 5 g/kg to about 50 g/kg; about 10 g/kg to about 50 g/kg; about 25 g/kg to about 50 g/kg; about 2.5 g/kg to about 7.5 g/kg; about 5 g/kg to about 10 g/kg; or about 10 g/kg to about 20 g/kg of the viscosity enhancer.

13. The method of claim 12, wherein the aqueous solution comprises about 5.5 g/kg of the viscosity enhancer.

14. The method of claim 8, wherein the aqueous solution comprises about 0.01 g/kg to about 5 g/kg; about 0.01 g/kg to about 2.5 g/kg; about 0.01 g/kg to about 1 g/kg; about 0.01 g/kg to about 0.75 g/kg; about 0.01 g/kg to about 0.5 g/kg; about 0.01 g/kg to about 0.25 g/kg; about 0.025 g/kg to about 5 g/kg; about 0.05 g/kg to about 5 g/kg; about 1 g/kg to about 5 g/kg; about 0.1 g/kg to about 5 g/kg; 0.1 g/kg to about 2.5 g/kg; about 0.1 g/kg to about 1 g/kg; about 0.1 g/kg to about 0.75 g/kg; about 0.1 g/kg to about 0.5 g/kg; about 0.1 g/kg to about 0.25 g/kg; about 0.25 g/kg to about 5 g/kg; about 0.5 g/kg to about 5 g/kg; about 1 g/kg to about 5 g/kg; about 2.5 g/kg to about 5 g/kg; about 0.25 g/kg to about 0.75 g/kg; about 0.5 g/kg to about 1 g/kg; or about 1 g/kg to about 2 g/kg of the surfactant.

15. The method of claim 14, wherein the aqueous solution comprises about 0.5 g/kg of the surfactant.

16. The method of claim 8, wherein the aqueous solution comprises about 5.5 g/kg of sodium carboxymethylcellulose and about 0.5 g/kg of polysorbate 80.

17. The method of claim 1, wherein the slurry comprises about 0.001 g/kg to about 5 g/kg; about 0.001 g/kg to about 2.5 g/kg; about 0.001 g/kg to about 1 g/kg; about 0.001 g/kg to about 0.75 g/kg; about 0.001 g/kg to about 0.5 g/kg; about 0.001 g/kg to about 0.25 g/kg; about 0.001 g/kg to about 0.01 g/kg; about 0.01 g/kg to about 5 g/kg; about 0.01 g/kg to about 2.5 g/kg; about 0.01 g/kg to about 1 g/kg; about 0.01 g/kg to about 0.75 g/kg; about 0.01 g/kg to about 0.5 g/kg; about 0.01 g/kg to about 0.25 g/kg; about 0.1 g/kg to about 2.5 g/kg; about 0.1 g/kg to about 1 g/kg; about 0.1 g/kg to about 0.75 g/kg; about 0.1 g/kg to about 0.5 g/kg; about 0.1 g/kg to about 0.25 g/kg; about 0.25 g/kg to about 5 g/kg; about 0.5 g/kg to about 5 g/kg; about 1 g/kg to about 5 g/kg; about 2.5 g/kg to about 5 g/kg; about 0.25 g/kg to about 0.75 g/kg; about 0.5 g/kg to about 1 g/kg; or about 1 g/kg to about 2 g/kg of the compound of Formula (I).

18. The method of claim 17, wherein the slurry comprises about 0.15 g/kg, about 0.35 g/kg, or about 1.15 g/kg of the compound of Formula (I).

19. The method of claim 1, wherein the compound of Formula (I) comprises no more than about 1% by weight of polymorph Form 9.

20. The method of claim 1, wherein the compound of Formula (I) comprises less than about 0.1% by weight of polymorph Form 9.

21. The method of claim 1, wherein the slurry comprises an excipient.

22. The method of claim 21, wherein the excipient comprises a surfactant.

23. The method of claim 22, wherein the surfactant is a polysorbate.

24. The method of claim 23, wherein the slurry comprises about 0.15 g/kg of the compound of Formula (I) and about 0.5 g/kg of polysorbate 80.

25. The method of claim 23, wherein the slurry comprises about 0.35 g/kg of the compound of Formula (I) and about 0.5 g/kg of polysorbate 80.

26. The method of claim 23, wherein the slurry comprises about 1.15 g/kg of the compound of Formula (I) and about 0.5 g/kg of polysorbate 80.

27. The method of claim 22, wherein the slurry comprises about 0.01 g/kg to about 5 g/kg; 0.01 g/kg to about 2.5 g/kg; about 0.01 g/kg to about 1 g/kg; about 0.01 g/kg to about 0.75 g/kg; about 0.01 g/kg to about 0.5 g/kg; about 0.01 g/kg to about 0.25 g/kg; about 0.025 g/kg to about 5 g/kg; about 0.05 g/kg to about 5 g/kg; about 1 g/kg to about 5 g/kg; about 0.1 g/kg to about 5 g/kg; 0.1 g/kg to about 2.5 g/kg; about 0.1 g/kg to about 1 g/kg; about 0.1 g/kg to about 0.75 g/kg; about 0.1 g/kg to about 0.5 g/kg; about 0.1 g/kg to about 0.25 g/kg; about 0.25 g/kg to about 5 g/kg; about 0.25 g/kg to about 2.5 g/kg; about 0.25 g/kg to about 0.75 g/kg; about 0.5 g/kg to about 5 g/kg; about 0.5 g/kg to about 2.5 g/kg; about 0.5 g/kg to about 1 g/kg; about 1 g/kg to about 5 g/kg; about 2.5 g/kg to about 5 g/kg; or about 1 g/kg to about 2 g/kg of the surfactant.

28. The method of claim 27, wherein the slurry comprises about 0.5 g/kg of the surfactant.

29. The method of claim 1, wherein the aqueous solution is a filtered mixture.

30. The method of claim 1, wherein the aqueous solution comprises a sterile diluent.

31. The method of claim 1, wherein the aqueous solution is a first sterilized mixture; the slurry is a second sterilized mixture; and the process comprises mixing the first sterilized mixture and the second sterilized mixture.

32. The method of claim 1, wherein the aqueous solution and the slurry are mixed to form a suspension comprising about 0.005 mg/mL to about 2.5 mg/mL, about 0.01 mg/mL to about 2.0 mg/mL, about 0.01 mg/mL to about 1 mg/mL, about 0.01 mg/mL to about 0.5 mg/mL, about 0.01 mg/mL to about 0.2 mg/mL, or about 0.015 mg/mL to about 0.115 mg/mL of the compound of Formula (I).

33. The method of claim 1, wherein the container comprises a suspension comprising about 0.005 mg/mL to about 2.5 mg/mL, about 0.005 mg/mL to about 2 mg/mL, about 0.001 mg/mL to about 2 mg/mL, about 0.01 mg/mL to about 1.8 mg/mL, about 0.015 mg/mL to about 0.115, about 0.025 mg/mL to about 1.6 mg/mL, about 0.05 mg/mL to about 1.5 mg/mL, about 0.075 mg/mL to about 1.25 mg/mL, about 0.1 mg/mL to about 1 mg/mL, or about 0.25 mg/mL to about 0.75 mg/mL of the compound of Formula (I).

34. The method of claim 1, wherein the container is selected from the group consisting of a vial, a bottle, an ampule, and a syringe.

35. The method of claim 34, wherein the vial is a glass vial, or a plastic vial made of polyethylene, polypropylene, polyolefins, polyethylene terephthalate, polyethylene terephthalate G, poly(vinyl chloride), and mixtures thereof.

36. The method of claim 1, wherein the container has a volume of 1 mL, 2 mL, 3 mL, 4 mL, 5 mL, 6 mL, 7 mL, 8 mL, 9 mL, or 10 mL.

37. The method of claim 36, wherein the container is a 3 mL polypropylene vial.

38. The method of claim 36, wherein the container is a 2 mL glass vial.

39. The method of claim 1, wherein the mixing is done aseptically.

40. The method of claim 1, wherein the filling is done aseptically.

41. The method of claim 1, wherein the filled container is terminally sterilized.

42. The method of claim 1, wherein the administration is intra-articular.

43. The method of claim 42, wherein the formulation is administered once.

44. The method of claim 42, wherein the formulation is administered more than once with each injection separated by about 3 months to about 60 months.

45. The method of claim 44, wherein the formulation is administered once monthly, every 3 months, every 6 months, or every 60 months.

* * * * *